(12) United States Patent
Ledbetter et al.

(10) Patent No.: US 9,790,479 B2
(45) Date of Patent: Oct. 17, 2017

(54) THERAPEUTIC NUCLEASE COMPOSITIONS AND METHODS

(71) Applicant: University of Washington, Seattle, WA (US)

(72) Inventors: Jeffrey A. Ledbetter, Seattle, WA (US); Martha Hayden-Ledbetter, Seattle, WA (US); Keith Elkon, Seattle, WA (US); Xizhang Sun, Seattle, WA (US)

(73) Assignee: University of Washington, Seattle, WA (US)

( * ) Notice: Subject to any disclaimer, the term of this patent is extended or adjusted under 35 U.S.C. 154(b) by 344 days.

(21) Appl. No.: 14/516,161

(22) Filed: Oct. 16, 2014

(65) Prior Publication Data

US 2015/0037871 A1    Feb. 5, 2015

Related U.S. Application Data

(60) Division of application No. 13/799,843, filed on Mar. 13, 2013, now abandoned, which is a division of application No. 13/197,731, filed on Aug. 3, 2011, now Pat. No. 8,841,416, which is a continuation of application No. PCT/US2010/055131, filed on Nov. 2, 2010.

(60) Provisional application No. 61/370,752, filed on Aug. 4, 2010, provisional application No. 61/257,458, filed on Nov. 2, 2009.

(51) Int. Cl.
| | |
|---|---|
| *C07H 21/04* | (2006.01) |
| *C12P 21/06* | (2006.01) |
| *C12N 5/02* | (2006.01) |
| *C12N 1/20* | (2006.01) |
| *C12N 15/00* | (2006.01) |
| *C12N 9/22* | (2006.01) |
| *C12N 11/06* | (2006.01) |
| *C12N 9/96* | (2006.01) |
| *C07K 16/18* | (2006.01) |
| *C07K 1/00* | (2006.01) |
| *A61K 38/00* | (2006.01) |

(52) U.S. Cl.
CPC .............. *C12N 9/22* (2013.01); *C07K 16/18* (2013.01); *C12N 9/96* (2013.01); *C12N 11/06* (2013.01); *A61K 38/00* (2013.01); *C07K 2319/30* (2013.01); *C12Y 301/27005* (2013.01); *Y02P 20/582* (2015.11)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,941,763 A | 3/1976 | Sarantakis |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,428,130 A | 6/1995 | Capon et al. |
| 5,453,269 A | 9/1995 | Haber et al. |
| 5,559,212 A | 9/1996 | Ardelt |
| 5,637,481 A | 6/1997 | Ledbetter et al. |
| 5,648,260 A | 7/1997 | Winter et al. |
| 5,658,570 A | 8/1997 | Newman et al. |
| 5,739,277 A | 4/1998 | Presta et al. |
| 5,834,250 A | 11/1998 | Wells et al. |
| 5,840,296 A | 11/1998 | Raines et al. |
| 5,840,840 A | 11/1998 | Rybak et al. |
| 5,869,046 A | 2/1999 | Presta et al. |
| 5,955,073 A | 9/1999 | Rybak et al. |
| 5,973,116 A | 10/1999 | Epenetos et al. |
| 5,989,830 A | 11/1999 | Davis et al. |
| 6,096,871 A | 8/2000 | Presta et al. |
| 6,121,022 A | 9/2000 | Presta et al. |
| 6,175,003 B1 | 1/2001 | Saxena |
| 6,194,551 B1 | 2/2001 | Idusogie et al. |
| 6,239,257 B1 | 5/2001 | Ardelt |
| 6,242,195 B1 | 6/2001 | Idusogie et al. |
| 6,277,375 B1 | 8/2001 | Ward |
| 6,280,991 B1 | 8/2001 | Raines |
| 6,348,343 B2 | 2/2002 | Lazarus et al. |
| 6,391,607 B1 | 5/2002 | Lazarus et al. |
| 6,482,626 B2 | 11/2002 | Baker et al. |
| 6,528,624 B1 | 3/2003 | Idusogie et al. |
| 6,538,124 B1 | 3/2003 | Idusogie et al. |
| 6,653,104 B2 | 11/2003 | Goldenberg |
| 6,660,843 B1 | 12/2003 | Feige et al. |
| 6,716,974 B1 | 4/2004 | Maciag et al. |
| 6,737,056 B1 | 5/2004 | Presta |
| 6,821,505 B2 | 11/2004 | Ward |
| 6,998,253 B1 | 2/2006 | Presta et al. |

(Continued)

FOREIGN PATENT DOCUMENTS

| | | |
|---|---|---|
| CL | 2438-2013 | 8/2013 |
| CL | 2013-02428 | 8/2014 |

(Continued)

OTHER PUBLICATIONS

Canadian Third Office Action, Canadian Application No. 2,779,615, Mar. 6, 2017, 8 pages.
Clark, E.A. et al., "CD16-Mediated Antibody Dependent Cellular Cytotoxicity is Required for B Cell Depletion by a Small Modular ImmunoPharmaceutical Specific for CD20," Blood, 2003, Abstract#2388, p. 646a, vol. 102, No. 11.
United States Restriction Requirement, U.S. Appl. No. 14/599,567, Apr. 6, 2017, 5 pages.
Chinese Fourth Office Action, Chinese Application No. 201280032451.2, Feb. 28, 2017, 4 pages (with concise explanation of relevance).
Indian First Examination Report, Indian Application No. 4709/CHENP/2012, Feb. 21, 2017, 9 pages.

(Continued)

*Primary Examiner* — Chun Dahle
(74) *Attorney, Agent, or Firm* — Fenwick & West LLP

(57) ABSTRACT

Hybrid nuclease molecules and methods for treating an immune-related disease or disorder in a mammal, and a pharmaceutical composition for treating an immune-related disease in a mammal.

84 Claims, 26 Drawing Sheets

(56) References Cited

U.S. PATENT DOCUMENTS

| | | |
|---|---|---|
| 7,033,572 B2 | 4/2006 | Goldenberg |
| 7,067,298 B2 | 6/2006 | Latham et al. |
| 7,074,592 B2 | 7/2006 | Ashkenazi et al. |
| 7,083,784 B2 | 8/2006 | Dall'Acqua et al. |
| 7,098,016 B2 | 8/2006 | Raines et al. |
| 7,118,751 B1 | 10/2006 | Ledbetter et al. |
| 7,247,302 B1 | 7/2007 | Rosok et al. |
| 7,317,091 B2 | 1/2008 | Lazar et al. |
| 7,364,731 B2 | 4/2008 | Idusogie et al. |
| 7,407,785 B2 | 8/2008 | Lazarus et al. |
| 7,416,875 B2 | 8/2008 | Raines et al. |
| 7,544,487 B2 | 6/2009 | Goldenberg et al. |
| 7,655,757 B2 | 2/2010 | Raines et al. |
| 7,662,925 B2 | 2/2010 | Lazar et al. |
| 7,754,208 B2 | 7/2010 | Ledbetter et al. |
| 7,754,209 B2 | 7/2010 | Ledbetter et al. |
| 7,807,409 B2 | 10/2010 | Kopetzki |
| 7,829,084 B2 | 11/2010 | Ledbetter et al. |
| 8,029,782 B2 | 10/2011 | Klink et al. |
| 8,067,548 B2 | 11/2011 | Wang et al. |
| 8,642,752 B2 | 2/2014 | Swayze et al. |
| 8,697,065 B2 | 4/2014 | Strong et al. |
| 8,841,416 B2 | 9/2014 | Ledbetter et al. |
| 8,937,157 B2 | 1/2015 | Ledbetter et al. |
| 2002/0103125 A1 | 8/2002 | Ashkenazi et al. |
| 2005/0054832 A1 | 3/2005 | Lazar et al. |
| 2005/0136049 A1 | 6/2005 | Ledbetter et al. |
| 2005/0158307 A1 | 7/2005 | Spies et al. |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2006/0040262 A1 | 2/2006 | Morris et al. |
| 2006/0235208 A1 | 10/2006 | Lazar et al. |
| 2006/0263774 A1 | 11/2006 | Clark et al. |
| 2007/0025982 A1 | 2/2007 | Ledbetter et al. |
| 2007/0059306 A1 | 3/2007 | Grosmaire et al. |
| 2007/0111281 A1 | 5/2007 | Sondermann et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0237779 A1 | 10/2007 | Ledbetter et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0057056 A1 | 3/2008 | Lazar et al. |
| 2008/0181892 A1 | 7/2008 | Ledbetter et al. |
| 2008/0227958 A1 | 9/2008 | Thompson et al. |
| 2008/0242845 A1 | 10/2008 | Lazar et al. |
| 2008/0279850 A1 | 11/2008 | Brady et al. |
| 2008/0293121 A1 | 11/2008 | Lazarus et al. |
| 2009/0148447 A1 | 6/2009 | Ledbetter et al. |
| 2009/0175867 A1 | 7/2009 | Thompson et al. |
| 2009/0196870 A1 | 8/2009 | Ledbetter et al. |
| 2009/0214539 A1 | 8/2009 | Grosmaire et al. |
| 2009/0258005 A1 | 10/2009 | Gill et al. |
| 2009/0274692 A1 | 11/2009 | Tan et al. |
| 2010/0015661 A1 | 1/2010 | Dubel et al. |
| 2010/0034820 A1 | 2/2010 | Ledbetter et al. |
| 2010/0099101 A1 | 4/2010 | Behrens et al. |
| 2010/0203052 A1 | 8/2010 | Ledbetter et al. |
| 2010/0279932 A1 | 11/2010 | Ledbetter et al. |
| 2010/0330089 A1 | 12/2010 | Damle et al. |
| 2011/0033483 A1 | 2/2011 | Thompson et al. |
| 2011/0081345 A1 | 4/2011 | Moore et al. |
| 2011/0091461 A1 | 4/2011 | Ledbetter et al. |
| 2011/0105729 A1 | 5/2011 | Ledbetter et al. |
| 2011/0123440 A1 | 5/2011 | Hansen et al. |
| 2011/0151515 A1 | 6/2011 | Heifetz et al. |
| 2011/0171208 A1 | 7/2011 | Tan et al. |
| 2012/0225066 A1 | 9/2012 | Ledbetter et al. |
| 2013/0089546 A1 | 4/2013 | Ledbetter et al. |
| 2013/0177561 A1 | 7/2013 | Ledbetter et al. |
| 2013/0183308 A1 | 7/2013 | Ledbetter et al. |
| 2013/0184334 A1 | 7/2013 | Ledbetter et al. |
| 2014/0044711 A1 | 2/2014 | Ledbetter et al. |
| 2014/0178379 A1 | 6/2014 | Ledbetter et al. |
| 2014/0227269 A1 | 8/2014 | Ledbetter et al. |
| 2015/0152399 A1 | 6/2015 | Ledbetter et al. |

FOREIGN PATENT DOCUMENTS

| | | |
|---|---|---|
| CN | 1852976 A | 10/2006 |
| CN | 101990439 A | 3/2011 |
| CN | 102770533 A | 11/2012 |
| EP | 0036676 | 9/1981 |
| EP | 0058481 | 8/1982 |
| EP | 0088046 | 9/1983 |
| EP | 0133988 | 3/1985 |
| EP | 0143949 | 6/1985 |
| JP | 2004-525630 A | 8/2004 |
| JP | 2006-512407 A | 4/2006 |
| JP | 2007-525443 A | 9/2007 |
| JP | 2012-537194 | 3/2013 |
| JP | 2014-508143 | 8/2014 |
| WO | WO 88/07089 | 9/1988 |
| WO | PCT/US93/00829 | 8/1993 |
| WO | WO 96/14339 | 5/1996 |
| WO | WO 98/05787 | 2/1998 |
| WO | WO 98/23289 | 6/1998 |
| WO | WO 99/25044 | 5/1999 |
| WO | WO 99/51642 | 10/1999 |
| WO | WO 99/58572 | 11/1999 |
| WO | WO 00/09560 | 2/2000 |
| WO | WO 00/32767 | 6/2000 |
| WO | WO 00/42072 | 7/2000 |
| WO | WO 01/02440 | 1/2001 |
| WO | WO 02/44215 | 6/2002 |
| WO | WO 02/060919 | 8/2002 |
| WO | WO 02/060955 | 8/2002 |
| WO | WO 02/072605 A2 | 9/2002 |
| WO | WO 02/096948 | 12/2002 |
| WO | WO 03/074569 | 9/2003 |
| WO | WO 2004/016750 | 2/2004 |
| WO | WO 2004/029207 | 4/2004 |
| WO | WO 2004/035752 | 4/2004 |
| WO | WO 2004/063351 | 7/2004 |
| WO | WO 2004/074455 | 9/2004 |
| WO | WO 2004/099249 | 11/2004 |
| WO | WO 2005/018572 | 3/2005 |
| WO | WO 2005/040217 | 5/2005 |
| WO | WO 2005/047327 | 5/2005 |
| WO | WO 2005/063808 | 7/2005 |
| WO | WO 2005/063815 | 7/2005 |
| WO | WO 2005/070963 | 8/2005 |
| WO | WO 2005/077981 | 8/2005 |
| WO | WO 2005/080586 | 9/2005 |
| WO | WO 2005/092925 | 10/2005 |
| WO | WO 2005/123780 | 12/2005 |
| WO | WO 2006/019447 | 2/2006 |
| WO | WO 2006/047350 | 5/2006 |
| WO | WO 2006/085967 | 8/2006 |
| WO | WO 2007/122511 | 11/2007 |
| WO | WO 2007/122511 A2 | 11/2007 |
| WO | WO 2007/141580 A2 | 12/2007 |
| WO | WO 2008/037311 A1 | 4/2008 |
| WO | WO 2009/015345 | 1/2009 |
| WO | WO 2009/064777 | 5/2009 |
| WO | WO 2011/053982 | 5/2011 |
| WO | WO 2012/149440 | 11/2012 |

OTHER PUBLICATIONS

Japanese Office Action, Japanese Application No. 2016-045546, Jan. 18, 2016, 6 pages (with concise explanation of relevance).
Korean Office Action, Korean Application No. 10-2012-7014363, Nov. 21, 2016, 4 pages (with concise explanation of relevance).
Mexican Third Office Action, Mexican Application No. 13/012612, Feb. 14, 2016, 12 pages.

(56) References Cited

OTHER PUBLICATIONS

Australian Second Examination Report, Australian Application No. 2016201790, Nov. 11, 2016, 3 pages.
Australian First Examination Report, Australian Application No. 2016202135, Nov. 11, 2016, 4 pages.
Chinese Third Office Action, Chinese Application No. 201280032451.2, Aug. 5, 2016, 11 pages.
European Examination Report, European Application No. 12777116.0, Oct. 25, 2016, 4 pages.
Guo, J. et al., "Clinical Applications of DNaseq," International Journal of Pathology and Clinical Medicine, Apr. 2009, pp. 125-129, vol. 29, No. 2 (with English abstract).
Indonesian Office Action, Indonesian Application No. WO0201305523, Sep. 20, 2016, 4 pages.
Israel Office Action, Israel Application No. 219475, Aug. 22, 2016, 7 pages (with concise explanation of relevance).
Ni, Y. et al., "Research Progress of DNaseq," International Journal of Pathology and Clinical Medicine, Dec. 2006, pp. 531-535, vol. 26, No. 6.
Prince, W.S. et al., "Pharmacodynamics of Recombinant Human DNase I in Serum," Clin. Exp. Immunol., 1998, pp. 289-296, vol. 113.
Zhao, W-P. et al., "Relationship Between RNA Released from Mouse Apoptotic Murine Splenocytes and Autoimmune Disease," Chinese Journal of Biochemistry and Molecular Biology, 2003, pp. 662-666, vol. 19, No. 5 (with English abstract).
Boix et al. Mol. Biosyst. 2007, 3:317-335.
Fujihara et al. Comparative Biochemistry and Physiology, Part B 163 (2012) 263-273.
Skolnick et al. Trends in Biotechnology, 18(1):34-39, 2000.
Whisstock et al., Quarterly reviews of Biophysics, 2003, 36:307-340.
Lazarus et al. JBC 1999, 274;14;9738-9743.
Nuclease Feb. 20, 2013, p. 1.
Davis, Jr., J.C. et al., "Recombinant Human Dnase I (rhDNase) in Patients with Lupus Nephritis," Lupus, 1999, pp. 68-76, vol. 8.
Berland, R., et al., "Toll-like Receptor 7-Dependent Loss of B Cell Tolerance in Pathogenic Autoantibody Knockin Mice," Immunity, Sep. 2006, pp. 429-440, vol. 25.
Bitonti, A.J. et al., "Pulmonary Delivery of an Erythropoietin Fc Fusion Protein in Non-Human Primates Through an Immunolobulin Transport Pathway," PNAS, Jun. 29, 2004, pp. 9763-9768, vol. 101, No. 26.
Brekke, O.H. et al., "Human IgG Isotype-Specific Amino Acid Residues Affecting Complement-Mediated Cell Lysis and Phagocytosis," European Journal of Immunology, 1994, pp. 2542-2547, vol. 24.
Brekke, O.H. et al., "Therapeutic Antibodies for Human Diseases at the Dawn of the Twenty-First Century," Nature Reviews, Jan. 2003, pp. 52-62, vol. 2.
Dubel, S., "Novel Recombinant Antibody Constructs and Fusion Proteins for Therapy and Research," Department of Biotechnology, Technical University of Braunschweig, Germany, Jun. 17, 2008, 15 pages.
Dwyer, M.A. et al., "Expression and Characterization of a DNase I-Fc Fusion Enzyme," The Journal of Biological Chemistry, Apr. 2, 1999, pp. 9738-9743, vol. 274, No. 14.
Gavalchin, J. et al., "The NZB X SWR Model of Lupus Nephritis. I. Cross-Reactive Idiotypes of Monoclonal Anti-DNA Antibodies in Relation to Antigenic Specificity, Charge, and Allotype. Identification of Interconnected Idiotype Families Inherited from the Normal SWR and the Autoimmune NZB Parents," The Journal of Immunology, Jan. 1, 1987, pp. 128-137, vol. 138.
GenBank Accession No. CAA11830, Nov. 20, 1998, 2 pages, [Online] Retrieved from the Internet<URL:http://www.ncbi.nlm.nih.giv/protein/CAA11830>-.
International Search Report and Written Opinion, PCT Application No. PCT/US10/55131, Apr. 29, 2011, 19 pages.
Invitation to Pay Additional Fees, and, Where Applicable, Protest Fee, PCT Application No. PCT/US10/55131, Feb. 9, 2011, 2 pages.

Linsley, P.S. et al., "CTLA-4 Is a Second Receptor for the B Cell Activation Antigen B7," J. Exp. Med., Sep. 1991, pp. 561-569, vol. 174.
Martinez-Valle, F. et al., "DNase 1 Activity in Patients with Systemic Lupus Erythematosus: Relationship with Epimediological, Clinical Immunological and Therapeutical Features," Lupus, 2009, pp. 418-423, vol. 18, No. 5.
Menzel, et al., "Human Antibody RNase Fusion Protein Targeting $CD30^+$ Lymphomas," Blood, Apr. 1, 2008, pp. 3830-3837, vol. 111, No. 7.
Pan, C.Q. et al., "$Ca^{2+}$-Dependent Activity of Human DNase I and Its Hyperactive Variants," Protein Science, 1999, pp. 1780-1788, vol. 8.
Pan, C.Q. et al., "Improved Potency of Hyperactive and Actin-Resistant Human DNase I Variants for Treatment of Cystic Fibrosis and Systemic Lupus Erythematosus," The Journal of Biological Chemistry, Jul. 17, 1998, pp. 18374-18381, vol. 273, No. 29.
Rodriguez, A.M. et al., "Identification, Localization and Expression of Two Novel Human Genes Similar to Deoxyribonuclease I," Genomics, 1997, pp. 507-513, vol. 42.
Yasuda, T. et al., "A Biochemical and Genetic Study on All Non-Synonymous Single Nucleotide Polymorphisms of the Gene Encoding Human Deoxyribonuclease I Potentially Relevant to Autoimmunity," The International Journal of Biochemistry & Cell Biology, 2010, pp. 1216-1225, vol. 42.
Zeng, Z. et al., "Cloning and Characterization of a Novel Human DNase," Biochemical and Biophysical Research Communication, 1997, pp. 499-504, vol. 231.
Canfield, Stephen M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).
PCT International Search Report and Written Opinion, PCT Application No. PCT/US12/35614, Sep. 4, 2012, 17 pages.
Fenton et al., "Anti-dsDNA Antibodies Promote Initiation, and Acquired Loss of Renal Dnase1 Promotes Progression of Lupus Nephritis in Autoimmune (NZBxNZW)F1 Mice," PloS One, 2009 (published online Dec. 2009), p. e8474, vol. 4, No. 12.
Chinese Office Action, Chinese Application No. 201080060471.1, Apr. 12, 2013, 20 pages.
New Zealand Examination Report, New Zealand Application No. 599842, Feb. 11, 2013, 3 pages.
United States Restriction Requirement, U.S. Appl. No. 13/505,421, Apr. 16, 2013, 8 pages.
European Extended Search Report, European Application No. 10827655.1, Jun. 24, 2013, 11 pages.
Macanovic, M. et al., "The Treatment of Systemic Lupus Erythematosus (SLE) in NZB/W $F_{sub.1}$ Hybrid Mice; Studies with recombinant Murine DNase and with Dexamethasone, " Clinical and Experimental Immunology, Nov. 1996, pp. 243-242, vol. 106, No. 2.
Beintema J.J. et al., "Differences in Glycosylation Pattern of Human Secretory Ribonucleases," Biochem. J., 1988, pp. 501-505, vol. 255.
Shak, S. et al., "Recombinant Human DNase I Reduces the Viscosity of Cystic Fibrosis Sputum," Proc. Natl. Acad. Sci., Dec. 1990, pp. 9188-9192, vol. 87.
Canadian Office Action, Canadian Application No. 2,779,615, Sep. 25, 2013, 5 pages.
GenBank Accession No. CAA55817.1 (May 20, 1994), Filipenko, M.L.et al., NCBI Sequence Viewer v2.0, 3 pages, [online] [Retrieved on Dec. 12, 2013] Retrieved from the Internet at <URL:http://www.ncbi.nlm.nih.gov/protein/CAA55817.1> pp. 1-3.
United States Office Action, U.S. Appl. No. 13/505,421, Oct. 22, 2013, 13 pages.
United States Restriction Requirement, U.S. Appl. No. 13/505,421, Aug. 6, 2013, 8 pages.
Video of Medicine Grand Rounds on Feb. 4, 2010 by Jeffrey Ledbetter, Research Professor of Medicine, Division of Rheumatology; Affiliate Associate Professor of Microbiology University of Washington School of Medicine, Can be Viewed at <http://depts.washington.edu/medweb/conferences/GRarchive.html# ledbett- er>.

(56) References Cited

OTHER PUBLICATIONS

Ledbetter, J.A., "Discovery of Biological Drugs: Seattle at the Leading Edge," Grand Rounds, Department of Medicine, University of Washington, Feb. 4, 2010, 36 pages.
Chinese Office Action, Chinese Application No. 201080060471.1, Feb. 27, 2014, 15 pages.
Australian Examination Report, Australian Application No. 2012249360, Mar. 7, 2014, 19 pages.
Australian First Office Action, Australian Application No. 2010313103, Mar. 14, 2014, 4 pages.
Australian First Office Action, Australian Application No. 2013203097, Mar. 14, 2014, 4 pages.
Chinese Second Office Action, Chinese Application No. 201080060471.1, Feb. 27, 2014, 15 pages.
Egyptian Office Action, Egyptian Application No. PCT1666/2013, May 24, 2014, 2 pages.
Georgian Office Action, Georgian Application No. AP 2012 013299, May 13, 2014, 2 pages, (with English summary).
United States Office Action, U.S. Appl. No. 14/174,167, May 8, 2014, 18 pages.
United States Restriction Requirement, U.S. Appl. No. 13/197,731, Aug. 17, 2012, 11 pages.
United States Restriction Requirement, U.S. Appl. No. 13/197,731, Nov. 16, 2012, 7 pages.
United States Office Action, U.S. Appl. No. 13/197,731, Feb. 27, 2013, 17 pages.
Australian Second Office Action, Australian Application No. 2012249360, Nov. 27, 2015, 3 pages.
Canadian First Office Action, Canadian Application No. 2,834,626, Feb. 5, 2015, 6 pages.
Canadian Second Office Action, Canadian Application No. 2,834,626, Jan. 12, 2016, 3 pages.
Canadian Second Office Action, Canadian Application No. 2,779,612, Dec. 8, 2015, 7 pages.
Chilean First Office Action, Chilean Application No. 03123-2013, Feb. 25, 2015, 13 pages (with concise explanation of relevance).
Chilean Second Office Action, Chilean Application No. 03123-2013, Nov. 13, 2015, 25 pages.
Chinese Third Office Action, Chinese Application No. 201080060471.1, Aug. 26, 2014, 12 pages.
Chinese Fourth Office Action, Chinese Application No. 201080060471.1, May 14, 2015, 9 pages
Chinese First Office Action, Chinese Application No. 201280032451.2, Dec. 11, 2014, 21 pages.
Chinese Second Office Action, Chinese Application No. 201280032451.2, Nov. 10, 2015, 17 pages.
Chinese Fifth Office Action, Chinese Application No. 201080060471.1, Dec. 16, 2015, 4 pages.
Colombian First Office Action, Colombian Application No. 13 279038, May 29, 2015, 13 pages (with concise explanation of relevance).
Eurasian Office Action, Eurasian Application No. 201391585/28, Jun. 25, 2015, 4 pages.
European Extended Search Report, European Application No. 12777116.0, Jun. 3, 2015, 7 pages.
Georgian Office Action, Georgian Application No. AP 2012 013299, Oct. 27, 2015, 3 pages (with concise explanation of relevance).
Gillies, S.D. et al., "Improving the Efficacy of Antibody-Interleukin 2 Fusion Proteins by Reducing Their Interaction with Fc Receptors," Cancer Research, May 1, 1999, pp. 2159-2166, vol. 59.
Israel First Office Action, Israel Application No. 219475, Jun. 19, 2014, 4 pages (with concise explanation of relevance).
Israel Second Office Action, Israel Application No. 219475, May 14, 2015, 6 pages (with concise exlanation of relevance).
Israel First Office Action, Israel Application No. 229074, Nov. 11, 2015, 5 pages (with concise explanation of relevance).
Japanese First Office Action, Japanese Application No. 2012-537194, Nov. 27, 2014, 28 pages.

Japanese Second Office Action, Japanese Application No. 2012-537194, Nov. 9, 2015, 15 pages (with concise explanation of relevance).
Jefferis, R. et al., "Interaction Sites on Human IgG-Fc for FcγR: Current Models," Immunology Letters, Jun. 3, 2002, pp. 57-65, vol. 82, No. 1-2.
Johnson, R.J. et al., "Inhibition of Human Pancreatic Ribonuclease by the Human Ribonuclease Inhibitor Protein," J. Mol. Biol., 2007, pp. 434-449, vol. 368.
Karasinska, J.M., "Searching for the Aircardi-Goutieres Syndrome Genes: TREX1 and Ribonuclease H2 Make the Cut," Clin. Genet., 2006, pp. 457-461, vol. 70.
Kenyan Office Action, Kenyan Application No. KE/P/2013/1931, Sep. 14, 2015, 5 pages.
Lovgren, T. et al., "Induction of Interferon-α by Immune Complexes or Liposomes Containing Systemic Lupus Erythematosus Autoantigen- and Sjogren's Syndrome Autoantigen-Associated RNA," Arthritis & Rheumatism, Jun. 2006, pp. 1917-1927, vol. 54, No. 6.
Mexican First Office Action, Mexican Application No. 12/005062, Jun. 9, 2014, 6 pages.
Mexican Second Office Action, Mexican Application No. 12/005062, Feb. 9, 2015, 13 pages.
Mexican Third Office Action, Mexican Application No. 12/005062, Oct. 2, 2015, 9 pages.
Mexican First Office Action, Mexican Application No. 13/012612, Jun. 26, 2015, 7 pages.
New Zealand Application No. 599842, Filed Nov. 2, 2010, Not yet published.
New Zealand Application No. 628189, Filed Nov. 2, 2010, Not yet published.
New Zealand Second Office Action, New Zealand Application No. 599842, Aug. 21, 2014, 3 pages.
New Zealand First Office Action, New Zealand Application No. 628189, Aug. 21, 2014, 3 pages.
New Zealand First Office Action, New Zealand Application No. 616989, Aug. 25, 2014, 2 pages.
New Zealand Third Office Action, New Zealand Application No. 599842, Dec. 12, 2014, 3 pages.
Sondermann, P. et al., "The 3.2 ANG Crystal Structure of the Human IgG1 Fc Frahment-FcγRIII Complex," Nature, Jul. 20, 2000, pp. 267-273, vol. 406, No. 6793.
Stavenhagen, J.B. et al., "Fc Optimization of Therapeutic Antibodies Enhances Their Ability to Kill Tumor Cells in Vitro and Controls Tumor Expansion in Vivo Via Lof-Affinity Activating Fcγ Receptors," Cancer Research, 2007, pp. 8882-8890, vol. 67.
Strohl, W.R., Curr. Opin. Biotechnol., (Nov. 11, 2009) vol. 20, p. 685-691.
Sun, X. et al., "Increased RNase Expression Reduces Inflammation and Prolongs Survival in TLR7 Transgenic Mice," The Journal of Immunology, Feb. 4, 2013, 9 pages.
Thai Office Action, Thai Application No. 1301006180, Apr. 23, 2015, 2 pages (with concise explanation of relevance).
United States Restriction Requirement, U.S. Appl. No. 13/197,731, Aug. 3, 2012, 11 pages.
United States Office Action, U.S. Appl. No. 13/505,421, Jun. 12, 2014, 13 pages.
United States Restriction Requirement, U.S. Appl. No. 14/174,167, Apr. 15, 2014, 6 pages.
United States Office Action, U.S. Appl. No. 14/174,167, Aug. 25, 2014, 12 pages.
United States Advisory Action, U.S. Appl. No. 14/174,167, Oct. 17, 2014, 4 pages.
Chan, A.G. et al., "Therapeutic Antibodies for Autoimmunity and Inflammation," Nature Reviews Immunology, May 2010, pp. 301-316, vol. 10.
European Examination Report, European Application No. 10827655.1, Feb. 12, 2016, 4 pages.
Japanese Office Action, Japanese Application No. 2014-508143, Mar. 23, 2016, 10 pages.
New Zealand First Examination Report, New Zealand Application No. 717205, Mar. 9, 2016, 3 pages.

(56) References Cited

OTHER PUBLICATIONS

New Zealand First Examination Report, New Zealand Application No. 717398, Mar. 15, 2016, 2 pages.
Colombian Office Action, Colombian Application No. 15 234237, May 12, 2016, 12 pages (with concise explanation of relevance).
Mexican Office Action, Mexican Application No. 13/012612, Feb. 9, 2016, 8 pages.
Ukrainian Office Action, Ukrainian Application No. A201312889, Jul. 13, 2016, 8 pages (with concise explanation of relevance).
Carsana, A. et al. "Structure of the Bovine Pancreatic Ribonuclease Gene: The Unique Intervening Sequence in the 5' Untranslated Region Contains a Promoter-Like Element," Nucleic Acids Research, Jun. 24, 1988, pp. 5491-5550, vol. 16, No. 12.
European Extended Search Report, European Application No. 16198956.1, dated May 4, 2017, 8 pages.
United States Office Action, U.S. Appl. No. 14/599,567, dated Jul. 21, 2017, 9 pages.

Figure 1

Figure 1 (Con't)

Figure 1 (Con't)

1: BDCA2 transfected COS sup
2: Control without enzyme
3: Mock transfected COS sup
4: Trex1-(Gly4S)4-Ig transfected COS sup
5: Trex1-(Gly4S)5-Ig transfected COS sup
6: human TREX1 positive control 1: BDCA2-Ig transfected COS sup (1ml) used as positive control
2: Mock COS sup (1ml) used as negative control
3: Trex1-(Gly4S)4-Ig transfected COS sup (1ml)
4: Trex1-(Gly4S)5-Ig transfected COS sup (1ml)

1. control
2. 2A3(600nM MTX)
3. 2A3(800nM MTX)
4. 3A5(300nM MTX)
5. 3A5(400nM MTX)
6. 8H8(600nM MTX)
7. bulk CHO sup 1,2,3,4,5: mDNase1l3-L-Ig transfected COS sup 2ul, 5ul, 10ul, 15ul and 20ul
6: mDNase1l3-NL-Ig transfected COS sup 20ul
7: mRNase-Ig transfected COS sup 20ul
8: COS sup 20ul A. Gel analysis of
Plasmid DNA Digestion B. DNase Alert Substrate
digestion/UV visualization 1: plasmid DNA mix
2: mock sup
3: 090210-8
4: 090210-9
5: 091210-8
6: 091210-14
7: DNAseI 1: neg. control ddH2O
2: DNase 1 (2 U)
3: mock transfected sup.
4: 090210-8
5: 090210-9
6: 091210-8
7: 091210-14

THERAPEUTIC NUCLEASE COMPOSITIONS AND METHODS

CROSS REFERENCE TO RELATED APPLICATIONS

This application claims the benefit of U.S. Ser. No. 13/799,843, filed Mar. 13, 2013, which claims the benefit of U.S. Ser. No. 13/197,731, filed Aug. 3, 2011, which claims the benefit of International Application No. PCT/US2010/055131, filed Nov. 2, 2010, which claims the benefit of U.S. Provisional Application No. 61/257,458, filed Nov. 2, 2009, and U.S. Provisional Application No. 61/370,752, filed Aug. 4, 2010; the entire disclosures of which are hereby incorporated by reference in their entirety for all purposes.

STATEMENT REGARDING FEDERALLY SPONSORED RESEARCH OR DEVELOPMENT

This invention was made with government support under grants NS065933 and AR048796 awarded by the National Institutes of Health. The government has certain rights in the invention.

REFERENCE TO A SEQUENCE LISTING

The instant application contains a Sequence Listing which has been submitted via EFS-Web and is hereby incorporated by reference in its entirety. Said ASCII copy, created on Jul. 28, 2015, is named 27991US_sequencelisting.txt, and is 369 kilobytes in size.

BACKGROUND

Excessive release of (ribo)nucleoprotein particles from dead and dying cells can cause lupus pathology by two mechanisms: (i) Deposition or in situ formation of chromatin/anti-chromatin complexes causes nephritis and leads to loss of renal function; and (ii) nucleoproteins activate innate immunity through toll-like receptor (TLR) 7, 8, and 9 as well as TLR-independent pathway(s). Release of nucleoproteins can serve as a potent antigen for autoantibodies in SLE, providing amplification of B cell and DC activation through co-engagement of antigen receptors and TLRs. Thus, there exists a need for a means to remove inciting antigens and/or attenuate immune stimulation, immune amplification, and immune complex mediated disease in subjects in need thereof.

SUMMARY

Disclosed herein is a hybrid nuclease molecule comprising a first nuclease domain and an Fc domain, wherein the first nuclease domain is operatively coupled to the Fc domain. In some embodiments, the hybrid nuclease molecule further includes a first linker domain, and the first nuclease domain is operatively coupled to the Fc domain by the first linker domain.

In some embodiments, a hybrid nuclease molecule is a polypeptide, wherein the amino acid sequence of the first nuclease domain comprises a human, wild-type RNase amino acid sequence, wherein the first linker domain is (Gly4Ser)n, where n is 0, 1, 2, 3, 4 or 5, wherein the amino acid sequence of the Fc domain comprises a human, wild-type IgG1 Fc domain amino acid sequence, and wherein the first linker domain is coupled to the C-terminus of the first nuclease domain and the N-terminus of the Fc domain. In some embodiments, a hybrid nuclease molecule is a polypeptide comprising or consisting of a sequence shown in Table 2. In some embodiments, a hybrid nuclease molecule is a polypeptide comprising SEQ ID NO:149. In some embodiments, a hybrid nuclease molecule is a polypeptide comprising SEQ ID NO:145. In some embodiments, a hybrid nuclease molecule is a polypeptide comprising SEQ ID NO:161. In some embodiments, a hybrid nuclease molecule is a polypeptide comprising SEQ ID NO:162. In some embodiments, a hybrid nuclease molecule is a polypeptide comprising SEQ ID NO:163.

In some embodiments, a hybrid nuclease molecule comprises wild-type, human DNase1 linked to wild-type, human IgG1. In some embodiments, a hybrid nuclease molecule comprises human DNase1 G105R A114F linked to a wild-type, human IgG1 Fc domain by a (gly4ser)n linker domain where n=0, 1, 2, 3, 4, or 5. In some embodiments, a hybrid nuclease molecule comprises wild-type, human RNase1 linked to wild-type, human IgG1 linked to wild-type, human DNase1. In some embodiments, a hybrid nuclease molecule comprises wild-type, human RNase1 linked to wild-type, human IgG1 linked to human DNase1 G105R A114F. In some embodiments, a hybrid nuclease molecule is a polypeptide, wherein the amino acid sequence of the first nuclease domain comprises a RNase amino acid sequence, wherein the first linker domain is between 5 and 32 amino acids in length, wherein the amino acid sequence of the Fc domain comprises a human, Fc domain amino acid sequence, and wherein the first linker domain is coupled to the C-terminus of the first nuclease domain and the N-terminus of the Fc domain. In some embodiments, the linker domain includes (gly4ser)5 and restriction sites BglII, AgeI, and XhoI. In some embodiments, a hybrid nuclease molecule is a polypeptide, wherein the amino acid sequence of the first nuclease domain comprises a human RNase amino acid sequence, wherein the first linker domain is a NLG peptide between 5 and 32 amino acids in length, wherein the amino acid sequence of the Fc domain comprises a human, wild-type Fc domain amino acid sequence, and wherein the first linker domain is coupled to the C-terminus of the first nuclease domain and the N-terminus of the Fc domain.

In some embodiments, the Fc domain binds to an Fc receptor on a human cell. In some embodiments, the serum half-life of the molecule is significantly longer than the serum half-life of the first nuclease domain alone. In some embodiments, the nuclease activity of the first nuclease domain of the molecule is the same or greater than the nuclease domain alone. In some embodiments, administration of the molecule to a mouse increases the survival rate of the mouse as measured by a mouse Lupus model assay.

In some embodiments, a hybrid nuclease molecule includes a leader sequence. In some embodiments, the leader sequence is human VK3LP peptide from the human kappa light chain family, and the leader sequence is coupled to the N-terminus of the first nuclease domain.

In some embodiments, the molecule is a polypeptide. In some embodiments, the molecule is a polynucleotide.

In some embodiments, the first nuclease domain comprises an RNase. In some embodiments, the RNase is a human RNase. In some embodiments, the RNase is a polypeptide comprising an amino acid sequence at least 90% similar to an RNase amino acid sequence set forth in Table 2. In some embodiments, the RNase is a human RNase A family member. In some embodiments, the RNase is a human pancreatic RNase1.

In some embodiments, the first nuclease domain comprises a DNase. In some embodiments, the DNase is a human DNase. In some embodiments, the DNase is a polypeptide comprising an amino acid sequence at least 90% similar to a DNase amino acid sequence set forth in Table 2. In some embodiments, the DNase is selected from the group consisting of human DNase I, TREX1, and human DNase 1L3.

In some embodiments, the Fc domain is a human Fc domain. In some embodiments, the Fc domain is a wild-type Fc domain. In some embodiments, the Fc domain is a mutant Fc domain. In some embodiments, the Fc domain is a human IgG1 Fc domain. In some embodiments, the Fc domain is a polypeptide comprising an amino acid sequence at least 90% similar to an Fc domain amino acid sequence set forth in Table 2.

In some embodiments, the first linker domain has a length of about 1 to about 50 amino acids. In some embodiments, the first linker domain has a length of about 5 to about 31 amino acids. In some embodiments, the first linker domain has a length of about 15 to about 25 amino acids. In some embodiments, the first linker domain has a length of about 20 to about 32 amino acids. In some embodiments, the first linker domain has a length of about 20 amino acids. In some embodiments, the first linker domain has a length of about 25 amino acids. In some embodiments, the first linker domain has a length of about 18 amino acids. In some embodiments, the first linker domain comprises a gly/ser peptide. In some embodiments, the gly/ser peptide is of the formula (Gly$_4$Ser)n, wherein n is a positive integer selected from the group consisting of 1, 2, 3, 4, 5, 6, 7, 8, 9, and 10. In some embodiments, the gly/ser peptide includes (Gly$_4$Ser)3. In some embodiments, the gly/ser peptide includes (Gly$_4$Ser)4. In some embodiments, the gly/ser peptide includes (Gly$_4$Ser)5. In some embodiments, the first linker domain includes at least one restriction site. In some embodiments, the first linker domain includes about 12 or greater nucleotides including at least one restriction site. In some embodiments, the first linker domain includes two or more restriction sites. In some embodiments, the first linker domain includes a plurality of restriction sites. In some embodiments, the first linker domain comprises an NLG peptide. In some embodiments, the first linker domain comprises an N-linked glycosylation site.

In some embodiments, the first nuclease domain is linked to the N-terminus of the Fc domain. In some embodiments, the first nuclease domain is linked to the C-terminus of the Fc domain.

In some embodiments, the hybrid nuclease molecule further includes a second nuclease domain. In some embodiments, the first and second nuclease domains are distinct nuclease domains. In some embodiments, the first and second nuclease domains are the same nuclease domains. In some embodiments, the second nuclease domain is linked to the C-terminus of the Fc domain. In some embodiments, the second nuclease domain is linked to the N-terminus of the Fc domain. In some embodiments, the second nuclease domain is linked to the C-terminus of the first nuclease domain. In some embodiments, the second nuclease domain is linked to the N-terminus of the first nuclease domain.

Also disclosed herein is a dimeric polypeptide comprising a first polypeptide and a second polypeptide, wherein the first polypeptide comprises a first nuclease domain, and an Fc domain, wherein the first nuclease domain is operatively coupled to the Fc domain. In some embodiments, the second polypeptide is a second hybrid nuclease molecule comprising a second nuclease domain, and a second Fc domain, wherein the second nuclease domain is operatively coupled to the second Fc domain.

Also disclosed herein is a pharmaceutical composition comprising at least one hybrid nuclease molecule and/or at least one dimeric polypeptide as described herein, and a pharmaceutically acceptable excipient.

Also disclosed herein is a nucleic acid molecule encoding a hybrid nuclease molecule disclosed herein. Also disclosed herein is a recombinant expression vector comprising a nucleic acid molecule disclosed herein. Also disclosed herein is a host cell transformed with a recombinant expression vector disclosed herein.

Also disclosed herein is a method of making a hybrid nuclease disclosed herein, comprising: providing a host cell comprising a nucleic acid sequence that encodes the hybrid nuclease molecule; and maintaining the host cell under conditions in which the hybrid nuclease molecule is expressed.

Also disclosed herein is a method for treating or preventing a condition associated with an abnormal immune response, comprising administering to a patient in need thereof an effective amount of an isolated hybrid nuclease molecule disclosed herein. In some embodiments, the condition is an autoimmune disease. In some embodiments, the autoimmune disease is selected from the group consisting of insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus (SLE), and connective tissue disease. In some embodiments, the autoimmune disease is SLE.

BRIEF DESCRIPTION OF THE SEVERAL
VIEWS OF THE DRAWINGS

These and other features, aspects, and advantages of the present invention will become better understood with regard to the following description, and accompanying drawings, where:

Figure 1:
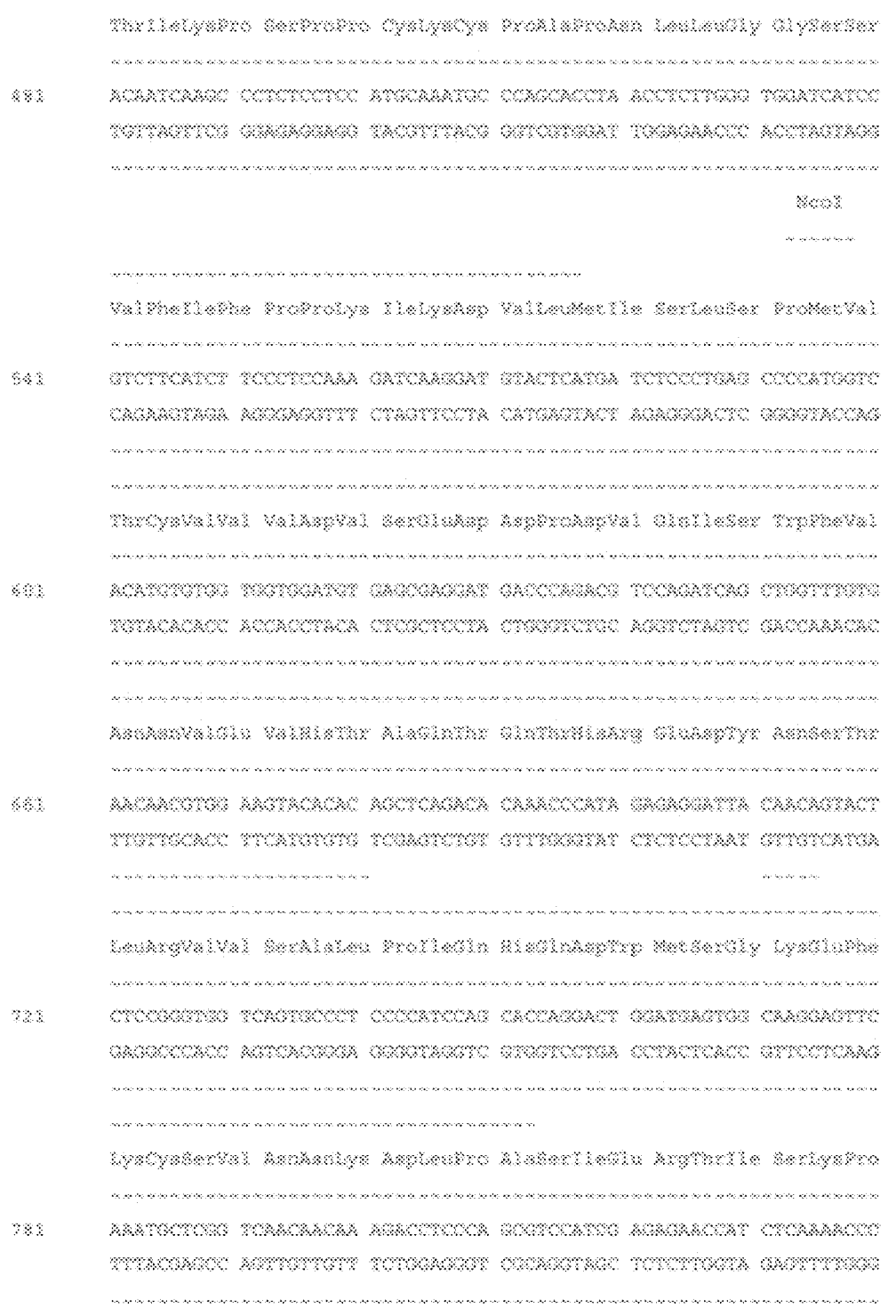

FIG. 1 shows the nucleotide and amino acid sequence of the mRNase-mIgG2a with mutations at P238S, K322S, and P331S. This sequence is listed in the sequence listing as huVK3LP+mrib1+mIgG2A-C-2S (SEQ ID NO:114).

Figure 23:
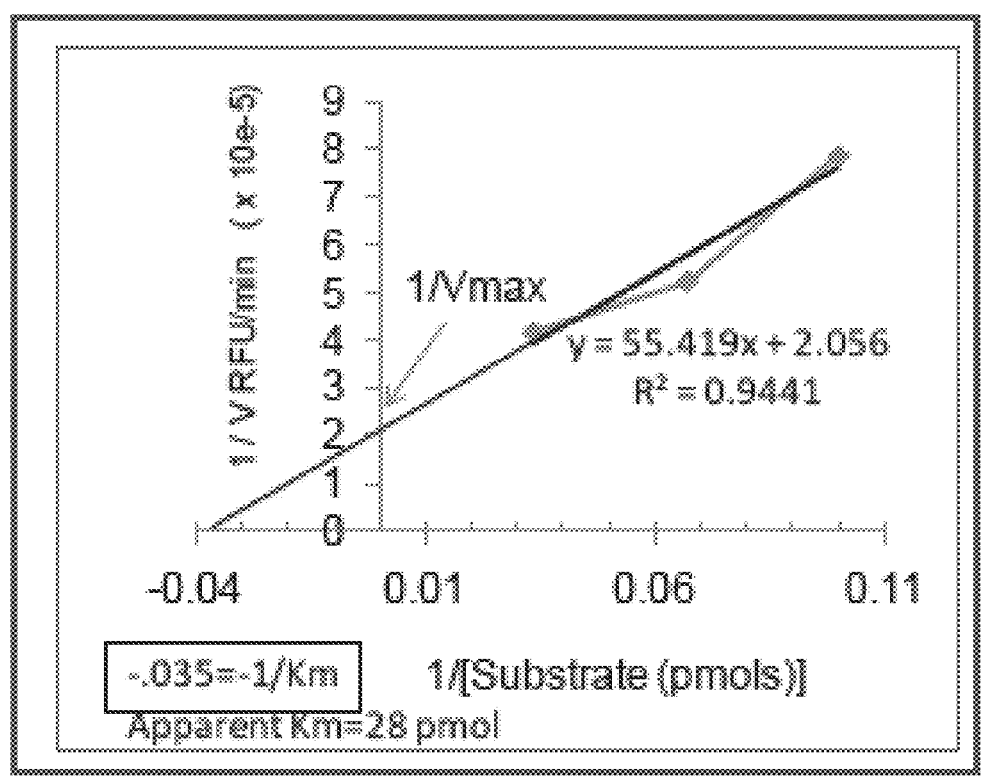

FIG. 23 shows enzyme kinetics assayed using the Rnase Alert Substrate (Ambion/IDT) and fluorescence quantified with a Spectramax M2 microplate Reader. Data was analyzed using Softmax Pro software (Molecular Devices). Reaction rates at different substrate concentrations were measured and the data shown as a Lineweaver-Burk plot. The apparent Km, corrected for volume is 280 nM.

Figure 24:
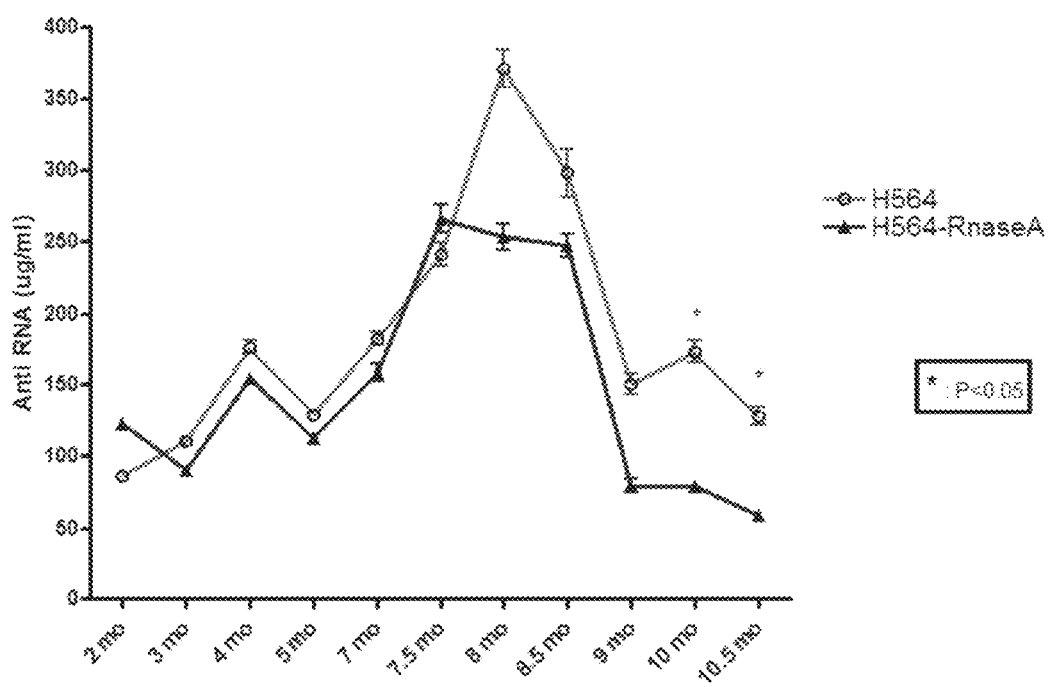

FIG. 24 shows the levels of anti-RNA antibodies in mouse sera from H564 and H564-RNaseA double transgenic mice at successive intervals as the transgenic mice aged.

DETAILED DESCRIPTION

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985); and Cassol et al., 1992; Rossolini et al., *Mol. Cell. Probes* 8:91-98, 1994). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "hybrid nuclease molecule" refers to polynucleotides or polypeptides that comprise at least one nuclease domain and at least one Fc domain. Hybrid nuclease molecules are also referred to as fusion protein(s) and fusion gene(s). For example, in one embodiment, a hybrid nuclease molecule can be a polypeptide comprising at least one Fc domain linked to a nuclease domain such as DNase and/or RNase. As another example, a hybrid nuclease molecule can include an RNase nuclease domain, a linker domain, and an Fc domain. SEQ ID NO:161 is an example of a hybrid nuclease molecule. Other examples are described in more detail below. In one embodiment a hybrid nuclease molecule of the invention can include additional modifications. In another embodiment, a hybrid nuclease molecule may be modified to add a functional moiety (e.g., PEG, a drug, or a label).

In certain aspects, the hybrid nuclease molecules of the invention can employ one or more "linker domains," such as polypeptide linkers. As used herein, the term "linker domain" refers to a sequence which connects two or more domains in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect a nuclease domain to an Fc domain. Preferably, such polypeptide linkers can provide flexibility to the polypeptide molecule. In certain embodiments the polypeptide linker is used to connect (e.g., genetically fuse) one or more Fc domains and/or one or more nuclease domains. A hybrid nuclease molecule of the invention may comprise more than one linker domain or peptide linker.

As used herein, the term "gly-ser polypeptide linker" refers to a peptide that consists of glycine and serine residues. An exemplary gly/ser polypeptide linker comprises the amino acid sequence Ser(Gly$_4$Ser)n. In one embodiment, n=1. In one embodiment, n=2. In another embodiment, n=3, i.e., Ser(Gly$_4$Ser)3. In another embodiment, n=4, i.e., Ser (Gly$_4$Ser)4. In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser (Gly$_4$Ser)n. In one embodiment, n=1. In one embodiment, n=2. In a preferred embodiment, n=3. In another embodiment, n=4. In another embodiment, n=5. In yet another embodiment, n=6.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, the term "Fc region" shall be defined as the portion of a native immunoglobulin formed by the respective Fc domains (or Fc moieties) of its two heavy chains.

As used herein, the term "Fc domain" refers to a portion of a single immunoglobulin (Ig) heavy chain. As such, Fc domain can also be referred to as "Ig" or "IgG." In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). In one embodiment, an Fc domain of the invention comprises at least the portion of an Fc molecule known in the art to be required for FcRn binding. In another embodiment, an Fc domain of the invention comprises at least the portion of an Fc molecule known in the art to be required for FcγR binding. In one embodiment, an Fc domain of the invention comprises at least the portion of an Fc molecule known in the art to be required for Protein A binding. In one embodiment, an Fc domain of the invention comprises at least the portion of an Fc molecule known in the art to be required for protein G binding. An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc domain includes molecules in monomeric or multimeric form, whether digested from whole antibody or produced by other means.

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain retains an effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting hybrid nuclease molecules. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

In one embodiment, a polypeptide of the invention consists of, consists essentially of, or comprises an amino acid sequence selected from Table 2 and functionally active variants thereof. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in Table 2. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence set forth in Table 2. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence set forth in Table 2.

In an embodiment, the peptides of the invention are encoded by a nucleotide sequence. Nucleotide sequences of the invention can be useful for a number of applications, including: cloning, gene therapy, protein expression and purification, mutation introduction, DNA vaccination of a host in need therof, antibody generation for, e.g., passive immunization, PCR, primer and probe generation, siRNA design and generation (see, e.g., the Dharmacon siDesign website), and the like. In an embodiment, the nucleotide sequence of the invention comprises, consists of, or consists essentially of, a nucleotide sequence selected from Table 2. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99° A identical to a nucleotide sequence set forth in Table 2. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in Table 2. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in Table 2.

Preferred hybrid nuclease molecules of the invention comprise a sequence (e.g., at least one Fc domain) derived from a human immunoglobulin sequence. However, sequences may comprise one or more sequences from another mammalian species. For example, a primate Fc domain or nuclease domain may be included in the subject sequence. Alternatively, one or more murine amino acids may be present in a polypeptide. In some embodiments, polypeptide sequences of the invention are not immunogenic and/or have reduced immunogenicity.

It will also be understood by one of ordinary skill in the art that the hybrid nuclease molecules of the invention may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. An isolated nucleic acid molecule encoding a non-natural variant of a hybrid nuclease molecule derived from an immunoglobulin (e.g., an Fc domain) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The peptide hybrid nuclease molecules of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The term "ameliorating" refers to any therapeutically beneficial result in the treatment of a disease state, e.g., an autoimmune disease state (e.g., SLE), including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Compositions

Hybrid Nuclease Molecules

In some embodiments, a composition of the invention includes a hybrid nuclease molecule. In some embodiments, a hybrid nuclease molecule includes a nuclease domain operatively linked to an Fc domain. In some embodiments, a hybrid nuclease molecule includes a nuclease domain linked to an Fc domain. In some embodiments the hybrid nuclease molecule is a nuclease protein. In some embodiments, the hybrid nuclease molecule is a nuclease polynucleotide.

In some embodiments, the nuclease domain is linked to the Fc domain via a linker domain. In some embodiments, the linker domain is a linker peptide. In some embodiments, the linker domain is a linker nucleotide. In some embodiments, the hybrid nuclease molecule includes a leader molecule, e.g., a leader peptide. In some embodiments, the leader molecule is a leader peptide positioned at the N-terminus of the nuclease domain. In some embodiments, the hybrid nuclease molecule will include a stop codon. In some embodiments, the stop codon will be at the C-terminus of the Fc domain.

Figure 12:
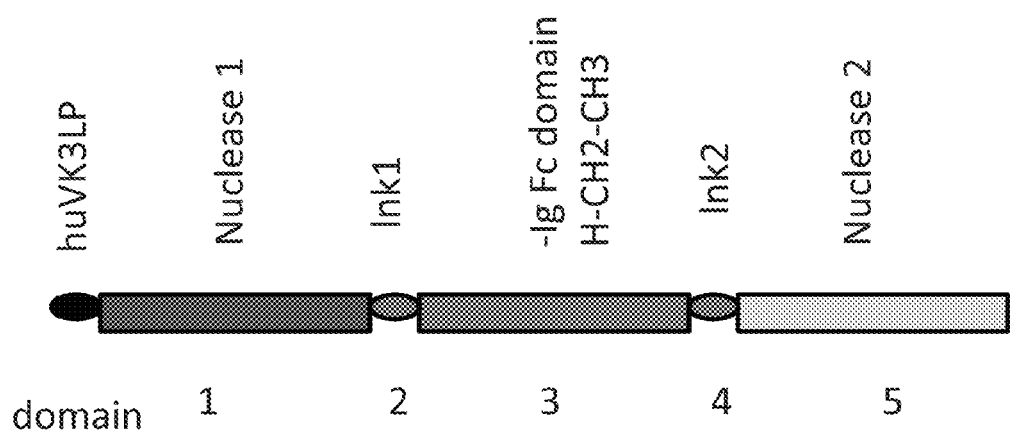
FIG. 12 shows a prototype structure for creating different embodiments of hybrid nuclease molecules.

In some embodiments, the hybrid nuclease molecule further includes a second nuclease domain. In some embodiments, the second nuclease domain is linked to the Fc domain via a second linker domain. In some embodiments, the second linker domain will be at the C-terminus of the Fc domain. FIG. 12 shows at least one embodiment of a hybrid nuclease molecule. In some embodiments, a hybrid nuclease molecule includes a sequence shown in Table 2.

In some embodiments, a hybrid nuclease molecule is an RNase molecule or DNase molecule or a multi-enzyme molecule (e.g., both RNase and DNase or two RNA or DNA nucleases with different specificity for substrate) attached to an Fc domain that specifically binds to extracellular immune complexes. In some embodiments, the Fc domain does not effectively bind Fcγ receptors. In one aspect, the hybrid nuclease molecule does not effectively bind C1q. In other aspects, the hybrid nuclease molecule comprises an in frame Fc domain from IgG1. In other aspects, the hybrid nuclease molecule further comprises mutations in the hinge, CH2, and/or CH3 domains. In other aspects, the mutations are P238S, P331S or N297S, and may include mutations in one or more of the three hinge cysteines. In some such aspects, the mutations in one or more of three hinge cysteines can be SCC or SSS. In other aspects, the molecules contain the SCC hinge, but are otherwise wild type for human IgG1 Fc CH2 and CH3 domains, and bind efficiently to Fc receptors, facilitating uptake of the hybrid nuclease molecule into the endocytic compartment of cells to which they are bound. In other aspects, the molecule has activity against single and/or double-stranded RNA substrates.

In some aspects, the activity of the hybrid nuclease molecule is detectable in vitro and/or in vivo. In some aspects, the hybrid nuclease molecule binds to a cell, a malignant cell, or a cancer cell and interferes with its biologic activity.

In another aspect, a multifunctional RNase molecule is provided that is attached to another enzyme or antibody having binding specificity, such as an scFv targeted to RNA or a second nuclease domain with the same or different specificities as the first domain.

In another aspect, a multifunctional DNase molecule is provided that is attached to another enzyme or antibody having binding specificity, such as an scFv targeted to DNA or a second nuclease domain with the same or different specificities as the first domain.

In another aspect, a hybrid nuclease molecule is adapted for preventing or treating a disease or disorder in a mammal by administering an hybrid nuclease molecule attached to an Fc region, in a therapeutically effective amount to the mammal in need thereof, wherein the disease is prevented or treated. In other aspects, the disease or disorder is an autoimmune disease or cancer. In some such aspects, the autoimmune disease is insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

In some embodiments, the targets of the RNase enzyme activity of RNase hybrid nuclease molecules are primarily extracellular, consisting of, e.g., RNA contained in immune complexes with anti-RNP autoantibody and RNA expressed on the surface of cells undergoing apoptosis. In some embodiments, the RNase hybrid nuclease molecule is active in the acidic environment of the endocytic vesicles. In some embodiments, an RNase hybrid nuclease molecule includes a wild-type (wt) Fc domain in order to, e.g, allow the molecule to bind FcR and enter the endocytic compartment through the entry pathway used by immune complexes. In some embodiments, an RNase hybrid nuclease molecule including a wt Fc domain is adapted to be active both extracellularly and in the endocytic environment (where TLR7 can be expressed). In some aspects, this allows an RNase hybrid nuclease molecule including a wt Fc domain to stop TLR7 signaling through previously engulfed immune complexes or by RNAs that activate TLR7 after viral infection. In some embodiments, the wt RNase of an RNase hybrid nuclease molecule is not resistant to inhibition by an RNase cytoplasmic inhibitor. In some embodiments, the wt RNase of an RNase hybrid nuclease molecule is not active in the cytoplasm of a cell.

In some embodiments, a hybrid nuclease molecule including a wt Fc domain is used for therapy of an autoimmune disease, e.g., SLE.

In some embodiments, Fc domain binding to an Fc receptor (FcR) is increased, e.g., via alterations of glycosylation and/or changes in amino acid sequence. In some embodiments, a hybrid nuclease molecule has one or more Fc alterations that increase FcR binding.

Alternative ways to construct a hybrid nuclease molecule attached to an Fc domain are envisioned. In some embodiments, the domain orientation can be altered to construct an Ig-RNase molecule or an Ig-DNase molecule or an RNase-Ig molecule or an RNase-Ig molecule that retains FcR binding and has active nuclease domains.

In some embodiments, DNase hybrid nuclease molecules include a wt Fc domain that can allow, e.g., the molecules to undergo endocytosis after binding FcR. In some embodiments, the DNase hybrid nuclease molecules can be active towards extracellular immune complexes containing DNA, e.g., either in soluble form or deposited as insoluble complexes.

In some embodiments, hybrid nuclease molecules include both DNase and RNase. In some embodiments, these hybrid nuclease molecules can improve the therapy of SLE because they can, e.g., digest immune complexes containing RNA, DNA, or a combination of both RNA and DNA; and when they further include a wt Fc domain, they are active both extracellularly and in the endocytic compartment where TLR7 and TLR9 can be located.

In some embodiments, linker domains include (gly4ser) 3, 4 or 5 variants that alter the length of the linker by 5 amino acid progressions. In another embodiment, a linker domain is approximately 18 amino acids in length and includes an N-linked glycosylation site, which can be sensitive to protease cleavage in vivo. In some embodiments, an N-linked glycosylation site can protect the hybrid nuclease molecules from cleavage in the linker domain. In some embodiments, an N-linked glycosylation site can assist in separating the folding of independent functional domains separated by the linker domain.

In some embodiments, hybrid nuclease molecules can include both mutant and/or wild type human IgG1 Fc domains. In some embodiments, the hybrid nuclease molecules can be expressed from both COS transient and CHO stable transfections. In some embodiments, both the CD80/86 binding and the RNase activity are preserved in a hybrid nuclease molecule. In some embodiments, hybrid nuclease molecules include DNase1L3-Ig-linker-RNase constructs. In some embodiments, a hybrid nuclease molecule includes a DNase1-Ig-linker-RNase construct or an RNase-Ig-linker-DNase construct. In some embodiments, fusion junctions between enzyme domains and the other domains of the hybrid nuclease molecule is optimized.

In some embodiments, hybrid nuclease molecules include DNase-Ig hybrid nuclease molecules and/or hybrid DNase-RNase hybrid nuclease molecules.

In some embodiments, a hybrid nuclease molecule includes TREX1. In some embodiments, a TREX1 hybrid nuclease molecule can digest chromatin. In some embodiments, a TREX1 hybrid nuclease molecule is expressed by a cell. In some embodiments, the expressed hybrid nuclease molecule includes murine TREX-1 and a murine (wt or mutant) Fc domain. In some embodiments, a 20-25 amino acid (aa) linker domain between TREX1 and the IgG hinge can be required to allow DNase activity. In some embodiments, a hybrid nuclease molecule with a 15 aa linker domain is not active. In some embodiments, use of the 20 and 25 amino acid linker domains (plus 2 or more amino acids to incorporate restriction sites) results in functional activity as measured by chromatin digestion. In some embodiments, a hydrophobic region of approximately 72 aa can be removed from the COOH end of TREX-1 prior to fusion to the Fc domain via the linker domain. In some embodiments, a 20 amino acid linker domain version of the hybrid nuclease molecule exhibits high expression levels compared to controls and/or other hybrid nuclease molecules. In some embodiments, kinetic enzyme assays are used to compare the enzyme activity of hybrid nuclease molecules and controls in a quantitative manner.

In some embodiments, further optimization of the fusion junction chosen for truncation of a TREX1 enzyme can be used to improve expression of the hybrid nuclease molecules.

In some embodiments, the hybrid nuclease molecule includes a human TREX1-linker-Ig Fc domain hybrid nuclease molecule with 20 and/or 25 aa linker domains. In some embodiments, the linker domain(s) are variants of a (gly4ser)4 or (gly4ser)5 cassette with one or more restriction sites attached for incorporation into the hybrid nuclease molecules construct. In some embodiments, because of the head-to-tail dimerization useful for TREX1 enzyme activity; a flexible, longer linker domain can be used to facilitate proper folding.

In some embodiments, the hybrid nuclease molecule is a TREX1-tandem hybrid nuclease molecule. In some embodiments, an alternative method for facilitating head-to-tail folding of TREX1 is to generate a TREX1-TREX1-Ig hybrid hybrid nuclease molecule that incorporates two TREX1 domains in tandem, followed by a linker domain and an Ig Fc domain. In some embodiments, positioning of TREX1 cassettes in a head-to-tail manner can be corrected for head-to tail folding on either arm of the immunoenzyme and introduce a single TREX1 functional domain into each arm of the molecule. In some embodiments, each immunoenzyme of a hybrid nuclease molecule has two functional TREX1 enzymes attached to a single IgG Fc domain.

In some embodiments, the hybrid nuclease molecule includes TREX1-linker1-Ig-linker2-RNase.

In some embodiments, the hybrid nuclease molecule includes RNase-Ig-linker-TREX1. In some embodiments, cassettes are derived for both amino and carboxyl fusion of each enzyme for incorporation into hybrid nuclease molecules where the enzyme configuration is reversed. In some embodiments, the RNase enzyme exhibits comparable functional activity regardless of its position in the hybrid nuclease molecules. In some embodiments, alternative hybrid nuclease molecules can be designed to test whether a particular configuration demonstrates improved expression and/or function of the hybrid nuclease molecule components.

In some embodiments, the hybrid nuclease molecule includes 1L3-Ig. In some embodiments, the 1L3 DNase is constructed from a murine sequence and expressed. In some embodiments, the enzyme is active. In some embodiments, a murine 1L3 DNase-Ig-RNase hybrid nuclease is constructed and expressed. In some embodiments, the molecule includes human 1L3-Ig, human 1L3-Ig-RNase, and/or human RNase-Ig-1L3.

In some embodiments, the hybrid nuclease molecule includes DNase1-Ig. In some embodiments, a naturally occurring variant allele, A114F, which shows reduced sensitivity to actin is included in a DNase1-Ig hybrid nuclease molecule. In some embodiments, this mutation is introduced into a hybrid nuclease molecule to generate a more stable derivative of human DNase1. In some embodiments, a DNase1-linker-Ig containing a 20 or 25 aa linker domain is made. In some embodiments, hybrid nuclease molecules include RNase-Ig-linker-DNase1 where the DNase1 domain is located at the COOH side of the Ig Fc domain. In some embodiments, hybrid nuclease molecules are made that incorporate DNase1 and include: DNase1-linker-Ig-linker2-RNase, and/or RNase-Ig-linker-DNase1.

Another aspect of the present invention is to use gene therapy methods for treating or preventing disorders, diseases, and conditions with one or more hybrid nuclease molecules. The gene therapy methods relate to the introduction of hybrid nuclease molecule nucleic acid (DNA, RNA and antisense DNA or RNA) sequences into an animal to achieve expression of the polypeptide or polypeptides of the present invention. This method can include introduction of one or more polynucleotides encoding a hybrid nuclease molecule polypeptide of the present invention operatively linked to a promoter and any other genetic elements necessary for the expression of the polypeptide by the target tissue.

In gene therapy applications, hybrid nuclease molecule genes are introduced into cells in order to achieve in vivo synthesis of a therapeutically effective genetic product. "Gene therapy" includes both conventional gene therapies where a lasting effect is achieved by a single treatment, and the administration of gene therapeutic agents, which involves the one time or repeated administration of a therapeutically effective DNA or mRNA. The oligonucleotides can be modified to enhance their uptake, e.g., by substituting their negatively charged phosphodiester groups by uncharged groups.

Fc Domains

In some embodiments, a hybrid nuclease molecule includes an Fc domain. Fc domains useful for producing the hybrid nuclease molecules of the present invention may be obtained from a number of different sources. In preferred embodiments, an Fc domain of the hybrid nuclease molecule is derived from a human immunoglobulin. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the hybrid nuclease molecule Fc domain or portion thereof may be derived from any immunoglobulin class, including IgM, IgG, IgD, IgA, and IgE, and any immunoglobulin isotype, including IgG1, IgG2, IgG3, and IgG4. In a preferred embodiment, the human isotype IgG1 is used.

A variety of Fc domain gene sequences (e.g. human constant region gene sequences) are available in the form of publicly accessible deposits. Constant region domains comprising an Fc domain sequence can be selected having a particular effector function (or lacking a particular effector function) or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The hybrid nuclease molecules of the invention may comprise one or more Fc domains (e.g., 2, 3, 4, 5, 6, 7, 8, 9, 10, or more Fc domains). In one embodiment, the Fc domains may be of different types. In one embodiment, at least one Fc domain present in the hybrid nuclease molecule comprises a hinge domain or portion thereof. In another embodiment, the hybrid nuclease molecule of the invention comprises at least one Fc domain which comprises at least one CH2 domain or portion thereof. In another embodiment, the hybrid nuclease molecule of the invention comprises at least one Fc domain which comprises at least one CH3 domain or portion thereof. In another embodiment, the hybrid nuclease molecule of the invention comprises at least one Fc domain which comprises at least one CH4 domain or portion thereof. In another embodiment, the hybrid nuclease molecule of the invention comprises at least one Fc domain which comprises at least one hinge domain or portion thereof and at least one CH2 domain or portion thereof (e.g, in the hinge-CH2 orientation). In another embodiment, the hybrid nuclease molecule of the invention comprises at least one Fc domain which comprises at least one CH2 domain or portion thereof and at least one CH3 domain or portion thereof (e.g, in the CH2-CH3 orientation). In another embodiment, the hybrid nuclease molecule of the invention comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the hybrid nuclease molecule comprises at least one complete Fc region derived from one or more immunoglobulin heavy chains (e.g., an Fc domain including hinge, CH2, and CH3 domains, although these need not be derived from the same antibody). In other embodiments, the hybrid nuclease molecule comprises at least two complete Fc domains derived from one or more immunoglobulin heavy chains. In preferred embodiments, the complete Fc domain is derived from a human IgG immunoglobulin heavy chain (e.g., human IgG1).

In another embodiment, a hybrid nuclease molecule of the invention comprises at least one Fc domain comprising a complete CH3 domain. In another embodiment, a hybrid nuclease molecule of the invention comprises at least one Fc domain comprising a complete CH2 domain. In another embodiment, a hybrid nuclease molecule of the invention comprises at least one Fc domain comprising at least a CH3 domain, and at least one of a hinge region, and a CH2 domain. In one embodiment, a hybrid nuclease molecule of the invention comprises at least one Fc domain comprising a hinge and a CH3 domain. In another embodiment, a hybrid nuclease molecule of the invention comprises at least one Fc domain comprising a hinge, a CH2, and a CH3 domain. In preferred embodiments, the Fc domain is derived from a human IgG immunoglobulin heavy chain (e.g., human IgG1).

The constant region domains or portions thereof making up an Fc domain of a hybrid nuclease molecule of the invention may be derived from different immunoglobulin molecules. For example, a polypeptide of the invention may comprise a CH2 domain or portion thereof derived from an IgG1 molecule and a CH3 region or portion thereof derived from an IgG3 molecule. In another example, a hybrid nuclease molecule can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In another embodiment, a hybrid nuclease molecule of the invention comprises one or more truncated Fc domains that are nonetheless sufficient to confer Fc receptor (FcR) binding properties to the Fc region. Thus, an Fc domain of a hybrid nuclease molecule of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In one embodiment, a hybrid nuclease molecule of the invention lacks one or more constant region domains of a complete Fc region, i.e., they are partially or entirely deleted. In a certain embodiments hybrid nuclease molecules of the invention will lack an entire CH2 domain (ΔCH2 constructs). Those skilled in the art will appreciate that such constructs may be preferred due to the regulatory properties of the CH2 domain on the catabolic rate of the antibody. In certain embodiments, hybrid nuclease molecules of the invention comprise CH2 domain-deleted Fc regions derived from a vector (e.g., from IDEC Pharmaceuticals, San Diego) encoding an IgG1 human constant region domain (see, e.g., WO 02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

Changes to Fc Amino Acids

In certain embodiments, an Fc domain employed in a hybrid nuclease molecule of the invention is altered, e.g., by amino acid mutation (e.g., addition, deletion, or substitution). As used herein, the term "Fc domain variant" refers to an Fc domain having at least one amino acid substitution as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

The amino acid substitution(s) of an Fc variant may be located at a position within the Fc domain referred to as corresponding to the portion number that that residue would be given in an Fc region in an antibody.

In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, the hybrid nuclease molecules of the invention comprise an Fc variant comprising more than one amino acid substitution. The hybrid nuclease molecules of the invention may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers an improvement in at least one effector function imparted by an Fc domain comprising said wild-type Fc domain (e.g., an improvement in the ability of the Fc domain to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The hybrid nuclease molecules of the invention may employ art-recognized Fc variants which are known to impart an improvement in effector function and/or FcR binding. Specifically, a hybrid nuclease molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648, 260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

In certain embodiments, a hybrid nuclease molecule of the invention comprises an amino acid substitution to an Fc domain which alters the antigen-independent effector functions of the antibody, in particular the circulating half-life of the antibody. Such hybrid nuclease molecules exhibit either increased or decreased binding to FcRn when compared to hybrid nuclease molecules lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the hybrid nuclease molecules of the invention exhibit reduced transport across the epithelium of kidney glomeruli from the vasculature. In another embodiment, the hybrid nuclease molecules of the invention exhibit reduced transport across the blood brain barrier (BBB) from the brain, into the vascular space. In one embodiment, a hybrid nuclease molecule with altered FcRn binding comprises at least one Fc domain (e.g., one or two Fc domains) having one or more amino acid substitutions within the "FcRn binding loop" of an Fc domain. Exemplary amino acid substitutions which altered FcRn binding activity are disclosed in International PCT Publication No. WO05/047327 which is incorporated by reference herein.

In other embodiments, a hybrid nuclease molecule of the invention comprises an Fc variant comprising an amino acid substitution which alters the antigen-dependent effector functions of the polypeptide, in particular ADCC or complement activation, e.g., as compared to a wild type Fc region. In exemplary embodiment, said hybrid nuclease molecules exhibit altered binding to an Fc gamma receptor (e.g., CD16). Such hybrid nuclease molecules exhibit either increased or decreased binding to FcR gamma when compared to wild-type polypeptides and, therefore, mediate enhanced or reduced effector function, respectively. Fc variants with improved affinity for FcγRs are anticipated to enhance effector function, and such molecules have useful applications in methods of treating mammals where target molecule destruction is desired. In contrast, Fc variants with decreased FcγR binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation. In one embodiment, the polypeptide comprising an Fc exhibits at least one altered antigen-dependent effector function selected from the group consisting of opsonization, phagocytosis, complement dependent cytotoxicity, antigen-dependent cellular cytotoxicity (ADCC), or effector cell modulation as compared to a polypeptide comprising a wild type Fc region.

In one embodiment the hybrid nuclease molecule exhibits altered binding to an activating FcγR (e.g. FcγI, FcγIIa, or FcγRIIIa). In another embodiment, the hybrid nuclease molecule exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

A hybrid nuclease molecule of the invention may also comprise an amino acid substitution which alters the glycosylation of the hybrid nuclease molecule. For example, the Fc domain of the hybrid nuclease molecule may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the hybrid nuclease molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO05/018572 and US Patent Publication No. 2007/0111281, which are incorporated by reference herein.

In other embodiments, a hybrid nuclease molecule of the invention comprises at least one Fc domain having engineered cysteine residue or analog thereof which is located at the solvent-exposed surface. Preferably the engineered cysteine residue or analog thereof does not interfere with an effector function conferred by the Fc. More preferably, the alteration does not interfere with the ability of the Fc to bind to Fc receptors (e.g. FcγRI, FcγRII, or FcγRIII) or complement proteins (e.g. Clq), or to trigger immune effector function (e.g., antibody-dependent cytotoxicity (ADCC), phagocytosis, or complement-dependent cytotoxicity (CDCC)). In preferred embodiments, the hybrid nuclease molecules of the invention comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the hybrid nuclease molecule of the invention may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the hybrid nuclease molecules of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the hybrid nuclease molecules of the invention may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Linker Domains

In some embodiments, a hybrid nuclease molecule includes a linker domain. In some embodiments, a hybrid nuclease molecule includes a plurality of linker domains. In some embodiments, the linker domain is a polypeptide linker. In certain aspects, it is desirable to employ a polypeptide linker to fuse one or more Fc domains to one or more nuclease domains to form a hybrid nuclease molecule.

In one embodiment, the polypeptide linker is synthetic. As used herein the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., an Fc domain sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc domains are juxtaposed to ensure proper folding and formation of a functional Fc domain. Preferably, a polypeptide linker compatible with the instant invention will be relatively non-immunogenic and not inhibit any non-covalent association among monomer subunits of a binding protein.

In certain embodiments, the hybrid nuclease molecules of the invention employ a polypeptide linker to join any two or more domains in frame in a single polypeptide chain. In one embodiment, the two or more domains may be independently selected from any of the Fc domains or nuclease domains discussed herein. For example, in certain embodiments, a polypeptide linker can be used to fuse identical Fc domains, thereby forming a homomeric Fc region. In other embodiments, a polypeptide linker can be used to fuse different Fc domains (e.g. a wild-type Fc domain and a Fc domain variant), thereby forming a heteromeric Fc region. In other embodiments, a polypeptide linker of the invention can be used to genetically fuse the C-terminus of a first Fc domain (e.g. a hinge domain or portion thereof, a CH2 domain or portion thereof, a complete CH3 domain or portion thereof, a FcRn binding portion, an FcγR binding portion, a complement binding portion, or portion thereof) to the N-terminus of a second Fc domain (e.g., a complete Fc domain).

In one embodiment, a polypeptide linker comprises a portion of an Fc domain. For example, in one embodiment, a polypeptide linker can comprise an immunoglobulin hinge domain of an IgG1, IgG2, IgG3, and/or IgG4 antibody. In another embodiment, a polypeptide linker can comprise a CH2 domain of an IgG1, IgG2, IgG3, and/or IgG4 antibody. In other embodiments, a polypeptide linker can comprise a CH3 domain of an IgG1, IgG2, IgG3, and/or IgG4 antibody. Other portions of an immunoglobulin (e.g. a human immunoglobulin) can be used as well. For example, a polypeptide linker can comprise a CH1 domain or portion thereof, a CL domain or portion thereof, a VH domain or portion thereof, or a VL domain or portion thereof. Said portions can be derived from any immunoglobulin, including, for example, an IgG1, IgG2, IgG3, and/or IgG4 antibody.

In exemplary embodiments, a polypeptide linker can comprise at least a portion of an immunoglobulin hinge region. In one embodiment, a polypeptide linker comprises an upper hinge domain (e.g., an IgG1, an IgG2, an IgG3, or IgG4 upper hinge domain). In another embodiment, a polypeptide linker comprises a middle hinge domain (e.g., an IgG1, an IgG2, an IgG3, or an IgG4 middle hinge domain). In another embodiment, a polypeptide linker comprises a lower hinge domain (e.g., an IgG1, an IgG2, an IgG3, or an IgG4 lower hinge domain).

In other embodiments, polypeptide linkers can be constructed which combine hinge elements derived from the same or different antibody isotypes. In one embodiment, the polypeptide linker comprises a chimeric hinge comprising at least a portion of an IgG1 hinge region and at least a portion of an IgG2 hinge region. In one embodiment, the polypeptide linker comprises a chimeric hinge comprising at least a portion of an IgG1 hinge region and at least a portion of an IgG3 hinge region. In another embodiment, a polypeptide linker comprises a chimeric hinge comprising at least a portion of an IgG1 hinge region and at least a portion of an IgG4 hinge region. In one embodiment, the polypeptide linker comprises a chimeric hinge comprising at least a portion of an IgG2 hinge region and at least a portion of an IgG3 hinge region. In one embodiment, the polypeptide linker comprises a chimeric hinge comprising at least a portion of an IgG2 hinge region and at least a portion of an IgG4 hinge region. In one embodiment, the polypeptide linker comprises a chimeric hinge comprising at least a portion of an IgG1 hinge region, at least a portion of an IgG2 hinge region, and at least a portion of an IgG4 hinge region. In another embodiment, a polypeptide linker can comprise an IgG1 upper and middle hinge and a single IgG3 middle hinge repeat motif. In another embodiment, a polypeptide linker can comprise an IgG4 upper hinge, an IgG1 middle hinge and a IgG2 lower hinge.

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula (Gly$_4$Ser)n, wherein n is a positive integer (e.g., 1, 2, 3, 4, or 5). A preferred gly/ser linker is (Gly$_4$Ser)4. Another preferred gly/ser linker is (Gly$_4$Ser)3. Another preferred gly/ser linker is (Gly$_4$Ser)5. In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as (Gly$_4$Ser)n).

In one embodiment, a polypeptide linker of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a polypeptide linker of the invention. In one embodiment, a polypeptide linker of the invention comprises a hinge domain which does not comprise a naturally occurring number of cysteines, i.e., the polypeptide linker comprises either fewer cysteines or a greater number of cysteines than a naturally occurring hinge molecule.

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a one preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. For example, mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term "about" indicates +/− two amino acid residues. Since linker length must be a positive integer, the length of from about 1 to about 50 amino acids in length, means a length of from 1 to 48-52 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Nuclease Domains

In certain aspects, a hybrid nuclease molecule includes a nuclease domain. Accordingly, the hybrid nuclease molecules of the invention typically comprise at least one nuclease domain and at least one linked Fc domain. In certain aspects, a hybrid nuclease molecule includes a plurality of nuclease domains.

In some embodiments, a nuclease domain is DNase. In some embodiments, the DNase is a Type I secreted DNase. In some embodiments, the DNase is DNase 1 and/or a DNase 1-like (DNaseL) enzyme, 1-3. In some embodiments, the DNase is TREX1.

In some embodiments, a nuclease domain is an RNase. In some embodiments, the RNase is an extracellular or secretory RNase of the RNase A superfamily, e.g., RNase A.

In one embodiment, the nuclease domain is operably linked (e.g., chemically conjugated or genetically fused (e.g., either directly or via a polypeptide linker)) to the N-terminus of an Fc domain. In another embodiment, the nuclease domain is operably linked (e.g., chemically conjugated or genetically fused (e.g., either directly or via a polypeptide linker)) to the C-terminus of an Fc domain. In other embodiments, a nuclease domain is operably linked (e.g., chemically conjugated or genetically fused (e.g., either directly or via a polypeptide linker)) via an amino acid side chain of an Fc domain. In certain exemplary embodiments, the nuclease domain is fused to an Fc domain via a human immunoglobulin hinge domain or portion thereof.

In certain embodiments, the hybrid nuclease molecules of the invention comprise two or more nuclease domains and at least one Fc domain. For example, nuclease domains may be operably linked to both the N-terminus and C-terminus of an Fc domain. In other exemplary embodiments, nuclease domains may be operably linked to both the N- and C-terminal ends of multiple Fc domains (e.g., two, three, four, five, or more Fc domains) which are linked together in series to form a tandem array of Fc domains.

In other embodiments, two or more nuclease domains are linked to each other (e.g., via a polypeptide linker) in series, and the tandem array of nuclease domains is operably linked (e.g., chemically conjugated or genetically fused (e.g., either directly or via a polypeptide linker)) to either the C-terminus or the N-terminus of a Fc domain or a tandem array of Fc domains. In other embodiments, the tandem array of nuclease domains is operably linked to both the C-terminus and the N-terminus of a Fc domain or a tandem array of Fc domains.

In other embodiments, one or more nuclease domains may be inserted between two Fc domains. For example, one or more nuclease domains may form all or part of a polypeptide linker of a hybrid nuclease molecule of the invention.

Preferred hybrid nuclease molecules of the invention comprise at least one nuclease domain (e.g., RNase or DNase), at least one linker domain, and at least one Fc domain.

In certain embodiments, the hybrid nuclease molecules of the invention have at least one nuclease domain specific for a target molecule which mediates a biological effect. In another embodiment, binding of the hybrid nuclease molecules of the invention to a target molecule (e.g. DNA or RNA) results in the reduction or elimination of the target molecule, e.g., from a cell, a tissue, or from circulation.

In certain embodiments, the hybrid nuclease molecules of the invention may comprise two or more nuclease domains. In one embodiment, the nuclease domains are identical, e.g., RNase and RNase, or TREX1 and TREX1. In another embodiment, the nuclease domains are different, e.g., DNase and RNase.

In other embodiments, the hybrid nuclease molecules of the invention may be assembled together or with other polypeptides to form binding proteins having two or more polypeptides ("multimers"), wherein at least one polypeptide of the multimer is a hybrid nuclease molecule of the invention. Exemplary multimeric forms include dimeric, trimeric, tetrameric, and hexameric altered binding proteins and the like. In one embodiment, the polypeptides of the multimer are the same (ie. homomeric altered binding proteins, e.g. homodimers, homotetramers). In another embodiment, the polypeptides of the multimer are different (e.g. heteromeric).

Methods of Making Hybrid Nuclease Molecules

The hybrid nuclease molecules of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Pharmaceutical Compositions and Therapeutic Methods of Use

In certain embodiments, a hybrid nuclease molecule is administered alone. In certain embodiments, a hybrid nuclease molecule is administered prior to the administration of at least one other therapeutic agent. In certain embodiments, a hybrid nuclease molecule is administered concurrent with the administration of at least one other therapeutic agent. In certain embodiments, a hybrid nuclease molecule is administered subsequent to the administration of at least one other therapeutic agent. In other embodiments, a hybrid nuclease molecule is administered prior to the administration of at least one other therapeutic agent. As will be appreciated by one of skill in the art, in some embodiments, the hybrid nuclease molecule is combined with the other agent/compound. In some embodiments, the hybrid nuclease molecule and other agent are administered concurrently. In some embodiments, the hybrid nuclease molecule and other agent are not administered simultaneously, with the hybrid nuclease molecule being administered before or after the agent is administered. In some embodiments, the subject receives both the hybrid nuclease molecule and the other agent during a same period of prevention, occurrence of a disorder, and/or period of treatment.

Pharmaceutical compositions of the invention can be administered in combination therapy, i.e., combined with other agents. In certain embodiments, the combination therapy comprises nuclease molecule, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for pharmaceutical compositions comprising a hybrid nuclease molecule together with a pharmaceutically acceptable diluent, carrier, solubilizer, emulsifier, preservative and/or adjuvant.

In certain embodiments, the invention provides for pharmaceutical compositions comprising a hybrid nuclease molecule and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, a hybrid nuclease molecule and/or a therapeutic molecule is linked to a half-life extending vehicle known in the art. Such vehicles include, but are not limited to, polyethylene glycol, glycogen (e.g., glycosylation of the hybrid nuclease molecule), and dextran. Such vehicles are described, e.g., in U.S. application Ser. No. 09/428,082, now U.S. Pat. No. 6,660,843 and published PCT Application No. WO 99/25044, which are hereby incorporated by reference for any purpose.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising a hybrid nuclease molecule, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a hybrid nuclease molecule, with or without at least one additional therapeutic agent, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired hybrid nuclease molecule, with or without additional therapeutic agents, in a pharmaceutically acceptable vehicle. In certain embodiments, a vehicle for parenteral injection is sterile distilled water in which a hybrid nuclease molecule, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a hybrid nuclease molecule, with or without at least one additional therapeutic agent, can be formulated as a dry powder for inhalation. In certain embodiments, an inhalation solution comprising a hybrid nuclease molecule, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, a hybrid nuclease molecule, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized In certain embodiments, at least one additional agent can be included to facilitate absorption of a hybrid nuclease molecule and/or any additional therapeutic agents.

In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a hybrid nuclease molecule, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a hybrid nuclease molecule, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D(-)-3-hydroxybutyric acid (EP 133,988). In certain embodiments, sustained release compositions can also include liposomes, which can be prepared by any of several methods known in the art. See, e.g., Eppstein et al., Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a hybrid nuclease molecule, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a hybrid nuclease molecule, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of a hybrid nuclease molecule and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising a hybrid nuclease molecule, with or without at least one additional therapeutic agent, in an ex vivo manner. In such instances, cells, tissues and/or organs that have been removed from the patient are exposed to a pharmaceutical composition comprising a hybrid nuclease molecule, with or without at least one additional therapeutic agent, after which the cells, tissues and/or organs are subsequently implanted back into the patient.

In certain embodiments, a hybrid nuclease molecule and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The hybrid nuclease molecules of the instant invention are particularly effective in the treatment of autoimmune disorders or abnormal immune responses. In this regard, it will be appreciated that the hybrid nuclease molecules of the present invention may be used to control, suppress, modulate, treat, or eliminate unwanted immune responses to both external and autoantigens. In yet other embodiments the polypeptides of the present invention may be used to treat immune disorders that include, but are not limited to, insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus, or connective tissue disease.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Construction of RNase-Ig Fusion Genes

Murine RNase 1 was amplified as a full-length cDNA from an EST library (from Dr. C. Raine, Albert Einstein School of Medicine, Bronx, N.Y.) who sent the clone to our laboratory without an MTA. Sequence specific 5' and 3' primers used were from the published sequences. The sequence of the clone was verified by sequencing analysis. The Genebank accession number is NCBI geneID 19752. Full length human RNase 1 was isolated from random primed and oligo dT primed cDNA derived from human pancreas total RNA (Ambion/Applied Biosystems, Austin, Tex.).

Once a full-length clone was isolated, primers were designed to create a fusion gene with the mouse IgG2a (SEQ ID NO:114) or human IgG1 (SEQ ID NO:110) Fc domains. Two different primers were designed for the 5' sequence fused at the amino terminus of the Fc tail; the first incorporated the native leader peptide from mouse (or human) RNase, while the second attached an AgeI site to the amino terminus of RNase at the predicted signal peptide cleavage site in order to fuse the RNase to a human VKIII leader peptide that we already had cloned and used for other expression studies. For the murine RNase, the sequence of the first primer is:

mribNL5'

30 mer (RNase 5' with native leader and HindIII+Kozak) gTT AAg CTT gCC ACC ATg ggT CTg gAg AAg TCC CTC ATT CTg-3' (SEQ ID NO:1)

The second primer creates a gene fusion junction between an existing leader sequence and the mature sequence at the 5' end of the RNase, at or near the predicted leader peptide cleavage site.

27 mer (RNase 5' mature sequence (no leader, with Age1 site)

(SEQ ID NO: 2)
5'-gAT ACC ACC ggT Agg gAA TCT gCA gCA CAg AAg TTT

CAg-3'

The sequence of the 3' primer for fusion to murine IgG2a at the carboxy end of RNase and the amino terminus of the Fc tail is as follows:

mrib3NH2

28 mer (RNase 3' end with XhoI site for fusion to mIgG2a).

(SEQ ID NO: 3)
5'-ggC TCg AgC ACA gTA gCA TCA AAg tGG ACT ggT ACg

TAg g-3'

Two more oligos were designed to create an -Ig-RNase fusion gene, where the -Ig tail is amino terminal to the RNase enzyme domain.

mrib5X 36 mer RNase 5' end with linker aa and XbaI site for fusion to carboxy end of Fc domain.

(SEQ ID NO: 4)
5'-AAA TCT AgA CCT CAA CCA ggT Agg gAA TCT gCA gCA

CAg AAg TTT CAg-3' mrib3X 31 mer RNase 3' end with two stop codons and XbaI site for fusion to carboxy end of Fc domain.

(SEQ ID NO: 5)
5'-TCT AgA CTA TCA CAC AgT AgC ATC AAA gTg gAC Tgg

TAC gTA g-3'

Example 2

Isolation of Anti-RNA or Anti-DNA scFvs from Monoclonal Antibody Expressing Hybridomas An anti-RNA hybridoma designated H564 was used to isolate V regions specific for RNA. Prior to harvesting, H564 anti-RNA hybridoma cells were kept in log phase growth for several days in RPMI 1640 media (Invitrogen/Life Technologies, Gaithersburg, Md.) supplemented with glutamine, pyruvate, DMEM non-essential amino acids, and penicillin-streptomycin. Cells were pelleted by centrifugation from the culture medium, and $2 \times 10^7$ cells were used to prepare RNA. RNA was isolated from the hybridoma cells using the QIAGEN RNAeasy kit (Valencia, Calif.) total RNA isolation kit and QIAGEN QIAshredder according to the manufacturer's instructions accompanying the kit. Four microgram (4 μg) of total RNA was used as template to prepare cDNA by reverse transcription. The RNA, 300 ng random primers, and 500 ng Oligo dT (12-18), and 1 μl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 μl in the presence of 5.times.second strand buffer and 0.1 M DTT provided with the enzyme. The reverse transcription reaction was allowed to proceed at 50° C. for one hour.

The cDNA generated in the reverse transcriptase reaction was purified by QIAquick PCR purification kits (QIAGEN, Valencia Calif.) and tailed with a poly-G sequence using terminal transferase (Invitrogen, Carlsbad, Calif.) according to manufacturer's instructions. Tailed cDNA was again purified by QIAquick PCR purification and eluted in 30 ul elution buffer (EB buffer) provided with the kits. Two microliters of tailed cDNA was used as template along with an anchor-tail 5' primer containing a poly-C domain, and constant region specific, degenerate 3' primers to amplify by PCR the variable regions for the light and heavy chain of the H564 antibody. The two variable chains were designed with restriction enzyme sites so that a scFv could be assembled by three way ligation of the two V regions to a linker sequence after amplification and restriction enzyme digestion.

A (gly4ser)4 peptide linker to be inserted between the two V regions was incorporated by amplification of this linker sequence by overlap extension PCR using overlapping primers encoding the two halves of the molecule. PCR fragments were isolated by agarose gel electrophoresis, fragments isolated by cutting the appropriate bands from the gel and purifying the amplified DNA using QIAquick gel extraction kits (QIAGEN, Valencia, Calif.). scFv derivatives from the H564 hybridoma were assembled as VH-linker-VL fusion genes that could be attached at either end of a larger -Ig fusion gene. The V.sub.H domain was amplified without a leader peptide, but included a 5' Age1 restriction site for fusion to the V.sub.L and a BglII restriction site at the 3' end for fusion to the linker domain.

The scFv-Ig was assembled by inserting the scFv HindIII-XhoI fragment into pDG containing the human IgG1 hinge, CH2, and CH3 regions, which was digested with restriction enzymes, HindIII and XhoI. After ligation, the ligation products were transformed into DH5-alpha bacteria. The scFv-Ig cDNA was subjected to cycle sequencing on a PE 9700 thermocycler using a 25-cycle program by denaturing at 96° C. for 10 seconds, annealing at 50° C. for 30 seconds, and extending at 72° C. for 4 minutes. The sequencing primers were pDG forward and reverse primers and an internal primer that annealed to the CH2 domain human in the IgG constant region portion. Sequencing reactions were performed using the Big Dye Terminator Ready Sequencing Mix v3.1 (PE-Applied Biosystems, Foster City, Calif.) according to the manufacturer's instructions. Samples were subsequently purified using Autoseq G25 columns (GE Healthcare) and the eluates dried in a Savant vacuum dryer, denatured in Template Suppression Reagent (PE-ABI), and analyzed on an ABI 310 Genetic Analyzer (PE-Applied Biosystems). The sequence was edited, translated, and analyzed using Vector Nti version 10.0 (Informax/Invitrogen, North Bethesda, Md.).

Construction of a Human RNaseI-hIgG1 (SEQ ID NO:125-127) Fusion Gene

Human RNase1 (SEQ ID NO:113) was isolated by PCR amplification from human pancreas total RNA obtained from Ambion/Applied Biosystems (Austin, Tex.). Four microgram (4 µg) of total RNA was used as template to prepare cDNA by reverse transcription. The RNA, 300 ng random primers, and 500 ng Oligo dT (12-18), and 1 ul 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 µl in the presence of second strand buffer and 0.1 M DTT provided with the enzyme. The reverse transcription reaction was allowed to proceed at 50° C. for one hour. Reactions were further purified by QIAquick PCR purification columns, and cDNA eluted in 40 microliters EB buffer prior to use in PCR reactions. Two microliters cDNA eluate were added to PCR reactions containing 50 pmol 5' and 3' primers specific for human RNase1, and 45 microliters of PCR high fidelity supermix (Invitrogen, Carlsbad, Calif.) was added to 0.2 ml PCR reaction tubes. PCR reactions were performed using a C1000 thermal cycler (BioRad, Hercules Calif.). Reactions included an initial denaturation step at 95° C. for 2 minutes, followed by 34 cycles with a 94° C., 30 sec denaturation, 50° C., 30 sec annealing, and 68° C., 1 minute extension step, followed by a final 4 minute extension at 72° C. Once wild type tails were isolated, the fragments were TOPO cloned into pCR2.1 vectors; DNA prepared using the QIAGEN spin plasmid miniprep kits according to manufacturer's instructions. Plasmid DNA was sequenced using ABI Dye Terminator v3.1 ready reaction mix according to manufacturer's instructions.

Example 3

Isolation of Human and Mouse -Fc Domains and Introduction of Mutations into the Coding Sequence For isolation of mouse (SEQ ID NO:114) and human -Fc domains (SEQ ID NO:110), RNA was derived from mouse or human tissue as follows. A single cell suspension was generated from mouse spleen in RPMI culture media. Alternatively, human PBMCs were isolated from fresh, whole blood using Lymphocyte Separation Media (LSM) Organon Teknika (Durham, N.C.), buffy coats harvested according to manufacturer's directions, and cells washed three times in PBS prior to use. Cells were pelleted by centrifugation from the culture medium, and 2×10⁷ cells were used to prepare RNA. RNA was isolated from the cells using the QIAGEN RNAeasy kit (Valencia, Calif.) total RNA isolation kit and QIAGEN QIAshredder columns according to the manufacturer's instructions accompanying the kits. One microgram (4 µg) of total RNA was used as template to prepare cDNA by reverse transcription. The RNA, 300 ng random primers, and 500 ng Oligo dT (12-18), and 1 µl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 µl in the presence of .second strand buffer and 0.1 M DTT provided with the enzyme. The reverse transcription reaction was allowed to proceed at 50° C. for one hour. cDNA was purified using QIAquick (QIAGEN) PCR purification columns according to manufacturer's directions, and eluted in 40 microliters EB buffer prior to use in PCR reactions.

Wild type mouse and human -Fc domains were isolated by PCR amplification using the cDNA described above as template. The following primers were used for initial amplification of wild type sequences, but incorporated the desired mutational changes in the hinge domain:

```
mahIgG1CH2M: 47 mer
                                           (SEQ ID NO: 6)
5'-tgtccaccgtgtccagcacctgaactcctgggtggatcgtcagtct tcc-3' hIgG1-5scc: 49 mer
                                           (SEQ ID NO: 7)
5'-agatctcgagcccaaatcttctgacaaaactcacacatgtccacc gtgt-3' mahIgG1S: 51 mer
                                           (SEQ ID NO: 8)
5'-tctagattatcatttacccggagacagagagaggctcttctgcgtg tagtg-3' muIgG2aCH2: 58mer
                                           (SEQ ID NO: 9)
5'-cctccatgcaaatgcccagcacctaacctcttgggtggatcatccg tcttcatcttcc-3' mIgG2a-5scc: 47mer
                                           (SEQ ID NO: 10)
5'-gaagatctcgagcccagaggtcccacaatcaagccctctcctcca-

3' mIgG2a3S: 48mer
                                           (SEQ ID NO: 11)
5'-gtttctagattatcatttacccggagtccgagagaagctcttagtc gt-3'
```

PCR reactions were performed using a C1000 thermal cycler (BioRad, Hercules Calif.) or an Eppendorf thermal cycler (ThermoFisher Scientific, Houston Tex.). Reactions included an initial denaturation step at 95° C. for 2 minutes, followed by 34 cycles with a 94° C., 30 sec denaturation, 50° C., 30 sec annealing, and 72° C., 1 minute extension step, followed by a final 4 minute extension at 72° C. Once wild type tails were isolated, the fragments were TOPO cloned into pCR2.1 vectors, DNA prepared using the QIAGEN spin plasmid miniprep kits according to manufacturer's instructions and clones sequenced using ABI Dye Terminator v3.1 sequencing reactions according to manufacturer's instructions.

DNA from the correct clones were used as templates in overlap extension PCRs to introduce mutations at the desired positions in the coding sequence for mouse IgG2a or human -IgG1. PCR reactions were set up using the full length wild type clones as template (1 microliter), 50 pmol 5' and 3' primers to PCR each portion of the -Fc domain up to and including the desired mutation site from each direction, and PCR hi fidelity Supermix (Invitrogen, Carlsbad Calif.), in 50 microliter reaction volumes using a short amplification cycle. As an example of the overlapping PCR mutagenesis, the primer combination used to introduce the P331S mutation into human -IgG1, was as follows:

A 5' subfragment was amplified using the full-length wild type clone as template, and the 5' primer was hIgG1-5scc: 5'-agatctcgagcccaaatcttctgacaaaactcacacatgtccaccgtgt-3' (SEQ ID NO:12), while the 3' primer was P331AS: 5'-gttttctcgatggaggctgggagggctttgttggagacc-3' (SEQ ID NO:13). A 3' subfragments was amplified using the full-length wild type clone as template and the 5' primer was P331S: 5'aaggtctccaacaaagccctcccagcctccatcga-gaaaacaatctcc-3' (SEQ ID NO:14), while the 3' primer was mahIgG1S: 5'-tctagattatcatttacccggagacagagagaggctcttct-gcgtgtagtg-3' (SEQ ID NO:15).

Once subfragments were amplified and isolated by agarose gel electrophoresis, they were purified by QIAquick gel purification columns and eluted in 30 microliters EB buffer according to manufacturer's instructions. Two rounds of PCR were then performed with the two subfragments as overlapping templates in new reactions. The cycler was paused and the 5' (hIgG1-5scc, see above) and 3' (mahIgG1S, see above) flanking primers were added to the reactions (50 pmol each). PCR amplifications were then carried out for 34 cycles at the conditions described for the wild type molecules above. Full length fragments were isolated by gel electrophoresis, and TOPO cloned into pCR2.1 vectors for sequence analysis. Fragments from clones with the correct sequence were then subcloned into expression vectors for creation of the different hybrid nuclease molecules described herein.

Example 4

Expression of RNAse-Ig (SEQ ID NO 124, 125, 126, 127, 174 (Nucleotide) or 160, 161, 162, 163, 175 (Amino Acid)), DNAse-Ig (SEQ ID NO: 118, 119, 120, 121, 122, 123, 186 (Nucleotide) or SEQ ID NO 154, 155, 156, 157, 158, 159, 187 (Amino Acid)), Multi-subunit Ig Fusion Constructs (SEQ ID NO: 115, 116, 117, 172, 176, 178, 180 (Nucleotide) or SEQ ID NO 151 152, 153, 173, 177, 179, 181 (Amino Acid)), and H564 scFv-Ig Fusion Proteins in Stable CHO Cell Lines This example illustrates expression of the different -Ig fusion genes described herein in eukaryotic cell lines and characterization of the expressed fusion proteins by SDS-PAGE and by IgG sandwich ELISA.

The -Ig fusion gene fragments with correct sequence were inserted into the mammalian expression vector pDG, and DNA from positive clones was amplified using QIAGEN plasmid preparation kits (QIAGEN, Valencia, Calif.). The recombinant plasmid DNA (100 µg) was then linearized in a nonessential region by digestion with AscI, purified by phenol extraction, and resuspended in tissue culture media, Excell 302 (Catalog #14312-79P, JRH Biosciences, Lenexa, Kans./SAFC). Cells for transfection, CHO DG44 cells, were kept in logarithmic growth, and $10^7$ cells harvested for each transfection reaction. Linearized DNA was added to the CHO cells in a total volume of 0.8 ml for electroporation.

Stable production of the -Ig fusion protein was achieved by electroporation of a selectable, amplifiable plasmid, pDG, containing the RNase-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 µg each of plasmid and carrier DNA was used to transfect $10^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2×DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Invitrogen/Life Technologies). Media for transfections under selection contained varying levels of methotrexate (Sigma-Aldrich) as selective agent, ranging from 50 nM to 1 µM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 50 nM methotrexate. Once clonal outgrowth was sufficient, serial dilutions of culture supernatants from master wells were screened for expression of -Ig fusion protein by use of an -IgG sandwich ELISA. Briefly, NUNC immulon II plates were coated overnight at 4° C. with 7.5 microgram/nil F(ab'2) goat anti-mouse IgG (KPL Labs, Gaithersburg, Md.) in PBS. Plates were blocked in PBS/3% BSA, and serial dilutions of culture supernatants incubated at room temperature for 2-3 hours. Plates were washed three times in PBS/0.05% Tween 20, and incubated with horseradish peroxidase conjugated F(ab'2)goat anti-mouse IgG2a (Southern Biotechnologies) and goat anti-mouse IgG (KPL) mixed together, each at 1:3500 in PBS/1.0% BSA, for 1-2 hours at room temperature. Plates were washed four times in PBS/0.05% Tween 20, and binding detected with SureBlue Reserve, TMB substrate (KPL Labs, Gaithersburg, Md.). Reactions were stopped by addition of equal volume of 1N HCl, and plates read at 450 nM on a Spectramax Pro plate reader (Microdevices, Sunnyvale Calif.). The clones with the highest production of the fusion protein were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the Excell 302 complete media contained an increased concentration of methotrexate, such that only the cells that amplified the DHFR plasmid could survive. The production level of the top four unamplified master wells from the RNase1g CHO transfectants ranged from 30-50 micrograms/ml culture. The amplified cultures are currently being assayed to determine production levels.

Supernatants were collected from CHO cells expressing the RNase-Ig, filtered through 0.2 um PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7), and bound protein was eluted using 0.1 M citrate buffer, pH 3.0. Fractions were collected and protein concentration was determined at 280 nM using a Nanodrop (Wilmington Del.) microsample spectrophotometer, and blank determination using 0.1 M citrate buffer, pH 3.0. Fractions containing fusion protein were pooled, and buffer exchange performed by serial spins in PBS using centricon concentrators followed by filtration through 0.2 μm filter devices, to reduce the possibility of endotoxin contamination. An extinction coefficient of 1.05 was determined using the protein analysis tools in the Vector Nti Version 10.0 Software package (Informax, North Bethesda, Md.) and the predicted cleavage site from the online ExPasy protein analysis tools.

Example 5

SDS-PAGE Analysis of RNaseIg Fusion Protein

Purified RNase-Ig (SEQ ID NO:115) was analyzed by electrophoresis on SDS-Polyacrylamide gels. Fusion protein samples were boiled in SDS sample buffer with and without reduction of disulfide bonds and applied to SDS 10% Tris-BIS gels (Catalog #NP0301, Novex, Carlsbad, Calif.). Five micrograms of each purified protein was loaded on the gels. The proteins were visualized after electrophoresis by Coomassie Blue staining (Pierce Gel Code Blue Stain Reagent, Catalog #24590, Pierce, Rockford, Ill.), and destaining in distilled water. Molecular weight markers were included on the same gel (Kaleidoscope Prestained Standards, Catalog #161-0324, Bio-Rad, Hercules, Calif.). Other samples were run as follows: Rnase-Ig fusion protein in the sampling buffer (62.5 mM Tris-HCl, pH6.8, 2% SDS, 10% glycerol, 0.01% Bromophenol blue) with and without 5% 2-mercaptoethanol) was loaded onto the 4-12% pre-cast gel (Bio-RAD). The gel was running at 100 volts until the dye ran off the gel. The gel was stained in the GelCode Blue (Thermo scientific) at room temperature overnight and then washed with water.

Figure 2:
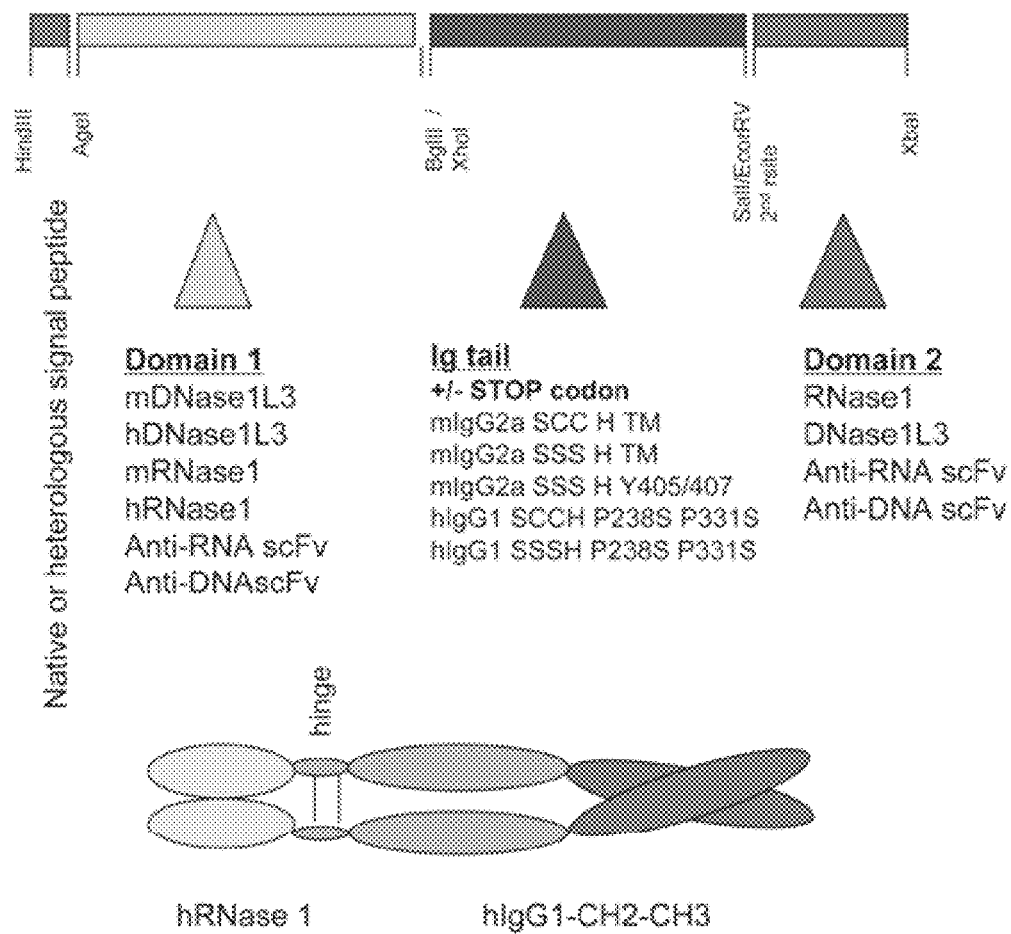
FIG. 2 shows a schematic diagram of some embodiments of hybrid nuclease molecules described herein.
Figure 3:
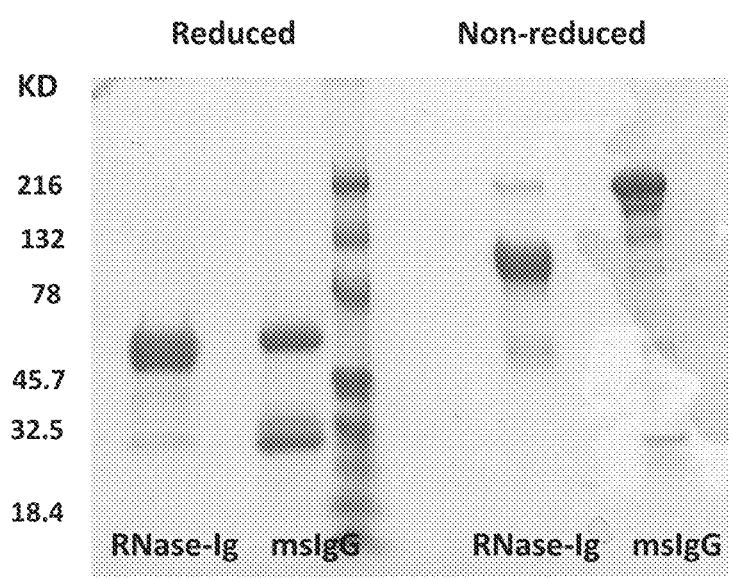
FIG. 3 shows the SDS-PAGE gel analysis of mRNase-mIgG2a-c under both reducing and non-reducing conditions.

FIG. 3 shows the RNase-Ig fusion protein compared to mouse IgG. Rnase-Ig was purified from supernatant transfected CHO cells by binding and elution from Protein A sepharose. The SDS-PAGE gel shows that Rnase-Ig is approximately 50 kDa when reduced and approximately 110 kDa when non-reduced.

Example 6

Detection of RNase-Ig in Mouse Sera

SRED Assay

The 2% agarose gel was prepared with distilled water. Poly-IC (Sigma) was dissolved in distilled water at 3 mg/ml and the gel plate was prepared as follows: 1.5 ml reaction buffer (0.2M Tris-HCl pH 7.0, 40 mM EDTA and 0.1 mg/ml ethidium bromide), 1 ml Poly-IC and 0.5 ml water were place in the tube and maintained at 50° C. for 5 min. 3 ml of the agarose (kept at 50° C.) was added to the tube. The mixture was immediately poured onto a glass plate. Sampling wells were punched in the gel. 2 μl of each serum sample was loaded into wells and the gel was incubated at 37° C. for 4 hours in the moist chamber. Then the gel was incubated in a buffer (20 mM sodium acetate pH5.2, 20 mg/ml ethidium bromide) on ice for 30 min. and read under UV.

Figure 4:
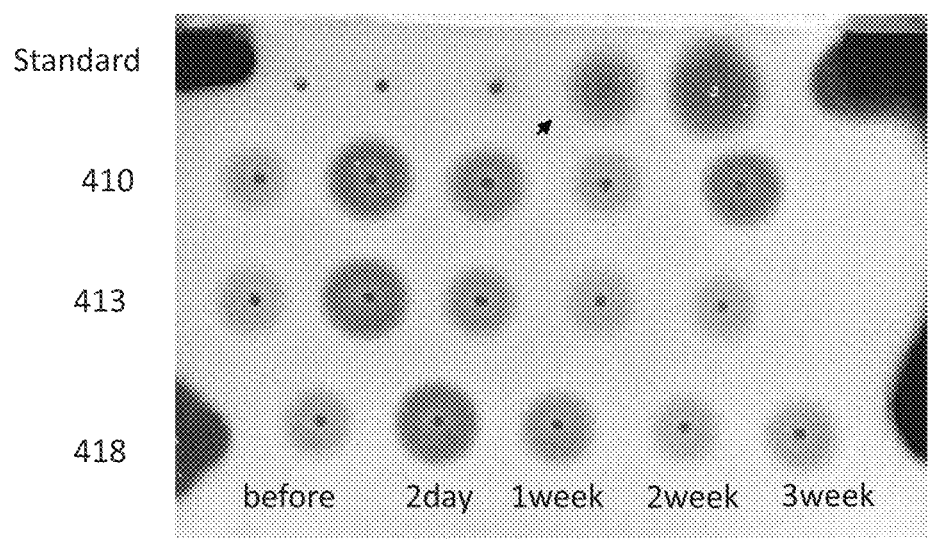
FIG. 4 shows gel immunoprecipitation analysis of mRNasemIg2a-c.

FIG. 4 shows RNase activity from three mice (410, 413, and 418) after intravenous injection of Rnase-Ig fusion protein (SEQ ID NO:150) (purified in this experiment from supernatant of transfected COS cells by binding and elution from protein A sepharose). A standard was used in the top row. Notice a second injection for mouse 410 (see arrow) after 2 weeks. 2 μl serum from each of three mice was loaded on 1% agarose gel containing 0.5 mg/ml poly-C. The gel was incubated for 4 hours in a moist chamber at 37° C., and then immersed in a buffer containing 20 mM sodium acetate and 20 ug/ml ethidium bromide for 30 min. The RNase activity is reflected by the size and intensity around the central well. This data shows that the RNase-Ig fusion protein has an extended half-life in mouse serum.

Example 7

Use of an Anti-RNA ELISA to Measure RNA Specific Antibodies in Mouse Sera

A 96-well plate (Nunc, Thermal fisher scientific) was coated with 50 μg/ml of Poly-L-Lysine (Sigma) overnight. After washing five times with PBS containing 0.05% Tween, the plate was coated with 10 μg/ml of yeast RNA in PBS at 4° C. overnight. After washing five times, the plate was blocked with PBS containing 1% BSA at room temperature for 2 hours. Serum samples at 1:50 dilution were added to the plate and incubated at 4° C. overnight. Hybridoma H564 (anti-RNA) culture medium was used as standard, using two-fold serial dilutions starting at 1:300. Detection antibody was anti-mouse IgG conjugated with alkaline phosphatase (Jackson Lab), and was added to the plate at 1:5000 for 1 hour at room temperature. Phosphatase substrate (Sigma) was dissolved in developing buffer (ThermoFisher Scientific) and added to the plate at 50 μl/well. Samples were read at 405 nm using a Spectramax Plus plate reader (Microdevices, Sunnyvale, Calif.).

Figure 5:
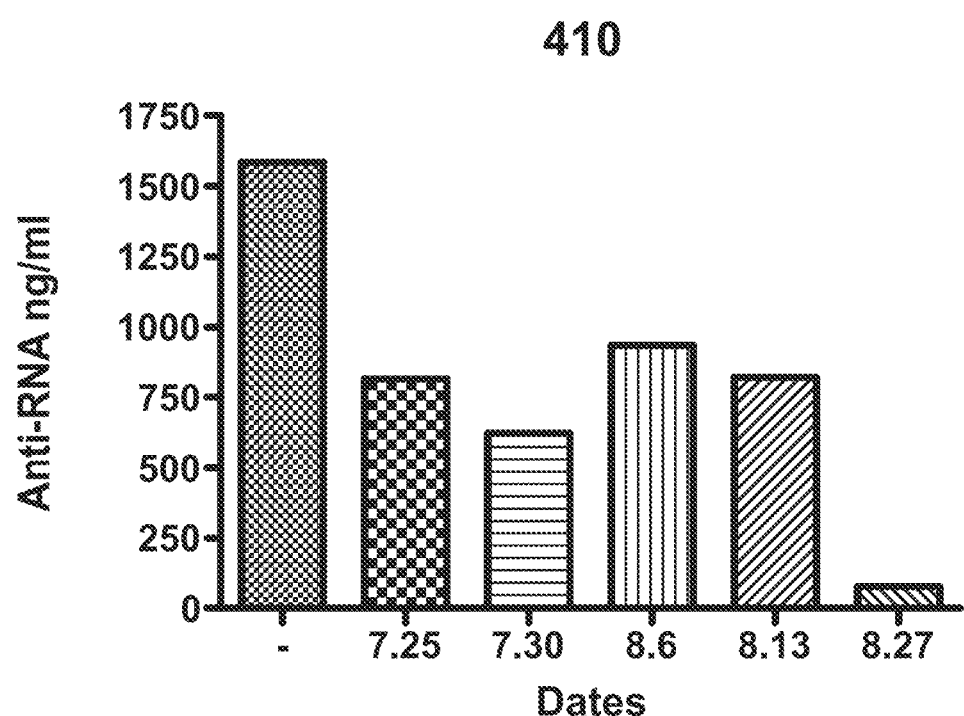
FIG. 5 shows an anti-RNA antibody ELISA titer before and after intravenous injection of RNase-Ig hybrid nuclease molecule from mouse 410. The data show that injection of RNase-Ig caused a reduction in titer of anti-RNA antibody that persisted for over 3 weeks.

FIG. 5 shows the results from the anti-RNA Antibody ELISA titer before and after intravenous injection of RNase-Ig fusion protein (SEQ ID NO:150) from mouse 410. The pre-coated Poly-L-lysine (50 μg/ml) plate was coated with 10 ug/ml yeast RNA. Serum (1:50) was loaded on the plate and incubated overnight at 4° C. Detection antibody was anti-mouse IgG-alkaline phosphatase (Jackson Labs) at 1:5000 for 1 hour at room temperature, and then phosphatase substrate was added and read at 405 nm. The data show that injection of Rnase-Ig caused a reduction in titer of anti-RNA antibody that persisted for over 3 weeks.

Figure 6:
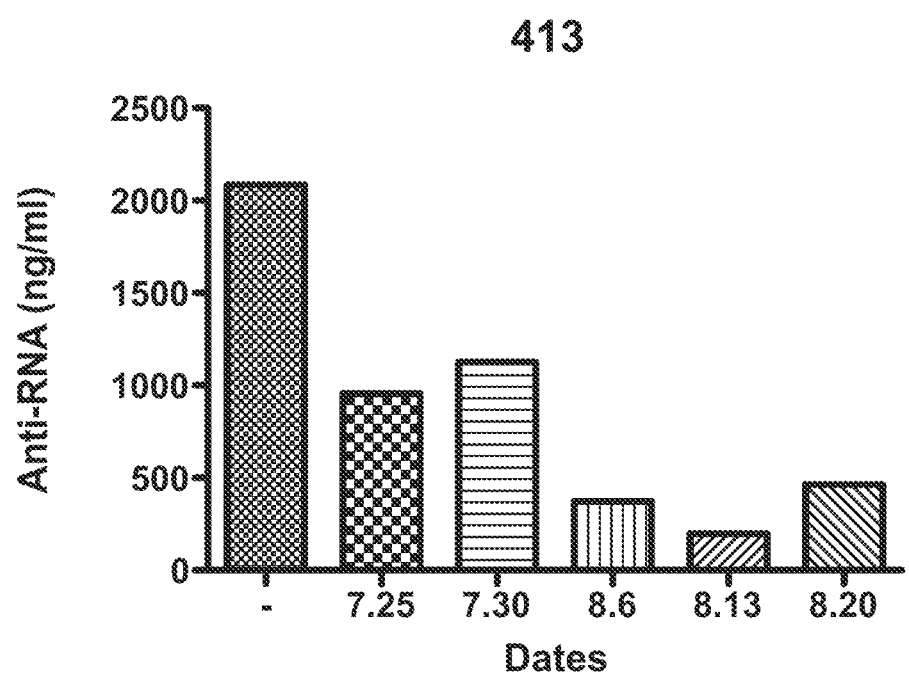
FIG. 6 shows that RNase-Ig addition abolished the induction of interferon-α from human peripheral blood mononuclear cells stimulated using immune complexes formed with serum from an SLE patient (J11) plus nuclear extract (NE). Titer of anti-RNA antibody was reduced after injection of RNase-Ig.

FIG. 6 shows the results from the anti-RNA Antibody ELISA titer before and after injection of RNase-Ig fusion protein (SEQ ID NO:150) within three weeks from mouse 413. The experiment was done as described for mouse 410. Titer of anti-RNA antibody was reduced after injection of Rnase-Ig.

Example 8

Figure 7:
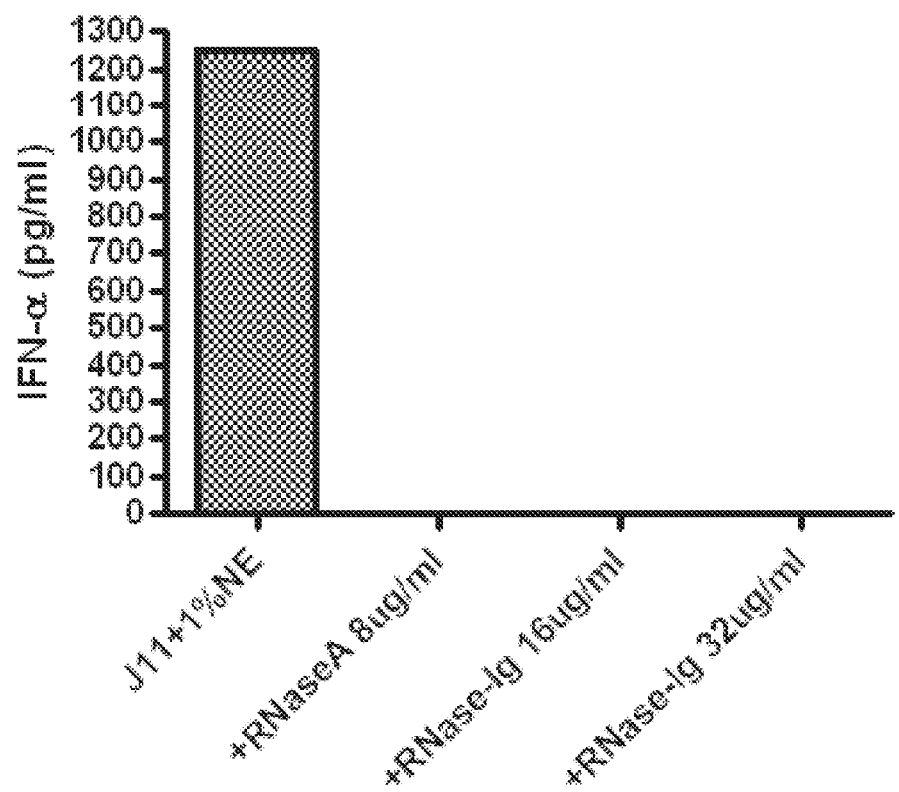
FIG. 7 shows that RNase-Ig addition abolished the induction of interferon-α from human peripheral blood mononuclear cells stimulated using immune complexes formed with serum from an SLE patient (J11) plus nuclear extract.

IFN-alpha Production by Human PBMCs is Inhibited by RNaseIg Addition to Cultures in vitro RNase-Ig (SEQ ID NO:150) addition abolished the induction of interferon-α from human peripheral blood mononuclear cells stimulated using immune complexes formed with serum from an SLE patient (J11) plus nuclear extract (NE). Briefly, ELISA plates were coated with 50 microliters 1:2500 capture antibody (anti-IFN alpha, PBL 21112-1, Piscataway, N.J.), and incubated overnight at 4° C. Plates were washed with PBS/0.05% Tween 20, blocked in PBS/1% BSA for 2 hours at room temperature, washed with PBS/0.05% Tween-20, and incubated with standard dilutions of IFN-alpha, or with serial dilutions of serum samples, and incubated 2 hours at room temperature. Plates were washed and incubated with 1:2000 detection antibody (PBL 31101-2, Piscataway, N.J.) in PBS/1% BSA. Plates were washed in PBS/0.05% Tween-20, and incubated with 50 microliters donkey anti-rabbit HRP (Jackson Immunoresearch, Westgrove, Pa.) at 1:12,000 in PBS/1% BSA. Plates were washed five times prior to addition of TMB substrate. Reactions were stopped by addition of ½ volume 2N $H_2SO_4$, and samples read at 450 nm on a Spectramax Pro plate reader (MicroDevices, Sunnyvale, Calif.). The results are shown in FIG. 7, which shows RNase-Ig addition abolished the induction of interferon-α from human peripheral blood mononuclear cells stimulated using immune complexes formed with serum from an SLE patient (J11) plus nuclear extract.

Example 9

Phenotype of TLR7.1×RNaseA Double Transgenic Mice

Figure 8:
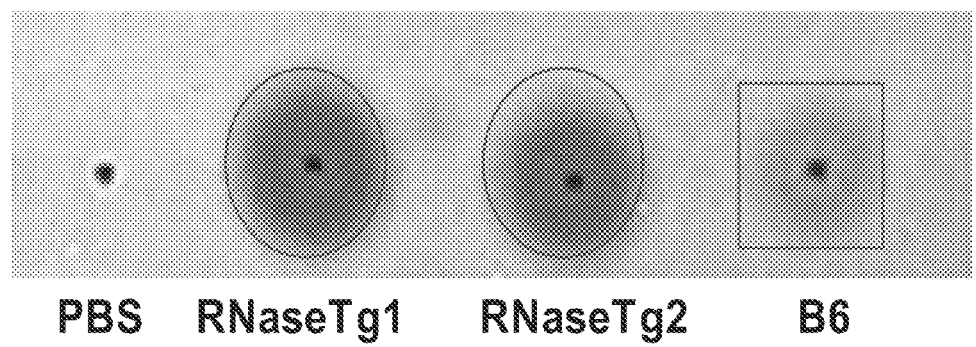
FIG. 8 shows single radial enzyme diffusion (SRED) analysis of serum from two RNase transgenic (Tg) mice compared to a normal B6 mouse.
Figure 9:
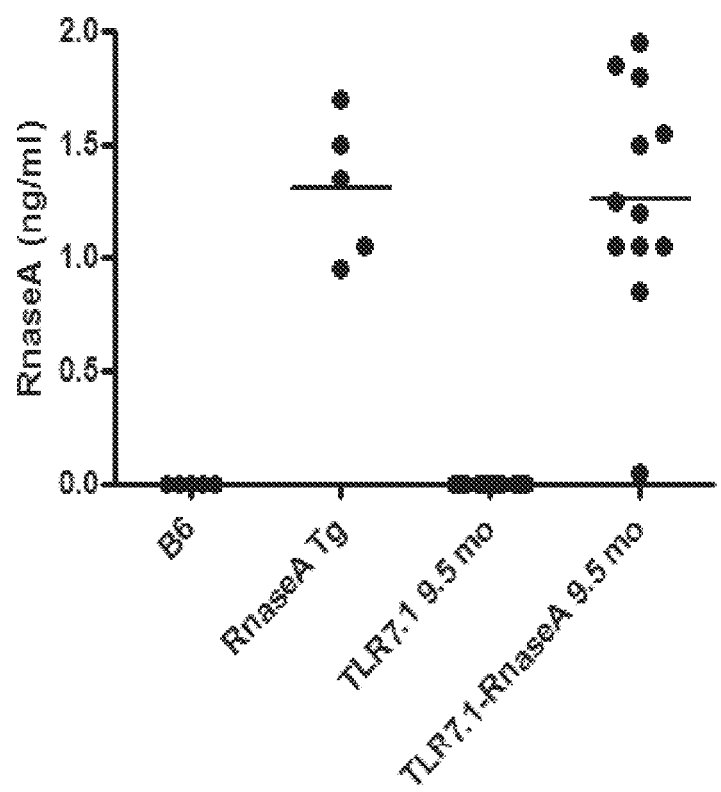
FIG. 9 shows the concentration of RNaseA in Tg and double Tg (DTg) mice measured by ELISA. Each dot represents the concentration measured in an individual mouse.

We have created mice that overexpress RNaseA (RNase Tg). This nuclease is expressed at high levels in RNase Tg mice (see FIG. 8). We have developed both a single radial diffusion (SRED) method (left panel) and a much more quantitative ELISA to quantify RNase in the serum (see FIG. 9). We crossed RNaseA Tg with TLR7.1 Tg mice to create the double Tg (DTg). TLR7.1 mice have 8-16 copies of TLR7 and develop a very aggressive, rapidly progressive lupus-like disease and start to die at 3 mo of age with a median survival of 6 mo. In a preliminary analysis, we bled DTg and littermate controls at 3 mo of age to see whether the DTg mice exhibited signs of improvement. As shown in FIG. 8, DTg mice had very high levels of RNase in their serum (equivalent to >13 U/ml RNase based on our standard with specific activity of 993 U/mg). RNaseA concentration in Tg and DTg mice was also measured by ELISA assay as shown in FIG. 9. The RNase A Tg and TLR7.1×RNaseA Dtg mice have RNase A serum concentrations between 1-2 ng/ml.

Detailed Method for Rnase A ELISA (Example 9, FIG. 9)
1. Coat plate with anti-RnaseA Abcam Ab(ab6610): 2.5-10 ug/ml O/N in 4 C.
2. Wash plate 3 times with 0.05% Tween/1× PBS
3. Block with 1% BSA in PBS for at least 1 hour
4. Wash plate 3 times with 0.05% Tween/1× PBS
5. Load samples. Sample dilutions at 1:50
6. Incubate Rm Temp for 2 hours
7. Wash plate 3 times with 0.05% Tween/1× PBS
8. Prepare dilution of biotin labeled Anti Rnase Ab at dilution of 1:4500 (2.2 ug/ml). Leave RT for 1 hour (Rockland 200-4688: 10 mg/ml).
9. Wash plate 3 times
10. Dilute StrepAV HRP (Biolegend 405210) 1:2500. Cover with foil and leave at RT for 25-30 min.
11. Wash 6 times, let the liquid sit in wells for at least 30 seconds in between washes.
12. Add BD OptEIA substrate A+B 1:1. Wait until color changes 5-10 min max. Don't let the top well standard go over 1.0. Add 80 ul. (Cat Nos: 51-2606KC; ReagentA, 51-2607KC; ReagentB)
13. Add 40 ul of 1M sulfuric acid to stop reaction Product/Reagent information:
RNaseA Ab: ab6610 (90 mg/ml)
ELISA buffer: 1% BSA in PBS
ELISA wash buffer: 0.05% Tween/1×PBS
Anti RNaseA biotin conjugated Ab: Rockland: 200-4688 (10 mg/ml)
Strep AV HRP: Biolegend 405210
BD OptEIA reagent A and B: 51-2606KC and 51-2607KC Example 10

Survival Curves for TLR7.1 Transgenic Mouse Strains

Figure 10:
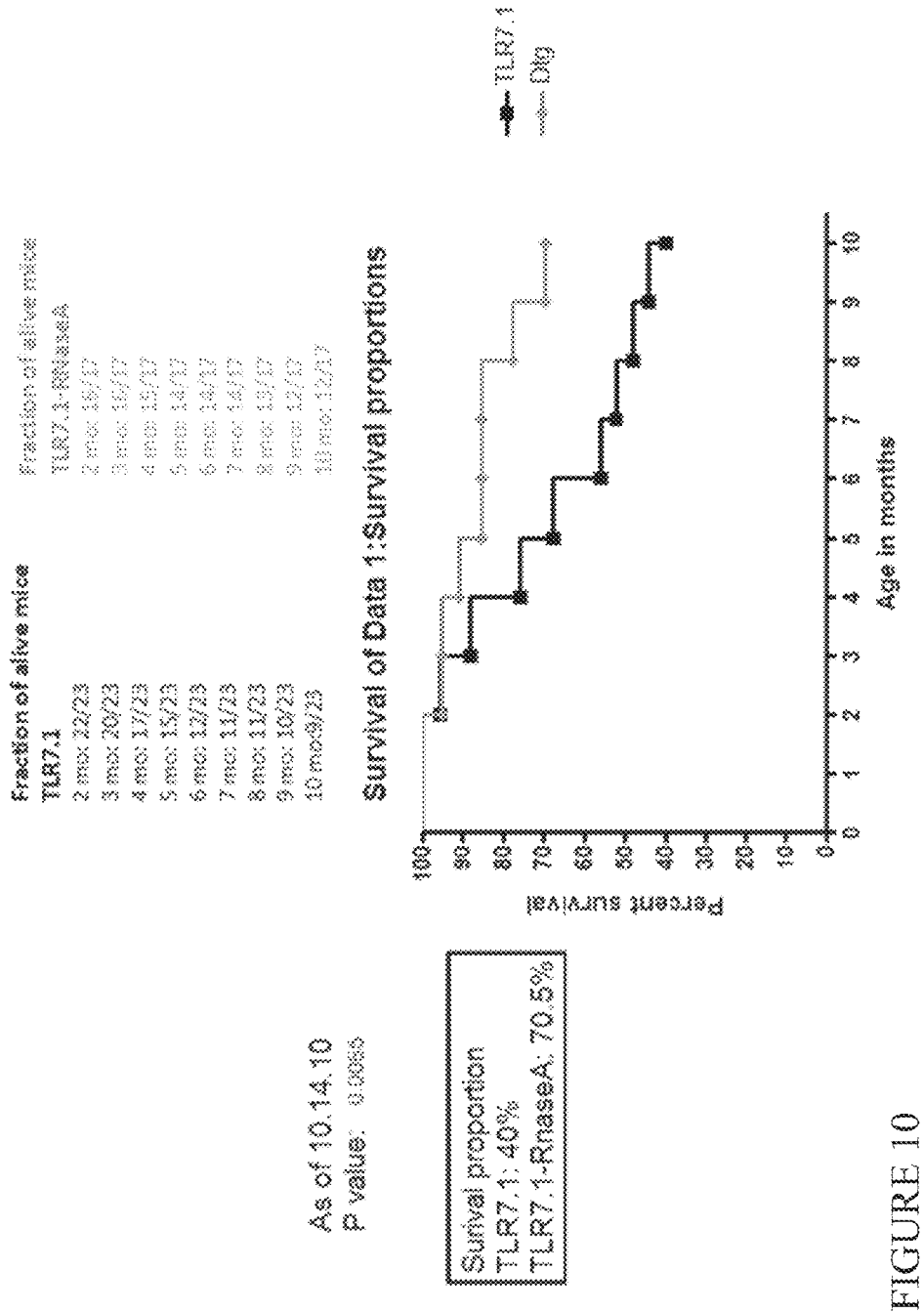
FIG. 10 shows survival of TLR7.1 Tg versus TLR7.1× RNaseA DTg mice

There was a highly significant difference between the DTg and the TLR7.1 littermate controls in survival. As shown in FIG. 10, at 10 months, 61% of TLR7.1 mice had died, whereas 31% of DTg mice had died. This data shows that overexpression of RNaseA exerted a strong therapeutic effect. The reasons why TLR7.1 mice die prematurely is not entirely clear, although severe anemia, thrombocytopenia, and glomerulonephritis could play a part. To determine whether red cell and platelet counts were positively impacted by RNaseA expression in the DTg mice, we performed blood counts but found no differences between the TLR7.1 and DTg mice. In contrast, there was a significant improvement in kidney histopathology in the DTg mice. We observed decreased deposition of IgG and C3 in DTg mice. PAS staining, which reflects inflammation in the mesangium was also reduced in DTg mice compared to TLR7.1 littermate controls. When we have now compared macrophage infiltration of the kidneys using anti-MAC-2 (galectin3) antibody (Lyoda et al. Nephrol Dial Transplat 22: 3451, 2007), there were many fewer mac-2 positive cells in the glomeruli of the DTg mice. The results of counting 20 glomeruli per mouse in 5 mice in each group revelaed mean+/−SE of 3.8+/−1.1 and 1.4+/−0.2 for single versus DTg respectively, p=0.05. In addition, we quantified glomerular tuft size and observed a significant reduction in glomerular tuft size in the DTg mice (179+/−41 versus 128+/−16.8 um2 in single versus DTg respectively, p=0.037). In summary, TLR7.1×RNaseA DTg mice survive longer than their single Tg TLR7.1 littermates and have less inflammation and injury in their kidneys.

Example 11

Analysis of IRGs in Spleens of TLR Tg Mice

Figure 11:
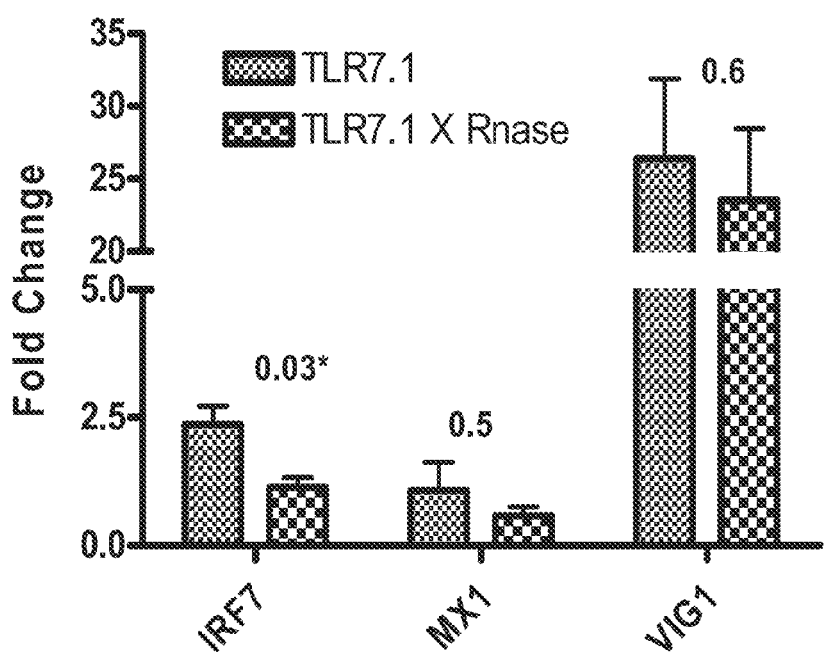
FIG. 11 shows quantitative PCR of IRGs in spleens of Tg versus DTg mice.

Analysis of interferon response genes (IRGs) in the spleens of TLR7.1 Tg and TLR7.1×RNaseA DTg mice mice showed that expression of the IRF7 gene was significantly lower in the DTg mice (p=0.03). Some other IRGs including MX1 and VIG1 were lower in DTg mice compared to Tg mice, but the differences were not significant. See FIG. 11. Quantitative PCR was performed as follows: total RNA was isolated from mouse spleens using the RNeasy mini kit (Qiagen, Valencia, Calif., USA), DNase treated using Turbo DNA-free (Applied Biosystems, Foster City, Calif., USA) and first-strand cDNA was produced with the RNA-to-cDNA kit (Applied Biosystems) using random primers. The 260/280 was between 1.7 and 2.0 for isolated RNA measured with a NanoDrop (Thermo Scientific, Waltham, Mass., USA). cDNA was diluted to an equivalent of 1 ng/ul total RNA and 8 ul were used per reaction. Primers for the reference gene (18s) and genes of interest (GOI) were synthesized (IDT, Coralville, Iowa, USA) and diluted to the appropriate concentrations for qPCR using molecular grade water. BLAST results of the primers show specific sequence homology only to the reference gene or GOI. Reactions in duplicate (20 ul) were run on an ABI Fast 7500 system using a 1:1 mix of template and primer to SensiMix SYBR low-ROX master mix (Bioline, London, UK). Relative quantification was calculated using the 2-ddCT method with age matched wild type B6 mice as baseline to determine fold changes for each GOI. The dissociation curves for the reactions show a single melt peak for each gene. The standard curve showed similar amplification efficiencies for each gene and that template concentrations were within the linear dynamic range for each of primer set.

Example 12

Structures for Generating Hybrid Nuclease Molecules

Hybrid nuclease molecules were designed to incorporate desired structures and functional activity of single enzyme or multi-enzyme structures as modular cassettes with compatible restriction enzyme sites for shuttling and domain exchange. The schematic structure of different embodiments of hybrid nuclease molecules is illustrated in FIG. 12. Primers are shown in Table 1. The nucleotide and amino acid sequences of representative hybrid nuclease molecules are shown in Table 2.

General Approach for Generation of Hybrid Nuclease Molecules

Human cDNAs were isolated from human pancreas RNA (Ambion) or human PBMC RNA from normal human peripheral blood lymphocytes (approximately 5×10e6) using QIAgen RNAeasy kits (Valencia, Calif.) and QIAshredder kits to homogenize cell lysates (Qiagen, Valencia, Calif.). Human PBMCs were isolated from heparinized human blood diluted 1:1 in D-PBS and layered over LSM Lymphocyte Separation Medium (MP Biomedicals, Irvine, Calif.) Ficoll gradients.

Mouse spleen RNA was isolated using QIAgen RNAeasy kits (Valencia, Calif.) from approximately 5×10e6 splenocytes. Cells were pelleted by centrifugation from the culture medium, and 5×10e6 cells were used to prepare RNA. RNA was isolated from the cells using the QIAGEN RNAeasy kit (Valencia, Calif.) total RNA isolation kit and QIAGEN QIAshredder according to the manufacturer's instructions accompanying the kit. One to two microgram (1-2 µg) of total RNA was used as template to prepare cDNA by reverse transcription. The RNA, 300 ng random primers, and 500 ng Oligo dT (12-18), and 1 µl 25 mM dNTPs were combined and denatured at 80° C. for 5 minutes prior to addition of enzyme. Superscript III reverse transcriptase (Invitrogen, Life Technologies) was added to the RNA plus primer mixture in a total volume of 25 µl in the presence of 5 times second strand buffer and 0.1 M DTT provided with the enzyme. The reverse transcription reaction was allowed to proceed at 50° C. for one hour.

Between 10-100 ng cDNA was used in PCR amplification reactions using primers specific for the nuclease gene of interest (RNaseA, RNase1, DNase1, Trex1, DNase1L3, etc.) For initial cloning reactions, primers were designed to isolate the full length cDNA or truncation products encoding the gene of interest. Full length or shortened PCR fragments were isolated by agarose gel electrophoresis, and purified using Qiagen QIAquick columns to remove nucleotides, primers, and unwanted amplified products. Purified fragments were cloned into pCR2.1 TOPO cloning vectors (Invitrogen, Carlsbad, Calif.) and transformed into TOP10 competent bacteria. Isolated colonies were picked into Luria Broth media containing 50 ug/ml carbenicillin, and grown overnight to isolate plasmids. TOPO clones were screened for inserts of the correct size by digestion with EcoRI (NEB, Ipswich, Mass.) restriction enzyme and agarose gel electrophoresis of digested fragments. DNA sequence analysis of positive clones was performed with ABI Ready Reaction Mix v 3.1 and analyzed using an ABI 3730 XL DNA sequencer. Once correct clones were obtained, further sequence modifications were designed and PCR reactions performed to generate the desired alleles or expression cassettes. Truncation products and alleles were generated by PCR mutagenesis using overlapping primers for introduction of mutations at specific positions in the genes. Linkers were synthesized by overlapping PCR using internal overlapping primers and successive rounds of PCR to attach additional sequence to each terminus Hybrid nuclease molecules were assembled as a string of several interchangeable cassettes. Molecules of the preferred embodiment contain a fixed leader peptide, a nuclease cassette, an optional cassette encoding a choice of several different polypeptide linkers, an -Ig Fc domain cassette with either a STOP codon or a linker at the carboxyl end of the CH3 domain, and for resolvICase type molecules, a second linker cassette, followed by a second nuclease cassette. FIG. 12 illustrate the cassette type structure of these hybrid nuclease molecules and examples of potential sequences inserted at each position. Once hybrid nuclease molecules were assembled, they were transferred to a mammalian expression plasmid pDG appropriate for transient expression in COS7 or other cells and stable expression in CHO DG44 cells using selection for DHFR with methotrexate.

Transient Expression of Hybrid Nuclease Molecules

COS-7 cells were transiently transfected with expression vector pDG containing hybrid nuclease molecule gene inserts. The day before transfection, cells were seeded at 4×10e5 cells per 60 mm dish in 4 ml DMEM (Thermo-Fisher/Mediatech cell gro)+10% FBS tissue culture media. DMEM basal media was supplemented with 4.5 g/L glucose, sodium pyruvate, L-glutamine 4 mM, and non-essential amino acids. Fetal bovine serum (Hyclone, Logan, Utah ThermoFisher Scientific) was added to media at 10% final volume. Cells were incubated at 37° C., 5% CO2 overnight and were approximately 40-80% confluent on the day of transfection. Plasmid DNA was prepared using Qiagen (Valencia, Calif.) QIAprep miniprep kits according to manufacturer's instructions, and eluted in 50 ul EB buffer. DNA concentrations were measured using a Nanodrop 1000 (Thermo Fisher Scientific, Wilmington Del.) spectrophotometer. Plasmid DNA was transfected using Polyfect (Qiagen, Valencia, Calif.) transfection reagent according to manufacturer's instructions, using 2.5 ug plasmid DNA per 60 mm dish and 15 ul polyfect reagent in 150 ul serum free DMEM transfection cocktails. After complex formation, reactions were diluted into 1 ml cell growth media containing serum and all supplements, and added drop-wise to the plates containing 3 ml fresh DMEM complete culture media. Transient transfections were incubated for 48-72 hours prior to harvesting culture supernatants for further analysis.

Generation of Stable CHO DG44 Transfectants Expressing the Hybrid Nuclease Molecules of Interest Stable production of the hybrid nuclease molecules was achieved by electroporation of a selectable, amplifiable plasmid, pDG, containing the nuclease-Ig cDNA under the control of the CMV promoter, into Chinese Hamster Ovary (CHO) cells. The pDG vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 µg each of plasmid and carrier DNA was used to transfect 10$^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2×DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Invitrogen/Life Technologies). Media for transfections under selection contained varying levels of methotrexate (Sigma-Aldrich) as selective agent, ranging from 50 nM to 1 µM. Electroporations were performed at 280 volts, 950 microFarads. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 50 nM methotrexate. Once clonal outgrowth was sufficient, serial dilutions of culture supernatants from master wells were screened for expression of hybrid nuclease molecules by use of an -IgG sandwich ELISA. Briefly, NUNC immulon II plates were coated overnight at 4° C. with 7.5 microgram/ml F(ab'2) goat anti-mouse IgG (KPL Labs, Gaithersburg, Md.) or 2 ug/ml goat anti-human or anti-mouse IgG (Jackson Immunoresearch, West Grove Pa.) in PBS. Plates were blocked in PBS/2-3% BSA, and serial dilutions of culture supernatants incubated at room temperature for 2-3 hours. Plates were washed three times in PBS/0.05% Tween 20, and incubated with horseradish peroxidase conjugated F(ab'2)goat anti-mouse IgG2a (Southern Biotechnologies) and goat anti-mouse IgG (KPL) mixed together, each at 1:3500 in PBS/1.0% BSA, or in horseradish peroxidase conjugated F(ab')2 goat anti-human IgG1 (Jackson Immunoresearch, West Grove, Pa.) at 1:2500 for 1-2 hours at room temperature. Plates were washed four times in PBS/0.05% Tween 20, and binding detected with SureBlue Reserve, TMB substrate (KPL Labs, Gaithersburg, Md.). Reactions were stopped by addition of equal volume of 1N HCl, and plates read at 450 nM on a Spectramax Pro plate reader (Microdevices, Sunnyvale Calif.). The clones with the highest production of the hybrid nuclease molecule were expanded into T25 and then T75 flasks to provide adequate numbers of cells for freezing and for scaling up production of the fusion protein. Production levels were further increased in cultures from the four best clones by progressive amplification in methotrexate containing culture media. At each successive passage of cells, the Excell 302 complete media contained an increased concentration of methotrexate, such that only the cells that amplified the DHFR plasmid could survive.

Supernatants were collected from CHO cells expressing the hybrid nuclease molecule, filtered through 0.2 µm PES express filters (Nalgene, Rochester, N.Y.) and were passed over a Protein A-agarose (IPA 300 crosslinked agarose) column (Repligen, Needham, Mass.). The column was washed with column wash buffer (90 mM Tris-Base, 150 mM NaCl, 0.05% sodium azide, pH 8.7), and bound protein was eluted using 0.1 M citrate buffer, pH 3.0. Fractions were collected and protein concentration was determined at 280 nM using a Nanodrop (Wilmington Del.) microsample spectrophotometer, and blank determination using 0.1 M citrate buffer, pH 3.0. Fractions containing hybrid nuclease molecules were pooled, and buffer exchange performed by serial spins in PBS using centricon concentrators followed by filtration through 0.2 µm filter devices, to reduce the possibility of endotoxin contamination.

Example 13

Analysis of Enzyme Kinetics for hRNase1-G88D-hIgG1 [SCCH-P238S-K322S-P331S1]

The human RNase1 sequence was isolated from human pancreas RNA by random primed cDNA reverse transcription and PCR amplification as described in Example 12 for nuclease molecules. The following primers at 50 pmol per reaction were used from the primer set listed in the PCR primer table.

hRNase5'age:
(SEQ ID NO: 16)
accggtaaggaatcccgggccaagaaattcc hRNase3'bx:
(SEQ ID NO: 17)
ctcgagatctgtagagtcctccacagaagcatcaaagtgg The mutant form of human RNase G88D was created by using the following two primers in PCR and overlap PCR reactions to introduce a mutation at position 88 that alters the resistance of the enzyme to the cytoplasmic inhibitor.

hRNaseG88D-S:
(SEQ ID NO: 18)
agactgccgcctgacaaacgactccaggtaccc hRNAseG88D-AS:
(SEQ ID NO: 19)
gggtacctggagtcgtttgtcaggcggcagtct Both wild type and mutant versions of human RNase1 were isolated and cloned as described for hybrid nuclease molecules above. The wild type sequence was cloned using the first two primers listed above. Once the RNase fragments were TOPO cloned and sequenced, the AgeI-XhoI cassettes were transferred to the pDG expression vector already containing the human VK3LP insert and the human IgG1-WT cassette. Constructs were verified by digestion, and plasmid DNA prepared for transient transfections. Once function was confirmed from small scale transient transfections, the molecules were stably transfected into CHO DG44 in order to express sufficient quantities for further in vitro analysis. The wild type human RNase1 fusion protein is shown in Table 2, hVK3LP-hRNase1-WT-hIgG1-WT (SEQ ID NO:163). Similarly, wild type human RNase1 was also expressed as a fusion gene with a (gly4ser)4 (SEQ ID NO:125 or SEQ ID NO:161) or (gly4ser)5 (SEQ ID NO:126 or SEQ ID NO:162) linker domain inserted between the hRNase cassette and the hIgG1 Fc domain. The G88D mutant of human RNase1 was also expressed as a fusion gene designated hVK3LP-hRNase-G88D-hIgG1-WT (SEQ ID NO:124 or 160) or hIgG1-SCCH-P238S-K322S-P331S (SEQ ID NO:174 or 175), listed in Table 2.

Figure 13:
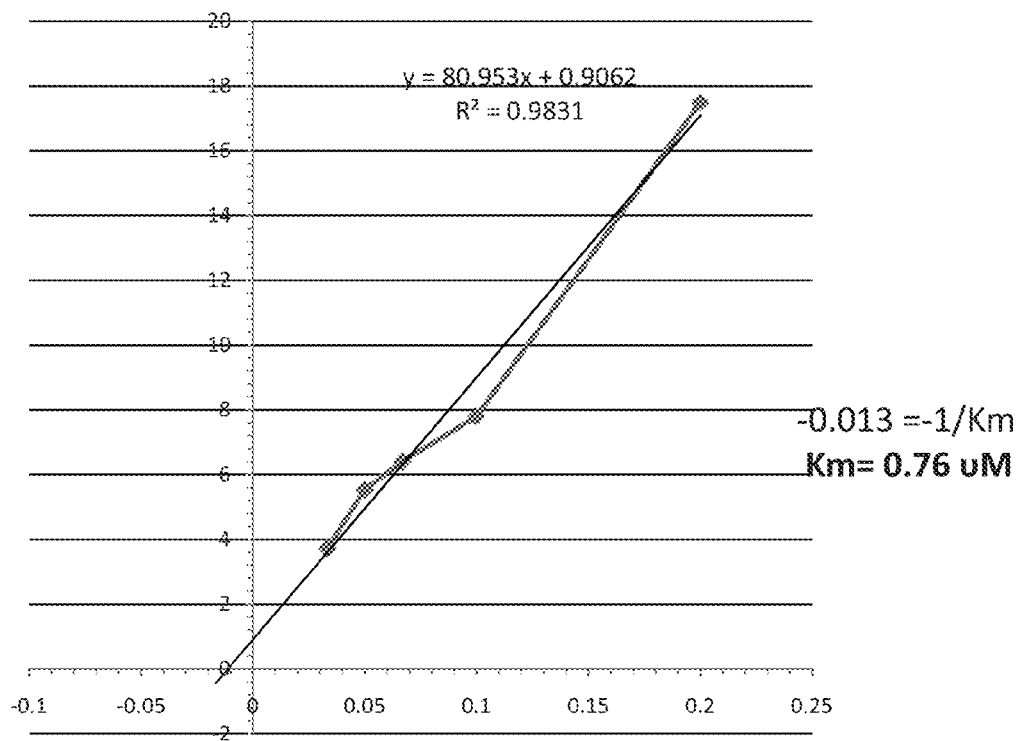
FIG. 13 shows the enzyme kinetics for hRNase1-G88D-hIgG1 SCCH-P238S-K322S-P331S hybrid nuclease molecules as measured using RNase Alert Substrate™.

The Lineweaver Burk plot of enzyme kinetics for the mutant hRNase1-G88D-hIgG1[SCCH-P2385-K3225-P3315] (SEQ ID NO:175) is shown in FIG. 13. To further define the functional characteristics of the bivalent RNase-Ig fusion protein, we performed preliminary determinations of the Michaelis constant, Km. Enzyme kinetics of purified human RNase1-Ig fusion protein was assayed using the RNase Alert Substrate (Ambion/IDT, San Diego, Calif.)

according to manufacturer's instructions and fluorescence assayed using a Spectramax M2 microplate reader (Molecular Devices, Sunnyvale, Calif.). Fluorescence data was collected at 30 second intervals over the course of a 30 minute incubation, and analyzed using SoftmaxPro Software (Molecular Devices) Reaction rates at different substrate concentrations were measured and the data is shown in the form of a Lineweaver Burke plot.

Example 14

Analysis of Binding of hRNase1-hIgG to Human Monocytic Lines

Figure 14:
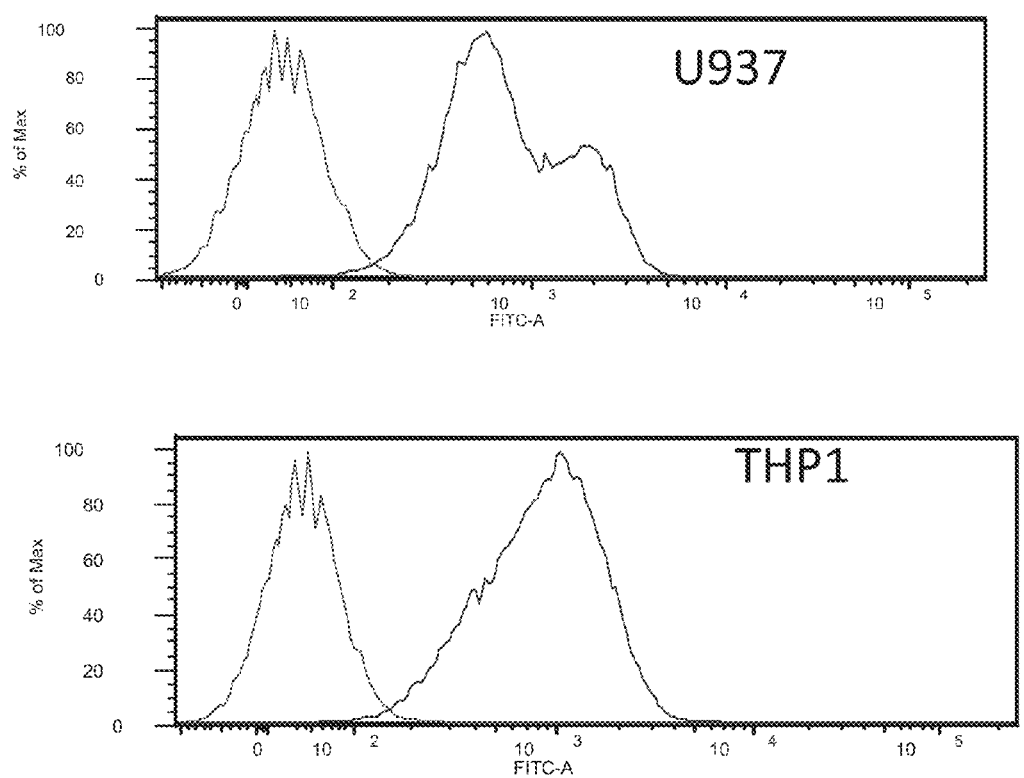
FIG. 14 shows the binding of hRNase1-WT-hIgG1-WT to human monocytic cell lines U937 and THP1. The peak on the left in both plots is control and the peak on the right in both plots is hRNase1-WT-hIgG1-WT.

Protein A purified hybrid nuclease molecules hRNase1-hIgG1-WT were incubated with human monocytic cell lines THP-1 or U937 to assess FcR mediated binding of the wild type or mutant Fc containing molecules. FIG. 14 shows the binding pattern of hRNase1-WT-hIgG1-WT (SEQ ID NO:161) to these two cell lines. Cells were incubated with 5 ug/ml purified fusion protein in PBS/2% FBS for 45 minutes on ice, washed three times in PBS/2% FBS, and incubated with FITC-goat anti-human IgG (Fc specific) (Jackson Immunoresearch, West Grove, Pa.) at 1:200 for 45 minutes on ice. Cells were washed two times in PBS/2% FBS and analyzed by flow cytometry using a FACS Canto (BD, Franklin Lakes, N.J.) flow cytometer, and FlowJo software (TreeStar, Ashland, Oreg.).

Example 15

IVIg Blocking of hRNase1-hIgG1 Binding to Human Monocytic Lines

Figure 15:
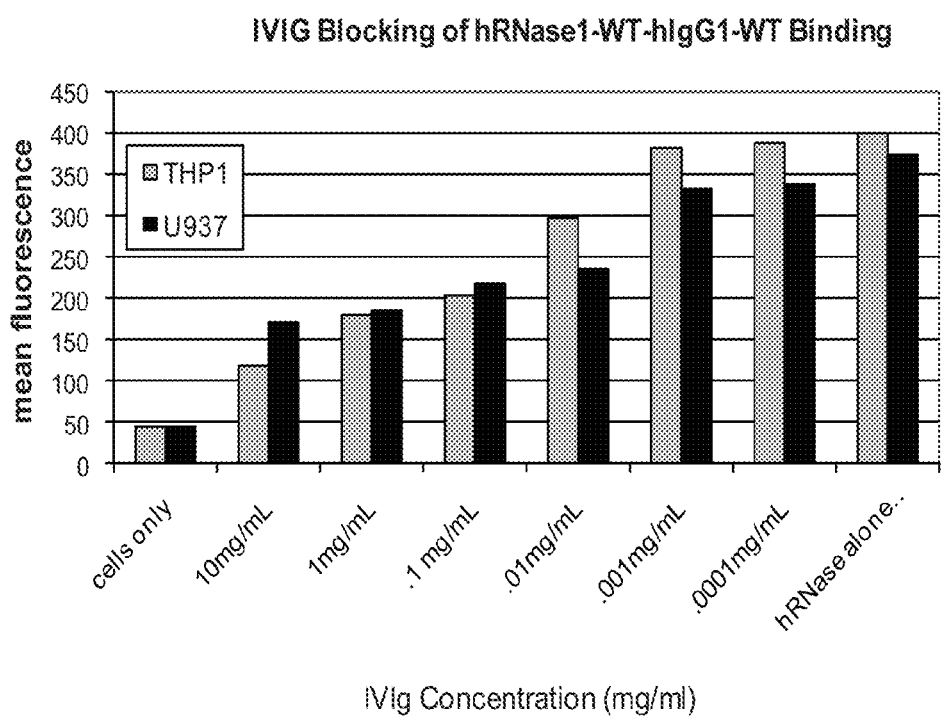
FIG. 15 shows the blocking activity of human IVIg for binding to U937 and THP-1 cells by hRNase1-WT-hIgG1-WT.

THP-1 or U937 cells were pre-incubated with IVIg starting at 10 mg/ml and performing 10-fold serial dilutions across the wells of a 96 well plate. Cells (approximately 1×10e6 per well) were incubated on ice for 45 minutes. Pre-bound cells were washed twice and AF750 conjugated hRNase1-WT-hIgG1-WT (SEQ ID NO:161) at approximately 5 ug/ml was added to each well. Binding reactions were incubated 45 minutes on ice, washed twice in PBS/2% FBS, and analyzed by flow cytometry as described above. IVIg was able to partially block the binding of the labeled nuclease fusion protein, but even at 10 mg/ml, there was still residual binding detectable above background. FIG. 15 shows the blocking activity of human IVIg for binding to U937 and THP-1 cells by hRNase1-WT-hIgG1-WT (SEQ ID NO:161).

Example 16

Trex1-Ig Activity Assay

Murine Trex1 was cloned from mouse cDNA using the primers listed below:
mTrex1-5'age: accggtatgggctcacagaccctgccccatggtcaca (SEQ ID NO:20)
mTrex1-3'bx: ctcgagatctgttgttccagtggtagccggagtgccgtacatg (SEQ ID NO:21)
PCR reactions were performed using 50 pmol each primer in a total volume of 50 ul, under an amplification profile of 94 C 30 sec; 50 C 60 sec; 68 C 90 sec for 35 cycles of amplification. PCR products were cloned into the pCR2.1 vector and TOPO clones screened as previously described for prototype nuclease fusion gene cloning. Once sequence was verified, the cassettes were subcloned into the pDG expression vector fused to the mIgG tail or co-cloned with one of the (g4s)n linkers to construct Trex1-lnk molecules with different length linkers. Plasmid isolates were transiently transfected into COS cells as described and stable CHO transfectants generated as described for prototype nuclease fusion genes.

Fusion genes were constructed encoding Trex1Ig as follows: the genes incorporate the human VK3 leader peptide fused to murine Trex1 truncated at the COOH terminus by 72 amino acids (to remove the intracellular nuclear targeting sequences) fused to a (gly4ser)4 (SEQ ID NO:130) or (gly4ser)5 linker (SEQ ID NO:131), fused to the murine IgG2a/c allele that incorporates some changes from the IgGc sequence of the Balb/c IgG2a allele.

Figure 16:
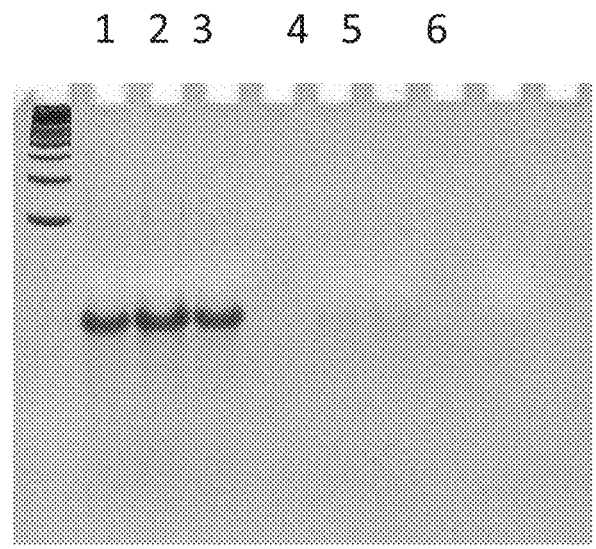
FIG. 16 shows the results of a DNA digestion assay by Trex1-(g4s)n-mIgG alternative forms.

The exonuclease activities of Trex1-Ig were measured in 30 ul reactions containing 20 mM Tris (pH7.5), 5 mM MgCl$_2$, 2 mM DTT, using a 36-mer oligonucleotide as substrate. Incubation reactions were allowed to proceed for 20-30 min at 37° C. Samples were subjected to electrophoresis on 23% polyacrylamide DNA gels overnight. Gels were incubated in TBE buffer containing 0.5 ug/ml ethidium bromide. The DNA was visualized by UV transilluminator, and photographed using a Kodak EDAS 290 digital camera equipped with ethidium bromide filters and analyzed using Kodak Molecular Imaging Software. The trex1 activity assay results for COS produced mTrex1-(g4s)4-mIgG2a-c (SEQ ID NO:166) and mTrex1-(g4s)5-mIgG2a-c (SEQ ID NO:167) are shown in FIG. 16.

Example 17

Figure 17:
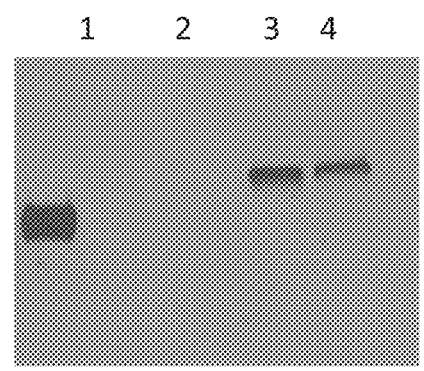
FIG. 17 shows the results of a Western Blot for trex1-(Gly4S)4-Ig and trex1-(Gly4S)5-Ig culture supernatants from COS-7 transient transfections.

Western Blot of mTrex1-Ig Single Hybrid Nuclease Molecules Produced by COS-7 Transient Transfection COS-7 cells were transiently transfected with plasmids containing hybrid nuclease molecules encoding Trex1-Ig as follows: the genes incorporate the human VK3 leader peptide fused to murine Trex1 truncated at the COOH terminus by 72 amino acids (to remove the nuclear envelope targeting sequences) fused to a (gly4ser)4 or (gly4ser)5 linker, fused to the murine IgG2a/c allele that incorporates some changes from the IgGc sequence from the Balb/c IgG2a allele. COS supernatants were harvested after 72 hours and 0.5-1.0 ml samples (depending on the experiment) were immunoprecipitated overnight at 4° C. with 100 ul protein A-agarose beads. Protein A beads were centrifuged and washed twice in PBS prior to resuspending in reducing SDS-PAGE loading buffer. Samples were heat treated at 100 C for 5 minutes, protein A beads centrifuged to pellet, and sample buffer loaded onto 10% SDS-PAGE gels. Samples were electrophoresed at 150 volts for 1.5-2 hours, and gels blotted to nitrocellulose membranes at 30 mAmp for 1 hour. Western blots were blocked in TBS/5% non-fat milk overnight. Blots were incubated with 1:2500 HRP (horseradish peroxidase) conjugated goat anti-mouse IgG2a/c (Fc specific, KPL) for 1.5 hours at room temperature, washed in PBS/0.5% Tween20 five or more times, and blots developed using ECL reagent. FIG. 17 shows a Western blot of immunoprecipitates from COS7 culture supernatants expressing mTrex1-(g4s)4 (SEQ ID NO:166) or (g4s)5-mIgG2a-c (SEQ ID NO:167) fusion proteins.

Example 18

Exonuclease Activity of DNase1L3Ig CHO Derived Fusion Protein

DNase1L3 was cloned from mouse spleen cDNA using the following primer pair to clone the mDNase1L3 including its native leader peptide sequence.

```
mdnase1L3-NL:
                                  (SEQ ID NO: 22)
GTT AAG CTT GCC ACC ATG TCC CTG CAC CCA GCT

TCC CCA CGC CTG

Mdnase1L3-3bx:
                                  (SEQ ID NO: 23)
CTC GAG ATC TGA GGA GCG ATT GCC TTT TTT TCT

CTT TTT GAG AG
```

Alternatively, PCR reactions were set up using the following primer pair to attach to the human VK3 leader peptide instead of the native leader.

```
mdnase1L3-age:
                                  (SEQ ID NO: 24)
ACC GGT CTA AGG CTC TGC TCC TTC AAT GTG AGG

TCC TTT GGA

Mdnase1L3-3bx:
                                  (SEQ ID NO: 25)
CTC GAG ATC TGA GGA GCG ATT GCC TTT TTT TCT

CTT TTT GAG AG
```

PCR reactions were performed using 50 pmol each primer in a total volume of 50 ul, under an amplification profile of 94 C 30 sec; 50 C 60 sec; 68 C 90 sec for 35 cycles of amplification. PCR products were cloned into the pCR2.1 vector and TOPO clones screened as previously described for prototype nuclease fusion gene cloning. Once sequence was verified, the cassettes were subcloned into the pDG expression vector fused to the mIgG tail. Plasmid isolates were transiently transfected into COS cells as described and stable CHO transfectants generated as described for prototype nuclease fusion genes.

Figure 18:
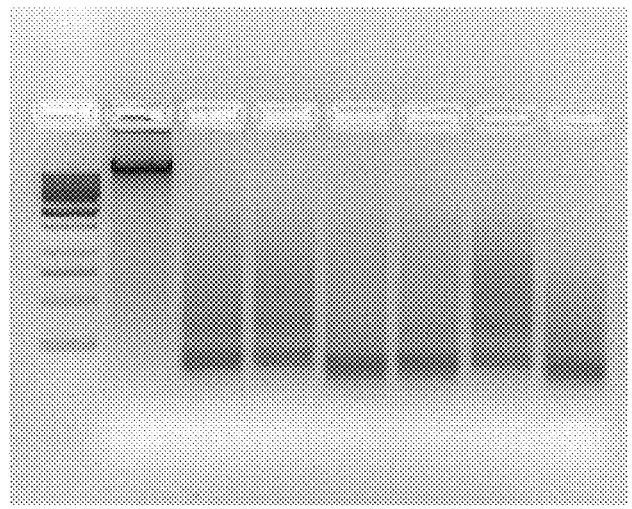
FIG. 18 shows DNA digestion patterns by different stably transfected CHO DG44 clones designated as 2A3, 3A5, and 8H8, expressing DNAse1L3-mIgG2a-c hybrid nuclease molecules.

The exonuclease activity in protein extracts from DNase1L3Ig (SEQ ID NO:185) CHO clones was measured in 30 ul reactions containing 20 mM Tris (pH7.5), 5 mM MgCl$_2$, 2 mM DTT, and a substrate. Incubation was 20-30 min at 37° C. Samples were then run on agarose DNA gel overnight. The gel was incubated in TBE buffer containing Ethidium bromide. The DNA was visualized under UV. The results of chromatin digestion analysis are shown in FIG. 18.

Example 19

Figure 19:
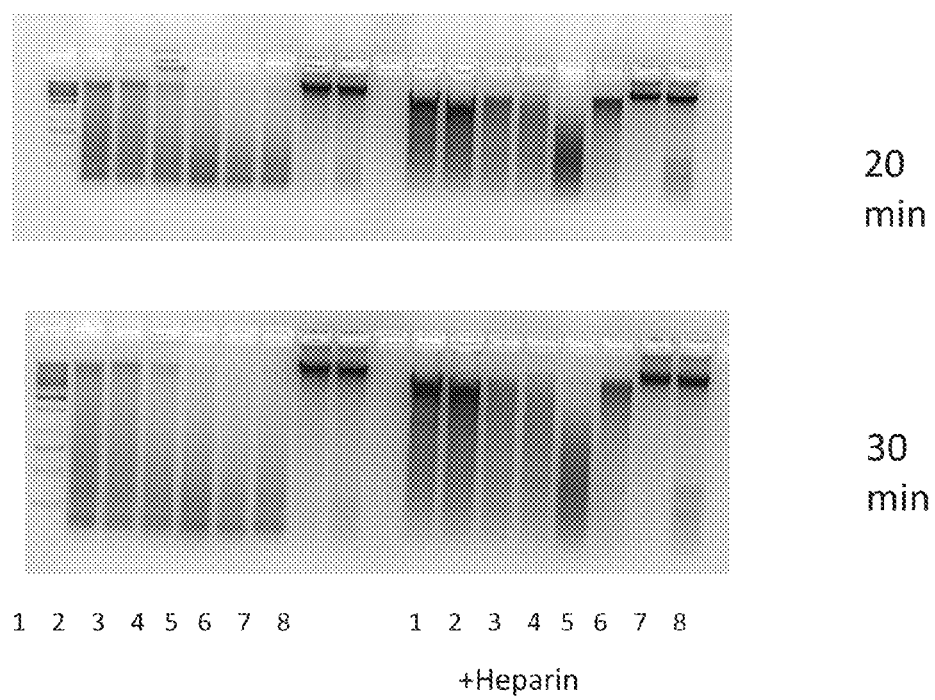
FIG. 19 shows DNA digestion patterns of decreasing amounts of DNase1L3-Ig hybrid nuclease molecules after various incubation times with and without heparin as an enzyme inhibitor.

Dose Titration of Increasing Volumes of CHO Supernatant for Exonuclease Activity FIG. 19 shows titration analysis of the exonuclease digestion patterns obtained from COS supernatants expressing DNase1L3Ig fusion proteins (SEQ ID NO:183 or 185). Nuclear DNA Degradation assays were performed as follows: HeLa cells were cultured in DMEM media and nuclei from 10e5 cells were isolated using NP-40 lysis. Nuclei were diluted into 200 ul reaction buffer containing 10 mM Hepes (pH 7.0), 50 mM NaCl, 2 mM MgCl$_2$, 2 mM CaCl$_2$, and 40 mM b-glycerophosphate. Nuclei were incubated for 3 hours at 37° C. in the volumes of culture supernatant indicated on the figure from DNase1L3 transfected COS cells. Nuclear DNA was isolated using QiAmp blood DNA minikit. DNA was analyzed by 1.5% agarose gel electrophoresis. For control reactions, heparin was used at 250 i.u./ml, to inhibit nuclease activity.

Example 20

Construction and Expression of DNase1-Ig Single and Dual Enzyme Hybrid Nuclease Molecules Naturally occurring alleles of human DNase1 or DNase1 like molecules have been reported. The A114F mutation has been previously reported to occur in natural variants of human DNAse1 like enzymes, and to result in actin resistance of the enzymes containing this sequence change. See Pan, C Q, Dodge T H, Baker D L, Prince W E, Sinicropi D V, and Lazarus R A. J Biol Chem 273: 18374-18381, (1998); Zhen A, Parmelee D, Hyaw H, Coleman T A, Su K, Zhang J, Gentz R, Ruben S, Rosen C, and Li Y. Biochem and Biophys Res Comm 231: 499-504 (1997); and Rodriguez A M, Rodin D, Nomura H, Morton C C, Weremowicz S, and Schneider M C. Genomics 42: 507-513 (1997), all of which are herein incorporated by reference.

Similarly, the G105R mutation has been reported recently as a single nucleotide polymorphism in the gene encoding human DNAse 1 that is polymorphic in some or all populations, and that is relevant to autoimmunity. (See Yasuda T, Ueki M, Takeshita H, Fujihara J, Kimura-Kataoka K, Lida R, Tsubota E, Soejima M, Koda Y, Dato H, Panduro A. Int J Biochem Cell Biol 42(7): 1216-1225 (2010), herein incorporated by reference). Allelic variants at this position resulted in high activity harboring DNase 1 isoforms relative to wild type. Another naturally occurring, polymorphic mutation (R21S) has also been reported to confer higher activity. (See Yasuda, supra)

SLE patients have been reported to have significantly decreased levels of DNase1 activity (See Martinez-Valle F, Balada E, Ordi-Ros J, Bujan-Rivas S, Sellas-Fernandez A, Vilardell-Tarres M. Lupus 18(5): 418-423 (2009), herein incorporated by reference).

Naturally occurring enzyme variants may thus be less immunogenic when administered to patients, since these isoforms occur in the human population. We reasoned that the combination of the actin resistant properties of alleles similar to A114F with the increased enzymatic activity of alleles like G105R would generate novel allelic variants of human DNase1 that might show improved clinical activity in vitro and in vivo. To our knowledge, ours is the first report of this new mutant form of DNase1 generated from a combination of two naturally occurring variants G105R and A114F.

Human DNase 1 was isolated as described previously from human pancreas RNA (Ambion), by random primed cDNA and PCR using the following primer sets:

```
5'hDNase1-age:
                                  (SEQ ID NO: 26)
GTT ACC GGT CTG AAG ATC GCA GCC TTC AAC ATC

CAG
```

-continued

```
5'hDNase1-bx:
                                           (SEQ ID NO: 27)
GTT CTC GAG ATC TTT CAG CAT CAC CTC CAC TGG

ATA GTG
```

Alternatively, the 3' DNase cassettes were amplified by PCR using the following primer pair.

```
3'hDNase1-RV:
                                           (SEQ ID NO: 28)
GTT GAT ATC CTG AAG ATC GCA GCC TTC AAC ATC

CAG

3'hDNase1-stop:
                                           (SEQ ID NO: 29)
GTT TCT AGA TTA TCA CTT CAG CAT CAC CTC CAC

TGG ATA GTG
```

PCR reactions were performed using 50 pmol each primer, 2 ul cDNA, in a total volume of 50 ul using Platinum PCR Supermix as previously described. The amplification profile was 94 C 30 sec; 55 C 30 sec; 68 C 90 sec for 35 cycles.

Once the wild type gene was amplified by PCR, the fragments were subjected to gel electrophoresis and 850 by fragments purified by QIAquick column purification. Fragments were cloned into pCR2.1, transformed by TOPO cloning according to manufacturer's instructions as described for the other constructs. Once sequence was verified, PCR primers were used to generate subfragments containing naturally occurring alleles for DNase1 that have been reported to improve specific activity and improve resistance to the inhibitory activity of actin. These subfragments contained overlapping sequence, permitting amplification of complete DNase1 subclones containing the desired allelic variations. COS 7 cells were transiently transfected in 60 mm dishes using Polyfect (Qiagen, Valencia, Calif.) transfection reagent. Plasmid DNA was prepared using the Qiagen QIAprep miniprep kits according to manufacturer's instructions. Plasmids were eluted in 50 ul EB buffer. DNA concentration was measured using the Nanodrop and an aliquot equivalent to 2.5 ug plasmid DNA used for each transfection reaction. Each DNase1g (SEQ ID NOS.: 118, 119, 120, 121, 122 or 123) or RNase-Ig-DNase (SEQ ID NOS.: 115, 116, 117) expression cassette was inserted into the mammalian expression vector pDG, a derivative of pcDNA3.1. Transfected cells were incubated for 72 hours at 37° C., 5% CO2 prior to harvest of culture supernatants for further analysis. Culture supernatants were harvested, residual cells centrifuged from the solution, and the liquid transferred to new tubes.

Figure 20:
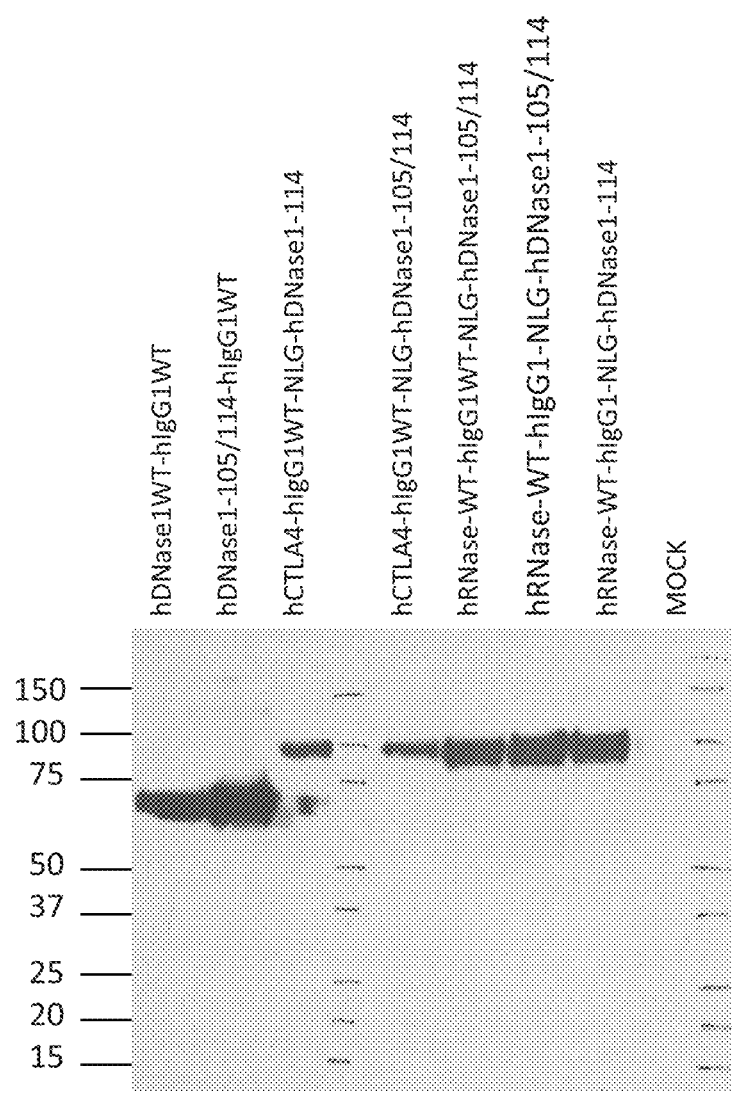
FIG. 20 shows a Western blot of immuneprecipitated fusion proteins from transiently transfected COS cells expressing different embodiments of hRNase1-Ig-hDNase1 or hDNase1-Ig hybrid nuclease molecules.

COS-7 cells were transiently transfected with plasmids containing human DNase1 wild type (SEQ ID NO:118) or naturally occurring DNase 1 mutant alleles (G105R and/or A114F) (SEQ ID NO:115, 116, or 117) fused to the wild type human IgG1 Fc domain. This hinge-CH2-CH3 cassette contains a single C→S mutation in the hinge region to eliminate the first cysteine in this domain since it is unpaired due to absence of its pairing partner present in the light chain of the antibody. In addition, more complex multi-nuclease fusion proteins were also expressed from COS cell transient transfections. Western blot analysis was performed on supernatants from transient transfectants. The molecules shown in FIG. 20 contain human DNase1 fused to the human IgG1 wild type Fc domain (SEQ ID NO:154, 155, 156, or 159) or include human RNase1 (wild type) fused to the SCC hinge-CH2-CH3 Fc domain of human IgG1, followed by a novel linker containing an N-linked glycosylation site to protect the linker domain from protease cleavage, and the wild type (SEQ ID NO:153) or mutant allele (SEQ ID NO:151 or 152) forms of human DNase1 at the carboxy terminus of the molecule. COS supernatants were harvested after 72 hours and 0.5-1.0 ml samples (depending on the experiment) were immunoprecipitated overnight at 4° C. with 100 ul protein A-agarose beads. Protein A beads were centrifuged and washed twice in PBS prior to resuspending in SDS-PAGE loading buffer, for NuPAGE gels—reducing or nonreducing LDS sample buffer. Samples were heated according to manufacturer's instructions, protein A beads centrifuged to pellet, and sample buffer loaded onto 5-12% NuPAGE gradient gels. Samples were electrophoresed at 150 volts for 1.5-2 hours, and gels blotted to nitrocellulose membranes at 30 mAmp for 1 hour. Western blots were blocked in TBS/5% non-fat milk overnight. Blots were incubated with 1:2500 HRP (horseradish peroxidase) conjugated goat anti-human IgG (Fc specific, Jackson Immunoresearch) or goat anti-mouse IgG for 1.5 hours at room temperature, washed in PBS/0.5% Tween20 five or more times, and blots developed using ECL reagent.

Example 22

Screening COS Supernatants for Nuclease Enzyme Activity

Figure 21:
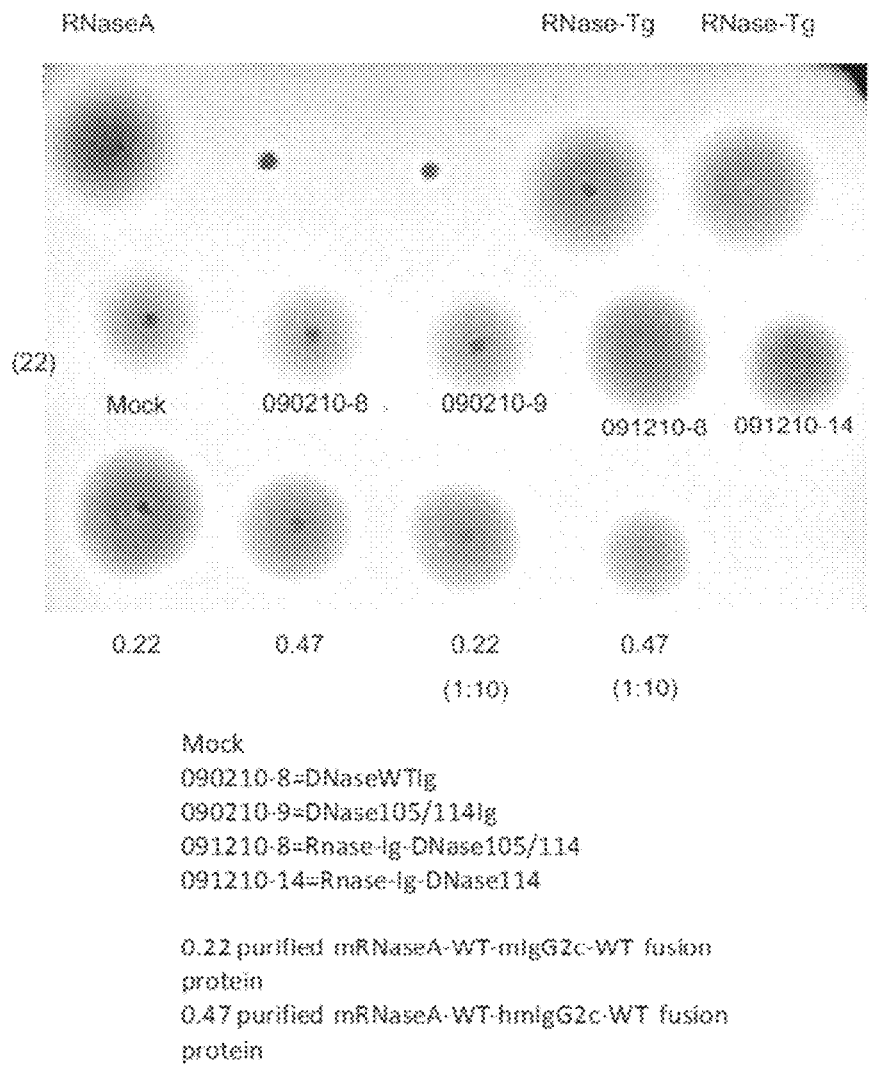
FIG. 21 shows SRED analysis to assess the presence of RNase activity in the COS supernatants expressing different embodiments of hRNase1-Ig-hDNase1 or hDNase1-Ig hybrid nuclease molecules.

FIG. 21 shows the results of RNase activity assays (SRED) analysis on harvested COS supernatants expressing hDNase1Ig and hRNase1-Ig-hDNase1 fusion proteins by SRED.

COS supernatants from transient transfections of the hDNaseIg single or multispecific nucleases were assayed for nuclease activity as follows. A 2% agarose gel was prepared with distilled water. Poly-C (Sigma) was dissolved in distilled water at 3 mg/ml. the gel plate was prepared as follows: 1.5 ml reaction buffer (0.2M Tris-HCl pH7.0, 40 mM EDTA and 0.1 mg/ml Ethidium bromide), 1 ml Poly-C and 0.5 ml water were place in the tube and maintained at 50 C for 5 min. 3 ml of the agarose (kept at 50 C) was added to the tube. The mixture was immediately poured onto glass plate. Sampling wells were punched in the gel. Approximately 2 ul of each sample was loaded and the gel was incubated at 37 C for 4 hours in the moist chamber. Then the gel was incubated in a buffer (20 mM sodium acetate pH5.2, 20 mg/ml Ethidium bromide) on ice for 30 min. Gels were photographed on a UV transilluminator using a Kodak digital camera DC290 system equipped with ethidium bromide filters and analyzed using Kodak Molecular Imaging software.

Figure 22:
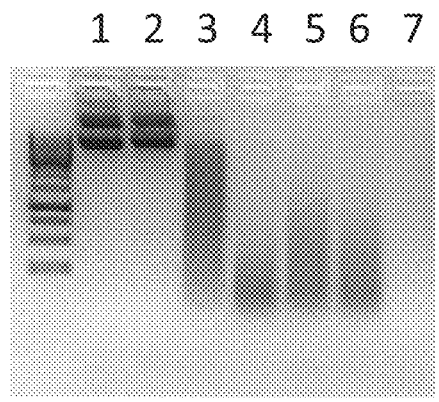
FIG. 22 shows a composite figure displaying results of DNase nuclease activity assays performed on COS supernatants from transfected cells. The description of the numbering (e.g., 090210-8 and 091210-8) from FIG. 21 applies to this figure as well.
Figure 22:
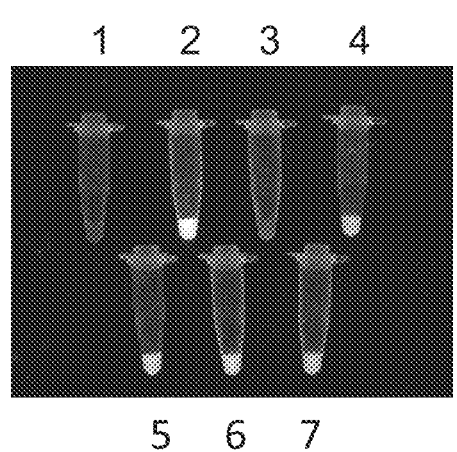

FIG. 22 shows a composite figure displaying results of DNase nuclease activity assays performed on COS supernatants from transfected cells. Culture supernatants were harvested 72 hours after transfecting the following clones of DNase1 wild type and mutant -Ig fusion proteins.: (1) 090210-8=hDNAse1-WT-hIgG1 WT (SEQ ID NO:154); (2) 090210-9=hDNase1-G105R; A114F-hIgG1 WT (SEQ ID NO:159); (3) 091210-8=hRNase1-WT-hIgG1-WT-DNase1-G105R; A114F (SEQ ID NO:151), and (4) 091210-14=hRNase-WT-hIgG1-WT-DNase1-A114F (SEQ ID NO:152).

The pH of the supernatants was adjusted to 0.0 with bicarbonate buffer to facilitate binding of expressed -Ig fusion proteins to protein A agarose beads. Panel A. of FIG. 22 shows gel electrophoresis analysis of plasmid DNA digestion: Protein A agarose slurry (50 ul per sample) was washed in PBS, and incubated overnight at 4° C. with 100 ul culture supernatant to immunoprecipitate -Ig fusion proteins. Immunoprecipitates were washed 4-5 times in 750 ul PBS, centrifuging at approximately 3500 rpm followed by aspiration of PBS. Final protein A precipitates were resuspended in 50 ul reaction buffer containing 20 mM Tris ph7.5. 2 mM CaCl2 and 2 mM MgCl2 containing 1.5 ug plasmid DNA (pDG expression vector). Reactions were incubated for 30 minutes at 37° C., heated at 65° C. for 5 min, and the DNA present in reactions analyzed by agarose gel electrophoresis on 1.5% TBE-agarose gels.

Panel B shows the results of a nuclease activity assay performed on the same culture supernatants using the DNase Alert Kit (IDT/Ambion). Reaction tubes containing lyophilized DNase Alert Substrate (50 pmoles) were resuspended with 5 ul nuclease free ddH2O supplied with the kit, 5 ul 10×DNase alert buffer, and 40 ul protein A slurry immunoprecipitated as follows: For these immunoprecipitations, 50 ul protein A agarose beads were incubated overnight with 50 ul culture supernatant. Samples were then washed 5 times with 0.75 ml PBS. Final protein A precipitates were resuspended in 80 ul nuclease free ddH2O, and 40 ul of the slurry (one half the precipitate) was transferred to the reaction tubes. Negative controls with mock transfected IP and ddH2O were also set up. A positive control was also set up containing DNase1 provided with the kit (2 units). Reactions were incubated 1 hour at 37° C., and exposed to short wave length UV transillumination to visualize fluorescence. Relative amounts of DNA digestion are indicated by degree of fluorescence.

Example 22

Examination of Mac-2 Positive Cells in DTg Mice

Early lupus mortality is usually due to nephritis or infection resulting from immunosuppression to treat nephritis. Therefore, an extremely important outcome for any new therapy is improvement in nephritis. While human studies are limited to quantitation of proteinuria and creatinine, in mice one can get an accurate assessment of inflammation and damage to the kidneys by histology and immunocytochemistry. We report that TLR7.1×RNase double transgenic (DTg) mice showed lower anti-RNA antibodies, less B cell activation, fewer immune deposits and less PAS positive staining glomeruli. We have further compared macrophage infiltration of the kidneys using the anti-Mac-2 (galectin3) antibody (Iyoda et al. Nephrol Dial Transplant 22: 3451, 2007). Frozen sections from kidneys obtained from single or double Tg were examined for numbers of Mac-2+ macrophages as well as glomerular size as described (Iyoda et al). Twenty randomly selected glomeruli (from the outer to inner side of the kidney) were counted for positive cells. There are many fewer mac-2 positive staining cells in the glomeruli of DTg as compared to single Tg mice (data not shown). The results of counting 20 glomeruli per mouse in a pilot study of n=4-5 in each group, revealed mean+/−SE of 3.8+/−1.1 and 1.4+/−0.2 for single versus DTg respectively, p=0.05. In addition, we quantified glomerular tuft size and observed a significant reduction in glomerular tuft size in the DTg mice (179.4+/−41 versus 128+/−16 8 um2 in single versus DTg respectively, p=0.037).

Example 23

Km of Purified Murine RNaseA-Ig Fusion Protein

To further define the functional characteristics of the bivalent RNase-Ig fusion protein (SEQ ID NO:150), we performed determinations of the Michaelis constant, Km. As shown in FIG. 23, the enzyme has a high affinity with a provisional Km of 280 nM (as a comparison, RNase A has a Km of 34 nM using polyC as substrate (delCardayre et al, Prot Eng 8:261, 1995)). FIG. 23 shows enzyme kinetics that were assayed using the Rnase Alert Substrate (Ambion/IDT) and fluorescence was quantified with a Spectramax M2 microplate Reader. Data was analyzed using Softmax Pro software (Molecular Devices). Reaction rates at different substrate concentrations were measured and the data shown as a Lineweaver-Burk plot. The apparent Km, corrected for volume is 280 nM.

Example 24

Analysis of 564Igi Tg Mice for Anti-RNA Antibodies

564 Igi Tg mice: Dr. Imanishi-Kara inserted the rearranged VDJ genes from the H564 hybridoma into the endogenous Igh and Igk loci to create the 564Igi mouse on a B6 background. Sera from these mice stained the cytoplasm and nucleoli of fixed cells indicating a predominant anti-RNA specificity. Consistent with this finding and of special relevance to this patent application, antibody production was inhibited when these mice were made TRL7 deficient indicating that the stimulus for antibody production is indeed RNA. This mouse strain develops late onset glomerulonephritis. We analyzed the expression of anti-RNA antibodies in mice transgenic for H564 and also double transgenic mice coexpressing 564Ig and RNase transgenes. FIG. 24 compares the levels of anti-RNA antibodies in mouse sera at successive intervals as these transgenic mice aged.

See Gavalchin, J., R. A. Seder, and S. K. Datta. 1987. The NZB X SWR model of lupus nephritis. I. Cross-reactive idiotypes of monoclonal anti-DNA antibodies in relation to antigenic specificity, charge, and allotype. Identification of interconnected idiotype families inherited from the normal SWR and the autoimmune NZB parents. *J. Immunol.* 138: 128-137; and Berland, R., L. Fernandez, E. Kari, J. H. Han, I. Lomakin, S. Akira, H. H. Wortis, J. F. Kearney, A. A. Ucci, and T. Imanishi-Kari. 2006. Toll-like receptor 7-dependent loss of B cell tolerance in pathogenic autoantibody knockin mice. *Immunity* 25:429-440.

Example 25

In vitro Assessment of Hybrid Nuclease Molecule Biological Activity

One or more hybrid nuclease molecules are purified, e.g., by affinity or ion exchange chromatography as previously described in the examples above. In some instances the hybrid nuclease molecule is a polypeptide. In some instances, the hybrid nuclease molecule includes one or more sequences from Table 2. In some instances the molecule is SEQ ID NO:161, 162, or 163. In some instances the molecule includes SEQ ID NO:145 and SEQ ID NO:149. In some instances the molecule is SEQ ID NO:151, 152, 153, 154, 155, 156, 157, 158, 159, 160, 161, 162, 163, 166, 167, 169, 170, 171, 173, 175, 177, 179, 181, 187, 189, 191, 193, 195, 197, 199, 201, 203, 205, or 207. The hybrid nuclease molecule can be any of those disclosed herein and any that can be constructed from the sequences disclosed herein (see Table 2), e.g., by taking a nuclease domain and linking it to an Fc domain; or, e.g., taking a nuclease domain and linking it to an Fc domain with a linker domain. Various linker domains (e.g., those described herein) can be used to link the Fc domains and/or nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. Molecules are assayed for the specific nuclease activity in vitro using qualitative assays to verify that they possess the desired nuclease function. Specific activities are generally then determined by fluorescence based kinetic assays utilizing substrates such as the RNase or DNase Alert Kit reagents, and a fluorescence plate reader set to take readings as a function of time. In addition, protein solutions are generally checked for endotoxin contamination using a commercially available kits, such as the Pyrotell Limulus Amebocyte Lysate (LAL) kit, 0.06 EU/ml detection limit from Cape Cod, Inc. (E. Palmouth, Mass.). Molecules are then assayed using a variety of in vitro assays for biological activity.

One series of in vitro assays will measure the effect of the molecules on cytokine production by human PBMC in response to various stimuli, in the presence or absence of the molecules in the cultures. Normal or patient human PBMC (approximately 1×10e6 cells) are cultured for 24, 48, or 96 hours depending on the assay. PBMC are cultured in the presence of stimuli such as TLR ligands, costimulatory antibodies, immune complexes, and normal or autoimmune sera. The effects of the molecules on cytokine production is measured using commercially available reagents, such as the antibody pair kits from Biolegend (San Diego, Calif.) for IL-6, IL-8, IL-10, IL-4, IFN-gamma, TNF-alpha. Culture supernatants from in vitro cultures are harvested at 24, 48 hours or later time points to determine the effects of the molcules on cytokine production. IFN-alpha production is measured using, e.g., anti-human IFN-alpha antibodies and standard curve reagents available from PBL interferon source (Piscataway, N.J.). A similar set of assays is performed using human lymphocyte subpopulations (isolated monocytes, B cells, pDCs, T cells, etc.); purified using, e.g., commercially available magnetic bead based isolation kits available from Miltenyi Biotech (Auburn, Calif.).

In addition, the effect of the molecules on expression of lymphocyte activation receptors such as CD5, CD23, CD69, CD80, CD86, and CD25 is assessed at various time points after stimulation. PBMC or isolated cell subpopulations are subjected to multi-color flow cytometry to determine how these molecules affect the expression of different receptors associated with immune cell activation.

Another set of assays will measure the effects of these molecules on the proliferation of different lymphocyte subpopulations in vitro. These assays will utilize, e.g., CFDA-SE staining (Invitrogen, Carlsbad, Calif.) of human PBMCs prior to stimulation. CFSE at 5 mM is diluted 1:3000 in PBS/0.5% BSA with 10e7-10e8 PBMCS or purified cell subsets and labeling reactions incubated for 3-4 minutes at 37 C prior to washing several times in RPMI/10% FBS to remove remaining CFSE. CFSE labeled cells are then incubated in co-culture reactions with various stimuli (TLR ligands, costimulatory antibodies, etc.) and the molecules for 4 days prior to analysis of cell proliferation by flow cytometry using dye-conjugated cell subpopulation specific antibodies.

The effect of these molecules on in vitro maturation of monocytes into DCs and macrophages is also assessed using both normal and patient PBMC samples.

The effectiveness of a hybrid nuclease molecule is demonstrated by comparing the results of an assay from cells treated with a hybrid nuclease molecule disclosed herein to the results of the assay from cells treated with control formulations. After treatment, the levels of the various markers (e.g., cytokines, cell-surface receptors, proliferation) described above are generally improved in an effective molecule-treated group relative to the marker levels existing prior to the treatment, or relative to the levels measured in a control group.

Example 26

Administration of a Hybrid Nuclease Molecule to a Mammal in Need Thereof

Mammals (e.g., mice, rats, rodents, humans, guinea pigs) are used in the study. Mammals are administered (e.g., intravenously) one or more hybrid nuclease molecules comprising one or more sequences from Table 2 or a control. In some instances the molecule is SEQ ID NO:161, 162, or 163. In some instances the molecule includes SEQ ID NO:145 and SEQ ID NO:149. In some instances the molecule is SEQ ID NO:151, 152, 153, 154, 155, 156, 157, 158, 159, 160, 161, 162, 163, 166, 167, 169, 170, 171, 173, 175, 177, 179, 181, 187, 189, 191, 193, 195, 197, 199, 201, 203, 205, or 207. The hybrid nuclease molecule can be any of those disclosed herein and any that can be constructed from the sequences disclosed herein (see Table 2), e.g., by taking a nuclease domain and linking it to an Fc domain; or, e.g., taking a nuclease domain and linking it to an Fc domain with a linker domain. Various linker domains (e.g., those described herein) can be used to link the Fc domains and/or nuclease domains. For example, linker domains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more amino acids in length can be used. In some instances the hybrid nuclease molecule is formulated a pharmaceutically acceptable carrier. In some instances the molecule is formulated as described in the pharmaceutical compositions section above. The hybrid nuclease molecule targets RNase and/or DNase.

Multiple rounds of doses are used where deemed useful. Effects on IFN-alpha levels, IFN-alpha response gene levels, autoantibody titers, kidney function and pathology, and/or circulating immune complex levels are monitored in the mammals. Similar studies are performed with different treatment protocols and administration routes (e.g., intramuscular administration, etc.). The effectiveness of a hybrid nuclease molecule is demonstrated by comparing the IFN-alpha levels, IFN-alpha response gene levels, autoantibody titers, kidney function and pathology, and/or circulating immune complex levels in mammals treated with a hybrid nuclease molecule disclosed herein to mammals treated with control formulations.

In an example, a human subject in need of treatment is selected or identified. The subject can be in need of, e.g., reducing a cause or symptom of SLE. The identification of the subject can occur in a clinical setting, or elsewhere, e.g., in the subject's home through the subject's own use of a self-testing kit.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

In another example, a rodent subject in need of treatment is selected or identified. The identification of the subject can occur in a laboratory setting or elsewhere.

At time zero, a suitable first dose of a hybrid nuclease molecule is administered to the subject. The hybrid nuclease molecule is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.
Tables

TABLE 1

| SEQ ID NO: | Name | Primer Listing for RNase and DNase -Ig Fusion Gene Constructs Sequence |
|---|---|---|
| | | human primers: |
| 30 | mahIgG1CH2M | tgtccaccgtgtccagcacctgaactcctgggtggatcgtcagtcttcc |
| 31 | huIgG1-H1 | agatctcgagcccaaatcttctgacaaaactcacacatgtccaccgtgt |
| 32 | hIgG1-5scc | gaagatctcgagcccaaatcttctgacaaaactcacacatgt |
| 33 | hIgG1SSSH | gttagatctcgagcccaaatcttctgacaaaactcacacatct |
| 34 | mahIgG1S | tctagattatcatttacccggagacagagagaggctcttctgcgtgtagtg |
| 35 | P331S | aaggtctccaacaaagccctcccagcctccatcgagaaaacaatctcc |
| 36 | P331AS | gttttctcgatggaggctgggagggctttgttggagacc |
| 37 | 5'hrnase | AAG CTT GCC ACC ATG GCT CTG GAG AAG TCT CTT GTC CGG CTC C |
| 38 | 3'hrnasebx | ctcgagatctgtagagtcctccacagaagcatcaaagtgg |
| 39 | 5'hrnaseage | accggtaaggaatcccgggccaagaaattcc |
| 40 | 3'hRNaseRV | gatatcccttccctgggcaaggaatcccgggccaagaaattccag |
| 41 | 3'hRNase-stop | gtttctagattattaggtagagtcctccacagaagcatcaaagtg |
| 42 | hdnase1L3-5NL | GGT AAG CTT GCC ACC ATG TCA CGG GAG CTG GCC CCA CTG CTG CTT |
| 43 | hdnase1L3-3bx | CTC GAG ATC TGA GGA GCG TTT GCT CTT TGT TTT CTT CCT TAG |
| 44 | hDNase1L3-5age | accggtatgaggatctgctccttcaacgtcaggtcctttgg |
| 45 | 5'hDNase1-age | GTT ACC GGT CTG AAG ATC GCA GCC TTC AAC ATC CAG |
| 46 | 5'hDNase1-bx | GTT CTC GAG ATC TTT CAG CAT CAC CTC CAC TGG ATA GTG |
| 47 | 3'hDNase1-RV | GTT GAT ATC CTG AAG ATC GCA GCC TTC AAC ATC CAG |
| 48 | 3'hDNase1-stop | GTT TCT AGA TTA TCA CTT CAG CAT CAC CTC CAC TGG ATA GTG |
| 49 | hDNase1 s105-114 | GAT GGC TGC GAG CCC TGC AGG AAC GAC ACC TTC AAC CGA GAG CCA TTC ATT GTC AGG TTC |

TABLE 1-continued

Primer Listing for RNase and DNase -Ig Fusion Gene Constructs

| SEQ ID NO: | Name | Sequence |
|---|---|---|
| 50 | hDNase1-as114-105 | GAA CCT GAC AAT GAA TGG CTC TCG GTT GAA GGT GTC GTT CCT GCA GGG CTC GCA GCC ATC |
| 51 | hDNase1-as114 | GGA GAA GAA CCT GAC AAT GAA TGG CTC TCG GTT GAA GGT |
| 52 | hDNase1-s114 | ACC TTC AAC CGA GAG CCA TTC ATT GTC AGG TTC TTC TCC |
| 53 | hTrex1-5'age | accggtatgggccctggagctcgcagacagggcag |
| 54 | hTrex1-3'bx | ctcgagatctttggtcctagcagaggctgtgacc |
| 55 | hTrex1-5'AX | accggtctcgagatgggccctggagctcgcagacagg |
| 56 | hTrex1-3'xho#2 | ctcgagtttggtcctagcagaggctgtgacc |

Murine Primers:

| SEQ ID NO: | Name | Sequence |
|---|---|---|
| 57 | mTrex1-5'age | accggtatgggctcacagaccctgccccatggtcaca |
| 58 | mTrex1-3'bx | ctcgagatctgttgttccagtggtagccggagtgccgtacatg |
| 59 | mdnase1L3-5NL | GTT AAG CTT GCC ACC ATG TCC CTG CAC CCA GCT TCC CCA CGC CTG |
| 60 | mdnase1L3-3bx | CTC GAG ATC TGA GGA GCG ATT GCC TTT TTT TCT CTT TTT GAG AG |
| 61 | mrib1-NL | gTT AAg CTT gCC ACC ATg ggT CTg gAg AAg TCC CTC ATT CTg |
| 62 | mrib3NH2 | ggC TCg AgC ACA gTA gCA TCA AAg tGG ACT ggT ACg TAg g |
| 63 | muIgG2aCH2 | cctccatgcaaatgcccagcacctaacctcttgggtggatcatccgtct tcatcttcc |
| 64 | mIgG2a-5 | agatctcgagcccagaggtcccacaatcaagccctctcctccatgcaaa tgcc |
| 65 | mIgG2a-5scc | gaagatctcgagcccagaggtcccacaatcaagccctctcctcca |
| 66 | muIgG2aSSSH | atcaagccctctcctccatctaaatccccagcacctaac |
| 67 | mIgG2aKP5 | agtggcaaggagttcaaatgctcggtcaagaagaaagacctcccagcgt ccatcgag |
| 68 | mIgG2aKP3 | ggttctctcgatggacgctgggaggtcttgttgttgaccgagcatttg aactcc |
| 69 | mIgG2a3S | gtttctagattatcatttacccggagtccgagagaagctcttagtcgt |

Other Primers for different tail mutations and for multispecific fusion genes:

| SEQ ID NO: | Name | Sequence |
|---|---|---|
| 70 | hIgG1-3ns-ns | gctagctccgtcgactttacccggagacagagagagg |
| 71 | K322S | gactggctgaatggcaaggagtacaagtgctcggtctccaacaaagccc tc |
| 72 | K322AS | gagggctttgttggagaccgagcacttgtaagacttgccattcagccag tc |
| 73 | hIgG1N297S | ccgcggggaggagcagtacagcagcacgtaccgtgtggtcagcgtc |
| 74 | hIgG1N297S3 | gacgctgaccacacggtacgtgctgctgtactgctcctcccgcgg |
| 75 | mIgG2aNS | gatatctctagatttacccggagtccgagagaagctcttagtcgt |

TABLE 1-continued

Primer Listing for RNase and DNase -Ig Fusion Gene Constructs

| SEQ ID NO: | Name | Sequence |
|---|---|---|
| 76 | mIgG2a3ns-sal | gatatctccggagtcgactttacccggagtccgagagaagctcttag |
| 77 | mIgG2N297S5 | cacaaacccatagagaggattacagcagtactctccgggtggtc |
| 78 | mIgG2N297S3 | gaccacccggagagtactgctgtaatcctctctatgggtttgag |
| 79 | | |
| 80 | g4s4clnk3 | GAT ATC ACC GGT AGA ACC ACC TCC ACC ACT CCC ACC TCC TCC AGT GCC TCC |
| 81 | g4s4clnk5 | GTC GAC TCC GGA GGA GGT GGC TCA GGT GGT GGA GGC AGT GGA GGA GGT GG |
| 82 | Nlnkgly5 | aaagtcgacggagctagcagccccgtgaacgtgagcagccccagcgtg |
| 83 | Nlnkgly3 | cccatgatatcctgcacgctggggctgctc |
| 84 | hdnase1age | ACC GGT ATG AGG ATC TGC TCC TTC AAC GTC AGG TCC TTT GG |
| 85 | hdnase1L3-3S | AGA TCT TTA TCA GGA GCG TTT GCT CTT TGT TTT CTT CCT TAG |
| 86 | mdnase1L3-3S | TCT AGA TTA TCA GGA GCG ATT GCC TTT TTT TCT CTT TTT GAG AG |
| 87 | mdnase1L3-age | ACC GGT CTA AGG CTC TGC TCC TTC AAT GTG AGG TCC TTT GGA |
| 88 | mrib-L5' | gAT ACC ACC ggT Agg gAA TCT gCA gCA CAg AAg TTT CAg |
| 89 | mrib5X | AAA TCT AgA CCT CAA CCA ggT Agg gAA TCT gCA gCA CAg AAg TTT CAg |
| 90 | mrib3X | TCT AgA CTA TCA CAC AgT AgC ATC AAA gTg gAC Tgg TAC gTA |
| 91 | hRNaseG88D-S | agactgccgcctgacaaacgactccaggtaccc |
| 92 | hRNaseG88D-AS | gggtacctggagtcgtttgtcaggcggcagtct |
| 93 | g4s5-5-1 | GGC TCA GGT GGT GGA GGA TCT GGA GGA GGT GGC TCA GGT GGT GGA GGA TCT G |
| 94 | g4s5-2s | GTT AGA TCT CTC CGG AGG AGG TGG CTC AGG TGG TGG AGG ATC TGG A |
| 95 | g4s5-asxho | CTC GAG ACT CCC ACC TCC TCC AGA TCC TCC ACC ACC TGA GCC ACC T |
| 96 | g4s4-5' | AAA GAT CTC TCC GGA GGA GGT GGC TCA GGT GGT GGA GGA TCT GGA GGA GG |
| 97 | g4s4-3' | CTC GAG ACC GGT AGA ACC ACC TCC ACC ACT CCC ACC TCC TCC AGA TCC TC |
| 98 | g4s5-5 | GTT AGA TCT CTC CGG AGG AGG TGG CTC A |
| 99 | g4s5-3 | ACC GGT CTC GAG ACT CCC ACC TCC TCC AGA TC |

TABLE 2

| SEQ ID NO: | DESCRIPTION | SEQUENCE (NUCLEOTIDE SEQUENCES ARE 5'-3') |
|---|---|---|
| 100 | g4s4lnk ("g4s4" disclosed as SEQ ID NO: 212) | agatctctccggaggaggtggctcaggtggtggaggatctggaggaggtgggag tggtggaggtggttctaccggtctcgag |
| 101 | G4S5-1 ("g4s5" disclosed as SEQ ID NO: 209) | agatctctccggaggaggtggctcaggtggtggaggatctggaggaggtggctc aggtggtggaggatctggaggaggtgggagtaccggtctcgag |
| 102 | G4S5-2 ("g4s5" disclosed as SEQ ID NO: 209) | agatctctccggaggaggtggctcaggtggtggaggatctggaggaggtggctc aggtggtggaggatctggaggaggtgggagtctcgag |
| 103 | 3'hRNase G88D | gtcgacggagctagcagccccgtgaacgtgagcagcccccagcgtgcaggatatc ccttccctgggcaaggaatcccgggccaagaaattccagcggcagcatatggac tcagacagttcccccagcagcagctccacctactgtaaccaaatgatgaggcgc cggaatatgacacaggggcggtgcaaaccagtgaacacctttgtgcacgagccc ctggtagatgtccagaatgtctgttccaggaaaaggtcacctgcaagaacggg cagggcaactgctacaagagcaactccagcatgcacatcacagactgccgcctg acaaacgactgccaggtaccccaactgtgcataccggaccagcccgaaggagaga cacatcattgtggcctgtgaagggagcccatatgtgccagtccactttgatgct tctgtggaggactctacctaataatctaga |
| 104 | hDNase1- 3'- G105R; A114F | gatatcctgaagatcgcagccttcaacatccagacatttggggagaccaagatg tccaatgccacccctcgtcagctacattgtgcagatcctgagccgctatgacatc gccctggtccaggaggtcagagacagccacctgactgccgtggggaagctgctg gacaacctcaatcaggatgcaccagacacctatcactacgtgtcagtgagcca ctgggacggaacagctataaggagcgctacctgttcgtgtacaggcctgaccag gtgtctgcggtggacagctactactacgatgatggctgcgagccctgcaggaac gacaccttcaaccgagagccattcattgtcaggttcttctcccggttcacagag gtcagggagtttgccattgttcccctgcatgcggccccgggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaagtgataatctaga |
| 105 | hDNase1- 3'-WT | gatatcctgaagatcgcagccttcaacatccagacatttggggagaccaagatg tccaatgccacccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccattcattgtcaggttcttctcccggttcacagag gtcagggagtttgccattgttcccctgcatgcggccccgggggacgcagtagcc gagatcgacgctctctatgacgtctacctggatgtccaagagaaatggggcttg gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc gtggttgcagggatgctgctccgaggcgccgttgttcccgactcggctcttccc tttaacttccaggctgcctatggcctgagtgaccaactggcccaagccatcagt gaccactatccagtggaggtgatgctgaaatgataatctaga |
| 106 | hDNase1- 3'A114F | gatatcctgaagatcgcagccttcaacatccagacatttggggagaccaagatg tccaatgccacccctcgtcagctacattgtgcagatcctgagccgctatgacatc gccctggtccaggaggtcagagacagccacctgactgccgtggggaagctgctg gacaacctcaatcaggatgcaccagacacctatcactacgtggtcagtgagcca ctgggacggaacagctataaggagcgctacctgttcgtgtacaggcctgaccag gtgtctgcggtggacagctactactacgatgatggctgcgagccctgcgggaac gacaccttcaaccgagagccattcattgtcaggttcttctcccggttcacagag gtcagggagtttgccattgttcccctgcatgcggccccgggggacgcagtagcc gagatcgacgctctctatgacgtctacctggatgtccaagagaaatggggctta gaggacgtcatgttgatgggcgacttcaatgcgggctgcagctatgtgagaccc tcccagtggtcatccatccgcctgtggacaagccccaccttccagtggctgatc cccgacagcgctgacaccacagctacacccacgcactgtgcctatgacaggatc |

TABLE 2-continued

| SEQ ID NO: | DESCRIPTION | SEQUENCE (NUCLEOTIDE SEQUENCES ARE 5'-3') |
|---|---|---|
| | | gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaagtgataatctaga |
| 107 | hDNase1-<br>5'-<br>G105R; A114F | accggtctgaagatcgcagccttcaacatccagacatttggggagaccaagatg<br>tccaatgccacccctcgtcagctacattgtgcagatcctgagccgctatgacatc<br>gccctggtccaggaggtcagagacagccacctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcaggaac<br>gacaccttcaaccgagagccattcattgtcaggttcttctcccggttcacagag<br>gtcagggagtttgccattgttcccctgcatgcggccccgggggacgcagtagcc<br>gagatcgacgctctctatgacgtctacctggatgtccaagagaaatggggcttg<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 108 | hDNase1-<br>5'-WT | accggtctgaagatcgcagccttcaacatccagacatttggggagaccaagatg<br>tccaatgccacccctcgtcagctacattgtgcagatcctgagccgctatgacatc<br>gccctggtccaggaggtcagagacagccacctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccattgtcaggttcttctcccggttcacagag<br>gtcagggagtttgccattgttcccctgcatgcggccccgggggacgcagtagcc<br>gagatcgacgctctctatgacgtctacctggatgtccaagagaaatggggcttg<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 109 | hDNase1-<br>5'-A114F | accggtctgaagatcgcagccttcaacatccagacatttggggagaccaagatg<br>tccaatgccacccctcgtcagctacattgtgcagatcctgagccgctatgacatc<br>gccctggtccaggaggtcagagacagccacctgactgccgtggggaagctgctg<br>gacaacctcaatcaggatgcaccagacacctatcactacgtggtcagtgagcca<br>ctgggacggaacagctataaggagcgctacctgttcgtgtacaggcctgaccag<br>gtgtctgcggtggacagctactactacgatgatggctgcgagccctgcgggaac<br>gacaccttcaaccgagagccattcattgtcaggttcttctcccggttcacagag<br>gtcagggagtttgccattgttcccctgcatgcggccccgggggacgcagtagcc<br>gagatcgacgctctctatgacgtctacctggatgtccaagagaaatggggctta<br>gaggacgtcatgttgatgggcgacttcaatgcgggctgcagctatgtgagaccc<br>tcccagtggtcatccatccgcctgtggacaagccccaccttccagtggctgatc<br>cccgacagcgctgacaccacagctacacccacgcactgtgcctatgacaggatc<br>gtggttgcagggatgctgctccgaggcgccgttgttcccgactcggctcttccc<br>tttaacttccaggctgcctatggcctgagtgaccaactggcccaagccatcagt<br>gaccactatccagtggaggtgatgctgaaagatctcgag |
| 110 | hIgG1<br>(SCC) | agatctcgagcccaaatcttctgacaaaactcacacatgtccaccgtgcccagc<br>acctgaactcctggggggaccgtcagtcttcctcttccccccaaaacccaagga<br>caccctcatgatctcccggacccctgaggtcacatgcgtggtggtggacgtgag<br>ccacgaagaccctgaggtcaagttcaactggtacgtggacggcgtggaggtgca<br>taatgccaagacaaagccgcgggaggagcagtacaacagcacgtaccgtgtggt<br>cagcgtcctcaccgtcctgcaccaggactggctgaatggcaaggagtacaagtg<br>caaggtctccaacaaagccctcccagcccccatcgagaaaaccatctccaaagc<br>caaagggcagccccgagaaccacaggtgtacaccctgcccccatcccgggatga<br>gctgaccaagaaccaggtcagcctgacctgcctggtcaaaggcttctatcccag<br>cgacatcgccgtggagtgggagagcaatgggcagccggagaacaactacaagac<br>cacgcctcccgtgctggactccgacggctccttcttcctctacagcaagctcac<br>cgtggacaagagcaggtggcagcaggggaacgtcttctcatgctccgtgatgca<br>tgaggctctgcacaaccactacacgcagaagagcctctctctgtctccgggtaa<br>atgataatctaga |
| 111 | hDNase1 +<br>VK3LP | gttaagcttgccaccatggaaaccccagcgcagcttctcttcctcctgctactc<br>tggctcccagataccaccggtctgaagatcgcagccttcaacatccagacattt<br>ggggagaccaagatgtccaatgccacccctcgtcagctacattgtgcagatcctg<br>agccgctatgacatcgccctggtccaggaggtcagagacagccacctgactgcc<br>gtggggaagctgctggacaacctcaatcaggatgcaccagacacctatcactac<br>gtggtcagtgagccactgggacggaacagctataaggagcgctacctgttcgt<br>gtacaggcctgaccaggtgtctgcggtggacagctactactacgatgatggctgc<br>gagccctgcgggaacgacaccttcaaccgagagccagccattgtcaggttcttc<br>tcccggttcacagaggtcagggagtttgccattgttcccctgcatgcggccccg<br>ggggacgcagtagccgagatcgacgctctctatgacgtctacctggatgtccaa |

TABLE 2-continued

| SEQ ID NO: | DESCRIPTION | SEQUENCE (NUCLEOTIDE SEQUENCES ARE 5'-3') |
|---|---|---|
| | | gagaaatggggcttggaggacgtcatgttgatgggcgacttcaatgcgggctgc<br>agctatgtgagaccctcccagtggtcatccatccgcctgtggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttcccttaacttccaggctgcctatggcctgagtgaccaactg<br>gcccaagccatcagtgaccactatccagtggaggtgatgctgaagtga |
| 112 | hDNase1L3 | atgtcacgggagctggccccactgctgcttctcctcctctccatccacagcgcc<br>ctggccatgaggatctgctccttcaacgtcaggtcctttggggaaagcaagcag<br>gaagacaagaatgccatggatgtcattgtgaaggtcatcaaacgctgtgacatc<br>atactcgtgatggaaatcaaggacagcaacaacaggatctgccccatactgatg<br>gagaagctgaacagaaattcaaggagaggcataacatacaactatgtgattagc<br>tctcggcttggaagaaacacatataaagaacaatatgcctttctctacaaggaa<br>aagctggtgtctgtgaagaggagttatcactaccatgactatcaggatggagac<br>gcagatgtgttttccagggagccctttgtggtctggttccaatctccccacact<br>gctgtcaaagacttcgtgattatcccctgcacaccaccccagagacatccgtt<br>aaggagatcgatgagttggttgaggtctacacggacgtgaaacaccgctggaag<br>gcggagaatttcattttcatgggtgacttcaatgccggctgcagctacgtcccc<br>aagaaggcctgaagaacatccgcttgaggactgaccccaggtttgtttggctg<br>atcggggaccaagaggacaccacggtgaagaagagcaccaactgtgcatatgac<br>aggattgtgcttagaggacaagaaatcgtcagttctgttgttcccaagtcaaac<br>agtgtttttgacttccagaaagcttacaagctgactgaagaggaggccctggat<br>gtcagcgaccacttccagttgaatttaaactacagtcttcaagggccttcacc<br>aacagcaaaaaatctgtcactctaaggaagaaaacaaagagcaaacgctcctag |
| 113 | human pancreatic ribonuclease | atgggtctggagaagtctcttgtccggctccttctgcttgtcctgatactgctg<br>gtgctgggctgggtccagcctccctgggcaaggaatcccgggcaagaaattc<br>cagcggcagcatatggactcagacagttccccagcagcagctccacctactgt<br>aaccaaatgatgaggcgccggaatatgacacaggggcggtgcaaaccagtgaac<br>acctttgtgcacgagcccctggtagatgtccagaatgtctgtttccaggaaaag<br>gtcacctgcaagaacgggcagggcaactgctacaagagcaactccagcatgcac<br>atcacagactgccgcctgacaaacggctccaggtaccccaactgtgcataccgg<br>accagcccgaaggagagacacatcattgtggcctgtgaagggagcccatatgtg<br>ccagtccactttgatgctactgtgtag |
| 114 | huVK3LP + mrib1 + mIgG2A-C-2S | gttaagcttgccaccatggaaaccccagcgcagcttctcttcctcctgctactc<br>tggctcccagataccaccggtaggaatctgcagcacagaagtttcagcggcag<br>cacatggatccagatggttcctccatcaacagccccacctactgcaaccaaatg<br>atgaaacgccgggatatgggcatgcaagcccgtgaacaccttcgtg<br>catgagcccttggcagatgtccaggccgtctgctcccaggaaaatgtcacctgc<br>aagaacaggaagagcaactgctacaagagcagctctgccctgcacatcactgac<br>tgccacctgaagggcaactccaagtatcccaactgtgactacaagaccactcaa<br>taccagaagcacatcattgtggcctgtgaagggaaccctctacgtaccagtccac<br>tttgatgctactgtgctcgagcccagaggtctcacaatcaagccctctcctcca<br>tgcaaatgcccagcacctaacctcttgggtggatcatccgtcttcatcttccct<br>ccaaagatcaaggatgtactcatgatctccctgagccccatggtcacatgtgtg<br>gtggtggatgtgagcgaggatgacccagacgtccagatcagctggtttgtgaac<br>aacgttggaagtacacacagctcagacacaaacccatagagaggattacaacagt<br>actctccgggtggtcagtgccctccccatccagcaccaggactggatgagtggc<br>aaggagttcaaatgctcggtcaacaacaaagacctcccagcgtccatcgagaga<br>accatctcaaaacccagagggccagtaagagctccacaggtatatgtcttgcct<br>ccaccagcagaagagatgactaagaaagagttcagtctgacctgcatgatcaca<br>ggcttcttacctgccgaaattgctgtggactggaccagcaatgggcgtacagag<br>caaaactacaagaacaccgcaacagtcctggactctgatggttcttacttcatg<br>tacagcaagctcagagtacaaaagagcacttgggaaagaggaagtcttttcgcc<br>tgctcagtggtccacgagggtctgcacaatcaccttacgactaagagcttctct<br>cggactccgggtaaatgataatctagaa |
| 115 | huVK3LP-hRNaseWT-hIgG1 (SCC)-NLG-hDNAse1-105-114 | aagcttgccgccatggaaaccccagcgcagcttctcttcctcctgctactctgg<br>ctcccagataccaccggtaaggaatctccgggccaagaaattccagcggcagcat<br>atggactcagacagttccccagcagcagctccacctactgtaaccaaatgatg<br>aggcgccggaatatgacacaggggcggtgcaaaccagtgaacacctttgtgcac<br>gagcccctggtagatgtccagaatgtctgtttccaggaaaaggtcacctgcaag<br>aacgggcagggcaactgctacaagagcagctctgccctgcacatcactgactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctgggggaccgtcagtcttc<br>ctcttccccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagcccctcccagcccc<br>atcgagaaaaccatctccaaagccaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc |

TABLE 2-continued

| SEQ ID NO: | DESCRIPTION | SEQUENCE (NUCLEOTIDE SEQUENCES ARE 5'-3') |
|---|---|---|
| | | ttcttcctctacagcaagctcaccgtggacaagagcaggtggcagcaggggaac
gtcttctcatgctccgtgatgcatgagggtctgcacaaccactacacgcagaag
agcctctctctgtctccgggtaaagtcgacggtgctagcagccatgtgaatgtg
agcagccctagcgtgcaggatatcctgaagatcgcagccttcaacatccagaca
tttggggagaccaagatgtccaatgccaccctcgtcagctacattgtgcagatc
ctgagccgctatgacatcgccctggtccaggaggtcagagacagccacctgact
gccgtggggaagctgctggacaacctcaatcaggatgcaccagacacctatcac
tacgtggtcagtgagccactgggacggaacagctataaggagcgctacctgttc
gtgtacaggcctgaccaggtgtctgcggtggacagctactactacgatgatggc
tgcgagccctgcgggaacgacaccttcaaccgagagccagccattgtcaggttc
ttctcccggttcacagaggtcagggagtttgccattgtccctgcatgcgcc
ccgggggacgcagtagccgagatcgacgctctctatgacgtctacctggatgtc
caagagaaatggggctcggaggacgtcatgttgatgggcgacttcaatgcgggc
tgcagctatgtgagaccctcccagtggtcatccatccgcctgtggacaagcccc
accttccagtggctgatccccgacagcgctgacaccacagctacacccacgcac
tgtgcctatgacaggatcgtggttgcagggatgctgctccgaggcgccgttgtt
cccgactcggctcttcccttttaacttccagnctgcctatggcctgagtgaccaa
ctggcccaagccatcagtgaccactatccagtggaggtgatgctgaagtgataa
tctaga |
| 116 | huVK3LP-
hRNaseWT-
hIgG1
(SCC)-
NLG-
hDNase1-
114F | aagcttgccgccatggaaacccagcgcagcttctcttcctcctgctactctgg
ctcccagataccaccggtaaggaatcccgggccaagaaattccagcggcagcat
atggactcagacagttccccagcagcagctccacctactgtaaccaaatgatg
aggcgccggaatatgacacaggggcggtgcaaaccagtgaacacctttgtgcac
gagccctggtagatgtccagaatgtctgtttccaggaaaaggtcacctgcaag
aacgggcagggcaactgctacaagagcaactccagcatgcacatcacagactgc
cgcctgacaaacggctccaggtaccccaactgtgcataccggaccagcccgaag
gagagacacatcattgtggcctgtgaagggagcccatatgtgccagtccacttt
gatgcttctgtggaggactctacagatctcgagcccaaatcttctgacaaaact
cacacatgtccaccgtgcccagcacctgaactcctggggggaccgtcagtcttc
ctcttccccccaaaacccaaggacacctcatgatctcccggacccctgaggtc
acatgcgtggtggtggacgtgagccacgaagaccctgaggtcaagttcaactgg
tacgtggacggcgtggaggtgcataatgccaagacaaagccgcgggaggagcag
tacaacagcacgtaccgtgtggtcagcgtcctcaccgtcctgcaccaggactgg
ctgaatggcaaggagtacaagtgcaaggtctccaacaaagcctcccagcccc
atcgagaaaaccatctccaaagccaaagggcagccccgagaaccacaggtgtac
accctgcccccatcccgggatgagctgaccaagaaccaggtcagcctgacctgc
ctggtcaaaggcttctatcccagcgacatcgccgtggagtgggagagcaatggg
cagccggagaacaactacaagaccacgcctcccgtgctggactccgacggctcc
ttcttcctctacagcaagctcaccgtggacaagagcaggtggcagcaggggaac
gtcttctcatgctccgtgatgcatgagggtctgcacaaccactacacgcagaag
agcctctctctgtctccgggtaaagtcgacggtgctagcagccatgtgaatgtg
agcagccctagcgtgcaggatatcctgaagatcgcagccttcaacatccagaca
tttggggagaccaagatgtccaatgccaccctcgtcagctacattgtgcagatc
ctgagccgctatgacatcgccctggtccaggaggtcagagacagccacctgact
gccgtggggaagctgctggacaacctcaatcaggatgcaccagacacctatcac
tacgtggtcagtgagccactgggacggaacagctataaggagcgctacctgttc
gtgtacaggcctgaccaggtgtctgcggtggacagctactactacgatgatggc
tgcgagccctgcgggaacgacaccttcaaccgagagccattcattgtcaggttc
ttctcccggttcacagaggtcagggagtttgccattgtccctgcatgcgcc
ccgggggacgcagtagccgagatcgacgctctctatgacgtctacctggatgtc
caagagaaatggggcttagaggacgtcatgttgatgggcgacttcaatgcgggc
tgcagctatgtgagaccctcccagtggtcatccatccgcctgtggacaagcccc
accttccagtggctgatccccgacagcgctgacaccacagctacacccacgcac
tgtgcctatgacaggatcgtggttgcagggatgctgctccgaggcgccgttgtt
cccgactcggctcttcccttttaacttccaggctgcctatggcctgagtgaccaa
ctggcccaagccatcagtgaccactatccagtggaggtgatgctgaagtgataa
tctaga |
| 117 | huVK3LP-
hRNaseWT-
hIgG1
(SCC)-
NLG-
hDNase1-
WT | aagcttgccgccatggaaacccagcgcagcttctcttcctcctgctactctgg
ctcccagataccaccggtaaggaatcccgggccaagaaattccagcggcagcat
atggactcagacagttccccagcagcagctccacctactgtaaccaaatgatg
aggcgccggaatatgacacaggggcggtgcaaaccagtgaacacctttgtgcac
gagccctggtagatgtccagaatgtctgtttccaggaaaaggtcacctgcaag
aacgggcagggcaactgctacaagagcaactccagcatgcacatcacagactgc
cgcctgacaaacggctccaggtaccccaactgtgcataccggaccagcccgaag
gagagacacatcattgtggcctgtgaagggagcccatatgtgccagtccacttt
gatgcttctgtggaggactctacagatctcgagcccaaatcttctgacaaaact
cacacatgtccaccgtgcccagcacctgaactcctggggggaccgtcagtcttc
ctcttccccccaaaacccaaggacacctcatgatctcccggacccctgaggtc
acatgcgtggtggtggacgtgagccacgaagaccctgaggtcaagttcaactgg
tacgtggacggcgtggaggtgcataatgccaagacaaagccgcgggaggagcag
tacaacagcacgtaccgtgtggtcagcgtcctcaccgtcctgcaccaggactgg
ctgaatggcaaggagtacaagtgcaaggtctccaacaaagcctcccagcccc
atcgagaaaaccatctccaaagccaaagggcagccccgagaaccacaggtgtac
accctgcccccatcccgggatgagctgaccaagaaccaggtcagcctgacctgc
ctggtcaaaggcttctatcccagcgacatcgccgtggagtgggagagcaatggg |

TABLE 2-continued

| SEQ ID NO: | DESCRIPTION | SEQUENCE (NUCLEOTIDE SEQUENCES ARE 5'-3') |
|---|---|---|
| | | cagccggagaacaactacaagaccacgcctcccgtgctggactccgacggctcc
ttcttcctctacagcaagctcaccgtggacaagagcaggtggcagcaggggaac
gtcttctcatgctccgtgatgcatgagggtctgcacaaccactacacgcagaag
agcctctctctgtctccgggtaaagtcgacggtgctagcagccatgtgaatgtg
agcagccctagcgtgcaggatatcctgaagatcgcagccttcaacatccagaca
tttggggagaccaagatgtccaatgccaccctcgtcagctacattgtgcagatc
ctgagccgctatgacatcgccctggtccaggaggtcagagacagccacctgact
gccgtggggaagctgctggacaacctcaatcaggatgcaccagacacctatcac
tacgtggtcagtgagccactgggacggaacagctataaggagcgctacctgttc
gtgtacaggcctgaccaggtgtctgcggtggacagctactactacgatgatggc
tgcgagccctgcgggaacgacaccttcaaccgagagccagccattgtcaggttc
ttctcccggttcacagaggtcagggagtttgccattgttcccctgcatgcggcc
ccgggggacgcagtagccgagtcgacgctctctatgacgtctacctggatgtc
caagagaaatggggcttggaggacgtcatgttgatgggcgacttcaatgcgggc
tgcagctatgtgagaccctcccagtggtcatccatccgcctgtggacaagcccc
accttccagtggctgatccccgacagcgctgacaccacagctacacccacgcac
tgtgcctatgacaggatcgtggttgcagggatgctgctccgaggcgccgttgtt
cccgactcggctcttccctttaacttccaggctgcctatggcctgagtgaccaa
ctgcccaagccatcagtgaccactatccagtggaggtgatgctgaaatgataa
tctaga |
| 118 | hVK3LP-
hDNase1
(WT)-
hIgG1
(SCC) | gttaagcttgccaccatggaaaccccagcgcagcttctcttcctcctgctactc
tggctcccagataccaccggtctgaagatcgcagccttcaacatccagacatt
ggggagaccaagatgtccaatgccaccctcgtcagctacattgtgcagatcctg
agccgctatgacatcgccctggtccaggaggtcagagacagccacctgactgcc
gtggggaagctgctggacaacctcaatcaggatgcaccagacacctatcactac
gtggtcagtgagccactgggacggaacagctataaggagcgctacctgttcgtg
tacaggcctgaccaggtgtctgcggtggacagctactactacgatgatggctgc
gagccctgcgggaacgacaccttcaaccgagagccagccattgtcaggttcttc
tcccggttcacagaggtcagggagtttgccattgttcccctgcatgcggccccg
ggggacgcagtagccgagtcgacgctctctatgacgtctacctggatgtccaa
gagaaatggggcttggaggacgtcatgttgatgggcgacttcaatgcgggctgc
agctatgtgagaccctcccagtggtcatccatccgcctgtggacaagccccacc
ttccagtggctgatccccgacagcgctgacaccacagctacacccacgcactgt
gcctatgacaggatcgtggttgcagggatgctgctccgaggcgccgttgttccc
gactcggctcttccctttaacttccaggctgcctatggcctgagtgaccaactg
cccaagccatcagtgaccactatccagtggaggtgatgctgaaagatctgag
cccaaatcttctgacaaaactcacacatgtccaccgtgcccagcacctgaactc
ctggggggaccgtcagtcttcctcttccccccaaaacccaaggacaccctcatg
atctcccggaccctgaggtcacatgcgtggtggtggacgtgagccacgaagac
cctgaggtcaagttcaactggtacgtggacggcgtggaggtgcataatgccaag
acaaagccgcgggaggagcagtacaacagcacgtaccgtgtggtcagcgtcctc
accgtcctgcaccaggactggctgaatggcaaggagtacaagtgcaaggtctcc
aacaaagccctcccagcccccatcgagaaaaccatctccaaagccaaagggcag
ccccgagaaccacaggtgtacaccctgcccccatcccgggatgagctgaccaag
aaccaggtcagcctgacctgcctggtcaaaggcttctatcccagcgacatcgcc
gtggagtgggagagcaatgggcagccggagaacaactacaagaccacgcctccc
gtgctggactccgacggctccttcttcctctacagcaagctcaccgtggacaag
agcaggtggcagcaggggaacgtcttctcatgctccgtgatgcatgaggctctg
cacaaccactacacgcagaagagcctctctctgtctccgggtaaatgataatct
aga |
| 119 | hVK3LP-
hDNase1-
A114F-
hIgG1 (SCC) | gttaagcttgccaccatggaaaccccagcgcagcttctcttcctcctgctactc
tggctcccagataccaccggtctgaagatcgcagccttcaacatccagacatt
ggggagaccaagatgtccaatgccaccctcgtcagctacattgtgcagatcctg
agccgctatgacatcgccctggtccaggaggtcagagacagccacctgactgcc
gtggggaagctgctggacaacctcaatcaggatgcaccagacacctatcactac
gtggtcagtgagccactgggacggaacagctataaggagcgctacctgttcgtg
tacaggcctgaccaggtgtctgcggtggacagctactactacgatgatggctgc
gagccctgcgggaacgacaccttcaaccgagagccagccattcattgtcaggttcttc
tcccggttcacagaggtcagggagtttgccattgttcccctgcatgcggccccg
ggggacgcagtagccgagtcgacgctctctatgacgtctacctggatgtccaa
gagaaatggggcttagaggacgtcatgttgatgggcgacttcaatgcgggctgc
agctatgtgagaccctcccagtggtcatccatccgcctgtggacaagccccacc
ttccagtggctgatccccgacagcgctgacaccacagctacacccacgcactgt
gcctatgacaggatcgtggttgcagggatgctgctccgaggcgccgttgttccc
gactcggctcttccctttaacttccaggctgcctatggcctgagtgaccaactg
cccaagccatcagtgaccactatccagtggaggtgatgctgaaagatctgag
cccaaatcttctgacaaaactcacacatgtccaccgtgcccagcacctgaactc
ctggggggaccgtcagtcttcctcttccccccaaaacccaaggacaccctcatg
atctcccggaccctgaggtcacatgcgtggtggtggacgtgagccacgaagac
cctgaggtcaagttcaactggtacgtggacggcgtggaggtgcataatgccaag
acaaagccgcgggaggagcagtacaacagcacgtaccgtgtggtcagcgtcctc
accgtcctgcaccaggactggctgaatggcaaggagtacaagtgcaaggtctcc
aacaaagccctcccagcccccatcgagaaaaccatctccaaagccaaagggcag
ccccgagaaccacaggtgtacaccctgcccccatcccgggatgagctgaccaag
aaccaggtcagcctgacctgcctggtcaaaggcttctatcccagcgacatcgcc |

TABLE 2-continued

| SEQ ID NO: | DESCRIPTION | SEQUENCE (NUCLEOTIDE SEQUENCES ARE 5'-3') |
|---|---|---|
| | | gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaatgataatct aga |
| 120 | hVK3LP-hDNase1-G105R; A114F-(G4S)4-hIgG1 (SCC) "(G4S)4" disclosed as SEQ ID NO: 212) | gttaagcttgccaccatggaaaccccagcgcagcttctcttcctcctgctactc tggctcccagataccaccggtctgaagatcgcagccttcaacatccagacattt ggggagaccaagatgtccaatgccaccctcgtcagctacattgtgcagatcctg agccgctatgacatcgccctggtccaggaggtcagagacagccacctgactgcc gtggggaagctgctggacaacctcaatcaggatgcaccagacacctatcactac gtggtcagtgagccactgggacggaacagctataaggagcgctacctgttcgtg tacaggcctgaccaggtgtctgcggtggacagctactactacgatgatggctgc gagccctgcaggaacgacaccttcaaccgagagccattcattgtcaggttcttc tcccggttcacagaggtcagggagtttgccattgttccctgcatgcggccccg ggggacgcagtagccgagatcgacgctctctatgacgtctacctggatgtccaa gagaaatggggcttggaggacgtcatgttgatgggcgacttcaatgcgggctgc agctatgtgagaccctcccagtggtcatccatccgcctgtggacaagccccacc ttccagtggctgatccccgacagcgctgacaccacagctacacccacgcactgt gcctatgacaggatcgtggttgcagggatgctgctccgaggcgccgttgttccc gactcggctcttcccttttaacttccaggctgcctatggcctgagtgaccaactg gcccaagccatcagtgaccactatccagtggaggtgatgctgaaagatctctcc ggaggaggtggctcaggtggtggaggatctggaggaggtggctcaggtggtgga ggttctaccggtctcgagcccaaatcttctgacaaaactcacacatgtccaccg tgcccagcacctgaactcctggggggaccgtcagtcttcctcttccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagccctcccagcccccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggtaaatgataatctaga |
| 121 | hVK3LP-hDNase1-G105R; A114F-(G4S)5-1-hIgG1 (SCC) "(G4S)5" disclosed as SEQ ID NO: 209) | gttaagcttgccaccatggaaaccccagcgcagcttctcttcctcctgctactc tggctcccagataccaccggtctgaagatcgcagccttcaacatccagacattt ggggagaccaagatgtccaatgccaccctcgtcagctacattgtgcagatcctg agccgctatgacatcgccctggtccaggaggtcagagacagccacctgactgcc gtggggaagctgctggacaacctcaatcaggatgcaccagacacctatcactac gtggtcagtgagccactgggacggaacagctataaggagcgctacctgttcgtg tacaggcctgaccaggtgtctgcggtggacagctactactacgatgatggctgc gagccctgcaggaacgacaccttcaaccgagagccattcattgtcaggttcttc tcccggttcacagaggtcagggagtttgccattgttccctgcatgcggccccg ggggacgcagtagccgagatcgacgctctctatgacgtctacctggatgtccaa gagaaatggggcttggaggacgtcatgttgatgggcgacttcaatgcgggctgc agctatgtgagaccctcccagtggtcatccatccgcctgtggacaagccccacc ttccagtggctgatccccgacagcgctgacaccacagctacacccacgcactgt gcctatgacaggatcgtggttgcagggatgctgctccgaggcgccgttgttccc gactcggctcttcccttttaacttccaggctgcctatggcctgagtgaccaactg gcccaagccatcagtgaccactatccagtggaggtgatgctgaaagatctctcc ggaggaggtggctcaggtggtggaggatctggaggaggtggctcaggtggtgga ggatctggaggaggtgggagtaccggtctcgagcccaaatcttctgacaaaact cacacatgtccaccgtgcccagcacctgaactcctggggggaccgtcagtcttc ctcttccccccaaaacccaaggacaccctcatgatctcccggacccctgaggtc acatgcgtggtggtggacgtgagccacgaagaccctgaggtcaagttcaactgg tacgtggacggcgtggaggtgcataatgccaagacaaagccgcgggaggagcag tacaacagcacgtaccgtgtggtcagcgtcctcaccgtcctgcaccaggactgg ctgaatggcaaggagtacaagtgcaaggtctccaacaaagccctcccagcccc atcgagaaaaccatctccaaagccaaagggcagccccgagaaccacaggtgtac accctgcccccatcccgggatgagctgaccaagaaccaggtcagcctgacctgc ctggtcaaaggcttctatcccagcgacatcgccgtggagtgggagagcaatggg cagccggagaacaactacaagaccacgcctcccgtgctggactccgacggctcc ttcttcctctacagcaagctcaccgtggacaagagcaggtggcagcaggggaac gtcttctcatgctccgtgatgcatgaggctctgcacaaccactacacgcagaag agcctctctctgtctccgggtaaatgataatctaga |
| 122 | hVK3LP-hDNase1-G105R; A114F-(G4S)5-2-hIgG1-(SCC) ("(G4S)5" | gttaagcttgccaccatggaaaccccagcgcagcttctcttcctcctgctactc tggctcccagataccaccggtctgaagatcgcagccttcaacatccagacattt ggggagaccaagatgtccaatgccaccctcgtcagctacattgtgcagatcctg agccgctatgacatcgccctggtccaggaggtcagagacagccacctgactgcc gtggggaagctgctggacaacctcaatcaggatgcaccagacacctatcactac gtggtcagtgagccactgggacggaacagctataaggagcgctacctgttcgtg tacaggcctgaccaggtgtctgcggtggacagctactactacgatgatggctgc |

TABLE 2-continued

| SEQ ID NO: | DESCRIPTION | SEQUENCE (NUCLEOTIDE SEQUENCES ARE 5'-3') |
|---|---|---|
| | disclosed as SEQ ID NO: 209) | gagccctgcaggaacgacaccttcaaccgagagccattcattgtcaggttcttc tcccggttcacagaggtcagggagtttgccattgttccctgcatgcggccccg ggggacgcagtagccgagatcgacgctctctatgacgtctacctggatgtccaa gagaaatggggcttggaggacgtcatgttgatgggcgacttcaatgcgggctgc agctatgtgagaccctccagtggtcatccatccgcctgtggacaagccccacc ttccagtggctgatccccgacagcgctgacaccacagctacacccacgcactgt gcctatgacaggatcgtggttgcagggatgctgctccgaggcgccgttgttccc gactcggctcttccctttaacttccaggctgcctatggcctgagtgaccaactg gcccaagccatcagtgaccactatccagtggaggtgatgctgaaagatctctcc ggaggaggtggctcaggtggtggaggatctggaggaggtggctcaggtggtgga ggatctggaggaggtgggagtctcgagcccaaatcttctgacaaaactcacaca tgtccaccgtgcccagcacctgaactcctgggggaccgtcagtcttcctcttc cccccaaaacccaaggacaccctcatgatctcccggacccctgaggtcacatgc gtggtggtggacgtgagccacgaagaccctgaggtcaagttcaactggtacgtg gacggcgtggaggtgcataatgccaagacaaagccgcgggaggagcagtacaac agcacgtaccgtgtggtcagcgtcctcaccgtcctgcaccaggactggctgaat ggcaaggagtacaagtgcaaggtctccaacaaagcccttccagccccatcgag aaaaccatctccaaagccaaagggcagccccgagaaccacaggtgtacaccctg cccccatcccgggatgagctgaccaagaaccaggtcagcctgacctgcctggtc aaaggcttctatcccagcgacatcgccgtggagtgggagagcaatgggcagccg gagaacaactacaagaccacgcctcccgtgctggactccgacggctccttcttc ctctacagcaagctcaccgtggacaagagcaggtggcagcaggggaacgtcttc tcatgctccgtgatgcatgaggctctgcacaaccactacacgcagaagagcctc tctctgtctccgggtaaatgataatctaga |
| 123 | hVK3LP- hDNase1- G105R; A114F- hIgG1(SCC) | gttaagcttgccaccatggaaaccccagcgcagcttctcttcctcctgctactc tggctcccagataccaccggtctgaagatcgcagccttcaacatccagacattt ggggagaccaagatgtccaatgccacccctcgtcagctacattgtgcagatcctg agccgctatgacatcgcccctggtccaggaggtcagagacagccacctgactgcc gtggggaagctgctggacaacctcaatcaggatgcaccagacacctatcactac gtggtcagtgagccactgggacggaacagctataaggagcgctacctgttcgtg tacaggcctgaccaggtgtctgcggtggacagctactactacgatgatggctgc gagccctgcaggaacgacaccttcaaccgagagccattcattgtcaggttcttc tcccggttcacagaggtcagggagtttgccattgttccctgcatgcggccccg ggggacgcagtagccgagatcgacgctctctatgacgtctacctggatgtccaa gagaaatggggcttggaggacgtcatgttgatgggcgacttcaatgcgggctgc agctatgtgagaccctccagtggtcatccatccgcctgtggacaagccccacc ttccagtggctgatccccgacagcgctgacaccacagctacacccacgcactgt gcctatgacaggatcgtggttgcagggatgctgctccgaggcgccgttgttccc gactcggctcttccctttaacttccaggctgcctatggcctgagtgaccaactg gcccaagccatcagtgaccactatccagtggaggtgatgctgaaagatctcgag cccaaatcttctgacaaaactcacacatgtccaccgtgcccagcacctgaactc ctgggggaccgtcagtcttcctcttcccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccttccagccccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaatgataatct aga |
| 124 | hVK3LP- hRNase(MT)- hIgG1(SCC) | gttaagcttgccaccatggaaaccccagcgcagcttctcttcctcctgctactc tggctcccagataccaccggtaaggaatcccgggccaagaaattccagcggcag catatggactcagacagttcccccagcagcagctccacctactgtaaccaaatg atgaggcgccgaatatgacacaggggcggtgcaaaccagtgaacaccttgtg cacgagcccctggtagatgtccagaatgtctgtttccaggaaaaggtcacctgc aagaacgggcagggcaactgctacaagagcaactccagcatgcacatcacagac tgccgcctgacaaacgactccaggtaccccaactgtgcataccggaccagcccg aaggagagacacatcattgtggcctgtgaagggagcccatatgtgccagtccac tttgatgcttctgtggaggactctacagatctcgagcccaaatcttctgacaaa actcacacatgtccaccgtgcccagcacctgaactcctgggggaccgtcagtc ttcctcttcccccaaaacccaaggacaccctcatgatctcccggacccctgag gtcacatgcgtggtggtggacgtgagccacgaagaccctgaggtcaagttcaac tggtacgtggacggcgtggaggtgcataatgccaagacaaagccgcgggaggag cagtacaacagcacgtaccgtgtggtcagcgtcctcaccgtcctgcaccaggac tggctgaatggcaaggagtacaagtgcaaggtctccaacaaagcccttccagcc cccatcgagaaaaccatctccaaagccaaagggcagccccgagaaccacaggtg tacaccctgcccccatcccgggatgagctgaccaagaaccaggtcagcctgacc tgcctggtcaaaggcttctatcccagcgacatcgccgtggagtgggagagcaat gggcagccggagaacaactacaagaccacgcctcccgtgctggactccgacggc |

TABLE 2-continued

| SEQ ID NO: | DESCRIPTION | SEQUENCE (NUCLEOTIDE SEQUENCES ARE 5'-3') |
|---|---|---|
| | | tccttcttcctctacagcaagctcaccgtggacaagagcaggtggcagcagggg aacgtcttctcatgctccgtgatgcatgaggctctgcacaaccactacacgcag aagagcctctctctgtctccgggtaaatgataatctaga |
| 125 | hVK3LP-hRNase(WT)-(G4S)4lnk-hIgG1 (SCC) ("(G4S)4" disclosed as SEQ ID NO: 212) | gttaagcttgccaccatggaaaccccagcgcagcttctcttcctcctgctactc tggctcccagataccaccggtaaggaatcccgggccaagaaattccagcggcag catatggactcagacagttcccccagcagcagctccacctactgtaaccaaatg atgaggcgccggaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtacccaactgtgcataccggaccagcccg aaggagagacacatcattgtgcctgtgaagggagcccatatgtgccagtccac tttgatgcttctgtggaggactctacagatctctccggaggaggtggctcaggt ggtggaggatctggaggaggtgggagtggtggaggtggttctaccggtctgag cccaaatcttctgacaaaactcacacatgtccaccgtgcccagcacctgaactc ctggggggaccgtcagtcttcctcttccccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagccctcccagcccccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaatgataatct aga |
| 126 | hVK3LP-hRNase(WT)-(G4S)5-2-lnk-hIgG1(SCC) ("(G4S)5" disclosed as SEQ ID NO: 209) | gttaagcttgccaccatggaaaccccagcgcagcttctcttcctcctgctactc tggctcccagataccaccggtaaggaatcccgggccaagaaattccagcggcag catatggactcagacagttcccccagcagcagctccacctactgtaaccaaatg atgaggcgccggaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtacccaactgtgcataccggaccagcccg aaggagagacacatcattgtgcctgtgaagggagcccatatgtgccagtccac tttgatgcttctgtggaggactctacagatctctccggaggaggtggctcaggt ggtggaggatctggaggaggtggctcaggtggtggaggatctggaggaggtggg agtctcgagcccaaatcttctgacaaaactcacacatgtccaccgtgcccagca cctgaactcctggggggaccgtcagtcttcctcttccccccaaaacccaaggac accctcatgatctcccggacccctgaggtcacatgcgtggtggtggacgtgagc cacgaagaccctgaggtcaagttcaactggtacgtggacggcgtggaggtgcat aatgccaagacaaagccgcgggaggagcagtacaacagcacgtaccgtgtggtc agcgtcctcaccgtcctgcaccaggactggctgaatggcaaggagtacaagtgc aaggtctccaacaaagccctcccagcccccatcgagaaaaccatctccaaagcc aaagggcagccccgagaaccacaggtgtacaccctgcccccatcccgggatgag ctgaccaagaaccaggtcagcctgacctgcctggtcaaaggcttctatcccagc gacatcgccgtggagtgggagagcaatgggcagccggagaacaactacaagacc acgcctcccgtgctggactccgacggctccttcttcctctacagcaagctcacc gtggacaagagcaggtggcagcaggggaacgtcttctcatgctccgtgatgcat gaggctctgcacaaccactacacgcagaagagcctctctctgtctccgggtaaa tgataatctaga |
| 127 | hVK3LP-hRNase(WT)-hIgG1(SCC) | gttaagcttgccaccatggaaaccccagcgcagcttctcttcctcctgctactc tggctcccagataccaccggtaaggaatcccgggccaagaaattccagcggcag catatggactcagacagttcccccagcagcagctccacctactgtaaccaaatg atgaggcgccggaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtacccaactgtgcataccggaccagcccg aaggagagacacatcattgtgcctgtgaagggagcccatatgtgccagtccac tttgatgcttctgtggaggactctacagatctcgagcccaaatcttctgacaaa actcacacatgtccaccgtgcccagcacctgaactcctggggggaccgtcagtc ttcctcttccccccaaaacccaaggacaccctcatgatctcccggacccctgag gtcacatgcgtggtggtggacgtgagccacgaagaccctgaggtcaagttcaac tggtacgtggacggcgtggaggtgcataatgccaagacaaagccgcgggaggag cagtacaacagcacgtaccgtgtggtcagcgtcctcaccgtcctgcaccaggac tggctgaatggcaaggagtacaagtgcaaggtctccaacaaagccctcccagcc cccatcgagaaaaccatctccaaagccaaagggcagccccgagaaccacaggtg tacaccctgcccccatcccgggatgagctgaccaagaaccaggtcagcctgacc tgcctggtcaaaggcttctatcccagcgacatcgccgtggagtgggagagcaat gggcagccggagaacaactacaagaccacgcctcccgtgctggactccgacggc tccttcttcctctacagcaagctcaccgtggacaagagcaggtggcagcagggg aacgtcttctcatgctccgtgatgcatgaggctctgcacaaccactacacgcag aagagcctctctctgtctccgggtaaatgataatctaga |

TABLE 2-continued

| SEQ ID NO: | DESCRIPTION | SEQUENCE (NUCLEOTIDE SEQUENCES ARE 5'-3') |
|---|---|---|
| 128 | murine Trex1 (FL) transcript variant 1 | atgggctcacagaccctgccccatggtcacatgcagaccctcatcttcttagac ctggaagccactggcctgccttcgtctcggcccgaagtcacagagctgtgcctg ctggctgtccacagacgtgctctggagaacacttccatttctcagggacatcca cctccagtgcccagaccgcccccgtgtggtggacaagctctctctgtgcattgct ccagggaaagcctgtagccctggggccagtgagatcacaggtctgagcaaagct gagctggaagtacaggggcgtcaacgcttcgatgacaacctggccatcctgctc cgagccttcctgcagcgccagccacagccttgctgccttgtggcacacaacggt gaccgctatgactttcctctgctccagacagagcttgctaggctgagcactccc agtcccctagatggtaccttctgtgtggacagcatcgctgccctaaaggccttg gaacaagctagcagcccctcagggaatggttcgaggaaaagctacagcctgggc agcatctacacccgcctgtactggcaagcaccgacagactcacatactgctgaa ggtgatgttctaaccctgctcagcatctgtcagtggaagccacaggccctactg cagtgggtggacgaacatgcccggccctttagcaccgtcaagcccatgtacggc actccggctaccactggaacaaccaacctaaggccacatgctgccacagctact acaccctggccacagccaatggaagtcccagcaatggcaggagcaggcgacct aagagtcctcctccagagaaggtcccagaagcccatcacaggagggctgctg gccccactgagcctgctgaccctcctgaccttggcaatagccactctgtatgga ctcttcctggcctcacctgggcagtaa |
| 129 | mTREX1minec | atgggctcacagaccctgccccatggtcacatgcagaccctcatcttcttagac ctggaagccactggcctgccttcgtctcggcccgaagtcacagagctgtgcctg ctggctgtccacagacgtgctctggagaacacttccatttctcagggacatcca cctccagtgcccagaccgcccccgtgtggtggacaagctctctctgtgcattgct ccagggaaagcctgtagccctggggccagtgagatcacaggtctgagcaaagct gagctggaagtacaggggcgtcaacgcttcgatgacaacctggccatcctgctc cgagccttcctgcagcgccagccacagccttgctgccttgtggcacacaacggt gaccgctatgactttcctctgctccagacagagcttgctaggctgagcactccc agtcccctagatggtaccttctgtgtggacagcatcgctgccctaaaggccttg gaacaagctagcagcccctcagggaatggttcgaggaaaagctacagcctgggc agcatctacacccgcctgtactggcaagcaccgacagactcacatactgctgaa ggtgatgttctaaccctgctcagcatctgtcagtggaagccacaggccctactg cagtgggtggacgaacatgcccggccctttagcaccgtcaagcccatgtacggc actccggctaccactggaacaacagatctcgag |
| 130 | murine Trex1-(G4S)4-mIgG2a-c ("(G4S)4"disclosed as SEQ ID NO: 212) | aagcttgccaccatggaaaccccagcgcagcttctcttcctcctgctactctgg ctcccagataccaccggtatgggctcacagaccctgccccatggtcacatgcag accctcatcttcttagacctggaagccactggcctgccttcgtctcggcccgaa gtcacagagctgtgcctgctggctgtccacagacgtgctctggagaacacttcc atttctcagggacatccacctccagtgcccagaccgcccccgtgtggtggacaag ctctctctgtgcattgctccagggaaagcctgtagccctggggccagtgagatc acaggtctgagcaaagctgagctggaagtacaggggcgtcaacgcttcgatgac aacctggccatcctgctccgagccttcctgcagcgccagccacagccttgctgc cttgtggcacacaacggtgaccgctatgactttcctctgctccagacagagctt gctaggctgagcactcccagtcccctagatggtaccttctgtgtggacagcatc gctgccctaaaggccttggaacaagctagcagcccctcagggaatggttcgagg aaaagctacagcctgggcagcatctacacccgcctgtactggcaagcaccgaca gactcacatactgctgaaggtgatgttctaaccctgctcagcatctgtcagtgg aagccacaggccctactgcagtgggtggacgaacatgcccggccctttagcacc gtcaagcccatgtacggcactccggctaccactggaacaacagatctctccgga ggaggtggctcaggtggtggagatctggaggaggtggctcagggagtggtgga ggtggttctacccggtctcgagcccagaggtcccacaatcaagccctctcctcca tgcaaatgcccagcacctaacctcttgggtggatcatccgtcttcatcttccct ccaaagatcaaggatgtactcatgatctccctgagccccatggtcacatgtgtg gtggtggatgtgagcgaggatgacccagacgtccagatcagctggtttgtgaac aacgtggaagtacacacagctcagacacaaacccatagagaggattacaacagt actctccgggtggtcagtgccctccccatccagcaccaggactggatgagtggc aaggagttcaaatgctcggtcaacaacaaagaccccagcgtccatcgagaga accatctcaaacccagagggccagtaagagctccacaggtatatgtcttgcct ccaccagcagaagagatgactaagaaagagttcagtctgacctgcatgatcaca ggcttcttacctgccgaaattgctgtggactggaccagcaatgggcgtacagag caaaactacaagaacaccgcaacagtcctggactctgatggttcttacttcatg tacagcaagctcagagtacaaaagagcacttgggaaagaggaagtcttttcgcc tgctcagtggtccacgagggtctgcacaatcaccttacgactaagagcttctct cggactccgggtaaatgataatctaga |
| 131 | murine Trex1-(G4S)5-mIgG2a-c ("(G4S)5" disclosed as SEQ ID NO: 209) | aagcttgccaccatggaaaccccagcgcagcttctcttcctcctgctactctgg ctcccagataccaccggtatgggctcacagaccctgccccatggtcacatgcag accctcatcttcttagacctggaagccactggcctgccttcgtctcggcccgaa gtcacagagctgtgcctgctggctgtccacagacgtgctctggagaacacttcc atttctcagggacatccacctccagtgcccagaccgcccccgtgtggtggacaag ctctctctgtgcattgctccagggaaagcctgtagccctggggccagtgagatc acaggtctgagcaaagctgagctggaagtacaggggcgtcaacgcttcgatgac aacctggccatcctgctccgagccttcctgcagcgccagccacagccttgctgc cttgtggcacacaacggtgaccgctatgactttcctctgctccagacagagctt gctaggctgagcactcccagtcccctagatggtaccttctgtgtggacagcatc gctgccctaaaggccttggaacaagctagcagcccctcagggaatggttcgagg aaaagctacagcctgggcagcatctacacccgcctgtactggcaagcaccgaca |

TABLE 2-continued

| SEQ ID NO: | DESCRIPTION | SEQUENCE (NUCLEOTIDE SEQUENCES ARE 5'-3') |
|---|---|---|
| | | gactcacatactgctgaaggtgatgttctaaccctgctcagcatctgtcagtgg aagccacaggccctactgcagtgggtggacgaacatgcccggcccttTagcacc gtcaagcccatgtacggcactccggctaccactggaacaacagatctctccgga ggaggtggctcaggtggtggaggatctggaggaggtggctcaggtggtggagga tctggaggaggtgggagtctcgagcccagaggtcccacaatcaagccctctcct ccatgcaaatgcccagcacctaacctcttgggtggatcatccgtcttcatcttc cctccaaagatcaaggatgtactcatgatctccctgagccccatggtcacatgt gtggtggtggatgtgagcgaggatgacccagacgtccagatcagctggtttgtg aacaacgtggaagtacacacagctcagacacaaacccatagagaggattacaac agtactctccgggtggtcagtgccctccccatccagcaccaggactggatgagt ggcaaggagttcaaatgctcggtcaacaacaaagacctcccagcgtccatcgag agaaccatctcaaaacccagagggccagtaagagctccacaggtatatgtcttg cctccaccagcagaagagatgactaagaaagagttcagtctgacctgcatgatc acaggcttcttacctgccgaaattgctgtggactggaccagcaatgggcgtaca gagcaaaactacaagaacaccgcaacagtcctggactctgatggttcttacttc atgtacagcaagctcagagtacaaaagagcacttgggaaagaggaagtcttttc gcctgctcagtggtccacgagggtctgcacaatcaccttacgactaagagcttc tctcggactccgggtaaatgataatctaga |
| 132 | NLG linker | gtcgacggcgcggccgccagccccgtgaacgtgagcagcccagcgtgcaggat atc |
| 133 | murine Trex1-Trex1-(G4S)5-mIgG2a-c ("(G4S)5" disclosed as SEQ ID NO: 209) | aagcttgccaccatggaaaccccagcgcagcttctcttcctcctgctactctgg ctcccagataccaccggtatgggctcacagaccctgcccatggtcacatgcag accctcatcttcttagacctggaagccactggcctgccttcgtctcggcccgaa gtcacagagctgtgcctgctggctgtccacagacgtgctctggagaacacttcc atttctcagggacatccacctccagtgcccagaccgccccgtgtggtggacaag ctctctctgtgcattgctccagggaaagcctgtagccctggggccagtgagatc acaggtctgagcaaagctgagctggaagtacaggggcgtcaacgcttcgatgac aacctggccatcctgctccgagccttcctgcagcgccagccacagccttgctgc cttgtggcacacaacggtgaccgctatgactttcctctgctccagacagagctt gctaggctgagcactcccagtccctagatggtaccttctgtgtggacagcatc gctgccctaaaggcttggaacaagctagcagcccctcagggaatggttcgagg aaaagctacagcctgggcagcatctacacccgcctgtactggcaagcaccgaca gactcacatactgctgaaggtgatgttctaaccctgctcagcatctgtcagtgg aagccacaggccctactgcagtgggtggacgaacatgcccggcccttTagcacc gtcaagcccatgtacggcactccggctaccactggaacaacagatctcatggc tcacagaccctgcccatggtcacatgcagaccctcatcttcttagacctggaa gccactggcctgccttcgtctcggcccgaagtcacagagctgtgcctgctggct gtccacagacgtgctctggagaacacttccatttctcagggacatccacctcca gtgcccagaccgccccgtgtggtggacaagctctctctgtgcattgctccaggg aaagcctgtagccctggggccagtgagatcacaggtctgagcaaagctgagctg gaagtacaggggcgtcaacgcttcgatgacaacctggccatcctgctccgagcc ttcctgcagcgccagccacagccttgctgccttgtggcacacaacggtgaccgc tatgactttcctctgctccagacagagcttgctaggctgagcactcccagtccc ctagatggtaccttctgtgtggacagcatcgctgccctaaaggcttggaacaa gctagcagcccctcagggaatggttcgaggaaaagctacagcctgggcagcatc tacacccgcctgtactggcaagcaccgacagactcacatactgctgaaggtgat gttctaaccctgctcagcatctgtcagtggaagccacaggccctactgcagtgg gtggacgaacatgcccggcccttTagcaccgtcaagcccatgtacggcactccg gctaccactggaacaacagatctctccggaggaggtggctcaggtggtggagga tctggaggaggtggctcaggtggtggaggatctggaggaggtgggagtctcgag cccagagggcccacaatcaagccctctcctccatgcaaatgcccagcacctaac ctcttgggtggatcatccgtcttcatcttccctccaaagatcaaggatgtactc atgatctccctgagccccatggtcacatgtgtggtggtggatgtgagcgaggat gacccagacgtccagatcagctggtttgtgaacaacgtggaagtacacacagct cagacacaaacccatagagaggattacaacagtactctccgggtggtcagtgcc ctccccatccagcaccaggactggatgagtggcaaggagttcaaatgctcggtc aacaacaaagacctcccagcgtccatcgagagaaccatctcaaaacccagaggg ccagtaagagctccacaggtatatgtcttgcctccaccagcagaagagatgact aagaaagagttcagtctgacctgcatgatcacaggcttcttacctgccgaaatt gctgtggactggaccagcaatgggcgtacagagcaaaactacaagaacaccgca acagtcctggactctgatggttcttacttcatgtacagcaagctcagagtacaa aagagcacttgggaaagaggaagtcttttcgcctgctcagtggtccacgagggt ctgcacaatcaccttacgactaagagcttctctcggactccgggtaaatgataa/ tctaga |
| 134 | huVK3LP-huTREX1-72aa-(g4s)4-hIgG1-(SCC) ("(g4s)4" | aagcttgccaccatggaaaccccagcgcagcttctcttcctcctgctactctgg ctcccagataccaccggtatgggctgagctcgagacaggcaggattgtg cagggaaggcctgagatgtgcttctgccaccccctaccccactccctcccctt cggatcttaacactgggcactcacacacccaccccatgctcctctccaggctca gcagcaggtacgtacccaaccatgggctcgcaggcctgccccggggcccatg cagaccctcatctttttcgacatggaggccactggcttgcccttctcccagccc aaggtcacgagctgtgcctgctggctgtccacagatgtgccctggagagcccc |

TABLE 2-continued

| SEQ ID NO: | DESCRIPTION | SEQUENCE (NUCLEOTIDE SEQUENCES ARE 5'-3') |
|---|---|---|
| | disclosed as SEQ ID NO: 212) | cccacctctcaggggccacctcccacagttcctccaccaccgcgtgtggtagac aagctctccctgtgtgtggctccggggaaggcctgcagccctgcagccagcgag atcacaggtctgagcacagctgtgctggcagcgcatgggcgtcaatgttttgat gacaacctggccaacctgctcctagccttcctgcgggcgcagccacagccctgg tgcctggtggcacacaatggtgaccgctacgacttccccctgctccaagcagag ctggctatgctgggcctcaccagtgctctggatggtgcctctgtgtggatagc atcactgcgctgaaggccctggagcgagcaagcagcccctcagaacacggccca aggaagagctacagcctaggcagcatctacactcgcctgtatgggcagtcccct ccagactcgcacacggctgagggtgatgtcctggccctgctcagcatctgtcag tggagaccacaggccctgctgcggtgggtggatgctcacgccaggcctttcggc accatcaggcccatgtatgggtcacagcctctgctaggaccaaagatctctcc ggaggaggtggctcaggtggtggaggatctggaggaggtgggagtggtggaggt ggttctaccggtctcgagcccaaatcttctgacaaaactcacacatgtccaccg tgcccagcacctgaactcctgggggaccgtcagtcttcctcttccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagcccttcccagcccccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggtaaatgataatctaga |
| 135 | huVK3LP-huTREx1-72aa-(g4s)5-hIgG1-(SCC) ("(g4s)5" disclosed as SEQ ID NO: 209) | aagcttgccaccatggaaaccccagcgcagcttctcttcctcctgctactctgg ctcccagataccaccggtatgggccctggagctcgcagacagggcaggattgtg cagggaaggcctgagatgtgcttctgcccaccccctaccccactccctcccctt cggatcttaacactgggcactcacacacccacccatgctcctctccaggctca gcagcaggtacgtacccaaccatgggctcgcaggccctgccccgggggccatg cagaccctcatctttttcgacatggaggccactggcttgccttctcccagccc aaggtcacggagctgtgcctgctggctgtccacagatgtgccctggagagcccc cccacctctcaggggccacctcccacagttcctccaccaccgcgtgtggtagac aagctctccctgtgtgtggctccggggaaggcctgcagcctgcagccagcgag atcacaggtctgagcacagctgtgctggcagcgcatgggcgtcaatgttttgat gacaacctggccaacctgctcctagccttcctgcgggcgccagccacagccctgg tgcctggtggcacacaatggtgaccgctacgacttccccctgctccaagcagag ctggctatgctgggcctcaccagtgctctggatggtgcctctgtgtggatagc atcactgcgctgaaggccctggagcgagcaagcagcccctcagaacacggccca aggaagagctacagcctaggcagcatctacactcgcctgtatgggcagtcccct ccagactcgcacacggctgagggtgatgtcctggccctgctcagcatctgtcag tggagaccacaggccctgctgcggtgggtggatgctcacgccaggcctttcggc accatcaggcccatgtatgggtcacagcctctgctaggaccaaagatctctcc ggaggaggtggctcaggtggtggaggatctggaggaggtggctcaggtggtgga ggatctggaggaggtgggagtctcgagcccaaatcttctgacaaaactcacaca tgtccaccgtgcccagcacctgaactcctgggggaccgtcagtcttcctcttc cccccaaaacccaaggacaccctcatgatctcccggacccctgaggtcacatgc gtggtggtggacgtgagccacgaagaccctgaggtcaagttcaactggtacgtg gacggcgtggaggtgcataatgccaagacaaagccgcgggaggagcagtacaac agcacgtaccgtgtggtcagcgtcctcaccgtcctgcaccaggactggctgaat ggcaaggagtacaagtgcaaggtctccaacaaagcccttcccagcccccatcgag aaaaccatctccaaagccaaagggcagccccgagaaccacaggtgtacaccctg cccccatcccgggatgagctgaccaagaaccaggtcagcctgacctgcctggtc aaaggcttctatcccagcgacatcgccgtggagtgggagagcaatgggcagccg gagaacaactacaagaccacgcctcccgtgctggactccgacggctccttcttc ctctacagcaagctcaccgtggacaagagcaggtggcagcaggggaacgtcttc tcatgctccgtgatgcatgaggctctgcacaaccactacacgcagaagagcctc tctctgtctccgggtaaatgataatctaga |
| 136 | g4s4lnk ("g4s4" disclosed as SEQ ID NO: 212) | ggggsggggsggggsggggs |
| 137 | G4S5-1 ("G4S5" disclosed as SEQ ID NO: 209) | ggggsggggsggggsggggsggggs |

TABLE 2-continued

| SEQ ID NO: | DESCRIPTION | SEQUENCE (NUCLEOTIDE SEQUENCES ARE 5'-3') |
|---|---|---|
| 138 | G4S5-2 ("G4S5" disclosed as SEQ ID NO: 209) | ggggsggggsggggsggggsggggs |
| 139 | hDNase1-3'-G105R; A114F | lkiaafniqtfgetkmsnatlvsyivqilsrydialvqevrdshltavgklldn lnqdapdtyhyvvseplgrnsykerylfvyrpdqvsavdsyyyddgcepcrndt fnrepfivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlagaisdhypvevmlk* |
| 140 | hDNase1-3'-WT | lkiaafniqtfgetkmsnatlvsyivqilsrydialvqevrdshltavgklldn lnqdapdtyhyvvseplgrnsykerylfvyrpdqvsavdsyyyddgcepcgndt fnrepaivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlagaisdhypvevmlk* |
| 141 | hDNase1-3'A114F | lkiaafniqtfgetkmsnatlvsyivqilsrydialvqevrdshltavgklldn lnqdapdtyhyvvseplgrnsykerylfvyrpdqvsavdsyyyddgcepcgndt fnrepfivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlagaisdhypvevmlk* |
| 142 | hDNase1-5'-G105R | lkiaafniqtfgetkmsnatlvsyivqilsrydialvqevrdshltavgklldn lnqdapdtyhyvvseplgrnsykerylfvyrpdqvsavdsyyyddgcepcrndt fnrepaivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlaqaisdhypvevmlk |
| 143 | hDNase1-5'-WT | lkiaafniqtfgetkmsnatlvsyivqilsrydialvqevrdshltavgklldn lnqdapdtyhyvvseplgrnsykerylfvyrpdqvsavdsyyyddgcepcgndt fnrepaivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlaqaisdhypvevmlk |
| 144 | hDNase1-5'-A114F | lkiaafniqtfgetkmsnatlvsyivqilsrydialvqevrdshltavgklldn lnqdapdtyhyvvseplgrnsykerylfvyrpdqvsavdsyyyddgcepcgndt fnrepfivrffsrftevrefaivplhaapgdavaeidalydvyldvqekwgled vmlmgdfnagcsyvrpsqwssirlwtsptfqwlipdsadttatpthcaydrivv agmllrgavvpdsalpfnfqaayglsdqlaqaisdhypvevmlk |
| 145 | hIgG1 (SCC) | lepkssdkthtcppcpapellggpsvflfppkpkdtlmisrtpevtcvvvdvsh edpevkfnwyvdgvevhnaktkpreeqynstyrvvsvltvlhqdwlngkeykck vsnkalpapiektiskakgqprepqvytlppsrdeltknqvsltclvkgfypsd iavewesngqpennykttppvldsdgsfflysklltvdksrwqqgnvfscsvmhe alhnhytqkslslspgk |
| 146 | hRNase-G88D-3' | kesrakkfqrqhmdsdsspsssstycnqmmrrrnmtqgrckpvntfvheplvdv qnvcfgekvtckngqgncyksnssmhitdcrltndsrypncayrtspkerhiiv acegspyvpvhfdasvedst* |
| 147 | human DNase1 + VK3LP | metpaqllflllllwlpdttglkiaafniqtfgetkmsnatlvsyivqilsrydi alvqevrdshltavgklldnlnqdapdtyhyvvseplgrnsykerylfvyrpdq vsavdsyyyddgcepcgndtfnrepaivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlagais dhypvevmlk* |
| 148 | DNase1L3 | msrelaplllllsihsalamricsfnvrsfgeskqedknamdvivkvikrcdi ilvmeikdsnnricpilmeklnrnsrrgitynyvissrlgrntykeqyaflyke klvsvkrsyhyhdyqdgdadvfsrepfvvwfgsphtavkdfviiplhttpetsv keidelvevytdvkhrwkaenfifmgdfnagcsyvpkkawknirlrtdprfvwl igdqedttvkkstncaydrivlrgqeivssvvpksnsvfdfqkayklteeeald vsdhfpvefklqssraftnskksvtlrkktkskrs* |
| 149 | human pancreatic ribonuclease | Mglekslvrllllvlillvlgwvqpslgkesrakkfqrqhmdsdsspsssstyc nqmmrrrnmtqgrckpvntfvheplvdvqnvcfgekvtckngqgncyksnssmh itdcrltngsrypncayrtspkerhiivacegspyvpvhfdasv*edst |
| 150 | huVK3LP + mrib1 + mIgG2A-C + 2S | metpaqllflllllwlpdttgresaaqkfqrqhmdpdgssinsptycnqmmkrrd mtngsckpvntfvhepladvgavcsqenvtcknrksncyksssalhitdchlkg nskypncdykttqyqkhiivacegnpyvpvhfdatvleprgltikpsppckcpa pnllggssvfifppkikdvlmislspmvtcvvvdvseddpdvqiswfvnnvevh taqtqthredynstlrvvsalpiqhqdwmsgkefkcsvnnkdlpasiertiskp |

TABLE 2-continued

| SEQ ID NO: | DESCRIPTION | SEQUENCE (NUCLEOTIDE SEQUENCES ARE 5'-3') |
|---|---|---|
| | | rgpvrapqvyvlpppaeemtkkefsltcmitgflpaeiavdwtsngrteqnykn<br>tatvldsdgsyfmysklrvqkstwergslfacsvvheglhnhlttksfsrtpgk<br>* |
| 151 | huVK3LP-<br>hRNaseWT-<br>hIgG1<br>(SCC)-<br>NLG-<br>hDNase1-<br>(G105R;<br>A114F) | metpaqllflllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstlepkssdkthtcpp<br>cpapellggpsvflfppkpkdtlmisrtpevtcvvvdvshedpevkfnwyvdgv<br>evhnaktkpreeqynstyrvvsvltvlhqdwlngkeykckvsnkalpapiekti<br>skakgqprepqvytlppsrdeltknqvsltclvkgfypsdiavewesngqpenn<br>ykttppvldsdgsfflyskltvdksrwqqgnvfscsvmheglhnhytqkslsls<br>pgkvdgasspvnvsspsvgdilkiaafniqtfgetkmsnatlvsyivqilsryd<br>ialvqevrdshltavgklldnlnqdapdtyhyvvseplgrnsykerylfvyrpd<br>qvsavdsyyyddgcepcrndtfnrepfivrffsrftevrefaivplhaapgdav<br>aeidalydvyldvqekwgsedvmlmgdfnagcsyvrpsqwssirlwtsptfqwl<br>ipdsadttatpthcaydrivvagmllrgavvpdsalpfnfqaayglsdqlaqai<br>sdhypvevmlk** |
| 152 | huVK3LP-<br>hRNaseWT-<br>hIgG1<br>(SCC)-<br>NLG-<br>hDNase1-<br>114F | metpaqllflllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstlepkssdkthtcpp<br>cpapellggpsvflfppkpkdtlmisrtpevtcvvvdvshedpevkfnwyvdgv<br>evhnaktkpreeqynstyrvvsvltvlhqdwlngkeykckvsnkalpapiekti<br>skakgqprepqvytlppsrdeltknqvsltclvkgfypsdiavewesngqpenn<br>ykttppvldsdgsfflyskltvdksrwqqgnvfscsvmheglhnhytqkslsls<br>pgkvdgasspvnvsspsvgdilkiaafniqtfgetkmsnatlvsyivqilsryd<br>ialvqevrdshltavgklldnlnqdapdtyhyvvseplgrnsykerylfvyrpd<br>qvsavdsyyyddgcepcgndtfnrepfivrffsrftevrefaivplhaapgdav<br>aeidalydvyldvqekwgledvmlmgdfnagcsyvrpsqwssirlwtsptfqwl<br>ipdsadttatpthcaydrivvagmllrgavvpdsalpfnfqaayglsdqlagai<br>sdhypvevmlk* |
| 153 | huVK3LP-<br>hRNaseWT-<br>hIgG<br>(SCC)-<br>NLG-<br>hDNAse1-<br>WT | metpaqllflllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstlepkssdkthtcpp<br>cpapellggpsvflfppkpkdtlmisrtpevtcvvvdvshedpevkfnwyvdgv<br>evhnaktkpreeqynstyrvvsvltvlhqdwlngkeykckvsnkalpapiekti<br>skakgqprepqvytlppsrdeltknqvsltclvkgfypsdiavewesngqpenn<br>ykttppvldsdgsfflyskltvdksrwqqgnvfscsvmheglhnhytqkslsls<br>pgkvdgasspvnvsspsvgdilkiaafniqtfgetkmsnatlvsyivqilsryd<br>ialvqevrdshltavgklldnlnqdapdtyhyvvseplgrnsykerylfvyrpd<br>qvsavdsyyyddgcepcgndtfnrepaivrffsrftevrefaivplhaapgdav<br>aeidalydvyldvqekwgledvmlmgdfnagcsyvrpsqwssirlwtsptfqwl<br>ipdsadttatpthcaydrivvagmllrgavvpdsalpfnfqaayglsdqlaqai<br>sdhypvevmlk* |
| 154 | hVK3LP-<br>hDNase1<br>(WT)-<br>hIgG1<br>(SCC) | metpaqllflllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcgndtfnrepaivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlagais<br>dhypvevmlklepkssdkthtcppcpapellggpsvflfppkpkdtlmisrtpe<br>vtcvvvdvshedpevkfnwyvdgvevhnakttkpreeqynstyrvvsvltvlhqd<br>wlngkeykckvsnkalpapiektiskakgqprepqvytlppsrdeltknqvslt<br>clvkgfypsdiavewesngqpennykttppvldsdgsfflyskltvdksrwqqg<br>nvfscsvmhealhnhytqkslslspgk* |
| 155 | hVK3LP-<br>hDNase1-<br>A114F-<br>hIgG1<br>(SCC) | metpaqllflllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgcepcgndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlagais<br>dhypvevmlklepkssdkthtcppcpapellggpsvflfppkpkdtlmisrtpe<br>vtcvvvdvshedpevkfnwyvdgvevhnakttkpreeqynstyrvvsvltvlhqd<br>wlngkeykckvsnkalpapiektiskakgqprepqvytlppsrdeltknqvslt<br>clvkgfypsdiavewesngqpennykttppvldsdgsfflyskltvdksrwqqg<br>nvfscsvmhealhnhytqkslslspgk* |
| 156 | hVK3LP-<br>hDNase1-<br>G105R; A114F-<br>(G4S)4-<br>hIgG1<br>(SCC)<br>("(G4S)4" | metpaqllflllllwlpdttglkiaafniqtfgetkmsnatlvsyivqilsrydi<br>alvqevrdshltavgklldnlnqdapdtyhyvvseplgrnsykerylfvyrpdq<br>vsavdsyyyddgceperndtfnrepfivrffsrftevrefaivplhaapgdava<br>eidalydvyldvqekwgledvmlmgdfnagcsyvrpsqwssirlwtsptfqwli<br>pdsadttatpthcaydrivvagmllrgavvpdsalpfnfqaayglsdqlagais<br>dhypvevmlkggggsggggsggggsggggslepkssdkthtcppcpapellggp<br>svflfppkpkdtlmisrtpevtcvvvdvshedpevkfnwyvdgvevhnakttkpr |

TABLE 2-continued

| SEQ ID NO: | DESCRIPTION | SEQUENCE (NUCLEOTIDE SEQUENCES ARE 5'-3') |
|---|---|---|
| | disclosed as SEQ ID NO: 212) | eeqynstyrvvsvltvlhqdwlngkeykckvsnkalpapiektiskakgqprep qvytlppsrdeltknqvsltclvkgfypsdiavewesngqpennykttppvlds dgsfflyskltvdksrwqqgnvfscsvmhealhnhytqkslslspgk* |
| 157 | hVK3LP-hDNase1G105R; A114F-(G4s)5-hIgG1 (SCC) ("(G4s)5" disclosed as SEQ ID NO: 209) | metpaqllflllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkggggsggggsggggsggggsggggslepkssdkthtcppcpape llggpsvflfppkpkdtlmisrtpevtcvvvdvshedpevkfnwyvdgvevhna ktkpreeqynstyrvvsvltvlhqdwlngkeykckvsnkalpapiektiskakg qprepqvytlppsrdeltknqvsltclvkgfypsdiavewesngqpennykttp pvldsdgsfflyskltvdksrwqqgnvfscsvmhealhnhytqkslslspgk* |
| 158 | hVK3LP-hDNase1-G105R; A114F-(G4S)5-2-hIgG1 (SCC) ("(G4S)5" disclosed as SEQ ID NO: 209) | metpaqllflllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkggggsggggsggggsggggsggggslepkssdkthtcppcpape llggpsvflfppkpkdtlmisrtpevtcvvvdvshedpevkfnwyvdgvevhna ktkpreeqynstyrvvsvltvlhqdwlngkeykckvsnkalpapiektiskakg qprepqvytlppsrdeltknqvsltclvkgfypsdiavewesngqpennykttp pvldsdgsfflyskltvdksrwqqgnvfscsvmhealhnhytqkslslspgk* |
| 159 | hVK3LP-hDNase1-G105R; A114F-hIgG1 (SCC) | metpaqllflllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlklepkssdkthtcppcpapellggpsvflfppkpkdtlmisrtpe vtcvvvdvshedpevkfnwyvdgvevhnaktkpreeqynstyrvvsvltvlhqd wlngkeykckvsnkalpapiektiskakgqprepqvytlppsrdeltknqvslt clvkgfypsdiavewesngqpennykttppvldsdgsfflyskltvdksrwqqg nvfscsvmhealhnhytqkslslspgk* |
| 160 | hVK3LP-hRNase1 (MT)-hIgG1 (SCC) | metpaqllflllwlpdttgkesrakkfqrqhmdsdsspsssstycnqmmrrrn mtqgrckpvntfvheplvdvqnvcfqekvtckngqgncyksnssmhitdcrltn dsrypncayrtspkerhiivacegspyvpvhfdasvedstlepkssdkthtcpp cpapellggpsvflfppkpkdtlmisrtpevtcvvvdvshedpevkfnwyvdgv evhnaktkpreeqynstyrvvsvltvlhqdwlngkeykckvsnkalpapiekti skakgqprepqvytlppsrdeltknqvsltclvkgfypsdiavewesngqpenn ykttppvldsdgsfflyskltvdksrwqqgnvfscsvmhealhnhytqkslsls pgk* |
| 161 | hVK3Lp-hRNase1 (WT)-(G4S)4lnk-hIgG1 (SCC) ("(G4S)4" disclosed as SEQ ID NO: 212) | metpaqllflllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstggggsggggsgggg sggggslepkssdkthtcppcpapellggpsvflfppkpkdtlmisrtpevtcv vvdvshedpevkfnwyvdgvevhnaktkpreeqynstyrvvsvltvlhqdwlng keykckvsnkalpapiektiskakgqprepqvytlppsrdeltknqvsltclvk gfypsdiavewesngqpennykttppvldsdgsfflyskltvdksrwqqgnvfs csvmhealhnhytqkslslspgk* |
| 162 | hVK3LP-hRNase (WT)-(G4S)5-2lnk-hIgG1 (SCC) ("(G4S)5" disclosed as SEQ ID NO: 209) | metpaqllflllwlpdttgkesrakkfqrqhmdsdsspsssstycnqmmrrrn mtqgrckpvntfvheplvdvqnvcfqekvtckngqgncyksnssmhitdcrltn gsrypncayrtspkerhiivacegspyvpvhfdasvedstggggsggggsgggg sggggsggggslepkssdkthtcppcpapellggpsvflfppkpkdtlmisrtp evtcvvvdvshedpevkfnwyvdgvevhnaktkpreeqynstyrvvsvltvlhq dwlngkeykckvsnkalpapiektiskakgqprepqvytlppsrdeltknqvsl tclvkgfypsdiavewesngqpennykttppvldsdgsfflyskltvdksrwqq gnvfscsvmhealhnhytqkslslspgk* |

TABLE 2-continued

| SEQ ID NO: | DESCRIPTION | SEQUENCE (NUCLEOTIDE SEQUENCES ARE 5'-3') |
|---|---|---|
| 163 | hVK3LP-hRNase (WT)-hIgG1 (SCC) | metpaqllflllllwlpdttgkesrakkfqrqhmdsdsspsssstycnqmmrrrnmtqgrckpvntfvheplvdvqnvcfgekvtckngqgncyksnssmhitdcrltngsrypncayrtspkerhiivacegspyvpvhfdasvedstlepkssdkthtcppcpapellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfypsdiavewesngqpennykttppvldsdgsfflysklvtvdksrwqqgnvfscsvmhealhnhytqkslslspgk* |
| 164 | murine Trex1 (FL)-transcript variant 1 | mgsqtlphghmqtlifldleatglpssrpevtelcllavhrralentsisqghppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttnlrphaatattplatangspsngrsrrpkspppekvpeapsqegllaplslltlltlaiatlyglflaspgq* |
| 165 | mouse Trex1minec | mgsqtlphghmqtlifldleatglpssrpevtelcllavhrralentsisqghppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttdle |
| 166 | murine Trex1-(G4S)4-mIgG2a-c ("(G4S)4" disclosed as SEQ ID NO: 212) | metpaqllflllllwlpdttgmgsqtlphghmqtlifldleatglpssrpevtelcllavhrralentsisqghpppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttggggsgggggsggggsggggsleprgptikpsppckcpapnllggssvfifppkikdvlmislspmvtcvvvdvseddpdvqiswfvnnvevhtaqtqthredynstlrvvsalpiqhqdwmsgkefkcsvnnkdlpasiertiskprgpvrapqvyvlpppaeemtkkefsltcmitgflpaeiavdwtsngrteqnykntatvldsdgsyfmysklrvqkstwergslfacsvvheglhnhlttksfsrtpgk* |
| 167 | murine Trex1-(G4S)5-mIgG2a-c ("(G4S)5" disclosed as SEQ ID NO: 209) | metpaqllflllllwlpdttgmgsqtlphghmqtlifldleatglpssrpevtelcllavhrralentsisqghpppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttggggsggggsggggsggggsggggsleprgptikpsppckcpapnllggssvfifppkikdvlmislspmvtcvvvdvseddpdvqiswfvnnvevhtaqtqthredynstlrvvsalpiqhqdwmsgkefkcsvnnkdlpasiertiskprgpvrapqvyvlpppaeemtkkefsltcmitgflpaeiavdwtsngrteqnykntatvldsdgsyfmysklrvqkstwergslfacsvvheglhnhlttksfsrtpgk* |
| 168 | NLGlnk | vdgasspvnvsspsvqdi |
| 169 | Murine Trex-Trex1-(G4s)5-mIgG2a-c ("(G4s)5" disclosed as SEQ ID NO: 209) | metpaqllflllllwlpdttgmgsqtlphghmqtlifldleatglpssrpevtelcllavhrralentsisqghpppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttmgsqtlphghmqtlifldleatglpssrpevtelcllavhrralentsisqghpppvprpprvvdklslciapgkacspgaseitglskaelevqgrqrfddnlaillraflqrqpqpcclvahngdrydfpllqtelarlstpspldgtfcvdsiaalkaleqasspsgngsrksyslgsiytrlywqaptdshtaegdvltllsicqwkpqallqwvdeharpfstvkpmygtpattgttggggsggggsggggsggggsggggsleprgptikpsppckcpapnllggssvfifppkikdvlmislspmvtcvvvdvseddpdvqiswfvnnvevhtaqtqthredynstlrvvsalpiqhqdwmsgkefkcsvnnkdlpasiertiskprgpvrapqvyvlpppaeemtkkefsltcmitgflpaeiavdwtsngrteqnykntatvldsdgsyfmysklrvqkstwergslfacsvvheglhnhlttksfsrtpgk* |
| 170 | huVK3LP-huTREX1-72aa-(g4s)4-hIgG1 (SCC) ("(g4s)4" disclosed as SEQ ID NO: 212) | metpaqllflllllwlpdttgmgpgarrqgrivqgrpemcfcppptplpplriltlgthtptpcsspgsaagtyptmgsqalppgpmqtliffdmeatglpfsqpkvtelcllavhrcalesppptsqgppptvpppprvvdklslcvapgkacspaaseitglstavlaahgrqcfddnlanlllaflrrqpqpwclvahngdrydfpllqaelamlgltsaldgafcvdsitalkalerasspsehgprksyslgsiytrlyggsppdshtaegdvlallsicqwrpqallrwvdaharpfgtirpmygvtasartkggggsggggsggggsggggslepkssdkthtcppcpapellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfypsdiavewesngqpennykttppvldsdgsfflysklvtvdksrwqqgnvfscsvmhealhnhytqkslslspgk* |
| 171 | huVK3LP-huTREX1- | metpaqllflllllwlpdttgmgpgarrqgrivqgrpemcfcppptplpplriltlgthtptpcsspgsaagtyptmgsgalppgpmqtliffdmeatglpfsqpkvte |

| SEQ ID NO: | DESCRIPTION | SEQUENCE (NUCLEOTIDE SEQUENCES ARE 5'-3') |
|---|---|---|
| | 72aa-(g4s)5-hIgG1 (SCC) ("(g4s)5" disclosed as SEQ ID NO: 209) | lcllavhrcalespptsqgppptvppppprvvdklslcvapgkacspaaseitgl stavlaahgrqcfddnlanlllaflrrqpqpwclvahngdrydfpllqaelaml gltsaldgafcvdsitalkalerassspsehgprksyslgsiytrlyggsppdsh taegdvlallsicqwrpqallrwvdaharpfgtirpmygvtasartkggggsgg ggsggggsggggsggggslepkssdkthtcppcpapellggpsvflfppkpkdt lmisrtpevtcvvvdvshedpevkfnwyvdgvevhnaktkpreeqynstyrvvs vltvlhqdwlngkeykckvsnkalpapiektiskakgqprepqvytlppsrdel tknqvsltclvkgfypsdiavewesngqpennykttppvldsdgsfflyskltv dksrwqqgnvfscsvmhealhnhytqkslslspgk* |
| 172 | huVK3LP-hDNase1-G105R; A114F-(G4S)4-hIgG1 (SCC)-NLG-hRNase1-WT ("(G4S)4" disclosed as SEQ ID NO: 212) | gttaagcttgccaccatggaaaccccagcgcagcttctcttcctcctgctactc tggctcccagataccaccggtctgaagatcgcagccttcaacatccagacatttggggagaccaagatgtccaatgccaccctcgtcagctacattgtgcagatcctg agccgctatgacatcgccctggtccaggaggtcagagacagccacctgactgcc gtggggaagctgctggacaacctcaatcaggatgcaccagacacctatcactac gtggtcagtgagccactgggacggaacagctataaggagcgctacctgttcgtg tacaggcctgaccaggtgtctgcggtggacagctactactacgatgatggctgc gagccctgcaggaacgacacccttcaaccgagagccattcattgtcaggttcttc tcccggttcacagaggtcagggagtttgccattgttccctgcatgcggccccg ggggacgcagtagccgagatcgacgctctctatgacgtctacctggatgtccaa gagaaatggggcttggaggacgtcatgttgatgggcgacttcaatgcgggctgc agctatgtgagaccctcccagtggtcatccatccgcctgtgggcaagcccacc ttccagtggctgatccccgacagcgctgacaccacagctacacccacgcactgt gcctatgacaggatcgtggttgcagggatgctgctccgaggcgccgttgttccc gactcggctcttcccttttaacttccaggctgcctatggcctgagtgaccaactg gcccaagccatcagtgaccactatccagtggaggtgatgctgaaagatctctcc ggaggaggtggctcaggtggtggaggatctggaggaggtgggagtggtggagspt ggttctaccggtctcgagcccaaatcttctgacaaaactcacacatgtccaccg tgcccagcacctgaactcctggggggaccgtcagtcttcctcttcccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagccctcccagcccccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggtaaagtcgacggagctagcagcccccgtgaacgtgagcagcccagcgtg caggatatcccttccctgggcaaggaatcccgggccaagaaattccagcggcag catatggactcagacagttcccccagcagcagctccacctactgtaaccaaatg atgaggcgccggaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtacccaactgtgcataccggaccagcccg aaggagagacacatcattgtggcctgtgaagggagcccatatgtgccagtccac tttgatgcttctgtggaggactctacctaataatctaga |
| 173 | huVK3LP-hDNase1-G105R; A114F-(G4S)4-hIgG1-(SCC)-NLG-hRNase1-WT ("(G4S)4" disclosed as SEQ ID NO: 212) | metpaqllflllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkgggsggggsggggsggggslepkssdkthtcppcpapellggp svflfppkpkdtlmisrtpevtcvvvdvshedpevkfnwyvdgvevhnaktkpr eeqynstyrvvsvltvlhqdwlngkeykckvsnkalpapiektiskakgqprep qvytlppsrdeltknqvsltclvkgfypsdiavewesngqpennykttppvlds dgsfflyskltvdksrwqqgnvfscsvmhealhnhytqkslslspgkvdgassp vnvsspsvgdikesrakkfqrqhmdsdsspssssstycnqmmrrrnmtqgrckpv ntfvheplvdvqnvcfgekvtckngqgncyksnssmhitdcrltngsrypncay rtspkerhiivacegspyvpvhfdasvedst* |
| 174 | huVK3LP-hRNAseG88D-hIgG1 (SCC)-P238S; K322S; P331S | gttaagcttgccaccatggaaaccccagcgcagcttctcttcctcctgctactc tggctcccagataccaccggtcttccctgggcaaggaatcccgggccaagaaa ttccagcggcagcatatggactcagacagttcccccagcagcagctccacctac tgtaaccaaatgatgaggcgccggaatatgacacaggggcggtgcaaaccagtg aacacctttgtgcacgagcccctggtagatgtccagaatgtctgtttccaggaa aaggtcacctgcaagaacgggcagggcaactgctacaagagcaactccagcatg cacatcacagactgccgcctgacaaacggctccaggtacccaactgtgcatac cggaccagcccgaaggagagacacatcattgtggcctgtgaagggagcccatat gtgccagtccactttgatgcttctgtggaggactctacagatctcgagcccaaa tcttctgacaaaactcacacatgtccaccgtgtccagcacctgaactcctgggt ggatcgtcagtcttcctcttccccccaaaacccaaggacactctcatgatctcc cggacccctgaggtcacgtgcgtggtggtggacgtgagccaggaagacccgag |

TABLE 2-continued

| SEQ ID NO: | DESCRIPTION | SEQUENCE (NUCLEOTIDE SEQUENCES ARE 5'-3') |
|---|---|---|
| | | gtccagttcaactggtacgtggacggcatggaggtgcataatgccaagacaaag
ccacgggaggagcagttcaacagcacgttccgtgtggtcagcgtcctcaccgtc
gtgcaccaggactggctgaacggcaaggagtacaagtgcaaggtctccaacaaa
gccctcccagcctccatcgagaaaacaatctccaaaaccaaagggcagccccga
gaaccacaggtgtacaccctgcccccatcccgggaggagatgaccaagaaccag
gtcagcctgacctgcctggtcaaaggcttctatcccagcgacatcgccgtggag
tgggagagcaatgggcagccggagaacaactacaacaccacgcctcccgtgctg
gactccgacggctccttctcctctacagcaagctcaccgtggacaagagcagg
tggcagcaggggaacgtcttctcatgctccgtgatgcatgaggctctgcacaac
cactacacgcagaagagcctctctctgtctccgggtaaatgataatctaga |
| 175 | huVK3LP-
hRNAseG88D-
hIgG1
(SCC)-
P238S; K322S;
P331S | metpaqllflllllwlpdttgkesrakkfqrqhmdsdsspsssstycnqmmrrrn
mtqgrckpvntfvheplvdvqnvcfqekvtckngqgncyksnssmhitdcrltn
dsrypncayrtspkerhiivacegspyvpvhfdasvedstlepkssdkthtcpp
cpapellggssvflfppkpkdtlmisrtpevtcvvvdvsqedpevqfnwyvdgm
evhnakttkpreeqfnstfrvvsvltvvhqdwlngkeykckvsnkalpasiekti
sktkgqprepqvytlppsreemtknqvsltclvkgfypsdiavewesngqpenn
ynttppvldsdgsfslyskltvdksrwqqgnvfscsvmhealhnhytqkslsls
pgk* |
| 176 | huVK3LP-
hDNase1-
G105R; A114F-
(G4S)5-
1-hIgG1-
(SCC)-
NLG-
hRNase1-
WT
("(G4S)5"
disclosed
as SEQ
ID NO:
209) | gttaagcttgccaccatggaaaccccagcgcagcttctcttcctcctgctactc
tggctcccagataccaccggtctgaagatcgcagccttcaacatccagacatt
ggggagaccaagatgtccaatgccaccctcgtcagctacattgtgcagatcctg
agccgctatgacatcgccctggtccaggaggtcagagacagccacctgactgcc
gtggggaagctgctggacaacctcaatcaggatgcaccagacacctatcactac
gtggtcagtgagccactgggacggaacagctataaggagcgctacctgttcgtg
tacaggcctgaccaggtgtctgcggtggacagctactactacgatgatggctgc
gagccctgcaggaacgacaccttcaaccgagagccattcattgtcaggttcttc
tcccggttcacagaggtcagggagtttgccattgttccctgcatgcggccccg
ggggacgcagtagccgagatcgacgctctctatgacgtctacctggatgtccaa
gagaaatggggcttggaggacgtcatgttgatgggcgacttcaatgcgggctgc
agctatgtgagaccctcccagtggtcatccatccgcctgtggacaagccccac
ttccagtggctgatcccgacagcgctgacaccacagctacacccacgcactgt
gcctatgacaggatcgtggttgcagggatgctgctccgaggcgccgttgttccc
gactcggctcttcccttttaacttccaggctgcctatgcctgagtgaccaactg
gcccaagccatcagtgaccactatccagtggaggtgatgctgaaagatctctcc
ggaggaggtggctcaggtggtggaggatctggaggaggtggctcaggtggtgga
ggatctggaggaggtgggagtaccggtctcgagcccaaatcttctgacaaaact
cacacatgtccaccgtgcccagccacctgaactcctgggggaccgtcagtcttc
ctcttccccccaaaacccaaggacaccctcatgatctcccggacccctgaggtc
acatgcgtggtggtggacgtgagccacgaagaccctgaggtcaagttcaactgg
tacgtggacggcgtggaggtgcataatgccaagacaaagccgcgggaggagcag
tacaacagcacgtaccgtgtggtcagcgtcctcaccgtcctgcaccaggactgg
ctgaatggcaaggagtacaagtgcaaggtctccaacaaagcccctcccagcccc
atcgagaaaaccatctccaaagccaaagggcagccccgagaaccacaggtgtac
accctgcccccatcccgggatgagctgaccaagaaccaggtcagcctgacctgc
ctggtcaaaggcttctatcccagcgacatcgccgtggagtgggagagcaatggg
cagccggagaacaactacaagaccacgcctcccgtgctggactccgacggctcc
ttcttcctctacagcaagctcaccgtggacaagagcaggtggcagcaggggaac
gtcttctcatgctccgtgatgcatgaggctctgcacaaccactacacgcagaag
agcctctctctgtctccgggtaaagtcgacggagctagcagccccgtgaacgtg
agcagcccagcgtgcaggatatccttccctgggcaaggaatcccgggccaag
aaattccagcggcagcatatggactcagacagttcccccagcagcagctccacc
tactgtaaccaaatgatgaggcgcggaatatgacacaggggcggtgcaaacca
gtgaacacctttgtgcacgagccctggtagatgtccagaatgtctgtttccag
gaaaaggtcaccgtcaagaacgggcagggcaactgctacaagagcaactccagc
atgcacatcacagactgccgcctgacaaacggctccaggtaccccaactgtgca
taccggaccagcccgaaggagagacacattgtggcctgtgaagggagccca
tatgtgccagtccactttgatgcttctgtggaggactctacctaataatctaga |
| 177 | huVK3LP-
hDNase1-
G105R; A114F-
(G4S)5-
1-hIgG1-
(SCC)-
NLG-
hRNase1-
WT
("(G4S)5"
disclosed
as SEQ
ID NO:
209) | metpaqllflllllwlpdttglkiaafniqtfgetkmsnatlvsyivqilsrydi
alvqevrdshltavgklldnlnqdapdtyhyvvseplgrnsykerylfvyrpdq
vsavdsyyyddgcepcrndtfnrepfivrffsrftevrefaivplhaapgdava
eidalydvyldvqekwgledvmlmgdfnagcsyvrpsqwssirlwtsptfqwli
pdsadttatpthcaydrivvagmllrgavvpdsalpfnfqaayglsdqlaqais
dhypvevmlkggggsggggsggggsggggsggggslepkssdkthtcppcpape
llggpsvflfppkpkdtlmisrtpevtcvvvdvshedpevkfnwyvdgvevhna
ktkpreeqynstyrvvsvltvlhqdwlngkeykckvsnkalpapiektiskakg
qprepqvytlppsrdeltknqvsltclvkgfypsdiavewesngqpennykttp
pvldsdgsfflyskltvdksrwqqgnvfscsvmhealhnhytqkslslspgkvd
gassppvnvsspsvqdikesrakkfqrqhmdsdsspsssstycnqmmrrrnmtqg
rckpvntfvheplvdvqnvcfqekvtckngqgncyksnssmhitdcrltngsry
pncayrtspkerhiivacegspyvpvhfdasvedst* |
| 178 | huVK3LP-
hDNase1- | gttaagcttgccaccatggaaaccccagcgcagcttctcttcctcctgctactc
tggctcccagataccaccggtctgaagatcgcagccttcaacatccagacatt |

TABLE 2-continued

| SEQ ID NO: | DESCRIPTION | SEQUENCE (NUCLEOTIDE SEQUENCES ARE 5'-3') |
|---|---|---|
| | G105R; A114F-(G4S)5-2-hIgG1-(SCC)-NLG-hRNase1-WT ("(G4S)5" disclosed as SEQ ID NO: 209) | ggggagaccaagatgtccaatgccaccctcgtcagctacattgtgcagatcctg
agccgctatgacatcgccctggtccaggaggtcagagacagccacctgactgcc
gtggggaagctgctggacaacctcaatcaggatgcaccagacacctatcactac
gtggtcagtgagccactgggacggaacagctataaggagcgctacctgttcgtg
tacaggcctgaccaggtgtctgcggtggacagctactactacgatgatggctgc
gagccctgcaggaacgacaccttcaaccgagagccattcattgtcaggttcttc
tcccggttcacagaggtcagggagtttgccattgttcccctgcatgcggccccg
ggggacgcagtagccgagatcgacgctctctatgacgtctacctggatgtccaa
gagaaatggggcttggaggacgtcatgttgatgggcgacttcaatgcgggctgc
agctatgtgagaccctcccagtggtcatccatccgcctgtggacaagccccacc
ttccagtggctgatccccgacagcgctgacaccacagctacacccacgcactgt
gcctatgacaggatcgtggttgcagggatgctgctccgaggcgccgttgttccc
gactcggctcttcccttaacttccaggctgcctatggcctgagtgaccaactg
gcccaagccatcagtgaccactatccagtggaggtgatgctgaaagatctctcc
ggaggaggtggctcaggtggtggaggatctggaggaggtggctcaggtggtgga
ggatctggaggaggtgggagtctcgagcccaaatcttctgacaaaactcacaca
tgtccaccgtgcccagcacctgaactcctgggggaccgtcagtcttcctcttc
cccccaaaacccaaggacaccctcatgatctcccggacccctgaggtcacatgc
gtggtggtggacgtgagccacgaagaccctgaggtcaagttcaactggtacgtg
gacggcgtggaggtgcataatgccaagacaaagccgcgggaggagcagtacaac
agcacgtaccgtgtggtcagcgtcctcaccgtcctgcaccaggactggctgaat
ggcaaggagtacaagtgcaaggtctccaacaaagccctcccagcccccatcgag
aaaaccatctccaaagccaaagggcagccccgagaaccacaggtgtacaccctg
cccccatcccgggatgagctgaccaagaaccaggtcagcctgacctgcctggtc
aaaggcttctatcccagcgacatcgccgtggagtgggagagcaatgggcagccg
gagaacaactacaagaccacgcctcccgtgctggactccgacggctccttcttc
ctctacagcaagctcaccgtggacaagagcaggtggcagcaggggaacgtcttc
tcatgctccgtgatgcatgaggctctgcacaaccactacacgcagaagagcctc
tctctgtctccgggtaaagtcgacggagctagcagccccgtgaacgtgagcagc
cccagcgtgcaggatatcccttccctgggcaaggaatcccgggcaagaaattc
cagcggcagcatatggactcagacagttcccccagcagcagctccacctactgt
aaccaaatgatgaggcgccggaatatgacacaggggcggtgcaaaccagtgaac
acctttgtgcacgagccctggtagatgtccagaatgtctgtttccaggaaaag
gtcacctgcaagaacgggcagggcaactgctacaagagcaactccagcatgcac
atcacagactgccgcctgacaaacggctccaggtacccccaactgtgcataccgg
accagcccgaaggagagacacatcattgtggcctgtgaagggagcccatatgtg
ccagtccactttgatgcttctgtggaggactctacctaataatctaga |
| 179 | huVK3LP-hDNase1-G105R; A114F-(G4S)5-2-hIgG1-(SCC)-NLG-hRNase1-WT ("(G4S)5" disclosed as SEQ ID NO: 209) | metpaqllflllwlpdttglkiaafniqtfgetkmsnatlvsyivqilsrydi
alvqevrdshltavgklldnlnqdapdtyhyvvseplgrnsykerylfvyrpdq
vsavdsyyyddgcepcrndtfnrepfivrffsrftevrefaivplhaapgdava
eidalydvyldvqekwgledvmlmgdfnagcsyvrpsqwssirlwtsptfqwli
pdsadttatpthcaydrivvagmllrgavvpdsalpfnfqaayglsdqlaqais
dhypvevmlkgggsggggsggggsggggsggggslepkssdkthtcppcpape
llggpsvflfppkpkdtlmisrtpevtcvvvdvshedpevkfnwyvdgvevhna
ktkpreeqynstyrvvsvltvlhqdwlngkeykckvsnkalpapiektiskakg
qprepqvytlppsrdeltknqvsltclvkgfypsdiavewesngqpennykttp
pvldsdgsfflyskltvdksrwqqgnvfscsvmhealhnhytqkslslspgkvd
gasspvnvsspsvqdikesrakkfqrqhmdsdsspsssstycnqmmrrrnmtqg
rckpvntfvheplvdvqnvcfqekvtckngqgncyksnssmhitdcrltngsry
pncayrtspkerhiivacegspyvpvhfdasvedst |
| 180 | huVK3LP-hDNase1 G105R; A114F-hIgG1-(SCC)-NLG-hRNase1-WT | gttaagcttgccaccatggaaaccccagcgcagcttctcttcctcctgctactc
tggctcccagataccaccggtctgaagatcgcagccttcaacatccagacattt
ggggagaccaagatgtccaatgccaccctcgtcagctacattgtgcagatcctg
agccgctatgacatcgccctggtccaggaggtcagagacagccacctgactgcc
gtggggaagctgctggacaacctcaatcaggatgcaccagacacctatcactac
gtggtcagtgagccactgggacggaacagctataaggagcgctacctgttcgtg
tacaggcctgaccaggtgtctgcggtggacagctactactacgatgatggctgc
gagccctgcaggaacgacaccttcaaccgagagccattcattgtcaggttcttc
tcccggttcacagaggtcagggagtttgccattgttcccctgcatgcggccccg
ggggacgcagtagccgagatcgacgctctctatgacgtctacctggatgtccaa
gagaaatggggcttggaggacgtcatgttgatgggcgacttcaatgcgggctgc
agctatgtgagaccctcccagtggtcatccatccgcctgtggacaagccccacc
ttccagtggctgatccccgacagcgctgacaccacagctacacccacgcactgt
gcctatgacaggatcgtggttgcagggatgctgctccgaggcgccgttgttccc
gactcggctcttcccttaacttccaggctgcctatggcctgagtgaccaactg
gcccaagccatcagtgaccactatccagtggaggtgatgctgaaagatctcgag
cccaaatcttctgacaaaactcacacatgtccaccgtgcccagcacctgaactc
ctgggggaccgtcagtcttcctcttccccccaaaacccaaggacaccctcatg
atctcccggacccctgaggtcacatgcgtggtggtggacgtgagccacgaagac
cctgaggtcaagttcaactggtacgtggacggcgtggaggtgcataatgccaag
acaaagccgcgggaggagcagtacaacagcacgtaccgtgtggtcagcgtcctc
accgtcctgcaccaggactggctgaatggcaaggagtacaagtgcaaggtctcc
aacaaagccctcccagcccccatcgagaaaaccatctccaaagccaaagggcag
ccccgagaaccacaggtgtacaccctgcccccatcccgggatgagctgaccaag |

TABLE 2-continued

| SEQ ID NO: | DESCRIPTION | SEQUENCE (NUCLEOTIDE SEQUENCES ARE 5'-3') |
|---|---|---|
| | | aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaagtcgacgga gctagcagcccgtgaacgtgagcagcccagcgtgcaggatatccctccctg ggcaaggaatcccgggccaagaaattccagcggcagcatatggactcagacagt tcccccagcagcagctccacctactgtaaccaaatgatgaggcgccggaatatg acacaggggcggtgcaaaccagtgaacacctttgtgcacgagcccctggtagat gtccagaatgtctgtttccaggaaaaggtcacctgcaagaacgggcagggcaac tgctacaagagcaactccagcatgcacatcacagactgccgcctgacaaacggc tccaggtacccaactgtgcataccggaccagcccgaaggagagacacatcatt gtggcctgtgaaggagcccatatgtgccagtccactttgatgcttctgtggag gactctacctaataatctaga |
| 181 | huVK3LP-hDNase1 G105R; A114F-hIgG1-(SCC)-NLG-hRNase1-WT | metpaqllflllllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivplhaapgdava eidalydvyldvqekwgledvmlmgdfnagcsyvrpsqwssirlwtsptfqwli pdsadttatpthcaydrivvagmllrgavvpdsalpnfqaayglsdqlaqais dhypvevmlklepkssdkthtcppcpapellggpsvflfppkpkdtlmisrtpe vtcvvvdvshedpevkfnwyvdgvevhnaktkpreeqynstyrvvsvltvlhqd wlngkeykckvsnkalpapiektiskakgqprepqvytlppsrdeltknqvslt clvkgfypsdiavewesngqpennykttppvldsdgsfflyskltvdksrwqqg nvfscsvmhealhnhytqkslslspgkvdgasspvnvsspsvqdikesrakkfq rqhmdsdssspsssstycnqmmrrrnmtqgrckpvntfvheplvdvqnvcfqekv tckngqgncyksnssmhitdcrltngsrypncayrtspkerhiivacegspyvp vhfdasvedst* |
| 182 | huVK3LP-mDNase1L3-mIgG2A-C (mut) | gaccaagcttgccaccatggaaacccagcgcagcttctcttcctcctgctact ctggctcccagataccaccggtctaaggctctgctccttcaatgtgaggtcctt tggagcgagcaagaaggaaaaccatgaagccatggatatcattgtgaagatcat caaacgctgtgaccttatactgttgatggaaatcaaggacagcagcaacaacat ctgtcccatgctgatggagaagctgaatggaaattcacgaagaagcacaacata caactatgtgattagttctcgacttggaagaaacacgtacaaagagcagtatgc cttcgtctacaaggagaagctggtgtctgtgaagacaaaataccactaccatga ctatcaggatggagacacagacgtgttttccaggagccctttgtggtttggtt ccattcccccttttactgctgtcaaggacttcgtgattgtcccttgcacacaac tcccgagacctccgttaaagagatagatgagctggtcgatgtctacacggatgt gagaagccagtggaagacagagaatttcatcttcatgggtgatttcaacgccgg ctgtagctatgtccccaagaaggcctggcagaacattcgtttgaggacggaccc caagtttgtttggctgattggggaccaagaggacactacggtcaagaagagtac cagctgtgcctatgacaggattgtgctttgtggacaagagatagtcaactccgt ggttccccgttccagtggcgtctttgactttcagaaagcttatgacttgtctga agaggaggccctggatgtcagtgatcacttccagttgagtttaagctacagtc ttcaagggccttcaccaacaacagaaaatctgtttctctcaaaaagagaaaaaa aggcaatcgctcctcagatctcgagcccagaggtctcacaatcaagccctctcc tccatgcaaatgcccagcacctaacctcttgggtggatcatccgtcttcatctt ccctccaaagatcaaggatgtactcatgatctccctgagcccatggtcacatg tgtggtggtggatgtgagcgaggatgacccagacgtccagatcagctggtttgt gaacaacgtggaagtacacacagctcagacacaaaccatagagaggattacaa cagtactctccgggtggtcagtgccctccccatccagcaccaggactggatgag tggcaaggagttcaaatgctcggtcaacaacaaagacctcccagcgtccatcga gagaaccatctcaaaacccagagggccagtaagagctccacaggtatatgtctt gcctccaccagcagaagagatgactaagaaagagttcagtctgacctgcatgat cacaggcttcttacctgccgaaattgctgtggactggaccagcaatgggcgtac agagcaaaactacaagaacaccgcaacagtcctggactctgatggttcttactt catgtacagcaagctcagagtacaaaagagcacttgggaaagaggaagtcttt cgcctgctcagtggtccacgagggtctgcacaatcaccttacgactaagagctt ctctcggactccgggtaaatgataatctagaa |
| 183 | huVK3LP-mDNase1L3-mIgG2A-C (mut) | metpaqllflllllwlpdttglrlcsfnvrsfgaskkenheamdiivkiikrcdl illmeikdssnnicpmlmeklngnsrrsttynyvissrlgrntykeqyafvyke klvsvktkyhydyqdgdtdvfsrepfvvwfhspftavkdfvivplhttpetsv keidelvdvytdvrsqwktenfifmgdfnagcsyvpkkawqnirlrtdpkfvwl igdqedttvkkststcaydrivlcgqeivnsvvprssgvfdfqkaydlseeeald vsdhfpvefklqssraftnnrksvslkkrkkgnrssdleprgltikpsppckcp apnllgssvfifppkikdvlmislspmvtcvvvdvseddpdvqiswfvnnvev htaqtqthredynstlrvvsalpiqhqdwmsgkefkcsvnnkdlpasiertisk prgpvrapqvyvlpppaeemtkkefsltcmitgflpaeiavdwtsngrteqnyk ntatvldsdgsyfmysklrvqkstwergslfacsvvheglhnhlttksfsrtpg k* |
| 184 | mDNase1L3-NL-mIgG2A_C (mut) | gagaccagcttgccccatgtccctgcacccagcttccccacgcctggcctcct gctgctcttcatccttgccctccatgacaccctggccctaaggctctgctcctt caatgtgaggtcctttggagcgagcaagaaggaaaaccatgaagccatggatat cattgtgaagatcatcaaacgctgtgaccttatactgttgatggaaatcaagga |

TABLE 2-continued

| SEQ ID NO: | DESCRIPTION | SEQUENCE (NUCLEOTIDE SEQUENCES ARE 5'-3') |
|---|---|---|
| | | cagcagcaacaacatctgtcccatgctgatggagaagctgaatggaaattcacg |
| | | aagaagcacaacatacaactatgtgattagttctcgacttggaagaaacacgta |
| | | caaagagcagtatgccttcgtctacaaggagaagctggtgtctgtgaagacaaa |
| | | ataccactaccatgactatcaggatggagacacagacgtgttttccaggagcc |
| | | ctttgtggtttggttccattccccctttactgctgtcaaggacttcgtgattgt |
| | | ccccttgcacacaactcccgagacctccgttaaagagatagatgagctggtcga |
| | | tgtctacacggatgtgagaagccagtggaagacagagaatttcatcttcatggg |
| | | tgatttcaacgccggctgtagctatgtccccaagaaggcctggcagaacattcg |
| | | tttgaggacggaccccaagtttgtttggctgattggggaccaagaggacactac |
| | | ggtcaagaagagtaccagctgtgcctatgacaggattgtgctttgtggacaaga |
| | | gatagtcaactccgtggttccccgttccagtggcgtctttgactttcagaaagc |
| | | ttatgacttgtctgangaggangcccctggatgtcagtgatcactttccagttga |
| | | gtttaagctacagtcttcaagggccttcaccaacaacagaaaatctgtttctct |
| | | caaaaagagaaaaaaaggcaatcgctcctcagatctcgagcccagaggtctcac |
| | | aatcaagccctctcctccatgcaaatgcccagcacctaacctcttgggtggatc |
| | | atccgtcttcatcttccctccaaagatcaaggatgtactcatgatctccctgag |
| | | ccccatggtcacatgtgtggtggtggatgtgagcgaggatgacccagacgtcca |
| | | gatcagctggtttgtgaacaacgtggaagtacacacagctcagacacaaaccca |
| | | tagagaggattacaacagtactctccgggtggtcagtgccctccccatccagca |
| | | ccaggactcgatgagtggcaaggagttcaaatgctcggtcaacaacaaagacct |
| | | cccagcgtccatcgagagaaccatctcaaaacccagagggccagtaagagctcc |
| | | acaggtatatgtcttgcctccaccagcagaagagatgactaagaaagagttcag |
| | | tctgacctgcatgatcacaggcttcttacctgccgaaattgctgtggactggac |
| | | cagcaatgggcgtacagagcaaaactacaagaacaccgcaacagtcctggactc |
| | | tgatggttcttacttcatgtacagcaagctcagagtacaaaagagcacttggga |
| | | aagaggaagtcttttcgcctgctcagtggtccacgagggtctgcacaatcacct |
| | | tacgactaagagcttctctcggactccgggtaaatgataatctagaa |
| 185 | mDNase1L3-<br>NL-<br>mIgG2A_C<br>(mut) | mslhpasprlaslllfilalhdtlalrlcsfnvrsfgaskkenheamdiivkii<br>krcdlillmeikdssnnicpmlmeklngnsrrsttynyvissrlgrntykeqya<br>fvykeklvsvktkyhyhdyqdgdtdvfsrepfvvwfhspftavkdfvivplhtt<br>petsvkeidelvdvytdvrsqwktenfifmgdfnagcsyvpkkawqnirlrtdp<br>kfvwligdqedttvkkstscaydrivlcgqeivnsvvprssgvfdfqkaydlsx<br>exaldvsdhfpvefklqssraftnnrksvslkkrkkgnrssdleprgltikpsp<br>pckcpapnllggssvfifppkikdvlmislspmvtcvvvdvseddpdvqiswfv<br>nnvevhtaqtqthredynstlrvvsalpiqhqdwmsgkefkcsvnnkdlpasie<br>rtiskprgpvrapqvyvlpppaeemtkkefsltcmitgflpaeiavdwtsngrt<br>eqnykntatvldsdgsyfmysklrvqkstwergslfacsvvheglhnhlttksf<br>srtpgk* |
| 186 | huVK3LP-<br>hDNase1L3-<br>hIgG1<br>(SCC)-<br>NLG-<br>hRNase1-<br>WT | gttaagcttgccaccatggaaaccccagcgcagcttctcttcctcctgctactc<br>tggctcccagataccaccggtatgaggatctgctccttcaacgtcaggtccttt<br>ggggaaagcaaggcaggaagacaagaatgccatggatgtcattgtgaaggtcatc<br>aaacgctgtgacatcatactcgtgatggaaatcaaggacagcaacaacaggatc<br>tgccccatactgatggaagctgaacagaaattcaaggagaggcataacatac<br>aactatgtgattagctctcggcttggaagaaacacatataaagaacaatatgcc<br>tttctctacaaggaaaagctggtgtctgtgaagaggagttatcactaccatgac<br>tatcaggatggagacgcagatgtgttttccagggagcccttttgtggtctggttc<br>caatctccccacactgctgtcaaagacttcgtgattatccccctgcacaccacc<br>ccagagacatccgttaaggagatcgatgagttggttgaggtctacacggacgtg<br>aaacaccgctggaaggcggagaattttcattttcatgggtgacttcaatgccggc<br>tgcagctacgtccccaagaaggcctggaagaacatccgcttgaggactgacccc<br>aggtttgtttggctgatcggggaccaagaggacaccacggtgaagaagagcacc<br>aactgtgcatatgacaggattgtgcttagaggacaagaaatcgtcagttctgtt<br>gttcccaagtcaaacagtgtttttgacttccagaaagcttacaagctgactgaa<br>gaggaggccctggatgtcagcgaccacttccagttgaatttaaactacagtct<br>tcaagggccttcaccaacagcaaaaaatctgtcactctaaggaagaaacaaag<br>agcaaacgctcagatctcgagcccaaatcttctgacaaaactcacacatgtcca<br>ccgtgcccagcacctgaactcctggggggaccgtcagtcttcctcttcccccca<br>aaacccaaggacaccctcatgatctcccggacccctgaggtcacatgcgtggtg<br>gtggacgtgagccacgaagaccctgaggtcaagttcaactggtacgtggacggc<br>gtggaggtgcataatgccaagacaaagccgcgggaggagcagtacaacagcacg<br>taccgtgtggtcagcgtcctcaccgtcctgcaccaggactggctgaatggcaag<br>gagtacaagtgcaaggtctccaacaaagcccctcccagcccccatcgagaaaacc<br>atctccaaagccaaagggcagccccgagaaccacaggtgtacaccctgcccca<br>tcccgggatgagctgaccaagaaccaggtcagcctgacctgcctggtcaaaggc<br>ttctatcccagcgacatcgccgtggagtgggagagcaatgggcagccggagaac<br>aactacaagaccacgcctcccgtgctggactccgacggctccttcttcctctac<br>agcaagctcaccgtggacaagagcaggtggcagcaggggaacgtcttctcatgc<br>tccgtgatgcatgaggctctgcacaaccactacacgcagaagagcctctctctg<br>tctccgggtaaagtcgacggagctagcagcccgtgaacgtgagcagcccagc<br>gtgcaggatatcccttcctgggcaaggaatcccgggcaagaaattccagcgg<br>cagcatatggactcagacagttccccccagcagcagctccacctactgtaaccaa<br>atgatgaggcgccggaatatgacacagggcggtgcaaaccagtgaacaccttt<br>gtgcacgagcccctggtagatgtccagaatgtctgtttccaggaaaaggtcacc<br>tgcaagaacgggcagggcaactgctacaagagcaactccagcatgcacatcaca<br>gactgccgcctgacaaacgcctccaggtacccccaactgtgcataccggaccagc |

TABLE 2-continued

| SEQ ID NO: | DESCRIPTION | SEQUENCE (NUCLEOTIDE SEQUENCES ARE 5'-3') |
|---|---|---|
| | | ccgaaggagagacacatcattgtggcctgtgaagggagcccatatgtgccagtc<br>cactttgatgcttctgtggaggactctacctaataatctaga |
| 187 | huVK3LP-<br>hDNase1L3-<br>hIgG1-<br>(SCC)-<br>NLG-<br>hRNase1-<br>WT | metpaqllflllllwlpdttgmricsfnvrsfgeskqedknamdvivkvikrcdi<br>ilvmeikdsnnricpilmeklnrnsrrgitynyvissrlgrntykeqyaflyke<br>klvsvkrsyhyhdyqdgdadvfsrepfvvwfqsphtavkdfviiplhttpetsv<br>keidelvevytdvkhrwkaenfifmgdfnagcsyvpkkawknirlrtdprfvwl<br>igdqedttvkkstncaydrivlrgqeivssvvpksnsvfdfqkayklteeeald<br>vsdhfpvefklgssraftnskksvtlrkktkskrslepkssdkthtcppcpape<br>llggpsvflfppkpkdtlmisrtpevtcvvvdvshedpevkfnwyvdgvevhna<br>ktkpreeqynstyrvvsvltvlhqdwlngkeykckvsnkalpapiektiskakg<br>qprepqvytlppsrdeltknqvsltclvkgfypsdiavewesngqpennykttp<br>pvldsdgsfflyskltvdksrwqqgnvfscsvmhealhnhytqkslslspgkvd<br>gasspvnvsspsvqdikesrakkfqrqhmdsdsspsssstycnqmmrrrnmtqg<br>rckpvntfvheplvdvqnvcfqekvtckngqgncyksnssmhitdcrltngsry<br>pncayrtspkerhiivacegspyvpvhfdasvedst* |
| 188 | huVK3LP-<br>hRNase1-<br>WT-<br>hIgG1-<br>(SCC)-<br>NLG-<br>hRNase1-<br>WT- | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagccctggtagatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctcgagcccaaatcttctgacaaaact<br>cacacatgtccaccgtgcccagcacctgaactcctgggggaccgtcagtcttc<br>ctcttcccccaaaacccaaggacaccctcatgatctcccggacccctgaggtc<br>acatgcgtggtggtggacgtgagccacgaagaccctgaggtcaagttcaactgg<br>tacgtggacggcgtggaggtgcataatgccaagacaaagccgcgggaggagcag<br>tacaacagcacgtaccgtgtggtcagcgtcctcaccgtcctgcaccaggactgg<br>ctgaatggcaaggagtacaagtgcaaggtctccaacaaagcccctcccagcccc<br>atcgagaaaaccatctccaaagccaaagggcagccccgagaaccacaggtgtac<br>accctgcccccatcccgggatgagctgaccaagaaccaggtcagcctgacctgc<br>ctggtcaaaggcttctatcccagcgacatcgccgtggagtgggagagcaatggg<br>cagccggagaacaactacaagaccacgcctcccgtgctggactccgacggctcc<br>ttcttcctctacagcaagctcaccgtggacaagagcaggtggcagcaggggaac<br>gtcttctcatgctccgtgatgcatgagggtctgcacaaccactacacgcagaag<br>agcctctctctgtctccgggtaaagtcgacggtgctagcagccatgtgaatgtg<br>agcagccctagcgtgcaggatatcccttccctgggcaaggaatcccgggccaag<br>aaattccagcggcagcatatggactcagacagttcccccagcagcagctccacc<br>tactgtaaccaaatgatgaggcgccggaatatgacacaggggcggtgcaaacca<br>gtgaacacctttgtgcacgagcccctggtagatgtctgtttccag<br>gaaaaggtcacctgcaagaacgggcagggcaactgctacaagagcaactccagc<br>atgcacatcacagactgccgcctgacaaacggctccaggtaccccaactgtgca<br>taccggaccagcccgaaggagagacacatcattgtggcctgtgaagggagccca<br>tatgtgccagtccactttgatgcttctgtggaggactctacctaataatctaga |
| 189 | huVK3LP-<br>hRNase1-<br>WT-<br>hIgG1-<br>(SCC)-<br>NLG-<br>hRNase1-<br>WT | metpaqllflllllwlpdttgkesrakkfqrqhmdsdsspsssstycnqmmrrrn<br>mtqgrckpvntfvheplvdvqnvcfqekvtckngqgncyksnssmhitdcrltn<br>gsrypncayrtspkerhiivacegspyvpvhfdasvedstlepkssdkthtcpp<br>cpapellggpsvflfppkpkdtlmisrtpevtcvvvdvshedpevkfnwyvdgv<br>evhnaktkpreeqynstyrvvsvltvlhqdwlngkeykckvsnkalpapiekti<br>skakgqprepqvytlppsrdeltknqvsltclvkgfypsdiavewesngqpenn<br>ykttppvldsdgsfflyskltvdksrwqqgnvfscsvmheglhnhytqkslsls<br>pgkvdgasshvnvsspsvqdikesrakkfqrqhmdsdsspsssstycnqmmrrr<br>nmtqgrckpvntfvheplvdvqnvcfqekvtckngqgncyksnssmhitdcrlt<br>ngsrypncayrtspkerhiivacegspyvpvhfdasvedst* |
| 190 | huVK3LP-<br>hRNase1-<br>WT-<br>(G4S)4-<br>hIgG1-<br>(SCC)-<br>NLG-<br>hRNase1-<br>WT<br>("(G4S)4"<br>disclosed<br>as SEQ<br>ID NO:<br>212) | aagcttgccgccatggaaaccccagcgcagcttctcttcctcctgctactctgg<br>ctcccagataccaccggtaaggaatcccgggccaagaaattccagcggcagcat<br>atggactcagacagttcccccagcagcagctccacctactgtaaccaaatgatg<br>aggcgccggaatatgacacaggggcggtgcaaaccagtgaacacctttgtgcac<br>gagccctggtagatgtctgtttccaggaaaaggtcacctgcaag<br>aacgggcagggcaactgctacaagagcaactccagcatgcacatcacagactgc<br>cgcctgacaaacggctccaggtaccccaactgtgcataccggaccagcccgaag<br>gagagacacatcattgtggcctgtgaagggagcccatatgtgccagtccacttt<br>gatgcttctgtggaggactctacagatctctcggaggaggtggctcaggtggt<br>ggaggatctggaggaggtgggagtggtggaggtggttctaccggtctcgagccc<br>aaatcttctgacaaaactcacacatgtccaccgtgcccagcacctgaactcctg<br>ggggaccgtcagtcttcctcttccccccaaaacccaaggacaccctcatgatc<br>tcccggacccctgaggtcacatgcgtggtggtggacgtgagccacgaagaccct<br>gaggtcaagttcaactggtacgtggacggcgtggaggtgcataatgccaagaca<br>aagccgcgggaggagcagtacaacagcacgtaccgtgtggtcagcgtcctcacc<br>gtcctgcaccaggactggctgaatggcaaggagtacaagtgcaaggtctccaac<br>aaagcccctcccagccccatcgagaaaaccatctccaaagccaaagggcagccc<br>cgagaaccacaggtgtacaccctgcccccatcccgggatgagctgaccaagaac |

TABLE 2-continued

| SEQ ID NO: | DESCRIPTION | SEQUENCE (NUCLEOTIDE SEQUENCES ARE 5'-3') |
|---|---|---|
| | | caggtcagcctgacctgcctggtcaaaggcttctatcccagcgacatcgccgtg gagtgggagagcaatgggcagccggagaacaactacaagaccacgcctcccgtg ctggactccgacggctccttcttcctctacagcaagctcaccgtggacaagagc aggtggcagcaggggaacgtcttctcatgctccgtgatgcatgagggtctgcac aaccactacacgcagaagagcctctctctgtctccgggtaaagtcgacggtgct agcagccatgtgaatgtgagcagccctagcgtgcaggatatcccttccctgggc aaggaatcccgggccaagaaattccagcggcagcatatggactcagacagttcc cccagcagcagctccacctactgtaaccaaatgatgaggcgccggaatatgaca caggggcggtgcaaaccagtgaacacctttgtgcacgagcccctggtagatgtc cagaatgtctgtttccaggaaaaggtcacctgcaagaacgggcagggcaactgc tacaagagcaactccagcatgcacatcacagactgccgcctgacaaacggctcc aggtaccccaactgtgcataccggaccagcccgaaggagagacacatcattgtg gcctgtgaagggagcccatatgtgccagtccactttgatgcttctgtggaggac tctacctaataatctaga |
| 191 | huVK3LP-<br>hRNase1-<br>WT-<br>(G4S)4-<br>hIgG1-<br>(SCC)-<br>NLG-<br>hRNase1-<br>WT<br>("(G4S)4"<br>disclosed<br>as SEQ<br>ID NO:<br>212) | metpaqllflllllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstggggsggggsggggs sggggslepkssdkthtcppcpapellggpsvflfppkpkdtlmisrtpevtcv vvdvshedpevkfnwyvdgvevhnaktkpreeqynstyrvvsvltvlhqdwlng keykckvsnkalpapiektiskakgqprepqvytlppsrdeltknqvsltclvk gfypsdiavewesngqpennykttppvldsdgsffflyskltvdksrwqqgnvfs csvmheglhnhytqkslslspgkvdgasshvnvsspsvqdikesrakkfqrqhm dsdssppssssstycnqmmrrrnmtqgrckpvntfvheplvdvqnvcfqekvtckn gqgncyksnssmhitdcrltngsrypncayrtspkerhiivacegspyvpvhfd asvedst* |
| 192 | huVK3LP-<br>hTREX1-<br>72AA-<br>(G4S)4-<br>hIgG1-<br>(SCC)-<br>NLG-<br>hRNase1-<br>WT<br>("(G4S)4"<br>disclosed<br>as SEQ<br>ID NO:<br>212) | aagcttgccaccatggaaaccccagcgcagcttctcttcctcctgctactctgg ctcccagataccaccggtatgggccctggagctcgcagacagggcaggattgtg cagggaaggcctgagatgtgcttctgcccaccccctaccccactccctcccctt cggatcttaacactgggcactcacacacccacccatgctcctctccaggctca gcagcaggtacgtacccaaccatgggctcgcaggccctgcccccgggcccatg cagaccctcatctttttcgacatggaggccactggcttgcccttctcccagccc aaggtcacggagctgtgcctgctggctgtccacagatgtgccctggagagcccc cccacctctcaggggccacctcccacagttcctccaccacgcgtgtggtagac aagctctccctgtgtgtggctcggggaaggcctgcagccctgcagcagcagg atcacaggtctgagcacagctgtgctggcagcgcatgggcgtcaatgttttgat gacaacctggccaacctgctcctagccttcctgcggcgccagccacagccctgg tgcctggtggcacacaatggtgaccgctacgacttcccccctgctccaagcagag ctggctatgctgggcctcaccagtgctctggatggtgcctcgtgtggataagc atcactgcgctgaaggccctggagcgagcaagcagcccctcagaacacggccca aggaagagctacagcctaggcagcatctacactcgcctgtatgggcagtcccct ccagactcgcacacggctgagggtgatgtcctggccctgctcagcatctgtcag tggagaccacaggccctgctgcggtgggtggatgctcacgccaggcctttcggc accatcaggcccatgtatggggtcacagcctctgctaggaccaaagatctctcc ggaggaggtggctcaggtggtggaggatctgaggaggtggagtggtggaggt ggttctaccggtctcgagcccaaatcttctgacaaaactcacacatgtccaccg tgcccagcacctgaactcctggggggaccgtcagtcttcctcttcccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatggcaaggag tacaagtgcaaggtctccaacaaagccctcccagcccccatcgagaaaaccatc tccaaagccaaagggcagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggtaaagtcgacggagctagcagccccgtgaacgtgagcagccccagcgtg caggatatcccttccctgggcaaggaatcccgggccaagaaattccagcggcag catatggactcagacagttcccccagcagcagctccacctactgtaaccaaatg atgaggcgccggaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtaccccaactgtgcataccggaccagcccg aaggagagacacatcattgtggcctgtgaagggagcccatatgtgccagtccac tttgatgcttctgtggaggactctacctaataatctaga |
| 193 | huVK3LP-<br>hTREX1-<br>72AA-<br>(G4S)4-<br>hIgG1- | metpaqllflllllwlpdttgmgpgarrqgrivqgrpemcfcppptplpplrilt lgthtptpcsspgsaagtyptmgsqalppgpmqtliffdmeatglpfsqpkvte lcllavhrcalesppsqgppptvppprrvvdklslcvapgkacspaaseitgl stavlaahgrqcfddnlanlllaflrrqpqpwclvahngdrydfpllqaelaml gltsaldgafcvdsitalkaleraspsehgprksyslgsiytrlygqsppdsh |

TABLE 2-continued

| SEQ ID NO: | DESCRIPTION | SEQUENCE (NUCLEOTIDE SEQUENCES ARE 5'-3') |
|---|---|---|
| | (SCC)-NLG-hRNase1-WT ("(G4S)4" disclosed as SEQ ID NO: 212) | taegdvlallsicqwrpqallrwvdaharpfgtirpmygvtasartkgggsgg ggsggggsggggslepkssdkthtcppcpapellggpsvflfppkpkdtlmisr tpevtcvvvdvshedpevkfnwyvdgvevhnaktkpreeqynstyrvvsvltvl hqdwlngkeykckvsnkalpapiektiskakgqprepqvytlppsrdeltknqv sltclvkgfypsdiavewesngqpennykttppvldsdgsfflyskltvdksrw qqgnvfscsvmhealhnhytqkslslspgkvdgasspvnvsspsvqdikesrak kfqrqhmdsdsspssssstycnqmmrrrnmtqgrckpvntfvheplvdvqnvcfq ekvtckngqgncyksnssmhitdcrltngsrypncayrtspkerhiivacegsp yvpvhfdasvedst* |
| 194 | huVK3LP-hRNase1-WT-hIgG1-(SCC)-NLG-hTREX1-72AA | aagcttgccgccatggaaaccccagcgcagcttctcttcctcctgctactctgg ctcccagataccaccggtaaggaatcccgggccaagaaattccagcggcagcat atggactcagacagttcccccagcagcagctccacctactgtaaccaaatgatg aggcgccggaatatgacacaggggcggtgcaaaccagtgaacaccttttgtgcac gagccctggtagatgtccagaatgtctgtttccaggaaaaggtcacctgcaag aacgggcagggcaactgctacaagagcaactccagcatgcacatcacagactgc cgcctgacaaacggctccaggtaccccaactgtgcataccggaccagcccgaag gagagacacatcattgtggcctgtgaagggagcccatatgtgccagtccacttt gatgcttctgtggaggactctacagatctcgagcccaaatcttctgacaaaact cacacatgtccaccgtgcccagcacctgaactcctgggggaccgtcagtcttc ctcttccccccaaaacccaaggacaccctcatgatctcccggacccctgaggtc acatgcgtggtggtggacgtgagccacgaagaccctgaggtcaagttcaactgg tacgtggacggcgtggaggtgcataatgccaagacaaagccgcgggaggagcag tacaacagcacgtaccgtgtggtcagcgtcctcaccgtcctgcaccaggactgg ctgaatggcaaggagtacaagtgcaaggtctccaacaaagcccctcccagcccc atcgagaaaaccatctccaaagccaaagggcagccccgagaaccacaggtgtac accctgcccccatcccgggatgagctgaccaagaaccaggtcagcctgacctgc ctggtcaaaggcttctatcccagcgacatcgccgtggagtgggagagcaatggg cagccggagaacaactacaagaccacgcctcccgtgctggactccgacggctcc ttcttcctctacagcaagctcaccgtggacaagagcaggtggcagcaggggaac gtcttctcatgctccgtgatgcatgagggtctgcacaaccactacacgcagaag agcctctctctgtctccgggtaaagtcgacggtgctagcagccatgtgaatgtg agcagcccagcgtgcaggatatcatgggccctggagctcgcagacagggcagg attgtgcagggaaggcctgagatgtgcttctgcccacccctaccccactccct ccccttcggatcttaacactgggcactcacacacccaccccatgctcctctcca ggctcagcagcaggtacgtacccaaccatgggctcgcaggccctgccccgggg cccatgcagaccctcatcttttttcgacatggaggccactggcttgcccttctcc cagcccaaggtcacggagctgtgcctgctggctgtccacagatgtgcctggag agcccccccacctctcaggggccacctcccacagttcctccaccaccgcgtgtg gtagacaagctctccctgtgtgtggcctccggggaaggcctgcagccctgcagcc agcgagatcacaggtctgagcacagctgtgctggcagcgcatgggcgtcaatgt tttgatgacaacctggccaacctgctcctagccttcctgcggcgccagccacag ccctggtgcctggtggcacaatggtgaccgctacgacttcccctgctccaa gcagagctggctatgctgggcctcaccagtgctctggatggtgccttctgtgtg gatagcatcactgcgctgaaggccctggagcgagcaagcagccctcagaacac ggcccaaggaagagctacagcctaggcagcatctacactcgcctgtatgggcag tcccctccagactcgcacacgctgagggtgatgtcctggccctgctcagcatc tgtcagtggagaccacaggccctgctgcggtgggtggatgctcacgccaggcct ttcggcaccatcaggcccatgtatggggtcacagcctctgctaggaccaaatga taatctaga |
| 195 | huVK3LP-hRNase1-WT-hIgG1-(SCC)-NLG-hTREX1-72AA | metpaqllflllllwlpdttgkesrakkfqrqhmdsdsspssssstycnqmmrrrn mtqgrckpvntfvheplvdvqnvcfqekvtckngqgncyksnssmhitdcrltn gsrypncayrtspkerhiivacegspyvpvhfdasvedstlepkssdkthtcpp cpapellggpsvflfppkpkdtlmisrtpevtcvvvdvshedpevkfnwyvdgv evhnaktkpreeqynstyrvvsvltvlhqdwlngkeykckvsnkalpapiekti skakgqprepqvytlppsrdeltknqvsltclvkgfypsdiavewesngqpenn ykttppvldsdgsfflyskltvdksrwqqgnvfscsvmheglhnhytqkslsls pgkvdgasshvnvsspsvqdimgpgarrqgrivqgrpemcfcppptplpplril tlgthtptpcsspgsaagtyptmgsqalppgpmqtliffdmeatglpfsqpkvt elcllavhrcalespptsqgpppptvppppprvvdklslcvapgkacspaaseitg lstavlaahgrqcfddnlanlllaflrrqpqpwclvahngdrydfpllqaelam lgltsaldgafcvdsitalkaleraspsehgprksyslgsiytrlygqsppds htaegdvlallsicqwrpqallrwvdaharpfgtirpmygvtasartk* |
| 196 | huVK3LP-hDNase1L3-(G4S)4-hIgG1-(SCC)-NLG-hRNase1-WT ("(G4S)4" | gttaagcttgccaccatggaaaccccagcgcagcttctcttcctcctgctactc tggctcccagataccaccggtatgaggatctgctcctcaacgtcaggtccttt ggggaaagcaagcaggaagacaagaatgccatggatgtcattgtgaaggtcatc aaacgctgacatcatactcgtagtgaaatcaaggacagcaagaggatc tgccccatactgatggagaagctgaacagaaattcaaggagaggcataacatac aactatgtgattagctctcggcttggaagaaacacatataaagaacaatatgcc tttctctacaagaaaagctggtgtctgtgaagaggagttatcactaccatgac tatcaggatggagacgcagatgtgttttccagggagccctttgtggtctggttc caatctccccacactgctgtcaaagacttcgtgattatccccctgcacaccacc |

TABLE 2-continued

| SEQ ID NO: | DESCRIPTION | SEQUENCE (NUCLEOTIDE SEQUENCES ARE 5'-3') |
|---|---|---|
| | disclosed as SEQ ID NO: 212) | ccagagacatccgttaaggagatcgatgagttggttgaggtctacacggacgtg aaacaccgctggaaggcggagaatttcattttcatgggtgacttcaatgccggc tgcagctacgtccccaagaaggcctggaagaacatccgcttgaggactgaccccc aggtttgtttggctgatcggggaccaagaggacaccacggtgaagaagagcacc aactgtgcatatgacaggattgtgcttagaggacaagaaatcgtcagttctgtt gttcccaagtcaaacagtgtttttgacttccagaaagcttacaagctgactgaa gaggaggcccctggatgtcagcgaccactttccagttgaatttaaactacagtct tcaagggccttcaccaacagcaaaaaatctgtcactctaaggaagaaaacaaag agcaaacgctcagatctctccggaggaggtggctcaggtggtggaggatctgga ggaggtgggagtggtggaggtggttctaccggtctcgagcccaaatcttctgac aaaactcacacatgtccaccgtgcccagcacctgaactcctgggggaccgtca gtcttcctcttccccccaaaacccaaggacaccctcatgatctcccggacccct gaggtcacatgcgtggtggtggacgtgagccacgaagaccctgaggtcaagttc aactggtacgtggacggcgtggaggtgcataatgccaagacaaagccgcgggag gagcagtacaacagcacgtaccgtgtggtcagcgtcctcaccgtcctgcaccag gactggctgaatggcaaggagtacaagtgcaaggtctccaacaaagcccctcca gcccccatcgagaaaaccatctccaaagccaaagggcagccccgagaaccacag gtgtacaccctgcccccatcccgggatgagctgaccaagaaccaggtcagcctg acctgcctggtcaaaggcttctatcccagcgacatcgccgtggagtgggagagc aatgggcagccggagaacaactacaagaccacgcctcccgtgctggactccgac ggctccttcttcctctacagcaagctcaccgtggacaagagcaggtggcagcag gggaacgtcttctcatgctccgtgatgcatgaggctctgcacaaccactacacg cagaagagcctctctctgtctccgggtaaagtcgacggtgctagcagccatgtg aatgtgagcagcccagcgtgcaggatatcccttccctgggcaaggaatcccgg gccaagaaattccagcggcagcatatggactcagacagttccccagcagcagc tccacctactgtaaccaaatgatgaggcgccggaatatgacacagggcggtgc aaaccagtgaacacctttgtgcacgagcccctggtagatgtccagaatgtctgt ttccaggaaaaggtcacctgcaagaacgggcagggcaactgctacaagagcaac tccagcatgcacatcacagactgccgcctgacaaacggctccaggtaccccaac tgtgcataccggaccagcccgaaggagagacatcattgtggcctgtgaaggg agcccatatgtgccagtccactttgatgcttctgtggaggactctacctaataa tctaga |
| 197 | huVK3LP-hDNase1L3-(G4S)4-hIgG1(SCC)-NLG-hRNase1-WT ("(G4S)4" disclosed as SEQ ID NO: 212) | metpaqllflllllwlpdttgmricsfnvrsfgeskqedknamdvivkvikrcdi ilvmeikdsnnricpilmeklnrnsrrgitynyvissrlgrntykeqyaflyke klvsvkrsyhyhdyqdgdadvfsrepfvvwfqsphtavkdfviiplhttpetsv keidelvevytdvkhrwkaenfifmgdfnagcsyvpkkawknirlrtdprfvwl igdqedttvkkstncaydrivlrggeivssvvpksnsvfdfqkaykltleeealdl vsdhfpvefklqssraftnskksvtlrkktkskrsgggggsgggggsgggggs slepkssdkthtcppcpapellggpsvflfppkpkdtlmisrtpevtcvvvdvs hedpevkfnwyvdgvevhnaktkpreeqynstyrvvsvltvlhqdwlngkeykc kvsnkalpapiektiskakgqprepqvytlppsrdeltknqvsltclvkgfyps diavewesngqpennykttppvldsdgsfflyskltvdksrwqqgnvfscsvmh eglhnhytqklslspgkvdgasshvnvsspsvqdikesrakkfqrqhmdsdss pssssstycnqmmrrrnmtqgrckpvntfvheplvdvqnvcfqekvtckngqgnc yksnssmhitdcrltngsrypncayrtspkerhiivacegspyvpvhfdasved st* |
| 198 | huVK3LP-hRNase1-WT-(G4S)4-hIgG1-(SCC)-NLG-hDNase1L3 ("(G4S)4" disclosed as SEQ ID NO: 212) | gttaagcttgccaccatggaaaccccagcgcagcttctcttcctcctgctactc tggctcccagataccaccggtaaggaatcccgggccaagaaattccagcggcag catatggactcagacagttccccagcagcagctccacctactgtaaccaaatg atgaggcgccggaatatgacacagggcggtgcaaaccagtgaacacctttgtg cacgagccctggtagatgtccagaatgtctgtttccaggaaaaggtcacctgc aagaacgggcagggcaactgctacaagagcaactccagcatgcacatcacagac tgccgcctgacaaacggctccaggtaccccaactgtgcataccggaccagcccg aaggagagacatcattgtggcctgtgaaggcagcccatatgtgccagtccatc tttgatgcttctgtggaggactctacagatctctccggaggaggtggctcaggt ggtgaggatctggaggaggtgggagtggtggaggtggttctaccggtctcgag cccaaatcttctgacaaaactcacacatgtccaccgtgcccagcacctgaactc ctgggggaccgtcagtcttcctcttccccccaaaacccaaggacaccctcatg atctcccggacccctgaggtcacatgcgtggtggtggacgtgagccacgaagac cctgaggtcaagttcaactggtacggacgcgtggaggtgcataatgccaag acaaagccgcggagagcagtacaacagcacgtaccgtgtggtcagcgtcctc accgtcctgcaccaggactggctgaatggcaaggagtacaagtgcaaggtctcc aacaaagcccctccagcccccatcgagaaaaccatctccaaagccaaagggcag ccccgagaaccacaggtgtacaccctgcccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaagtcgacggt gctagcagccatgtgaatgtgagcagcccagcgtgcaggatatcatggatc tgctccttcaacgtcaggtcctttgggaaagcaagcaggaagacaagaatgcc atggatgtcattgtgaaggtcatcaaacgctgtgacatcatactcgtgatggaa atcaaggacagcaacaacaggatctgccccatactgatgagaagctgaacaga aattcaaggagaggcataacatacaactatgtgattagctctcggcttgaaga aacacatataaagaacaatatgcctttctctacaaggaaaagctggtgtctgtg |

TABLE 2-continued

| SEQ ID NO: | DESCRIPTION | SEQUENCE (NUCLEOTIDE SEQUENCES ARE 5'-3') |
|---|---|---|
| | | aagaggagttatcactaccatgactatcaggatggagacgcagatgtgttttcc<br>agggagcccttttgtggtctggttccaatctccccacactgctgtcaaagacttc<br>gtgattatcccctgcacaccaccccagagacatccgttaaggagatcgatgag<br>ttggttgaggtctacacggacgtgaaacaccgctggaaggcggagaatttcatt<br>ttcatgggtgacttcaatgccggctgcagctacgtccccaagaaggcctggaag<br>aacatccgcttgaggactgaccccaggtttgtttggctgatcggggaccaagag<br>gacaccacggtgaagaagagcaccaactgtgcatatgacaggattgtgcttaga<br>ggacaagaaatcgtcagttctgttgttcccaagtcaaacagtgttttgacttc<br>cagaaagcttacaagctgactgaagaggaggccctggatgtcagcgaccactt<br>ccagttgaatttaaactacagtcttcaagggcttcaccaacagcaaaaaatct<br>gtcactctaaggaagaaaacaaagagcaaacgctcctaatgatctaga |
| 199 | huVK3LP-<br>hRNase1-<br>WT-<br>(G4S)4-<br>hIgG1-<br>(SCC)-<br>NLG-<br>hDNase1L3<br>("(G4S)4"<br>disclosed<br>as SEQ<br>ID NO:<br>212) | metpaqllflllwlpdttgkesrakkfqrqhmdsdsspssssstycnqmmrrrn<br>mtqgrckpvntfvheplvdvqnvcfqekvtckngqgncyksnssmhitdcrltn<br>gsrypncayrtspkerhiivacegspyvpvhfdasvedstggggsggggsgggg<br>sggggslepkssdkthtcppcpapellggpsvflfppkpkdtlmisrtpevtcv<br>vvdvshedpevkfnwyvdgvevhnaktkpreeqynstyrvvsvltvlhqdwlng<br>keykckvsnkalpapiektiskakgqprepqvytlppsrdeltknqvsltclvk<br>gfypsdiavewesngqpennykttppvldsdgsfflyskltvdksrwqqgnvfs<br>csvmhealhnhytqkslslspgkvdgasshvnvssspsvqdimricsfnvrsfge<br>skqedknamdvivkvikrcdiilvmeikdsnnricpilmeklnrnsrrgityny<br>vissrlgrntykeqyaflykeklvsvkrsyhyhdyqdgdadvfsrepfvvwfqs<br>phtavkdfviiplhttpetsvkeidelvevytdvkhrwkaenfifmgdfnagcs<br>yvpkkawknirlrtdprfvwligdqedttvkkstncaydrivlrgqeivssvvp<br>ksnsvfdfqkaykltheeealdvsdhfpvefklqssraftnskksvtlrkktksk<br>rs* |
| 200 | huVK3LP-<br>hDNase1-<br>G105R; A114F-<br>(G4S)4-<br>hIgG1-<br>(SCC)-<br>NLG-<br>hTREX1-<br>72AA<br>("(G4S)4"<br>disclosed<br>as SEQ<br>ID NO:<br>212) | gttaagcttgccaccatggaaaccccagcgcagcttctcttcctcctgctactc<br>tggctcccagataccaccggtctgaagatcgcagccttcaacatccagacatt<br>ggggagaccaagatgtccaatgccacccctcgtcagctacattgtgcagatcctg<br>agccgctatgacatcgccctggtccaggaggtcaggagacagcacctgactgcc<br>gtggggaagctgctggacaaccntcaatcaggatgcaccagacacctatcactac<br>gtggtcagtgagccactgggacggaacagctactactacgatgatggctgc<br>gagccctgcaggaacgacacctcaaccgagagccattcattgtcaggttcttc<br>tcccggttcacagaggtcagggagtttgccattgttcccctgcatgcggccccg<br>ggggacgcagtagccgagatcgacgctctctatgacgtctacctggatgtccaa<br>gagaaatgggcttggaggacgtcatgttgatgggcgacttcaatgcgggctgc<br>agctatgtgagaccctcccagtggtcatccatccgcctgtgggacaagccccacc<br>ttccagtggctgatccccgacagcgctgacaccacagctacacccacgcactgt<br>gcctatgacaggatcgtggttgcagggatgctgctccgaggcgccgttgttccc<br>gactcggctcttcccttttaacttccaggctgcctatggcctgagtgaccaactg<br>gcccaagccatcagtgaccactatccagtggaggtgatgctgaaagatctctcc<br>ggaggaggtggctcaggtggtggaggatctggaggaggtggagtggtggaggt<br>ggttctaccggtctcgagcccaaatcttctgacaaaactcacacatgtccaccg<br>tgcccagcacctgaactcctgggggaccgtcagtcttcctcttccccccaaaa<br>cccaaggacacccctcatgatctcccggaccccgaggtcacatgcgtggtggtg<br>gacgtgagccacgaagaccctgaggtcaagttcaactggtacgtggacggcgtg<br>gaggtgcataatgccaagacaaagccgcgggaggagcagtacaacagcacgtac<br>cgtgtggtcagcgtcctcaccgtcctgcaccaggactggctgaatggcaaggag<br>tacaagtgcaaggtctccaacaaagcccctcccagccccatcgagaaaaccatc<br>tccaaagccaaagggcagccccgagaaccacaggtgtacaccctgccccatcc<br>cgggatgagctgaccaagaaccaggtcagcctgacctgcctggtcaaaggcttc<br>tatcccagcgacatcgccgtggagtgggagagcaatgggcagccggagaacaac<br>tacaagaccacgcctcccgtgctggactccgacggctccttcttcctctacagc<br>aagctcaccgtggacaagagcaggtggcagcaggggaacgtcttctcatgctcc<br>gtgatgcatgaggctctgcacaaccactacacgcagaagagcctctctctgtct<br>ccgggtaaaagtcgacggtgctagcagccatgtgaatgtgagcagccctagcgtg<br>caggatatcatgggccctggagctcgcagacagggcaggattgtgcagggaagg<br>cctgagatgtgcttctgcccaccccctacccactccctccccttcggatctta<br>acactgggcactcacacacccaccccatgctcctctccaggctcagcagcaggt<br>acgtacccaaccatgggctcgcaggccctgccccggggcccatgcagaccctc<br>atcttttcgacatggaggccactggcttgcccttctcccagcccaaggtcacg<br>gagctgtgcctgctggctgtccacagatgtgccctggagagccccccacctct<br>caggggccacctcccacagttcctccaccaccgcgtgtggtagacaagctctcc<br>ctgtgtgtggctccggggaaggcctgcagccctgcagccagcgagatcacaggt<br>ctgagcacagctgtgctggcagcgcatgggcgtcaatgttttgatgacaacctg<br>gccaacctgctcctagccttcctgcggcgccagccacagcccctggtgcctggtg<br>gcacacaatggtgaccgctacgacttccccctgctccaagcagagctggctatg<br>ctgggcctcaccagtgctctggatggtgcctctgtgtggatagcatcactgcg<br>ctgaaggccctggagcgagcaagcagcccctcagaacacggcccaaggaagagc<br>tacagcctaggcagcatctacactcgcctgtatgggcagtcccctccagactcg<br>cacacggctgagggtgatgtcctggccctgctcagcatctgtcagtggagacca<br>caggccctgctgcggtgggtggatgctcacgccaggcctttcggcaccatcagg<br>cccatgtatgggtcacagcctctgctaggaccaaatgataatctaga |

TABLE 2-continued

| SEQ ID NO: | DESCRIPTION | SEQUENCE (NUCLEOTIDE SEQUENCES ARE 5'-3') |
| --- | --- | --- |
| 201 | huVK3LP-hDNase1-G105R; A114F-(G4S)4-hIgG1-(SCC)-NLG-hTREX1-72AA ("(G4S)4" disclosed as SEQ ID NO: 212) | metpaqllflllwlpdttglkiaafniqtfgetkmsnatlvsyivqilsrydi alvqevrdshltavgklldnlnqdapdtyhyvvseplgrnsykerylfvyrpdq vsavdsyyyddgcepcrndtfnrepfivrffsrftevrefaivrplhaapgdava eidalydvyldvqekwgledvmlmgdfnagcsyvrpsqwssirlwtsptfqwli pdsadttatpthcaydrivvagmllrgavvpdsalpfnfqaayglsdqlaqais dhypvevmlkggggsggggsggggsggggslepkssdkthtcppcpapellggp svflfppkpkdtlmisrtpevtcvvvdvshedpevkfnwyvdgvevhnaktkpr eeqynstyrvvsvltvlhqdwlngkeykckvsnkalpapiektiskakgqprep qvytlppsrdeltknqvsltclvkgfypsdiavewesngqpennykttppvlds dgsfflyskltvdksrwqqgnvfscsvmhealhnhytqkslslspgkvdgassh vnvssspsvqdimgpgarrqgrivqgrpemcfcpppptplpplriltlgthtptpc sspgsaagtyptmgsqalppgpmqtliffdmeatglpfsqpkvtelcllavhrc alesppt sqgppptvppppr vvdklslcvapgkacspaaseitglstavlaahg rqcfddnlanlllaflrrqpqpwclvahngdrydfpllqaelamlgltsaldga fcvdsitalkalerassp sehgprksyslgsiytrlygqsppdshtaegdvlal lsicqwrpqallrwvdaharpfgtirpmygvtasartk* |
| 202 | huVK3LP-hTREX1-72AA (G4S)4-hIgG1-(SCC)-NLG-hDNase1-G105R; A114F ("(G4S)4" disclosed as SEQ ID NO: 212) | aagcttgccaccatggaaaccccagcgcagcttctcttcctcctgctactctgg ctcccagataccaccggtatgggccctggagctcgcagacagggcaggattgtg cagggaaggcctgagatgtgcttctgcccacccctaccccactccctcccctt cggatcttaacactgggcactcacacacccccatgctcctctccaggctca gcagcaggtacgtaccccaaccatgggctcgcaggcctgccccggggcccatg cagaccctcatcttttcgacatggaggccactggcttgcccttctcccagccc aaggtcacggagctgtgcctgctggctgtccacagatgtgccctggagagccc cccaccctctcagggg ccacctcccacagttcctccaccaccgcgtgtggtagac aagctctccctgtgtgtggctccggggaaggcctgcagcctgcagccagcgag atcacaggtctgagcacagctgtgctggcagcgcatgggcgtcaatgttttgat gacaacctggccaacctgctcctagccttcctgcgggcgcagccacagccctgg tgcctggtggcacacaatggtgaccgctacgacttcccctgctccaagcagag ctggctatgctgggcctcaccagtgctctggatggtgcctttctgtgtggatagc atcactgcgctgaaggcccggagcgagcaagcagcccctcagaacacggccca aggaagagctacagcctaggcagcatctacactcgcctgtatgggcagtcccct ccagactcgcacacggctgagggtgatgtcctggcccctgctcagcatctgtcag tggagaccacaggccctgctgcggtgggtggatgctcacgccaggcctttcggc accatcaggcccatgtatggggtcacagcctctgctaggaccaaagatctctcc ggaggaggtggctcaggtggtggaggatctggaggaggtgggagtggtggaggt ggttctaccggtctcgagcccaaatcttctgacaaaactcacacatgtccaccg tgcccagcacctgaactcctggggggaccgtcagtcttcctcttcccccccaaaa cccaaggacaccctcatgatctcccggacccctgaggtcacatgcgtggtggtg gacgtgagccacgaagaccctgaggtcaagttcaactggtacgtggacggcgtg gaggtgcataatgccaagacaaagccgcgggaggagcagtacaacagcacgtac cgtgtggtcagcgtcctcaccgtcctgcaccaggactggctgaatgggcaaggag tacaagtgcaaggtctccaacaaagccctcccagcccccatcgagaaaaccatc tccaaagccaaaggg cagccccgagaaccacaggtgtacaccctgcccccatcc cgggatgagctgaccaagaaccaggtcagcctgacctgcctggtcaaaggcttc tatcccagcgacatcgccgtggagtgggagagcaatgggcagccggagaacaac tacaagaccacgcctcccgtgctggactccgacggctccttcttcctctacagc aagctcaccgtggacaagagcaggtggcagcaggggaacgtcttctcatgctcc gtgatgcatgaggctctgcacaaccactacacgcagaagagcctctctctgtct ccgggtaaagtcgacggtgctagcagccatgtgaatgtgagcagccctagcgtg caggatatcctgaagatcgcagccttcaacatccagacatttggggagaccaag atgtccaatgccacccctcgtcagctacattgtgcagatcctgagccgctatgac atcgccctggtccaggaggtcagagacagccacctgactgccgtggggaagctg ctggacaacctcaatcaggatgcaccagacacctatcactacgtggtcagtgag ccactgggacggaacagctataaggagcgctacctgttcgtgtacagacctgac caggtgtctgccggtggacagctactactacgatgatggctgcgagccctgcggg aacgacaccttcaaccgagagccagccattgtcaggttcttctcccggttcaca gaggtcagggagtttgccattgttccctgcatgcgggccccggggacgcagta gccgagatcgacgctctctatgcgtctacctggatgtccaagagaaatgggc tcggaggacgtcatgttgatggggcgacttcaatgcgggctgcagctatgtgaga ccctcccagtggtcatccatccgcctgtgacaagcccaccttccagtggctg atccccgacagcgctgacaccacagctacacccacgcactgtgcctatgacagg atcgtggttgcagggatgctgctccgaggcgccgttgttcccgactcggctctt ccctttaacttccagnctgcctatggcctgagtgaccaactggcccaagccatc agtgaccactatccagtggaggtgatgctgaagtgataatctaga |
| 203 | huVK3LP-hTREX1-72AA (G4S)4-hIgG1-(SCC)-NLG-hDNase1-G105R; A114F ("(G4S)4" | metpaqllflllwlpdttgmgpgarrqgrivqgrpemcfcpppptplpplrilt lgthtptpcsspgsaagtyptmgsqalppgpmqtliffdmeatglpfsqpkvte lcllavhrcalesppt sqgppptvpppprvvdklslcvapgkacspaaseitgl stavlaahgrqcfddnlanlllaflrrqpqpwclvahngdrydfpllqaelaml gltsaldgafcvdsitalkalerassp sehgprksyslgsiytrlygqsppdsh taegdvlallsicqwrpqallrwvdaharpfgtirpmygvtasartkggggsgg ggsggggsggggslepkssdkthtcppcpapellggpsvflfppkpkdtlmisr tpevtcvvvdvshedpevkfnwyvdgvevhnaktkpreeqynstyrvvsvltvl hqdwlngkeykckvsnkalpapiektiskakgqprepqvytlppsrdeltknqv sltclvkgfypsdiavewesngqpennykttppvldsdgsfflyskltvdksrw |

TABLE 2-continued

| SEQ ID NO: | DESCRIPTION | SEQUENCE (NUCLEOTIDE SEQUENCES ARE 5'-3') |
|---|---|---|
| | disclosed as SEQ ID NO: 212) | qqgnvfscsvmhealhnhytqkslslspgkvdgasshvnvsspsvqdilkiaaf niqtfgetkmsnatlvsyivqilsrydialvqevrdshltavgklldnlnqdap dtyhyvvseplgrnsykerylfvyrpdqvsavdsyyyddgcepogndtfnrepa ivrffsrftevrefaivplhaapgdavaeidalydvyldvqekwgsedvmlmgd fnagcsyvrpsqwssirlwtsptfqwlipdsadttatpthcaydrivvagmllr gavvpdsalpfnfqxayglsdqlagaisdhypvevmlk* |
| 204 | huVK3LP-hRNase1-WT-(G4S)4-hIgG1-(SCC)-NLG-hTREX1-72AA ("(G4S)4" disclosed as SEQ ID NO: 212) | gttaagcttgccaccatggaaaccccagcgcagcttctcttcctcctgctactc tggctcccagataccaccggtaaggaatcccgggccaagaaattccagcggcag catatggactcagacagttcccccagcagcagctccacctactgtaaccaaatg atgaggcgccgaatatgacacaggggcggtgcaaaccagtgaacacctttgtg cacgagcccctggtagatgtccagaatgtctgtttccaggaaaaggtcacctgc aagaacgggcagggcaactgctacaagagcaactccagcatgcacatcacagac tgccgcctgacaaacggctccaggtaccccaactgtgcataccggaccagcccg aaggagagacacatcattgtggcctgtgaagggagcccatatgtgccagtccac tttgatgcttctgtggaggactctacagatctctccggaggaggtggctcaggt ggtggaggatctggaggaggtgggagtggtggaggtggttctaccggtctcgag cccaaatcttctgacaaaactcacacatgtccaccgtgcccagcacctgaactc ctgggggaccgtcagtcttcctcttcccccaaaacccaaggacaccctcatg atctcccggacccctgaggtcacatgcgtggtggtggacgtgagccacgaagac cctgaggtcaagttcaactggtacgtggacggcgtggaggtgcataatgccaag acaaagccgcgggaggagcagtacaacagcacgtaccgtgtggtcagcgtcctc accgtcctgcaccaggactggctgaatggcaaggagtacaagtgcaaggtctcc aacaaagcccttcccagccccatcgagaaaaccatctccaaagccaaagggcag ccccgagaaccacaggtgtacaccctgccccatcccgggatgagctgaccaag aaccaggtcagcctgacctgcctggtcaaaggcttctatcccagcgacatcgcc gtggagtgggagagcaatgggcagccggagaacaactacaagaccacgcctccc gtgctggactccgacggctccttcttcctctacagcaagctcaccgtggacaag agcaggtggcagcaggggaacgtcttctcatgctccgtgatgcatgaggctctg cacaaccactacacgcagaagagcctctctctgtctccgggtaaagtcgacggt gctagcagccatgtgaatgtgcagcccctagcgtgcaggatatcatgggccct ggagctcgcagacagggcaggattgtgcagggaaggcctgagatgtgcttctgc ccaccccctaccccactccctcccctttcggatcttaacactgggcactcacaca cccacccccatgctcctctccaggctcagcagcaggtacgtacccaaccatgggc tcgcaggccctgccccgggggccatgcagaccctcatctttttcgcatggag gccactggcttgcccttctcccagccaaggtcacggagctgtgcctgctggct gtccacagatgtgccctggagagcccccccacctctcaggggccacctcccaca gttcctccaccaccgcgtgtggtagacaagctctccctgtgtgtggctccgggg aaggcctgcagccctgcagccagccagagatcacaggtctgagcacagctgctg gcagcgcatgggcgtcaatgttttgatgacaacctggccaacctgctcctagcc ttcctgcgggcgccagccacagccctggtgcctggtggcacacaatggtgaccgc tacgacttcccctgctccaagcagagctggctatgctgggcctcaccagtgct ctggatggtgccttctgtgtggatagcatcactgcgctgaaggccctggagcga gcaagcagcccctcagaacacggcccaaggaagagctacagcctaggcagcatc tacactcgcctgtatgggcagtcccctccagactcgcacacggctgagggtgat gtcctggcccctgctcagcatctgtcagtggagaccacaggccctgctgcggtgg gtggatgctcacgccaggcctttcggcaccatcaggcccatgtatggggtcaca gcctctgctaggaccaaatgataatctaga |
| 205 | huVK3LP-hRNase1-WT-(G4S)4-hIgG1-(SCC)-NLG-hTREX1-72AA ("(G4S)4" disclosed as SEQ ID NO: 212) | metpaqllflllllwlpdttgkesrakkfqrqhmdsdsspssssstycnqmmrrrn mtqggrckpvntfvheplvdvqnvcfqekvtckngqgncyksnssmhitdcrltn gsrypncayrtspkerhiivacegspyvpvhfdasvedstgggsggggsgggg sggggslepkssdkthtcppcpapellggpsvflfppkpkdtlmisrtpevtcv vvdvshedpevkfnwyvdgvevhnaktkpreeqynstyrvvsvltvlhqdwlng keykckvsnkalpapiektiskakgqprepqvytlppsrdeltknqvsltclvk gfypsdiavewesngqpennykttppvldsdgsffyskltvdksrwqqgnvfs csvmhealhnhytqkslslspgkvdgasshvnvsspsvqdimgpgarrqgrivq grpemcfcppptplpplriltlgthtptpcsspgsaagtyptmgsgalppgpmq tliffdmeatglpfsqpkvtelcllavhrcalesppstsqgppptvppppvvdk lslcvapgkacspaaseitglstavllaahgrqcfddnlanlllaflrrqpqpwc lvahngdrydfpllqaelamlgltsaldgafcvdsitalkaleraspsehgpr ksyslgsiytrlyggsppdshtaegdvlallsicqwrpqallrwvdaharpfgt irpmygvtasartk* |
| 206 | huVK3LP-hDNase1L3-hIgG1-(SCC)-NLG-hTREX1-72AA | gttaagcttgccaccatggaaaccccagcgcagcttctcttcctcctgctactc tggctcccagataccaccggtatgaggatctgctccttcaacgtcaggtccttt ggggaaagcaagcaggaagacaagaatgccatggatgtcattgtgaaggtcatc aaacgctgtgacatcatactcgtgatggaaatcaaggacagcaacaacagtgc tgccccatactgatgagaagctgaacagaaattcaaggagaggcataacatac aactatgtgattagctctcggcttggaagaaacacatataaagaacaatatgcc tttctctacaaggaaaagctggtgtctgtgaagaggagttatcactaccatgac tatcaggatggagacgcagatgtgttttccagggagccctttgtggtctggttc caatctccccacactgctgtcaaagacttcgtgattatcccctgcacaccacc ccagagacatccgttaaggagtcgatgagttggttgaggtctacacgacgtg aaacaccgctggaaggcggagaatttcattttcatgggtgacttcaatgccggc tgcagctacgtccccaagaaggcctggaagaacatccgcttgaggactgaccc aggtttgtttggctgatcggggaccaagaggacaccacggtgaagaagagcacc |

TABLE 2-continued

| SEQ ID NO: | DESCRIPTION | SEQUENCE (NUCLEOTIDE SEQUENCES ARE 5'-3') |
|---|---|---|
| | | aactgtgcatatgacaggattgtgcttagaggacaagaaatcgtcagttctgtt
gttcccaagtcaaacagtgtttttgacttccagaaagcttacaagctgactgaa
gaggaggccctggatgtcagcgaccactttccagttgaatttaaactacagtct
tcaagggccttcaccaacagcaaaaaatctgtcactctaaggaagaaaacaaag
agcaaacgctcagatctcgagcccaaatcttctgacaaaactcacacatgtcca
ccgtgcccagcacctgaactcctgggggaccgtcagtcttcctcttcccccca
aaacccaaggacaccctcatgatctcccggacccctgaggtcacatgcgtggtg
gtggacgtgagccacgaagaccctgaggtcaagttcaactggtacgtggacggc
gtggaggtgcataatgccaagacaaagccgcgggaggagcagtacaacagcacg
taccgtgtggtcagcgtcctcaccgtcctgcaccaggactggctgaatggcaag
gagtacaagtgcaaggtctccaacaaagcccctcccagcccccatcgagaaaacc
atctccaaagccaaagggcagccccgagaaccacaggtgtacaccctgcccca
tcccgggatgagctgaccaagaaccaggtcagcctgacctgcctggtcaaaggc
ttctatcccagcgacatcgccgtggagtgggagagcaatgggcagccggagaac
aactacaagaccacgcctcccgtgctggactccgacggctccttcttcctctac
agcaagctcaccgtggacaagagcaggtggcagcaggggaacgtcttctcatgc
tccgtgatgcatgaggctctgcacaaccactacacgcagaagagcctctctctg
tctccgggtaaagtcgacggagctagcagccccgtgaacgtgagcagccccagc
gtgcaggatatcatgggccctggagctcgcagacagggcaggattgtgcaggga
aggcctgagatgtgcttctgcccacccccctaccccactccctccccttcggatc
ttaacactgggcactcacacacccaccccatgctcctctccaggctcagcagca
ggtacgtacccaaccatgggctcgcaggccctgccccccgggggcccatgcagacc
ctcatcttttcgacatggaggccactggcttgccttctcccagcccaaggtc
acggagctgtgcctgctggctgtccacagatgtgccctggagagccccccccacc
tctcaggggccacctcccacagttcctccaccaccgcgtgtggtagacaagctc
tccctgtgtgtggctccggggaaggcctgcagccctgcagccagcgagatcaca
ggtctgagcacagctgtgctggcagcgcatgggcgtcaatgttttgatgacaac
ctggccaacctgctcctagccttcctgcggcgccagccacagccctggtgcctg
gtggcacacaatggtgaccgctacgacttccccctgctccaagcagagctggct
atgctgggcctcaccagtgctctggatggtgccttctgtgtggatagcatcact
gcgctgaaggccctggagcgagcaagcagccctcagaacacggcccaaggaag
agctacagcctaggcagcatctacactcgcctgtatgggcagtcccctccagac
tcgcacacggctgagggtgatgtcctggccctgctcagcatctgtcagtggaga
ccacaggccctgctgcggtgggtggatgctcacgccaggcctttcggcaccatc
aggcccatgtatgggtcacagcctctgctaggaccaaatgataatctaga |
| 207 | huVK3LP-
hDNase1L3-
hIgG1-
(SCC)-
NLG-
hTREX1-
72AA | metpaqllfllllwlpdttgmricsfnvrsfgeskqedknamdvivkvikrcdi
ilvmeikdsnnricpilmeklnrnsrrgitynyvissrlgrntykeqyaflyke
klvsvkrsyhyhdyqdgdadvfsrepfvvwfqsphtavkdfviiplhttpetsv
keidelvevytdvkhrwkaenfifmgdfnagcsyvpkkawknirlrtdprfvwl
igdqedttvkkstncaydrivlrgqeivssvvpksnsvfdfqkayklteeeald
vsdhfpvefklqssraftnskksvtlrkktkskrsdlepkssdkthtcppcpap
ellggpsvflfppkpkdtlmisrtpevtcvvvdvshedpevkfnwyvdgvevhn
aktkpreeqynstyrvvsvltvlhqdwlngkeykckvsnkalpapiektiskak
gqprepqvytlppsrdeltknqvsltclvkgfypsdiavewesngqpennyktt
ppvldsdgsffflysklttvdksrwqqgnvfscsvmhealhnhytqkslslspgkv
dgasspvnvsspsvgdimgpgarrqgrivqgrpemcfcppptplpplriltlgt
htptpcsspgsaagtyptmgsgalppgpmqtliffdmeatglpfsqpkvtelcl
lavhrcalesppttsqgppptvppppprvvdklslcvapgkacspaaseitglsta
vlaahgrqcfddnlanlllaflrrqpqpwclvahngdrydfpllqaelamlglt
saldgafcvdsitalkalerassspsehgprksyslgsiytrlyggsppdshtae
gdvlallsicqwrpqallrwvdaharpfgtirpmygvtasartk* |

The invention claimed is:

1. A nucleic acid comprising a nucleotide sequence encoding a hybrid nuclease molecule comprising human RNase 1 operatively coupled with or without a linker to an Fc domain, and human DNase I operatively coupled with or without a linker to the Fc domain, wherein the Fc domain is a human immunoglobulin Fc domain or a mutant human immunoglobulin Fc domain.

2. The nucleic acid of claim 1, wherein the human RNase 1 is linked to the N-terminus of the Fc domain and the human DNase I is linked to the C-terminus of the Fc domain.

3. The nucleic acid of claim 1, wherein the human RNase 1 is linked to the C-terminus of the Fc domain and the human DNase I is linked to the N-terminus of the Fc domain.

4. The nucleic acid of claim 1, wherein the Fc domain comprises a human IgG1 Fc domain.

5. The nucleic acid of claim 2, wherein the Fc domain comprises a human IgG1 Fc domain.

6. The nucleic acid of claim 3, wherein the Fc domain comprises a human IgG1 Fc domain.

7. The nucleic acid of claim 1, wherein the Fc domain is a mutant Fc domain that has reduced binding to Fc receptors on human cells.

8. The nucleic acid of claim 1, wherein the nucleotide sequence comprises a first linker domain, a second linker domain, or both, wherein when the nucleotide sequence comprises a first linker domain, the human RNase 1 is operatively coupled to the Fc domain by the first linker domain, and when the nucleotide sequence comprises a second linker domain, the human DNase I is operatively coupled to the Fc domain by the second linker domain.

9. The nucleic acid of claim 8, wherein the nucleotide sequence comprises a first linker domain and a second linker domain.

10. The nucleic acid of claim 9, wherein the first linker domain comprises a nucleotide sequence encoding a gly/ser peptide of the formula (Gly$_4$Ser)n (SEQ ID NO: 210), wherein n is a positive integer selected from the group consisting of 1, 2, 3, 4, 5, 6, 7, 8, 9, and 10, and the second linker domain comprises a nucleotide sequence encoding an NLG peptide comprising the amino acid sequence set forth in SEQ ID NO: 168, wherein the first linker domain is coupled to the C-terminus of the human RNase 1 and the N-terminus of the Fc domain, and wherein the second linker domain is coupled to the C-terminus of the Fc domain and the N-terminus of the human DNase I.

11. The nucleic acid of claim 8, wherein the first linker domain comprises a nucleotide sequence encoding a gly/ser peptide of the formula (Gly$_4$Ser)n (SEQ ID NO: 210), wherein n is a positive integer selected from the group consisting of 1, 2, 3, 4, 5, 6, 7, 8, 9, and 10.

12. The nucleic acid of claim 8, wherein the second linker domain comprises a nucleotide sequence encoding an NLG peptide comprising the amino acid sequence set forth in SEQ ID NO: 168.

13. The nucleic acid of claim 1, wherein the Fc domain comprises a nucleotide sequence encoding a mutant human IgG1 Fc domain comprising one or more of the mutations selected from P238S, P331S, K322S, N297S, wherein numbering is according to the EU index.

14. The nucleic acid of claim 2, wherein the Fc domain comprises a nucleotide sequence encoding a mutant human IgG1 Fc domain comprising one or more of the mutations selected from P238S, P331S, K322S, N297S, wherein numbering is according to the EU index.

15. The nucleic acid of claim 12, wherein the Fc domain comprises a nucleotide sequence encoding a mutant human IgG1 Fc domain comprising one or more of the mutations selected from P238S, P331S, K322S, N297S, wherein numbering is according to the EU index.

16. The nucleic acid of claim 1, wherein the nucleotide sequence further comprises a nucleotide sequence encoding a leader sequence.

17. The nucleic acid of claim 16, wherein the leader sequence is human VK3LP peptide, and wherein the leader sequence is coupled to the N-terminus of the human RNase 1.

18. The nucleic acid of claim 8, wherein the first linker domain, the second linker domain, or both, comprise a nucleic acid sequence encoding a gly/ser peptide.

19. The nucleic acid of claim 18, wherein the gly/ser peptide is of the formula (Gly$_4$Ser)n, (SEQ ID NO: 210), wherein n is a positive integer selected from the group consisting of 1, 2, 3, 4, 5, 6, 7, 8, 9, and 10.

20. The nucleic acid of claim 19, wherein the gly/ser peptide comprises (Gly$_4$Ser)3 (SEQ ID NO: 211), (Gly$_4$Ser)4 (SEQ ID NO: 212), or (Gly$_4$Ser)5 (SEQ ID NO:209).

21. The nucleic acid of claim 8, wherein the first linker domain, the second linker domain, or both, comprise a nucleotide sequence encoding an NLG peptide comprising the amino acid sequence set forth in SEQ ID NO: 168.

22. The nucleic acid of claim 21, wherein the NLG peptide comprises an N-linked glycosylation site.

23. The nucleic acid of claim 1, wherein the human RNase 1 comprises a nucleic acid sequence encoding the amino acid sequence set forth in SEQ ID NO:149, with or without a leader sequence.

24. The nucleic acid of claim 23, wherein the Fc domain comprises a nucleotide sequence encoding the amino acid sequence set forth in SEQ ID NO:145.

25. The nucleic acid of claim 23, wherein the human DNase I comprises a nucleotide sequence encoding the amino acid sequence set forth in SEQ ID NO:143.

26. The nucleic acid of claim 23, wherein the human DNase I comprises a nucleotide sequence encoding a G105R mutation as set forth in SEQ ID NO: 142.

27. The nucleic acid of claim 26, wherein the Fc domain is a mutant human IgG1 Fc domain comprising a nucleotide sequence encoding one or more of the mutations selected from P238S, P331S, K322S, and N297S, numbering is according to the EU index.

28. The nucleic acid of claim 27, wherein the Fc domain comprises a nucleotide sequence encoding a P238S mutation, numbering is according to the EU index.

29. The nucleic acid of claim 23, wherein the human DNase I comprises a nucleotide sequence encoding mutations G105R and A114F as set forth in SEQ ID NO:139.

30. The nucleic acid of claim 29 further comprising a linker domain comprising a nucleotide sequence encoding an NLG peptide comprising the amino acid sequence set forth in SEQ ID NO: 168, and wherein the linker domain is coupled to the C-terminus of the human Fc domain and the N-terminus of human DNase I.

31. The nucleic acid of claim 29, wherein the Fc domain comprises a nucleotide sequence encoding a mutant human IgG1 Fc domain comprising one or more of the mutations selected from P238S, P331S, K322S, N297S, numbering is according to the EU index.

32. The nucleic acid of claim 31, wherein the Fc domain comprises a nucleotide sequence encoding a P238S mutation, numbering is according to the EU index.

33. The nucleic acid of claim 1, wherein the human RNase 1 comprises a nucleotide sequence encoding the amino acid sequence set forth in SEQ ID NO: 149, without a leader sequence.

34. The nucleic acid of claim 33, wherein the leader sequence comprises a nucleotide sequence encoding the amino acid sequence set forth in SEQ ID NO: 224.

35. The nucleic acid of claim 1, wherein the human RNase 1 comprises a nucleotide sequence encoding mutation G88D as set forth in SEQ ID NO: 146.

36. The nucleic acid of claim 33, wherein the Fc domain comprises a nucleotide sequence encoding the amino acid sequence set forth in SEQ ID NO: 145.

37. The nucleic acid of claim 33, wherein the Fc domain comprises a nucleotide sequence encoding a mutant human IgG1 Fc domain comprising one or more of the mutations selected from P238S, P331S, K322S, and N297S, numbering is according to the EU index.

38. The nucleic acid of claim 37, wherein the Fc domain comprises a nucleotide sequence encoding a P238S mutation, numbering is according to the EU index.

39. The nucleic acid of claim 34, wherein the Fc domain comprises a nucleotide sequence encoding the amino acid sequence set forth in SEQ ID NO: 145.

40. The nucleic acid of claim 34, wherein the Fc domain comprises a nucleotide sequence encoding a mutant human IgG1 Fc domain comprising one or more of the mutations selected from P238S, P331S, K322S, and N297S, numbering is according to the EU index.

41. The nucleic acid of claim 40, wherein the Fc domain comprises a nucleotide sequence encoding a P238S mutation, numbering is according to the EU index.

42. The nucleic acid of claim 37, wherein the human DNase I comprises a nucleotide sequence encoding mutations G105R and A114F as set forth in SEQ ID NO: 139.

43. The nucleic acid of claim 40, wherein the human DNase I comprises a nucleotide sequence encoding mutations G105R and A114F as set forth in SEQ ID NO: 139.

44. A nucleic acid comprising a nucleotide sequence encoding a hybrid nuclease molecule comprising (a) the amino acid sequence set forth in SEQ ID NO: 151, with or without a leader sequence, or (b) the amino acid sequence set forth in SEQ ID NO: 151, with or without a leader sequence and comprising one or more Fc mutations selected from P238S, P331S, K322S, and N297S, numbering is according to the EU index.

45. The nucleic acid of claim 44, wherein the leader sequence comprises a nucleotide sequence encoding the amino acid sequence set forth in SEQ ID NO: 225.

46. The nucleic acid of claim 44, comprising a nucleotide sequence encoding the amino acid sequence set forth in SEQ ID NO:151 without a leader sequence and comprising one or more of the Fc mutations selected from P238S, P331S, K322S, and N297S, numbering is according to the EU index.

47. The nucleic acid of claim 46, wherein the Fc domain comprises a nucleotide sequence encoding a P238S mutation, numbering is according to the EU index.

48. The nucleic acid of claim 44 comprising a nucleotide sequence encoding the amino acid sequence set forth in SEQ ID NO:151 without a leader sequence.

49. The nucleic acid of claim 44, wherein Fc domain comprises a nucleotide sequence encoding a P238S mutation, numbering is according to the EU index.

50. The nucleic acid of claim 1, wherein the Fc domain comprises a nucleotide sequence encoding a mutant human IgG1 Fc domain comprising a substitution of one or more of three hinge region cysteine residues with serine.

51. The nucleic acid of claim 2, wherein the Fc domain comprises a nucleotide sequence encoding a mutant human IgG1 Fc domain comprising a substitution of one or more of three hinge region cysteine residues with serine.

52. The nucleic acid of claim 13, wherein the mutant human IgG1 Fc domain comprises a nucleotide sequence encoding a substitution of one or more of three hinge region cysteine residues with serine.

53. The nucleic acid of claim 42, wherein the mutant human IgG1 Fc domain comprises a nucleotide sequence encoding a substitution of one or more of three hinge region cysteine residues with serine.

54. The nucleic acid of claim 27, wherein the Fc domain comprises a nucleotide sequence encoding a P331S mutation, numbering is according to the EU index.

55. The nucleic acid of claim 31, wherein the Fc domain comprises a nucleotide sequence encoding a P331S mutation, numbering is according to the EU index.

56. The nucleic acid of claim 37, wherein the Fc domain comprises a nucleotide sequence encoding a P331S mutation, numbering is according to the EU index.

57. The nucleic acid of claim 40, wherein the Fc domain comprises a nucleotide sequence encoding a P331S mutation, numbering is according to the EU index.

58. The nucleic acid of claim 46, wherein the Fc domain comprises a nucleotide sequence encoding a P331S mutation, numbering is according to the EU index.

59. The nucleic acid of claim 48, wherein the Fc domain comprises a nucleotide sequence encoding a P331S mutation, numbering is according to the EU index.

60. The nucleic acid of claim 37, wherein the human DNase I comprises a nucleotide sequence encoding the amino acid sequence set forth in SEQ ID NO: 143.

61. The nucleic acid of claim 40, wherein the human DNase I comprises a nucleotide sequence encoding the amino acid sequence set forth in SEQ ID NO: 143.

62. A nucleic acid comprising a nucleotide sequence encoding the amino acid sequence of SEQ ID NO: 152, with or without a leader sequence.

63. A nucleic acid of claim 62 comprising a nucleotide sequence encoding the amino acid sequence of SEQ ID NO: 152 without a leader sequence.

64. A nucleic acid comprising a nucleotide sequence encoding the amino acid sequence of SEQ ID NO: 153, with or without a leader sequence.

65. A nucleic acid of claim 64 comprising a nucleotide sequence encoding the amino acid sequence of SEQ ID NO: 153 without a leader sequence.

66. A nucleic acid comprising a nucleotide sequence encoding the amino acid sequence of SEQ ID NO: 173, with or without a leader sequence.

67. A nucleic acid of claim 66 comprising a nucleotide sequence encoding the amino acid sequence of SEQ ID NO: 173 without a leader sequence.

68. A nucleic acid comprising a nucleotide sequence encoding the amino acid sequence of SEQ ID NO: 177, with or without a leader sequence.

69. A nucleic acid of claim 68 comprising a nucleotide sequence encoding the amino acid sequence of SEQ ID NO: 177 without a leader sequence.

70. A nucleic acid comprising a nucleotide sequence encoding the amino acid sequence of SEQ ID NO: 179, with or without a leader sequence.

71. A nucleic acid of claim 70 comprising a nucleotide sequence encoding the amino acid sequence of SEQ ID NO: 179 without a leader sequence.

72. A nucleic acid comprising a nucleotide sequence encoding the amino acid sequence of SEQ ID NO: 181, with or without a leader sequence.

73. A nucleic acid of claim 72 comprising a nucleotide sequence encoding the amino acid sequence of SEQ ID NO: 181 without a leader sequence.

74. A nucleic acid comprising a nucleotide sequence encoding a human RNase 1 operatively linked with or without a linker to the N-terminus of a mutant human IgG1

Fc domain, and human DNase I operatively linked with or without a linker to the C-terminus of the mutant Fc domain, wherein the human RNase 1 comprises a nucleotide sequence encoding the amino acid sequence set forth in SEQ ID NO: 149, with or without a leader sequence, and wherein the human DNase I comprises a nucleotide sequence encoding the amino acid sequence set forth in SEQ ID NO: 139.

75. The nucleic acid of claim 74, wherein the human RNase 1 comprises a nucleotide sequence encoding the amino acid sequence set forth in SEQ ID NO: 149, without a leader sequence.

76. The nucleic acid of claim 75, wherein the mutant Fc domain comprises a nucleotide sequence encoding one or more of the mutations selected from P238S, P331S, K322S, and N297S, numbering is according to the EU index.

77. The nucleic acid of claim 76, wherein the mutant Fc domain comprises a nucleotide sequence encoding a P238S mutation, numbering is according to the EU index.

78. The nucleic acid of claim 76, wherein the mutant Fc domain comprises a nucleotide sequence encoding a P331S mutation, numbering is according to the EU index.

79. The nucleic acid of claim 76, wherein the mutant Fc domain comprises a nucleotide sequence encoding a substitution of one or more of three hinge region cysteine residues with serine.

80. The nucleic acid of claim 79 wherein the nucleotide sequence comprises a linker domain comprising a nucleotide sequence encoding an NLG peptide comprising the amino acid sequence set forth in SEQ ID NO: 168, and wherein the linker domain is coupled to the C-terminus of the human Fc domain and the N-terminus of human DNase I.

81. A recombinant expression vector comprising a nucleic acid according to claim 1.

82. A host cell transformed with the recombinant expression vector according to claim 81.

83. A method of making a homodimer, comprising: providing the host cell of claim 82 and maintaining the host cell under conditions in which the nucleic acid is expressed as a homodimer.

84. The method of claim 83, further comprising isolating the homodimer.

* * * * *

SEQUENCE LISTING

<160> NUMBER OF SEQ ID NOS: 225

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttaagcttg ccaccatggg tctggagaag tccctcattc tg                         42

<210> SEQ ID NO 2
<211> LENGTH: 39

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gataccaccg gtagggaatc tgcagcacag aagtttcag                            39

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggctcgagca cagtagcatc aaagtggact ggtacgtagg                           40

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaatctagac ctcaaccagg tagggaatct gcagcacaga agtttcag                  48

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctagactat cacacagtag catcaaagtg gactggtacg tag                       43

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtccaccgt gtccagcacc tgaactcctg ggtggatcgt cagtcttcc                 49

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agatctcgag cccaaatctt ctgacaaaac tcacacatgt ccaccgtgt                 49

<210> SEQ ID NO 8
<211> LENGTH: 51
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 8
tctagattat catttacccg gagacagaga gaggctcttc tgcgtgtagt g          51

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cctccatgca aatgcccagc acctaacctc ttgggtggat catccgtctt catcttcc          58

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gaagatctcg agcccagagg tcccacaatc aagccctctc ctcca          45

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gtttctagat tatcatttac ccggagtccg agagaagctc ttagtcgt          48

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
agatctcgag cccaaatctt ctgacaaaac tcacacatgt ccaccgtgt          49

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gttttctcga tggaggctgg gagggctttg ttggagacc          39

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaggtctcca acaaagccct cccagcctcc atcgagaaaa caatctcc                    48

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctagattat catttacccg gagacagaga gaggctcttc tgcgtgtagt g                51

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accggtaagg aatcccgggc caagaaattc c                                      31

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcgagatct gtagagtcct ccacagaagc atcaaagtgg                             40

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agactgccgc ctgacaaacg actccaggta ccc                                    33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggtacctgg agtcgtttgt caggcggcag tct                                    33

<210> SEQ ID NO 20
<211> LENGTH: 37
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 20
accggtatgg gctcacagac cctgccccat ggtcaca                              37

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctcgagatct gttgttccag tggtagccgg agtgccgtac atg                       43

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttaagcttg ccaccatgtc cctgcaccca gcttccccac gcctg                     45

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctcgagatct gaggagcgat tgccttttttt tctcttttttg agag                    44

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
accggtctaa ggctctgctc cttcaatgtg aggtcctttg ga                        42

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcgagatct gaggagcgat tgccttttttt tctcttttttg agag                    44

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 26
gttaccggtc tgaagatcgc agccttcaac atccag                                36

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gttctcgaga tctttcagca tcacctccac tggatagtg                             39

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttgatatcc tgaagatcgc agccttcaac atccag                                36

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtttctagat tatcacttca gcatcacctc cactggatag tg                         42

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgtccaccgt gtccagcacc tgaactcctg ggtggatcgt cagtcttcc                  49

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agatctcgag cccaaatctt ctgacaaaac tcacacatgt ccaccgtgt                  49

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaagatctcg agcccaaatc ttctgacaaa actcacacat gt                           42

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttagatctc gagcccaaat cttctgacaa aactcacaca tct                          43

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctagattat catttacccg gagacagaga gaggctcttc tgcgtgtagt g                 51

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaggtctcca acaaagccct cccagcctcc atcgagaaaa caatctcc                     48

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gttttctcga tggaggctgg gagggctttg ttggagacc                               39

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aagcttgcca ccatggctct ggagaagtct cttgtccggc tcc                          43

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctcgagatct gtagagtcct ccacagaagc atcaaagtgg                                40

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
accggtaagg aatcccgggc caagaaattc c                                         31

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatatccctt ccctgggcaa ggaatcccgg gccaagaaat tccag                          45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtttctagat tattaggtag agtcctccac agaagcatca aagtg                          45

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtaagcttg ccaccatgtc acgggagctg gccccactgc tgctt                          45

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctcgagatct gaggagcgtt tgctctttgt tttcttcctt ag                             42

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
accggtatga ggatctgctc cttcaacgtc aggtcctttg g                    41

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gttaccggtc tgaagatcgc agccttcaac atccag                              36

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttctcgaga tctttcagca tcacctccac tggatagtg                           39

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gttgatatcc tgaagatcgc agccttcaac atccag                              36

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtttctagat tatcacttca gcatcacctc cactggatag tg                       42

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gatggctgcg agccctgcag gaacgacacc ttcaaccgag agccattcat tgtcaggttc    60

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gaacctgaca atgaatggct ctcggttgaa ggtgtcgttc ctgcagggct cgcagccatc    60

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggagaagaac ctgacaatga atggctctcg gttgaaggt                            39

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
accttcaacc gagagccatt cattgtcagg ttcttctcc                            39

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
accggtatgg gccctggagc tcgcagacag ggcag                                35

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctcgagatct ttggtcctag cagaggctgt gacc                                 34

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
accggtctcg agatgggccc tggagctcgc agacagg                              37

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctcgagtttg gtcctagcag aggctgtgac c                                    31

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
accggtatgg gctcacagac cctgccccat ggtcaca                              37

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctcgagatct gttgttccag tggtagccgg agtgccgtac atg                       43

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gttaagcttg ccaccatgtc cctgcaccca gcttccccac gcctg                     45

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctcgagatct gaggagcgat tgccttttttt tctcttttttg agag                    44

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gttaagcttg ccaccatggg tctggagaag tccctcattc tg                        42

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggctcgagca cagtagcatc aaagtggact ggtacgtagg                           40

<210> SEQ ID NO 63
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cctccatgca aatgcccagc acctaacctc ttgggtggat catccgtctt catcttcc         58

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agatctcgag cccagaggtc ccacaatcaa gccctctcct ccatgcaaat gcc              53

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaagatctcg agcccagagg tcccacaatc aagccctctc ctcca                      45

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atcaagccct ctcctccatc taaatcccca gcacctaac                             39

<210> SEQ ID NO 67
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agtggcaagg agttcaaatg ctcggtcaag aagaaagacc tcccagcgtc catcgag         57

<210> SEQ ID NO 68
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggttctctcg atggacgctg ggaggtcttt gttgttgacc gagcatttga actcc           55

-continued

```
<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtttctagat tatcatttac ccggagtccg agagaagctc ttagtcgt                    48

<210> SEQ ID NO 70
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gctagctccg tcgactttac ccggagacag agagagg                                37

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gactggctga atggcaagga gtacaagtgc tcggtctcca acaaagccct c                 51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gagggctttg ttggagaccg agcacttgta agacttgcca ttcagccagt c                 51

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccgcgggagg agcagtacag cagcacgtac cgtgtggtca gcgtc                        45

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gacgctgacc acacggtacg tgctgctgta ctgctcctcc cgcgg                        45

<210> SEQ ID NO 75
```

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gatatctcta gatttacccg gagtccgaga gaagctctta gtcgt            45

<210> SEQ ID NO 76
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gatatctccg gagtcgactt tacccggagt ccgagagaag ctcttag          47

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cacaaaccca tagagaggat tacagcagta ctctccgggt ggtc             44

<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gaccacccgg agagtactgc tgtaatcctc tctatgggtt tgag             44

<210> SEQ ID NO 79

<400> SEQUENCE: 79

000

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gatatcaccg gtagaaccac ctccaccact cccacctcct ccagtgcctc c      51

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtcgactccg aggaggtgg ctcaggtggt ggaggcagtg gaggaggtgg        50

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aaagtcgacg gagctagcag ccccgtgaac gtgagcagcc ccagcgtg         48

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cccatgatat cctgcacgct ggggctgctc                             30

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
accggtatga ggatctgctc cttcaacgtc aggtcctttg g                41

<210> SEQ ID NO 85
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agatctttat caggagcgtt tgctctttgt tttcttcctt ag               42

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tctagattat caggagcgat tgccttttt tctcttttg agag               44

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
accggtctaa ggctctgctc cttcaatgtg aggtcctttg ga             42

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gataccaccg gtagggaatc tgcagcacag aagtttcag                39

<210> SEQ ID NO 89
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aaatctagac ctcaaccagg tagggaatct gcagcacaga agtttcag       48

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tctagactat cacacagtag catcaaagtg gactggtacg ta             42

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agactgccgc ctgacaaacg actccaggta ccc                       33

<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gggtacctgg agtcgtttgt caggcggcag tct                       33

<210> SEQ ID NO 93
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggctcaggtg gtggaggatc tgaggaggt ggctcaggtg gtggaggatc tg    52

<210> SEQ ID NO 94
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gttagatctc tccggaggag gtggctcagg tggtggagga tctgga    46

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctcgagactc ccacctcctc cagatcctcc accacctgag ccacct    46

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aaagatctct ccggaggagg tggctcaggt ggtggaggat ctggaggagg    50

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ctcgagaccg gtagaaccac ctccaccact cccacctcct ccagatcctc    50

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gttagatctc tccggaggag gtggctca    28

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
accggtctcg agactcccac ctcctccaga tc    32

<210> SEQ ID NO 100
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agatctctcc ggaggaggtg gctcaggtgg tggaggatct ggaggaggtg ggagtggtgg    60
aggtggttct accggtctcg ag                                             82

<210> SEQ ID NO 101
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
agatctctcc ggaggaggtg gctcaggtgg tggaggatct ggaggaggtg gctcaggtgg    60
tggaggatct ggaggaggtg ggagtaccgg tctcgag                             97

<210> SEQ ID NO 102
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
agatctctcc ggaggaggtg gctcaggtgg tggaggatct ggaggaggtg gctcaggtgg    60
tggaggatct ggaggaggtg ggagtctcga g                                   91

<210> SEQ ID NO 103
<211> LENGTH: 462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gtcgacggag ctagcagccc cgtgaacgtg agcagcccca gcgtgcagga tatcccttcc    60
ctgggcaagg aatcccgggc caagaaattc cagcggcagc atatggactc agacagttcc   120
cccagcagca gctccaccta ctgtaaccaa atgatgaggc gccggaatat gacacagggg   180
cggtgcaaac cagtgaacac ctttgtgcac gagcccctgg tagatgtcca gaatgtctgt   240
ttccaggaaa aggtcacctg caagaacggg cagggcaact gctacaagag caactccagc   300
atgcacatca cagactgccg cctgacaaac gactccaggt accccaactg tgcataccgg   360
accagcccga aggagagaca catcattgtg gcctgtgaag ggagcccata tgtgccagtc   420
cactttgatg cttctgtgga ggactctacc taataatcta ga                      462

<210> SEQ ID NO 104
<211> LENGTH: 798
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 104

| | |
|---|---|
| gatatcctga agatcgcagc cttcaacatc cagacatttg gggagaccaa gatgtccaat | 60 |
| gccaccctcg tcagctacat tgtgcagatc ctgagccgct atgacatcgc cctggtccag | 120 |
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcag gaacgacacc ttcaaccgag agccattcat tgtcaggttc | 360 |
| ttctcccggt tcacagaggt cagggagttt gccattgttc ccctgcatgc ggccccgggg | 420 |
| gacgcagtag ccgagatcga cgctctctat gacgtctacc tggatgtcca agagaaatgg | 480 |
| ggcttggagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaagtgat aatctaga | 798 |

<210> SEQ ID NO 105
<211> LENGTH: 798
<212> TYPE: DNA
<213> ORGANISM: Homo sapiens

<400> SEQUENCE: 105

| | |
|---|---|
| gatatcctga agatcgcagc cttcaacatc cagacatttg gggagaccaa gatgtccaat | 60 |
| gccaccctcg tcagctacat tgtgcagatc ctgagccgct atgacatcgc cctggtccag | 120 |
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcgg gaacgacacc ttcaaccgag agccagccat tgtcaggttc | 360 |
| ttctcccggt tcacagaggt cagggagttt gccattgttc ccctgcatgc ggccccgggg | 420 |
| gacgcagtag ccgagatcga cgctctctat gacgtctacc tggatgtcca agagaaatgg | 480 |
| ggcttggagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaaatgat aatctaga | 798 |

<210> SEQ ID NO 106
<211> LENGTH: 798
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106

```
gatatcctga agatcgcagc cttcaacatc cagacatttg gggagaccaa gatgtccaat      60
gccaccctcg tcagctacat tgtgcagatc ctgagccgct atgacatcgc cctggtccag     120
gaggtcagag acagccacct gactgccgtg gggaagctgc tggacaacct caatcaggat     180
gcaccagaca cctatcacta cgtggtcagt gagccactgg gacggaacag ctataaggag     240
cgctacctgt tcgtgtacag gcctgaccag gtgtctgcgg tggacagcta ctactacgat     300
gatggctgcg agccctgcgg gaacgacacc ttcaaccgag agccattcat tgtcaggttc     360
ttctcccggt tcacagaggt cagggagttt gccattgttc ccctgcatgc ggccccgggg     420
gacgcagtag ccgagatcga cgctctctat gacgtctacc tggatgtcca agagaaatgg     480
ggcttagagg acgtcatgtt gatgggcgac ttcaatgcgg gctgcagcta tgtgagaccc     540
tcccagtggt catccatccg cctgtggaca agccccacct tccagtggct gatccccgac     600
agcgctgaca ccacagctac acccacgcac tgtgcctatg acaggatcgt ggttgcaggg     660
atgctgctcc gaggcgccgt tgttcccgac tcggctcttc cctttaactt ccaggctgcc     720
tatggcctga gtgaccaact ggcccaagcc atcagtgacc actatccagt ggaggtgatg     780
ctgaagtgat aatctaga                                                    798

<210> SEQ ID NO 107
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
accggtctga agatcgcagc cttcaacatc cagacatttg gggagaccaa gatgtccaat      60
gccaccctcg tcagctacat tgtgcagatc ctgagccgct atgacatcgc cctggtccag     120
gaggtcagag acagccacct gactgccgtg gggaagctgc tggacaacct caatcaggat     180
gcaccagaca cctatcacta cgtggtcagt gagccactgg gacggaacag ctataaggag     240
cgctacctgt tcgtgtacag gcctgaccag gtgtctgcgg tggacagcta ctactacgat     300
gatggctgcg agccctgcag gaacgacacc ttcaaccgag agccattcat tgtcaggttc     360
ttctcccggt tcacagaggt cagggagttt gccattgttc ccctgcatgc ggccccgggg     420
gacgcagtag ccgagatcga cgctctctat gacgtctacc tggatgtcca agagaaatgg     480
ggcttggagg acgtcatgtt gatgggcgac ttcaatgcgg gctgcagcta tgtgagaccc     540
tcccagtggt catccatccg cctgtggaca agccccacct tccagtggct gatccccgac     600
agcgctgaca ccacagctac acccacgcac tgtgcctatg acaggatcgt ggttgcaggg     660
atgctgctcc gaggcgccgt tgttcccgac tcggctcttc cctttaactt ccaggctgcc     720
tatggcctga gtgaccaact ggcccaagcc atcagtgacc actatccagt ggaggtgatg     780
ctgaaagatc tcgag                                                       795

<210> SEQ ID NO 108
<211> LENGTH: 795
<212> TYPE: DNA
<213> ORGANISM: Homo sapiens

<400> SEQUENCE: 108
accggtctga agatcgcagc cttcaacatc cagacatttg gggagaccaa gatgtccaat      60
gccaccctcg tcagctacat tgtgcagatc ctgagccgct atgacatcgc cctggtccag     120
```

| | |
|---|---|
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcgg gaacgacacc ttcaaccgag agccagccat tgtcaggttc | 360 |
| ttctcccggt tcacagaggt cagggagttt gccattgttc ccctgcatgc ggccccgggg | 420 |
| gacgcagtag ccgagatcga cgctctctat gacgtctacc tggatgtcca agagaaatgg | 480 |
| ggcttggagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaaagatc tcgag | 795 |

<210> SEQ ID NO 109
<211> LENGTH: 795
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

| | |
|---|---|
| accggtctga agatcgcagc cttcaacatc cagacatttg gggagaccaa gatgtccaat | 60 |
| gccaccctcg tcagctacat tgtgcagatc ctgagccgct atgacatcgc cctggtccag | 120 |
| gaggtcagag acagccacct gactgccgtg gggaagctgc tggacaacct caatcaggat | 180 |
| gcaccagaca cctatcacta cgtggtcagt gagccactgg gacggaacag ctataaggag | 240 |
| cgctacctgt tcgtgtacag gcctgaccag gtgtctgcgg tggacagcta ctactacgat | 300 |
| gatggctgcg agccctgcgg gaacgacacc ttcaaccgag agccattcat tgtcaggttc | 360 |
| ttctcccggt tcacagaggt cagggagttt gccattgttc ccctgcatgc ggccccgggg | 420 |
| gacgcagtag ccgagatcga cgctctctat gacgtctacc tggatgtcca agagaaatgg | 480 |
| ggcttagagg acgtcatgtt gatgggcgac ttcaatgcgg gctgcagcta tgtgagaccc | 540 |
| tcccagtggt catccatccg cctgtggaca agccccacct tccagtggct gatccccgac | 600 |
| agcgctgaca ccacagctac acccacgcac tgtgcctatg acaggatcgt ggttgcaggg | 660 |
| atgctgctcc gaggcgccgt tgttcccgac tcggctcttc cctttaactt ccaggctgcc | 720 |
| tatggcctga gtgaccaact ggcccaagcc atcagtgacc actatccagt ggaggtgatg | 780 |
| ctgaaagatc tcgag | 795 |

<210> SEQ ID NO 110
<211> LENGTH: 715
<212> TYPE: DNA
<213> ORGANISM: Homo sapiens

<400> SEQUENCE: 110

| | |
|---|---|
| agatctcgag cccaaatctt ctgacaaaac tcacacatgt ccaccgtgcc cagcacctga | 60 |
| actcctgggg ggaccgtcag tcttcctctt ccccccaaaa cccaaggaca cctcatgat | 120 |
| ctcccggacc cctgaggtca catgcgtggt ggtggacgtg agccacgaag accctgaggt | 180 |
| caagttcaac tggtacgtgg acggcgtgga ggtgcataat gccaagacaa agccgcggga | 240 |

```
ggagcagtac aacagcacgt accgtgtggt cagcgtcctc accgtcctgc accaggactg    300
gctgaatggc aaggagtaca agtgcaaggt ctccaacaaa gccctcccag cccccatcga    360
gaaaaccatc tccaaagcca agggcagcc ccgagaacca caggtgtaca ccctgccccc     420
atcccgggat gagctgacca agaaccaggt cagcctgacc tgcctggtca aaggcttcta    480
tcccagcgac atcgccgtgg agtgggagag caatgggcag ccggagaaca actacaagac    540
cacgcctccc gtgctggact ccgacggctc cttcttcctc tacagcaagc tcaccgtgga    600
caagagcagg tggcagcagg ggaacgtctt ctcatgctcc gtgatgcatg aggctctgca    660
caaccactac acgcagaaga gcctctctct gtctccgggt aaatgataat ctaga         715

<210> SEQ ID NO 111
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gttaagcttg ccaccatgga aacccagcg cagcttctct tcctcctgct actctggctc      60
ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
ctggtccagg aggtcagaga cagccacctg actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcggg aacgacacct caaccgaga gccagccatt     420 gtcaggttct ctcccggtt cacagaggtc agggagtttg ccattgttcc cctgcatgcg     480 gccccgggg acgcagtagc cgagatcgac gctctctatg acgtctacct ggatgtccaa     540
gagaaatggg gcttggagga cgtcatgttg atgggcgact tcaatgcggg ctgcagctat    600
gtgagaccct cccagtggtc atccatccgc tgtggacaa gccccacctt ccagtggctg      660
atccccgaca gcgctgacac cacagctaca cccacgcact gtgccatga caggatcgtg      720 gttgcaggga tgctgctccg aggcgccgtt gttcccgact cggctcttcc cttaacttc      780 caggctgcct atggcctgag tgaccaactg gcccaagcca tcagtgacca ctatccagtg    840
gaggtgatgc tgaagtga                                                  858

<210> SEQ ID NO 112
<211> LENGTH: 918
<212> TYPE: DNA
<213> ORGANISM: Homo sapiens

<400> SEQUENCE: 112
atgtcacggg agctggcccc actgctgctt ctcctcctct ccatccacag cgccctggcc     60
atgaggatct gctccttcaa cgtcaggtcc tttgggaaa gcaagcagga agacaagaat    120
gccatggatg tcattgtgaa ggtcatcaaa cgctgtgaca tcatactcgt gatggaaatc    180
aaggacagca acaacaggat ctgccccata ctgatggaga agctgaacag aaattcaagg    240
agaggcataa catacaacta tgtgattagc tctcggcttg aagaaacac atataaagaa     300 caatatgcct ttctctacaa ggaaaagctg gtgtctgtga agaggagtta tcactaccat    360
gactatcagg atggagacgc agatgtgttt tccagggagc cctttgtggt ctggttccaa    420
```

```
tctccccaca ctgctgtcaa agacttcgtg attatccccc tgcacaccac cccagagaca      480
tccgttaagg agatcgatga gttggttgag gtctacacgg acgtgaaaca ccgctggaag      540
gcggagaatt tcattttcat gggtgacttc aatgccggct gcagctacgt ccccaagaag      600
gcctggaaga acatccgctt gaggactgac cccaggtttg tttggctgat cggggaccaa      660
gaggacacca cggtgaagaa gagcaccaac tgtgcatatg acaggattgt gcttagagga      720
caagaaatcg tcagttctgt tgttcccaag tcaaacagtg tttttgactt ccagaaagct      780
tacaagctga ctgaagagga ggccctggat gtcagcgacc actttccagt tgaatttaaa      840
ctacagtctt caagggcctt caccaacagc aaaaaatctg tcactctaag gaagaaaaca      900
aagagcaaac gctcctag                                                    918

<210> SEQ ID NO 113
<211> LENGTH: 459
<212> TYPE: DNA
<213> ORGANISM: Homo sapiens

<400> SEQUENCE: 113
atgggtctgg agaagtctct tgtccggctc cttctgcttg tcctgatact gctggtgctg       60
ggctgggtcc agccttccct gggcaaggaa tcccgggcca agaaattcca gcggcagcat      120
atggactcag acagttcccc cagcagcagc tccacctact gtaaccaaat gatgaggcgc      180
cggaatatga cacaggggcg gtgcaaacca gtgaacacct tgtgcacga gcccctggta      240 gatgtccaga atgtctgttt ccaggaaaag gtcacctgca agaacgggca gggcaactgc      300
tacaagagca actccagcat gcacatcaca gactgccgcc tgacaaacgg ctccaggtac      360
cccaactgtg cataccggac cagcccgaag gagagacaca tcattgtggc ctgtgaaggg      420
agcccatatg tgccagtcca ctttgatgct actgtgtag                             459

<210> SEQ ID NO 114
<211> LENGTH: 1162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gttaagcttg ccaccatgga accccagcg cagcttctct tcctcctgct actctggctc       60
ccagatacca ccggtaggga atctgcagca cagaagtttc agcggcagca catggatcca      120
gatggttcct ccatcaacag ccccacctac tgcaaccaaa tgatgaaacg ccgggatatg      180
acaaatgggt catgcaagcc cgtgaacacc ttcgtgcatg agcccttggc agatgtccag      240
gccgtctgct cccaggaaaa tgtcacctgc aagaacagga gagcaactg ctacaagagc      300 agctctgccc tgcacatcac tgactgccac ctgaagggca actccaagta tcccaactgt      360
gactacaaga ccactcaata ccagaagcac atcattgtgg cctgtgaagg aaccccctac      420
gtaccagtcc actttgatgc tactgtgctc gagcccagag gtctcacaat caagccctct      480
cctccatgca aatgcccagc acctaacctc ttgggtggat catccgtctt catcttccct      540
ccaaagatca aggatgtact catgatctcc ctgagcccca tggtcacatg tgtggtggtg      600
gatgtgagcg aggatgaccc agacgtccag atcagctggt ttgtgaacaa cgtggaagta      660
cacacagctc agacacaaac ccatagagag gattacaaca gtactctccg ggtggtcagt      720
gccctcccca tccagcacca ggactggatg agtggcaagg agttcaaatg ctcggtcaac      780
```

```
aacaaagacc tcccagcgtc catcgagaga accatctcaa aacccagagg gccagtaaga      840
gctccacagg tatatgtctt gcctccacca gcagaagaga tgactaagaa agagttcagt      900
ctgacctgca tgatcacagg cttcttacct gccgaaattg ctgtggactg gaccagcaat      960
gggcgtacag agcaaaacta caagaacacc gcaacagtcc tggactctga tggttcttac     1020
ttcatgtaca gcaagctcag agtacaaaag agcacttggg aaagaggaag tcttttcgcc     1080
tgctcagtgg tccacgaggg tctgcacaat caccttacga ctaagagctt ctctcggact     1140
ccgggtaaat gataatctag aa                                              1162
```

<210> SEQ ID NO 115
<211> LENGTH: 2004
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1921)..(1921)
<223> OTHER INFORMATION: a, c, t, g, unknown or other

<400> SEQUENCE: 115

```
aagcttgccg ccatggaaac cccagcgcag cttctcttcc tcctgctact ctggctccca       60
gataccaccg gtaaggaatc ccgggccaag aaattccagc ggcagcatat ggactcagac      120
agttccccca gcagcagctc cacctactgt aaccaaatga tgaggcgccg gaatatgaca      180
caggggcggt gcaaaccagt gaacaccttt gtgcacgagc cctggtagaa tgtccagaat      240
gtctgtttcc aggaaaaggt cacctgcaag aacgggcagg gcaactgcta caagagcaac      300
tccagcatgc acatcacaga ctgccgcctg acaaacggct ccaggtaccc caactgtgca      360
taccggacca gcccgaagga gagacacatc attgtggcct gtgaagggag cccatatgtg      420
ccagtccact ttgatgcttc tgtggaggac tctacagatc tcgagcccaa atcttctgac      480
aaaactcaca catgtccacc gtgcccagca cctgaactcc tggggggacc gtcagtcttc      540
ctcttccccc caaaacccaa ggacaccctc atgatctccc ggacccctga ggtcacatgc      600
gtggtggtgg acgtgagcca cgaagaccct gaggtcaagt tcaactggta cgtggacggc      660
gtggaggtgc ataatgccaa gacaaagccg cgggaggagc agtacaacag cacgtaccgt      720
gtggtcagcg tcctcaccgt cctgcaccag gactggctga atggcaagga gtacaagtgc      780
aaggtctcca acaaagccct cccagccccc atcgagaaaa ccatctccaa agccaaaggg      840
cagccccgag aaccacaggt gtacaccctg cccccatccc gggatgagct gaccaagaac      900
caggtcagcc tgacctgcct ggtcaaaggc ttctatccca gcgacatcgc cgtggagtgg      960
gagagcaatg ggcagccgga gaacaactac aagaccacgc ctcccgtgct ggactccgac     1020
ggctccttct tcctctacag caagctcacc gtggacaaga gcaggtggca gcaggggaac     1080
gtcttctcat gctccgtgat gcatgagggt ctgcacaacc actacacgca gaagagcctc     1140
tctctgtctc cgggtaaagt cgacggtgct agcagccatg tgaatgtgag cagccctagc     1200
gtgcaggata tcctgaagat cgcagccttc aacatccaga catttgggga gaccaagatg     1260
tccaatgcca ccctcgtcag ctacattgtg cagatcctga gccgctatga catcgccctg     1320
gtccaggagg tcagagacag ccacctgact gccgtgggga gctgctggaa caacctcaat     1380
caggatgcac cagacaccta tcactacgtg gtcagtgagc cactgggacg gaacagctat     1440
aaggagcgct acctgttcgt gtacaggcct gaccaggtgt ctgcggtgga cagctactac     1500
```

| | |
|---|---|
| tacgatgatg gctgcgagcc ctgcgggaac gacaccttca accgagagcc agccattgtc | 1560 |
| aggttcttct cccggttcac agaggtcagg gagtttgcca ttgttcccct gcatgcggcc | 1620 |
| ccggggacg cagtagccga gatcgacgct ctctatgacg tctacctgga tgtccaagag | 1680 |
| aaatggggct cggaggacgt catgttgatg ggcgacttca atgcgggctg cagctatgtg | 1740 |
| agaccctccc agtggtcatc catccgcctg tggacaagcc ccaccttcca gtggctgatc | 1800 |
| cccgacagcg ctgacaccac agctacaccc acgcactgtg cctatgacag gatcgtggtt | 1860 |
| gcagggatgc tgctccgagg cgccgttgtt cccgactcgg ctcttcccctt taacttccag | 1920 |
| nctgcctatg gcctgagtga ccaactggcc caagccatca gtgaccacta tccagtggag | 1980 |
| gtgatgctga agtgataatc taga | 2004 |

<210> SEQ ID NO 116
<211> LENGTH: 2004
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 116

| | |
|---|---|
| aagcttgccg ccatggaaac cccagcgcag cttctcttcc tcctgctact ctggctccca | 60 |
| gataccaccg gtaaggaatc ccgggccaag aaattccagc ggcagcatat ggactcagac | 120 |
| agttccccca gcagcagctc cacctactgt aaccaaatga tgaggcgccg gaatatgaca | 180 |
| caggggcggt gcaaaccagt gaacaccttt gtgcacgagc cctggtaga tgtccagaat | 240 |
| gtctgtttcc aggaaaaggt cacctgcaag aacgggcagg gcaactgcta caagagcaac | 300 |
| tccagcatgc acatcacaga ctgccgcctg acaaacggct ccaggtaccc caactgtgca | 360 |
| taccggacca gcccgaagga gagacacatc attgtggcct gtgaagggag cccatatgtg | 420 |
| ccagtccact tgatgcttc tgtggaggac tctacagatc tcgagcccaa atcttctgac | 480 |
| aaaactcaca catgtccacc gtgcccagca cctgaactcc tggggggacc gtcagtcttc | 540 |
| ctcttccccc caaaacccaa ggacaccctc atgatctccc ggacccctga ggtcacatgc | 600 |
| gtggtggtgg acgtgagcca cgaagaccct gaggtcaagt tcaactggta cgtggacggc | 660 |
| gtggaggtgc ataatgccaa gacaaagccg cgggaggagc agtacaacag cacgtaccgt | 720 |
| gtggtcagcg tcctcaccgt cctgcaccag gactggctga atggcaagga gtacaagtgc | 780 |
| aaggtctcca acaaagccct cccagccccc atcgagaaaa ccatctccaa agccaaaggg | 840 |
| cagccccgag aaccacaggt gtacaccctg cccccatccc gggatgagct gaccaagaac | 900 |
| caggtcagcc tgacctgcct ggtcaaaggc ttctatccca gcgacatcgc cgtggagtgg | 960 |
| gagagcaatg ggcagccgga gaacaactac aagaccacgc ctcccgtgct ggactccgac | 1020 |
| ggctccttct tcctctacag caagctcacc gtggacaaga gcaggtggca gcaggggaac | 1080 |
| gtcttctcat gctccgtgat gcatgagggt ctgcacaacc actacacgca gaagagcctc | 1140 |
| tctctgtctc cgggtaaagt cgacggtgct agcagccatg tgaatgtgag cagccctagc | 1200 |
| gtgcaggata tcctgaagat cgcagccttc aacatccaga catttgggga gaccaagatg | 1260 |
| tccaatgcca ccctcgtcag ctacattgtg cagatcctga gccgctatga catcgccctg | 1320 |
| gtccaggagg tcagagacag ccacctgact gccgtgggga gctgctggaa caacctcaat | 1380 |
| caggatgcac cagacaccta tcactacgtg gtcagtgagc cactgggacg gaacagctat | 1440 |
| aaggagcgct acctgttcgt gtacaggcct gaccaggtgt ctgcggtgga cagctactac | 1500 |

```
tacgatgatg gctgcgagcc ctgcgggaac gacaccttca accgagagcc attcattgtc    1560
aggttcttct cccggttcac agaggtcagg gagtttgcca ttgttcccct gcatgcggcc    1620 ccggggacg cagtagccga gatcgacgct ctctatgacg tctacctgga tgtccaagag     1680
aaatggggct tagaggacgt catgttgatg ggcgacttca atgcgggctg cagctatgtg    1740
agaccctccc agtggtcatc catccgcctg tggacaagcc ccaccttcca gtggctgatc    1800
cccgacagcg ctgacaccac agctacaccc acgcactgtg cctatgacag gatcgtggtt    1860
gcagggatgc tgctccgagg cgccgttgtt cccgactcgg ctcttcccct taacttccag    1920
gctgcctatg gcctgagtga ccaactggcc caagccatca gtgaccacta tccagtggag    1980
gtgatgctga agtgataatc taga                                            2004
```

<210> SEQ ID NO 117
<211> LENGTH: 2004
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
aagcttgccg ccatggaaac cccagcgcag cttctcttcc tcctgctact ctggctccca    60
gataccaccg gtaaggaatc ccgggccaag aaattccagc ggcagcatat ggactcagac    120
agttccccca gcagcagctc cacctactgt aaccaaatga tgaggcgccg gaatatgaca    180
caggggcggt gcaaaccagt gaacaccttt gtgcacgagc cctggtaga tgtccagaat    240 gtctgtttcc aggaaaaggt cacctgcaag aacgggcagg gcaactgcta caagagcaac    300
tccagcatgc acatcacaga ctgccgcctg acaaacggct ccaggtaccc caactgtgca    360
taccggacca gcccgaagga gagacacatc attgtggcct gtgaagggag cccatatgtg    420
ccagtccact tgatgcttc tgtggaggac tctacagatc tcgagcccaa atcttctgac    480
aaaactcaca catgtccacc gtgcccagca cctgaactcc tggggggacc gtcagtcttc    540
ctcttccccc caaaacccaa ggacaccctc atgatctccc ggaccctga ggtcacatgc    600 gtggtggtgg acgtgagcca cgaagaccct gaggtcaagt tcaactggta cgtggacggc    660
gtggaggtgc ataatgccaa gacaaagccg cgggaggagc agtacaacag cacgtaccgt    720
gtggtcagcg tcctcaccgt cctgcaccag gactggctga atggcaagga gtacaagtgc    780
aaggtctcca acaaagccct cccagccccc atcgagaaaa ccatctccaa agccaaaggg    840
cagccccgag aaccacaggt gtacaccctg cccccatccc gggatgagct gaccaagaac    900
caggtcagcc tgacctgcct ggtcaaaggc ttctatccca gcgacatcgc cgtggagtgg    960
gagagcaatg ggcagccgga gaacaactac aagaccacgc ctcccgtgct ggactccgac    1020
ggctccttct cctctacag caagctcacc gtggacaaga gcaggtggca gcagggaac     1080 gtcttctcat gctccgtgat gcatgagggt ctgcacaacc actacacgca gaagagcctc    1140
tctctgtctc cgggtaaagt cgacggtgct agcagccatg tgaatgtgag cagccctagc    1200
gtgcaggata tcctgaagat cgcagccttc aacatccaga catttgggga gaccaagatg    1260
tccaatgcca ccctcgtcag ctacattgtg cagatcctga ccgctatga catcgccctg    1320 gtccaggagg tcagagacag ccacctgact gccgtgggga agctgctgga caacctcaat    1380
caggatgcac cagacaccta tcactacgtg gtcagtgagc cactgggacg gaacagctat    1440
aaggagcgct acctgttcgt gtacaggcct gaccaggtgt ctgcggtgga cagctactac    1500
```

```
tacgatgatg gctgcgagcc ctgcgggaac gacaccttca accgagagcc agccattgtc    1560
aggttcttct cccggttcac agaggtcagg gagtttgcca ttgttcccct gcatgcggcc    1620 ccggggacg cagtagccga gatcgacgct ctctatgacg tctacctgga tgtccaagag     1680
aaatggggct tggaggacgt catgttgatg ggcgacttca atgcgggctg cagctatgtg    1740
agaccctccc agtggtcatc catccgcctg tggacaagcc ccaccttcca gtggctgatc    1800
cccgacagcg ctgacaccac agctacaccc acgcactgtg cctatgacag gatcgtggtt    1860
gcagggatgc tgctccgagg cgccgttgtt cccgactcgg ctcttcccctt taacttccag    1920 gctgcctatg gcctgagtga ccaactggcc caagccatca gtgaccacta tccagtggag    1980
gtgatgctga aatgataatc taga                                           2004
```

<210> SEQ ID NO 118
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118

```
gttaagcttg ccaccatgga aaccccagcg cagcttctct tcctcctgct actctggctc    60
ccagatacca ccggtctgaa gatcgcagcc ttcaacatcc agacatttgg ggagaccaag   120
atgtccaatg ccaccctcgt cagctacatt gtgcagatcc tgagccgcta tgacatcgcc   180
ctggtccagg aggtcagaga cagccacctg actgccgtgg ggaagctgct ggacaacctc   240
aatcaggatg caccagacac ctatcactac gtggtcagtg agccactggg acggaacagc   300
tataaggagc gctacctgtt cgtgtacagg cctgaccagg tgtctgcggt ggacagctac   360
tactacgatg atggctgcga gccctgcggg aacgacacct caaccgaga gccagccatt   420 gtcaggttct ctcccggtt cacagaggtc agggagtttg ccattgttcc cctgcatgcg   480
gccccggggg acgcagtagc cgagatcgac gctctctatg acgtctacct ggatgtccaa    540
gagaaatggg gcttggagga cgtcatgttg atgggcgact tcaatgcggg ctgcagctat    600
gtgagaccct cccagtggtc atccatccgc ctgtggacaa gccccacctt ccagtggctg    660
atccccgaca cgctgacac acagctacac cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct cgagcccaaa tcttctgaca aaactcacac atgtccaccg    900
tgcccagcac ctgaactcct ggggggaccg tcagtcttcc tcttcccccc aaaacccaag   960
gacaccctca tgatctcccg gacccctgag gtcacatgcg tggtggtgga cgtgagccac    1020
gaagaccctg aggtcaagtt caactggtac gtggacggcg tggaggtgca taatgccaag    1080
acaaagccgc gggaggagca gtacaacagc acgtaccgtg tggtcagcgt cctcaccgtc    1140
ctgcaccagg actggctgaa tggcaaggag tacaagtgca aggtctccaa caaagccctc    1200
ccagccccca tcgagaaaac catctccaaa gccaaagggc agccccgaga accacaggtg    1260
tacaccctgc cccatcccg ggatgagctg accaagaacc aggtcagcct gacctgcctg    1320
gtcaaaggct tctatcccag cgacatcgcc gtggagtggg agagcaatgg gcagccggag    1380
aacaactaca agaccacgcc tcccgtgctg gactccgacg gctccttctt cctctacagc    1440
aagctcaccg tggacaagag caggtggcag caggggaacg tcttctcatg ctccgtgatg    1500
```

```
catgaggctc tgcacaacca ctacacgcag aagagcctct ctctgtctcc gggtaaatga    1560
taatctaga                                                           1569
```

<210> SEQ ID NO 119
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
gttaagcttg ccaccatgga acccccagcg cagcttctct tcctcctgct actctggctc     60
ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
ctggtccagg aggtcagaga cagccaccct actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcggg aacgacacct caaccgaga gccattcatt    420 gtcaggttct tctcccggtt cacagaggtc agggagtttg ccattgttcc cctgcatgcg    480 gccccgggg acgcagtagc cgagatcgac gctctctatg acgtctacct ggatgtccaa    540
gagaaatggg gcttagagga cgtcatgttg atgggcgact tcaatgcggg ctgcagctat    600
gtgagaccct cccagtggtc atccatccgc ctgtggacaa gccccacctt ccagtggctg    660
atccccgaca gcgctgacac cacagctaca cccacgcact gtgcctatga caggatcgtg    720
gttgcaggga tgctgctccg aggcgccgtt gttcccgact cggctcttcc cttaacttc    780 caggctgcct atggcctgag tgaccaactg gcccaagcca tcagtgacca ctatccagtg    840
gaggtgatgc tgaaagatct cgagcccaaa tcttctgaca aaactcacac atgtccaccg    900
tgcccagcac ctgaactcct ggggggaccg tcagtcttcc tcttccccc aaaacccaag    960 gacaccctca tgatctcccg gacccctgag gtcacatgcg tggtggtgga cgtgagccac   1020
gaagaccctg aggtcaagtt caactggtac gtggacggcg tggaggtgca taatgccaag   1080
acaaagccgc gggaggagca gtacaacagc acgtaccgtg tggtcagcgt cctcaccgtc   1140
ctgcaccagg actggctgaa tggcaaggag tacaagtgca aggtctccaa caaagccctc   1200
ccagccccca tcgagaaaac catctccaaa gccaaagggc agccccgaga accacaggtg   1260
tacaccctgc cccatcccg ggatgagctg accaagaacc aggtcagcct gacctgcctg   1320
gtcaaaggct tctatcccag cgacatcgcc gtggagtggg agagcaatgg gcagccggag   1380
aacaactaca agaccacgcc tcccgtgctg gactccgacg gctccttctt cctctacagc   1440
aagctcaccg tggacaagag caggtggcag caggggaacg tcttctcatg ctccgtgatg   1500
catgaggctc tgcacaacca ctacacgcag aagagcctct ctctgtctcc gggtaaatga   1560
taatctaga                                                          1569
```

<210> SEQ ID NO 120
<211> LENGTH: 1641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
gttaagcttg ccaccatgga aaccccagcg cagcttctct tcctcctgct actctggctc    60
ccagatacca ccggtctgaa gatcgcagcc ttcaacatcc agacatttgg ggagaccaag   120
atgtccaatg ccaccctcgt cagctacatt gtgcagatcc tgagccgcta tgacatcgcc   180
ctggtccagg aggtcagaga cagccacctg actgccgtgg ggaagctgct ggacaacctc   240
aatcaggatg caccagacac ctatcactac gtggtcagtg agccactggg acggaacagc   300
tataaggagc gctacctgtt cgtgtacagg cctgaccagg tgtctgcggt ggacagctac   360
tactacgatg atggctgcga gccctgcagg aacgacacct caaccgaga gccattcatt   420
gtcaggttct tctcccggtt cacagaggtc agggagtttg ccattgttcc cctgcatgcg   480
gccccggggg acgcagtagc cgagatcgac gctctctatg acgtctacct ggatgtccaa   540
gagaaatggg gcttggagga cgtcatgttg atgggcgact tcaatgcggg ctgcagctat   600
gtgagaccct cccagtggtc atccatccgc ctgtggacaa gccccacctt ccagtggctg   660
atccccgaca gcgctgacac cacagctaca cccacgcact gtgcctatga caggatcgtg   720
gttgcaggga tgctgctccg aggcgccgtt gttcccgact cggctcttcc ctttaacttc   780
caggctgcct atgccctgag tgaccaactg cccaagcca tcagtgacca ctatccagtg   840
gaggtgatgc tgaaagatct ctccggagga ggtggctcag gtggtggagg atctggagga   900
ggtgggagtg gtggaggtgg ttctaccggt ctcgagccca atcttctga caaaactcac   960
acatgtccac cgtgcccagc acctgaactc ctggggggac cgtcagtctt cctcttcccc  1020
ccaaaaccca aggacaccct catgatctcc cggacccctg aggtcacatg cgtggtggtg  1080
gacgtgagcc acgaagaccc tgaggtcaag ttcaactggt acgtggacgg cgtggaggtg  1140
cataatgcca agacaaagcc gcgggaggag cagtacaaca gcacgtaccg tgtggtcagc  1200
gtcctcaccg tcctgcacca ggactggctg aatggcaagg agtacaagtg caaggtctcc  1260
aacaaagccc tcccagcccc catcgagaaa accatctcca aagccaaagg gcagccccga  1320
gaaccacagg tgtacaccct gcccccatcc cgggatgagc tgaccaagaa ccaggtcagc  1380
ctgacctgcc tggtcaaagg cttctatccc agcgacatcg ccgtggagtg ggagagcaat  1440
gggcagccgg agaacaacta caagaccacg cctcccgtgc tggactccga cggctccttc  1500
ttcctctaca gcaagctcac cgtggacaag agcaggtggc agcaggggaa cgtcttctca  1560
tgctccgtga tgcatgaggc tctgcacaac cactacacgc agaagagcct ctctctgtct  1620
ccgggtaaat gataatctag a                                           1641
```

<210> SEQ ID NO 121
<211> LENGTH: 1656
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121

```
gttaagcttg ccaccatgga aaccccagcg cagcttctct tcctcctgct actctggctc    60
ccagatacca ccggtctgaa gatcgcagcc ttcaacatcc agacatttgg ggagaccaag   120
atgtccaatg ccaccctcgt cagctacatt gtgcagatcc tgagccgcta tgacatcgcc   180
ctggtccagg aggtcagaga cagccacctg actgccgtgg ggaagctgct ggacaacctc   240
aatcaggatg caccagacac ctatcactac gtggtcagtg agccactggg acggaacagc   300
```

| | |
|---|---|
| tataaggagc gctacctgtt cgtgtacagg cctgaccagg tgtctgcggt ggacagctac | 360 |
| tactacgatg atggctgcga gccctgcagg aacgacacct tcaaccgaga gccattcatt | 420 |
| gtcaggttct tctcccggtt cacagaggtc agggagtttg ccattgttcc cctgcatgcg | 480 |
| gccccggggg acgcagtagc cgagatcgac gctctctatg acgtctacct ggatgtccaa | 540 |
| gagaaatggg gcttggagga cgtcatgttg atgggcgact tcaatgcggg ctgcagctat | 600 |
| gtgagaccct cccagtggtc atccatccgc ctgtggacaa gccccacctt ccagtggctg | 660 |
| atccccgaca gcgctgacac cacagctaca cccacgcact gtgcctatga caggatcgtg | 720 |
| gttgcaggga tgctgctccg aggcgccgtt gttcccgact cggctcttcc ctttaacttc | 780 |
| caggctgcct atggcctgag tgaccaactg gcccaagcca tcagtgacca ctatccagtg | 840 |
| gaggtgatgc tgaaagatct ctccggagga ggtggctcag gtggtggagg atctggagga | 900 |
| ggtggctcag gtggtggagg atctggagga ggtgggagta ccggtctcga gcccaaatct | 960 |
| tctgacaaaa ctcacacatg tccaccgtgc ccagcacctg aactcctggg gggaccgtca | 1020 |
| gtcttcctct tccccccaaa acccaaggac accctcatga tctcccggac ccctgaggtc | 1080 |
| acatgcgtgg tggtggacgt gagccacgaa gaccctgagg tcaagttcaa ctggtacgtg | 1140 |
| gacggcgtgg aggtgcataa tgccaagaca aagccgcggg aggagcagta caacagcacg | 1200 |
| taccgtgtgg tcagcgtcct caccgtcctg caccaggact ggctgaatgg caaggagtac | 1260 |
| aagtgcaagg tctccaacaa agccctccca gcccccatcg agaaaaccat ctccaaagcc | 1320 |
| aaagggcagc cccgagaacc acaggtgtac accctgcccc catcccggga tgagctgacc | 1380 |
| aagaaccagg tcagcctgac ctgcctggtc aaaggcttct atcccagcga catcgccgtg | 1440 |
| gagtgggaga gcaatgggca gccggagaac aactacaaga ccacgcctcc cgtgctggac | 1500 |
| tccgacggct ccttcttcct ctacagcaag ctcaccgtgg acaagagcag gtggcagcag | 1560 |
| gggaacgtct tctcatgctc cgtgatgcat gaggctctgc acaaccacta cacgcagaag | 1620 |
| agcctctctc tgtctccggg taaatgataa tctaga | 1656 |

<210> SEQ ID NO 122
<211> LENGTH: 1650
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 122

| | |
|---|---|
| gttaagcttg ccaccatgga aaccccagcg cagcttctct tcctcctgct actctggctc | 60 |
| ccagatacca ccggtctgaa gatcgcagcc ttcaacatcc agacatttgg ggagaccaag | 120 |
| atgtccaatg ccaccctcgt cagctacatt gtgcagatcc tgagccgcta tgacatcgcc | 180 |
| ctggtccagg aggtcagaga cagccacctg actgccgtgg ggaagctgct ggacaacctc | 240 |
| aatcaggatg caccagacac ctatcactac gtggtcagtg agccactggg acggaacagc | 300 |
| tataaggagc gctacctgtt cgtgtacagg cctgaccagg tgtctgcggt ggacagctac | 360 |
| tactacgatg atggctgcga gccctgcagg aacgacacct tcaaccgaga gccattcatt | 420 |
| gtcaggttct tctcccggtt cacagaggtc agggagtttg ccattgttcc cctgcatgcg | 480 |
| gccccggggg acgcagtagc cgagatcgac gctctctatg acgtctacct ggatgtccaa | 540 |
| gagaaatggg gcttggagga cgtcatgttg atgggcgact tcaatgcggg ctgcagctat | 600 |
| gtgagaccct cccagtggtc atccatccgc ctgtggacaa gccccacctt ccagtggctg | 660 |

```
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct ctccggagga ggtggctcag gtggtggagg atctggagga    900
ggtggctcag gtggtggagg atctggagga ggtgggagtc tcgagcccaa atcttctgac    960
aaaactcaca catgtccacc gtgcccagca cctgaactcc tggggggacc gtcagtcttc   1020
ctcttccccc caaaacccaa ggacaccctc atgatctccc ggacccctga ggtcacatgc   1080
gtggtggtgg acgtgagcca cgaagaccct gaggtcaagt tcaactggta cgtggacggc   1140
gtggaggtgc ataatgccaa gacaaagccg cgggaggagc agtacaacag cacgtaccgt   1200
gtggtcagcg tcctcaccgt cctgcaccag gactggctga atggcaagga gtacaagtgc   1260
aaggtctcca acaaagccct cccagccccc atcgagaaaa ccatctccaa agccaaaggg   1320
cagccccgag aaccacaggt gtacaccctg cccccatccc gggatgagct gaccaagaac   1380
caggtcagcc tgacctgcct ggtcaaaggc ttctatccca gcgacatcgc cgtggagtgg   1440
gagagcaatg ggcagccgga gaacaactac aagaccacgc ctcccgtgct ggactccgac   1500
ggctccttct tcctctacag caagctcacc gtggacaaga gcaggtggca gcaggggaac   1560
gtcttctcat gctccgtgat gcatgaggct ctgcacaacc actacacgca gaagagcctc   1620
tctctgtctc cgggtaaatg ataatctaga                                    1650
```

<210> SEQ ID NO 123
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
gttaagcttg ccaccatgga aacccagcg cagcttctct tcctcctgct actctggctc     60
ccagatacca ccggtctgaa gatcgcagcc ttcaacatcc agacatttgg ggagaccaag   120
atgtccaatg ccaccctcgt cagctacatt gtgcagatcc tgagccgcta tgacatcgcc   180
ctggtccagg aggtcagaga cagccacctg actgccgtgg ggaagctgct ggacaacctc   240
aatcaggatg caccagacac ctatcactac gtggtcagtg agccactggg acggaacagc   300
tataaggagc gctacctgtt cgtgtacagg cctgaccagg tgtctgcggt ggacagctac   360
tactacgatg atggctgcga gccctgcagg aacgacacct tcaaccgaga gccattcatt   420
gtcaggttct ctcccggtt cacagaggtc agggagtttg ccattgttcc cctgcatgcg   480 gccccgggg acgcagtagc cgagatcgac gctctctatg acgtctacct ggatgtccaa   540
gagaaatggg gcttggagga cgtcatgttg atggcgact tcaatgcggg ctgcagctat   600
gtgagaccct cccagtggtc atccatccgc ctgtggacaa gccccacctt ccagtggctg   660
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct cgagcccaaa tcttctgaca aaactcacac atgtccaccg   900
tgcccagcac ctgaactcct ggggggaccc tcagtcttcc tcttcccccc aaaacccaag   960
gacaccctca tgatctcccg gacccctgag gtcacatgcg tggtggtgga cgtgagccac  1020
```

```
gaagaccctg aggtcaagtt caactggtac gtggacggcg tggaggtgca taatgccaag    1080
acaaagccgc gggaggagca gtacaacagc acgtaccgtg tggtcagcgt cctcaccgtc    1140
ctgcaccagg actggctgaa tggcaaggag tacaagtgca aggtctccaa caaagccctc    1200
ccagccccca tcgagaaaac catctccaaa gccaagggc agccccgaga ccacaggtg     1260 tacaccctgc ccccatcccg ggatgagctg accaagaacc aggtcagcct gacctgcctg    1320
gtcaaaggct tctatcccag cgacatcgcc gtggagtggg agagcaatgg gcagccggag    1380
aacaactaca agaccacgcc tcccgtgctg gactccgacg gctccttctt cctctacagc    1440
aagctcaccg tggacaagag caggtggcag caggggaacg tcttctcatg ctccgtgatg    1500
catgaggctc tgcacaacca ctacacgcag aagagcctct ctctgtctcc gggtaaatga    1560
taatctaga                                                            1569

<210> SEQ ID NO 124
<211> LENGTH: 1173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gttaagcttg ccaccatgga aaccccagcg cagcttctct tcctcctgct actctggctc      60
ccagatacca ccggtaagga atcccgggcc aagaaattcc agcggcagca tatggactca     120
gacagttccc ccagcagcag ctccacctac tgtaaccaaa tgatgaggcg ccggaatatg     180
acacaggggc ggtgcaaacc agtgaacacc tttgtgcacg agcccctggt agatgtccag     240
aatgtctgtt ccaggaaaaa ggtcacctgc aagaacgggc agggcaactg ctacaagagc     300
aactccagca tgcacatcac agactgccgc ctgacaaacg actccaggta ccccaactgt     360
gcataccgga ccagcccgaa ggagagacac atcattgtgg cctgtgaagg agcccctat     420 gtgccagtcc actttgatgc ttctgtggag gactctacag atctcgagcc caaatcttct     480
gacaaaactc acacatgtcc accgtgccca gcacctgaac tcctgggggg accgtcagtc     540
ttcctcttcc ccccaaaacc caaggacacc ctcatgatct cccggacccc tgaggtcaca     600
tgcgtggtgg tggacgtgag ccacgaagac cctgaggtca agttcaactg gtacgtggac     660
ggcgtggagg tgcataatgc caagacaaag ccgcggagg agcagtacaa cagcacgtac     720
cgtgtggtca gcgtcctcac cgtcctgcac caggactggc tgaatggcaa ggagtacaag     780
tgcaaggtct ccaacaaagc cctcccagcc ccatcgaga aaccatctc caaagccaaa     840 gggcagcccc gagaaccaca ggtgtacacc ctgcccccat cccgggatga gctgaccaag     900
aaccaggtca gcctgacctg cctggtcaaa ggcttctatc cagcgacat cgccgtggag     960 tgggagagca atgggcagcc ggagaacaac tacaagacca cgcctcccgt gctggactcc    1020
gacggctcct tcttcctcta cagcaagctc accgtggaca agagcaggtg gcagcagggg    1080
aacgtcttct catgctccgt gatgcatgag gctctgcaca accactacac gcagaagagc    1140
ctctctctgt ctccgggtaa atgataatct aga                                 1173

<210> SEQ ID NO 125
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 125

```
gttaagcttg ccaccatgga aacccagcg cagcttctct tcctcctgct actctggctc      60
ccagatacca ccggtaagga atcccgggcc aagaaattcc agcggcagca tatggactca    120
gacagttccc ccagcagcag ctccacctac tgtaaccaaa tgatgaggcg ccggaatatg    180
acacagggc ggtgcaaacc agtgaacacc tttgtgcacg agccctggt agatgtccag      240
aatgtctgtt tccaggaaaa ggtcacctgc aagaacgggc agggcaactg ctacaagagc    300
aactccagca tgcacatcac agactgccgc ctgacaaacg gctccaggta ccccaactgt    360
gcataccgga ccagcccgaa ggagagacac atcattgtgg cctgtgaagg agcccatat    420
gtgccagtcc actttgatgc ttctgtggag gactctacag atctctccgg aggaggtggc    480
tcaggtggtg gaggatctgg aggaggtggg agtggtggag tggttctac cggtctcgag     540
cccaaatctt ctgacaaaac tcacacatgt ccaccgtgcc cagcacctga actcctgggg    600
ggaccgtcag tcttcctctt ccccccaaaa cccaaggaca ccctcatgat ctcccggacc    660
cctgaggtca catgcgtggt ggtggacgtg agccacgaag accctgaggt caagttcaac    720
tggtacgtgg acggcgtgga ggtgcataat gccaagacaa agccgcggga ggagcagtac    780
aacagcacgt accgtgtggt cagcgtcctc accgtcctgc accaggactg gctgaatggc    840
aaggagtaca agtgcaaggt ctccaacaaa gccctcccag cccccatcga gaaaaccatc    900
tccaaagcca agggcagcc cgagaaccag gtgtaca ccctgccccc atcccgggat        960
gagctgacca agaaccaggt cagcctgacc tgcctggtca aaggcttcta tcccagcgac   1020
atcgccgtgg agtgggagag caatgggcag ccggagaaca actacaagac cacgcctccc   1080
gtgctggact ccgacggctc cttcttcctc tacagcaagc tcaccgtgga caagagcagg   1140
tggcagcagg ggaacgtctt ctcatgctcc gtgatgcatg aggctctgca caaccactac   1200
acgcagaaga gcctctctct gtctccgggt aaatgataat ctaga                   1245
```

<210> SEQ ID NO 126
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
gttaagcttg ccaccatgga aacccagcg cagcttctct tcctcctgct actctggctc      60
ccagatacca ccggtaagga atcccgggcc aagaaattcc agcggcagca tatggactca    120
gacagttccc ccagcagcag ctccacctac tgtaaccaaa tgatgaggcg ccggaatatg    180
acacagggc ggtgcaaacc agtgaacacc tttgtgcacg agccctggt agatgtccag      240
aatgtctgtt tccaggaaaa ggtcacctgc aagaacgggc agggcaactg ctacaagagc    300
aactccagca tgcacatcac agactgccgc ctgacaaacg gctccaggta ccccaactgt    360
gcataccgga ccagcccgaa ggagagacac atcattgtgg cctgtgaagg agcccatat    420
gtgccagtcc actttgatgc ttctgtggag gactctacag atctctccgg aggaggtggc    480
tcaggtggtg gaggatctgg aggaggtggc tcaggtggtg gaggatctgg aggaggtggg   540
agtctcgagc ccaaatcttc tgacaaaact cacacatgtc caccgtgccc agcacctgaa   600
ctcctggggg gaccgtcagt cttcctcttc ccccaaaac ccaaggacac cctcatgatc    660
tcccggaccc ctgaggtcac atgcgtggtg gtggacgtga gccacgaaga ccctgaggtc   720
```

```
aagttcaact ggtacgtgga cggcgtggag gtgcataatg ccaagacaaa gccgcgggag      780
gagcagtaca acagcacgta ccgtgtggtc agcgtcctca ccgtcctgca ccaggactgg      840
ctgaatggca aggagtacaa gtgcaaggtc tccaacaaag ccctcccagc ccccatcgag      900 aaaccatct ccaaagccaa agggcagccc cgagaaccac aggtgtacac cctgccccca      960
tcccgggatg agctgaccaa gaaccaggtc agcctgacct gcctggtcaa aggcttctat     1020
cccagcgaca tcgccgtgga gtgggagagc aatgggcagc cggagaacaa ctacaagacc     1080
acgcctcccg tgctggactc cgacggctcc ttcttcctct acagcaagct caccgtggac     1140
aagagcaggt ggcagcaggg gaacgtcttc tcatgctccg tgatgcatga ggctctgcac     1200
aaccactaca cgcagaagag cctctctctg tctccgggta atgataatc taga            1254
```

<210> SEQ ID NO 127
<211> LENGTH: 1173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
gttaagcttg ccaccatgga aaccccagcg cagcttctct tcctcctgct actctggctc       60
ccagatacca ccggtaagga atcccgggcc aagaaattcc agcggcagca tatggactca      120
gacagttccc ccagcagcag ctccacctac tgtaaccaaa tgatgaggcg ccggaatatg      180
acacaggggc ggtgcaaacc agtgaacacc tttgtgcacg agcccctggt agatgtccag      240
aatgtctgtt tccaggaaaa ggtcacctgc aagaacgggc agggcaactg ctacaagagc      300
aactccagca tgcacatcac agactgccgc ctgacaaacg gctccaggta ccccaactgt      360
gcataccgga ccagcccgaa ggagagacac atcattgtgg cctgtgaagg gagcccatat      420
gtgccagtcc actttgatgc ttctgtggag gactctacag atctcgagcc caaatcttct      480
gacaaaactc acacatgtcc accgtgccca gcacctgaac tcctgggggg accgtcagtc      540
ttcctcttcc cccccaaaacc caaggacacc ctcatgatct cccggacccc tgaggtcaca      600
tgcgtggtgg tggacgtgag ccacgaagac cctgaggtca agttcaactg gtacgtggac      660
ggcgtggagg tgcataatgc caagacaaag ccgcgggagg agcagtacaa cagcacgtac      720
cgtgtggtca gcgtcctcac cgtcctgcac caggactggc tgaatggcaa ggagtacaag      780
tgcaaggtct ccaacaaagc cctcccagcc cccatcgaga aaaccatctc caaagccaaa      840
gggcagcccc gagaaccaca ggtgtacacc ctgcccccat cccgggatga gctgaccaag      900
aaccaggtca gcctgacctg cctggtcaaa ggcttctatc ccagcgacat cgccgtggag      960
tgggagagca atgggcagcc ggagaacaac tacaagacca cgcctcccgt gctggactcc     1020
gacggctcct tcttcctcta cagcaagctc accgtggaca agagcaggtg gcagcagggg     1080
aacgtcttct catgctccgt gatgcatgag gctctgcaca accactacac gcagaagagc     1140
ctctctctgt ctccgggtaa atgataatct aga                                   1173
```

<210> SEQ ID NO 128
<211> LENGTH: 945
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
atgggctcac agaccctgcc ccatggtcac atgcagaccc tcatcttctt agacctggaa        60
gccactggcc tgccttcgtc tcggcccgaa gtcacagagc tgtgcctgct ggctgtccac       120
agacgtgctc tggagaacac ttccatttct cagggacatc cacctccagt gcccagaccg       180
ccccgtgtgg tggacaagct ctctctgtgc attgctccag ggaaagcctg tagccctggg       240
gccagtgaga tcacaggtct gagcaaagct gagctggaag tacaggggcg tcaacgcttc       300
gatgacaacc tggccatcct gctccgagcc ttcctgcagc gccagccaca gccttgctgc       360
cttgtggcac acaacggtga ccgctatgac tttcctctgc tccagacaga gcttgctagg       420
ctgagcactc ccagtcccct agatggtacc ttctgtgtgg acagcatcgc tgccctaaag       480
gccttggaac aagctagcag cccctcaggg aatggttcga ggaaaagcta cagcctgggc       540
agcatctaca cccgcctgta ctggcaagca ccgacagact cacatactgc tgaaggtgat       600
gttctaaccc tgctcagcat ctgtcagtgg aagccacagg ccctactgca gtgggtggac       660
gaacatgccc ggccctttag caccgtcaag cccatgtacg gcactccggc taccactgga       720
acaaccaacc taaggccaca tgctgccaca gctactacac ccctggccac agccaatgga       780
agtcccagca atggcaggag caggcgacct aagagtcctc ctccagagaa ggtcccagaa       840
gccccatcac aggaggggct gctggcccca ctgagcctgc tgaccctcct gaccttggca       900
atagccactc tgtatggact cttcctggcc tcacctgggc agtaa                       945
```

<210> SEQ ID NO 129
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
atgggctcac agaccctgcc ccatggtcac atgcagaccc tcatcttctt agacctggaa        60
gccactggcc tgccttcgtc tcggcccgaa gtcacagagc tgtgcctgct ggctgtccac       120
agacgtgctc tggagaacac ttccatttct cagggacatc cacctccagt gcccagaccg       180
ccccgtgtgg tggacaagct ctctctgtgc attgctccag ggaaagcctg tagccctggg       240
gccagtgaga tcacaggtct gagcaaagct gagctggaag tacaggggcg tcaacgcttc       300
gatgacaacc tggccatcct gctccgagcc ttcctgcagc gccagccaca gccttgctgc       360
cttgtggcac acaacggtga ccgctatgac tttcctctgc tccagacaga gcttgctagg       420
ctgagcactc ccagtcccct agatggtacc ttctgtgtgg acagcatcgc tgccctaaag       480
gccttggaac aagctagcag cccctcaggg aatggttcga ggaaaagcta cagcctgggc       540
agcatctaca cccgcctgta ctggcaagca ccgacagact cacatactgc tgaaggtgat       600
gttctaaccc tgctcagcat ctgtcagtgg aagccacagg ccctactgca gtgggtggac       660
gaacatgccc ggccctttag caccgtcaag cccatgtacg gcactccggc taccactgga       720
acaacagatc tcgag                                                         735
```

<210> SEQ ID NO 130
<211> LENGTH: 1593
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
aagcttgcca ccatggaaac cccagcgcag cttctcttcc tcctgctact ctggctccca      60
gataccaccg gtatgggctc acagaccctg ccccatggtc acatgcagac cctcatcttc     120
ttagacctgg aagccactgg cctgccttcg tctcggcccg aagtcacaga gctgtgcctg     180
ctggctgtcc acagacgtgc tctggagaac acttccattt ctcagggaca tccacctcca     240
gtgcccagac cgcccgtgt ggtggacaag ctctctctgt gcattgctcc agggaaagcc      300
tgtagccctg gggccagtga gatcacaggt ctgagcaaag ctgagctgga agtacagggg     360
cgtcaacgct tcgatgacaa cctggccatc ctgctccgag ccttcctgca gcgccagcca     420
cagccttgct gccttgtggc acacaacggt gaccgctatg actttcctct gctccagaca     480
gagcttgcta ggctgagcac tcccagtccc ctagatggta ccttctgtgt ggacagcatc     540
gctgccctaa aggccttgga caagctagc agcccctcag ggaatggttc gaggaaaagc      600
tacagcctgg gcagcatcta cacccgcctg tactggcaag caccgacaga ctcacatact     660
gctgaaggtg atgttctaac cctgctcagc atctgtcagt ggaagccaca ggccctactg     720
cagtgggtgg acgaacatgc ccggcccttt agcaccgtca agcccatgta cggcactccg     780
gctaccactg gaacaacaga tctctccgga ggaggtggct caggtggtgg aggatctgga     840
ggaggtggct cagggagtgg tggaggtggt tctaccggtc tcgagcccag aggtcccaca     900
atcaagccct ctcctccatg caaatgccca gcacctaacc tcttgggtgg atcatccgtc     960
ttcatcttcc ctccaaagat caaggatgta ctcatgatct ccctgagccc catggtcaca    1020
tgtgtggtgg tggatgtgag cgaggatgac ccagacgtcc agatcagctg gtttgtgaac    1080
aacgtggaag tacacacagc tcagacacaa acccatagag aggattacaa cagtactctc    1140
cgggtggtca gtgccctccc catccagcac caggactgga tgagtggcaa ggagttcaaa    1200
tgctcggtca acaacaaaga cctcccagcg tccatcgaga gaaccatctc aaaacccaga    1260
gggccagtaa gagctccaca ggtatatgtc ttgcctccac cagcagaaga gatgactaag    1320
aaagagttca gtctgacctg catgatcaca ggcttcttac ctgccgaaat tgctgtggac    1380
tggaccagca atgggcgtac agagcaaaac tacaagaaca ccgcaacagt cctggactct    1440
gatggttctt acttcatgta cagcaagctc agagtacaaa agagcacttg ggaaagagga    1500
agtcttttcg cctgctcagt ggtccacgag ggtctgcaca atcaccttac gactaagagc    1560
ttctctcgga ctccgggtaa atgataatct aga                                 1593
```

<210> SEQ ID NO 131
<211> LENGTH: 1596
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
aagcttgcca ccatggaaac cccagcgcag cttctcttcc tcctgctact ctggctccca      60
gataccaccg gtatgggctc acagaccctg ccccatggtc acatgcagac cctcatcttc     120
ttagacctgg aagccactgg cctgccttcg tctcggcccg aagtcacaga gctgtgcctg     180
ctggctgtcc acagacgtgc tctggagaac acttccattt ctcagggaca tccacctcca     240
gtgcccagac cgcccgtgt ggtggacaag ctctctctgt gcattgctcc agggaaagcc      300
tgtagccctg gggccagtga gatcacaggt ctgagcaaag ctgagctgga agtacagggg     360
```

```
cgtcaacgct tcgatgacaa cctggccatc ctgctccgag ccttcctgca gcgccagcca    420
cagccttgct gccttgtggc acacaacggt gaccgctatg actttcctct gctccagaca    480
gagcttgcta ggctgagcac tcccagtccc ctagatggta ccttctgtgt ggacagcatc    540
gctgccctaa aggccttgga acaagctagc agcccctcag ggaatggttc gaggaaaagc    600
tacagcctgg gcagcatcta cacccgcctg tactggcaag caccgacaga ctcacatact    660
gctgaaggtg atgttctaac cctgctcagc atctgtcagt ggaagccaca ggccctactg    720
cagtgggtgg acgaacatgc ccggcccttt agcaccgtca agcccatgta cggcactccg    780
gctaccactg gaacaacaga tctctccgga ggaggtggct caggtggtgg aggatctgga    840
ggaggtggct caggtggtgg aggatctgga ggaggtggga gtctcgagcc cagaggtccc    900
acaatcaagc cctctcctcc atgcaaatgc ccagcaccta acctcttggg tggatcatcc    960
gtcttcatct tccctccaaa gatcaaggat gtactcatga tctccctgag ccccatggtc   1020
acatgtgtgg tggtggatgt gagcgaggat gacccagacg tccagatcag ctggtttgtg   1080
aacaacgtgg aagtacacac agctcagaca caaacccata gagaggatta caacagtact   1140
ctccgggtgg tcagtgccct ccccatccag caccaggact ggatgagtgg caaggagttc   1200
aaatgctcgg tcaacaacaa agacctccca gcgtccatcg agagaaccat ctcaaaaccc   1260
agagggccag taagagctcc acaggtatat gtcttgcctc caccagcaga agagatgact   1320
aagaaagagt tcagtctgac ctgcatgatc acaggcttct tacctgccga aattgctgtg   1380
gactggacca gcaatgggcg tacagagcaa aactacaaga acaccgcaac agtcctggac   1440
tctgatggtt cttacttcat gtacagcaag ctcagagtac aaaagagcac ttgggaaaga   1500
ggaagtcttt tcgcctgctc agtggtccac gagggtctgc acaatcacct tacgactaag   1560
agcttctctc ggactccggg taaatgataa tctaga                             1596
```
<210> SEQ ID NO 132
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132

```
gtcgacggcg cggccgccag ccccgtgaac gtgagcagcc ccagcgtgca ggatatc        57
```

<210> SEQ ID NO 133
<211> LENGTH: 2328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
aagcttgcca ccatggaaac cccagcgcag cttctcttcc tcctgctact ctggctccca     60
gataccaccg gtatgggctc acagaccctg ccccatggtc acatgcagac cctcatcttc    120
ttagacctgg aagccactgg cctgccttcg tctcggcccg aagtcacaga gctgtgcctg    180
ctggctgtcc acagacgtgc tctggagaac acttccattt ctcagggaca tccacctcca    240
gtgcccagac cgccccgtgt ggtggacaag ctctctctgt gcattgctcc agggaaagcc    300
tgtagccctg gggccagtga gatcacaggt ctgagcaaag ctgagctgga agtacagggg    360
```

```
cgtcaacgct tcgatgacaa cctggccatc ctgctccgag ccttcctgca gcgccagcca    420
cagccttgct gccttgtggc acacaacggt gaccgctatg actttcctct gctccagaca    480
gagcttgcta ggctgagcac tcccagtccc ctagatggta ccttctgtgt ggacagcatc    540
gctgccctaa aggccttgga acaagctagc agcccctcag ggaatggttc gaggaaaagc    600
tacagcctgg gcagcatcta cacccgcctg tactggcaag caccgacaga ctcacatact    660
gctgaaggtg atgttctaac cctgctcagc atctgtcagt ggaagccaca ggccctactg    720
cagtgggtgg acgaacatgc ccggcccttt agcaccgtca agcccatgta cggcactccg    780
gctaccactg gaacaacaga tctcatgggc tcacagaccc tgccccatgg tcacatgcag    840
accctcatct tcttagacct ggaagccact ggcctgcctt cgtctcggcc gaagtcaca     900
gagctgtgcc tgctggctgt ccacagacgt gctctggaga cacttccat ttctcaggga     960
catccacctc cagtgcccag accgcccgt gtggtggaca agctctctct gtgcattgct    1020
ccagggaaag cctgtagccc tggggccagt gagatcacag gtctgagcaa agctgagctg    1080
gaagtacagg ggcgtcaacg cttcgatgac aacctggcca tcctgctccg agccttcctg    1140
cagcgccagc cacagccttg ctgccttgtg gcacacaacg gtgaccgcta tgactttcct    1200
ctgctccaga cagagcttgc taggctgagc actcccagtc ccctagatgg taccttctgt    1260
gtggacagca tcgctgccct aaaggccttg aacaagcta gcagcccctc agggaatggt    1320
tcgaggaaaa gctacagcct gggcagcatc tacacccgcc tgtactggca agcaccgaca    1380
gactcacata ctgctgaagg tgatgttcta accctgctca gcatctgtca gtggaagcca    1440
caggccctac tgcagtgggt ggacgaacat gcccggccct ttagcaccgt caagcccatg    1500
tacggcactc cggctaccac tggaacaaca gatctctccg gaggaggtgg ctcaggtggt    1560
ggaggatctg gaggaggtgg ctcaggtggt ggaggatctg gaggaggtgg gagtctcgag    1620
cccagaggtc ccacaatcaa gcctctcct ccatgcaaat gcccagcacc taacctcttg    1680
ggtggatcat ccgtcttcat cttccctcca aagatcaagg atgtactcat gatctccctg    1740
agccccatgg tcacatgtgt ggtggtggat gtgagcgagg atgacccaga cgtccagatc    1800
agctggtttg tgaacaacgt ggaagtacac acagctcaga cacaaaccca tagagaggat    1860
tacaacagta ctctccgggt ggtcagtgcc ctccccatcc agcaccagga ctggatgagt    1920
ggcaaggagt tcaaatgctc ggtcaacaac aaagacctcc cagcgtccat cgagagaacc    1980
atctcaaaac ccagagggcc agtaagagct ccacaggtat atgtcttgcc tccaccagca    2040
gaagagatga ctaagaaaga gttcagtctg acctgcatga tcacaggctt cttacctgcc    2100
gaaattgctg tggactggac cagcaatggg cgtacagagc aaaactacaa gaacaccgca    2160
acagtcctgg actctgatgg ttcttacttc atgtacagca agctcagagt acaaaagagc    2220
acttgggaaa gaggaagtct tttcgcctgc tcagtggtcc acgagggtct gcacaatcac    2280
cttacgacta gagcttctc tcggactccg ggtaaatgat aatctaga                 2328
```

<210> SEQ ID NO 134
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
aagcttgcca ccatggaaac cccagcgcag cttctcttcc tcctgctact ctggctccca    60
```

-continued

```
gataccaccg gtatgggccc tggagctcgc agacagggca ggattgtgca gggaaggcct      120
gagatgtgct tctgcccacc ccctacccca ctccctcccc ttcggatctt aacactgggc      180
actcacacac ccaccccatg ctcctctcca ggctcagcag caggtacgta cccaaccatg      240
ggctcgcagg ccctgccccc ggggcccatg cagaccctca tcttttttcga catggaggcc     300 actggcttgc ccttctccca gcccaaggtc acggagctgt gcctgctggc tgtccacaga      360
tgtgccctgg agaccccccc cacctctcag gggccacctc ccacagttcc tccaccaccg      420
cgtgtggtag acaagctctc cctgtgtgtg gctccgggga aggcctgcag ccctgcagcc      480
agcgagatca caggtctgag cacagctgtg ctggcagcgc atgggcgtca atgttttgat      540
gacaacctgg ccaacctgct cctagccttc ctgcggcgcc agccacagcc ctggtgcctg      600
gtggcacaca atggtgaccg ctacgacttc cccctgctcc aagcagagct ggctatgctg      660
ggcctcacca gtgctctgga tggtgccttc tgtgtggata gcatcactgc gctgaaggcc      720
ctggagcgag caagcagccc ctcagaacac ggcccaagga gagctacag cctaggcagc       780 atctacactc gcctgtatgg gcagtcccct ccagactcgc acacggctga gggtgatgtc      840
ctggccctgc tcagcatctg tcagtggaga ccacaggccc tgctgcggtg ggtggatgct      900
cacgccaggc ctttcggcac catcaggccc atgtatgggg tcacagcctc tgctaggacc      960
aaagatctct ccggaggagg tggctcaggt ggtggaggat ctggaggagg tgggagtggt     1020
ggaggtggtt ctaccggtct cgagcccaaa tcttctgaca aaactcacac atgtccaccg     1080
tgcccagcac ctgaactcct gggggggaccg tcagtcttcc tcttcccccc aaaacccaag    1140
gacaccctca tgatctcccg gacccctgag gtcacatgcg tggtggtgga cgtgagccac     1200
gaagaccctg aggtcaagtt caactggtac gtggacggcg tggaggtgca taatgccaag     1260
acaaagccgc gggaggagca gtacaacagc acgtaccgtg tggtcagcgt cctcaccgtc     1320
ctgcaccagg actggctgaa tggcaaggag tacaagtgca aggtctccaa caaagccctc     1380
ccagccccca tcgagaaaac catctccaaa gccaaagggc agccccgaga accacaggtg     1440
tacaccctgc cccatcccg ggatgagctg accaagaacc aggtcagcct gacctgcctg      1500
gtcaaaggct tctatcccag cgacatcgcc gtggagtggg agagcaatgg gcagccggag     1560
aacaactaca agaccacgcc tcccgtgctg gactccgacg gctccttctt cctctacagc     1620
aagctcaccg tggacaagag caggtggcag caggggaacg tcttctcatg ctccgtgatg     1680
catgaggctc tgcacaacca ctacacgcag aagagcctct ctctgtctcc gggtaaatga     1740
taatctaga                                                              1749
```

<210> SEQ ID NO 135
<211> LENGTH: 1758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
aagcttgcca ccatggaaac cccagcgcag cttctcttcc tcctgctact ctggctccca       60
gataccaccg gtatgggccc tggagctcgc agacagggca ggattgtgca gggaaggcct      120
gagatgtgct tctgcccacc ccctacccca ctccctcccc ttcggatctt aacactgggc      180
actcacacac ccaccccatg ctcctctcca ggctcagcag caggtacgta cccaaccatg      240
ggctcgcagg ccctgccccc ggggcccatg cagaccctca tcttttttcga catggaggcc     300
```

```
actggcttgc ccttctccca gcccaaggtc acggagctgt gcctgctggc tgtccacaga    360
tgtgccctgg agagccccc cacctctcag gggccacctc ccacagttcc tccaccaccg     420
cgtgtggtag acaagctctc cctgtgtgtg gctccgggga aggcctgcag ccctgcagcc    480
agcgagatca caggtctgag cacagctgtg ctggcagcgc atgggcgtca atgttttgat    540
gacaacctgg ccaacctgct cctagccttc ctgcggcgcc agccacagcc ctggtgcctg    600
gtggcacaca atggtgaccg ctacgacttc cccctgctcc aagcagagct ggctatgctg    660
ggcctcacca gtgctctgga tggtgccttc tgtgtggata gcatcactgc gctgaaggcc    720
ctggagcgag caagcagccc ctcagaacac ggcccaagga gagctacag cctaggcagc      780 atctacactc gcctgtatgg gcagtcccct ccagactcgc acacggctga gggtgatgtc    840
ctggccctgc tcagcatctg tcagtggaga ccacaggccc tgctgcggtg ggtggatgct    900
cacgccaggc ctttcggcac catcaggccc atgtatgggg tcacagcctc tgctaggacc    960
aaagatctct ccggaggagg tggctcaggt ggtggaggat ctggaggagg tggctcaggt    1020
ggtggaggat ctggaggagg tgggagtctc gagcccaaat cttctgacaa aactcacaca    1080
tgtccaccgt gcccagcacc tgaactcctg gggggaccgt cagtcttcct cttcccccca    1140
aaacccaagg acaccctcat gatctcccgg acccctgagg tcacatgcgt ggtggtggac    1200
gtgagccacg aagaccctga ggtcaagttc aactggtacg tggacggcgt ggaggtgcat    1260
aatgccaaga caaagccgcg ggaggagcag tacaacagca cgtaccgtgt ggtcagcgtc    1320
ctcaccgtcc tgcaccagga ctggctgaat ggcaaggagt acaagtgcaa ggtctccaac    1380
aaagccctcc cagcccccat cgagaaaacc atctccaaag ccaagggca gccccgagaa     1440 ccacaggtgt acaccctgcc cccatcccgg gatgagctga ccaagaacca ggtcagcctg    1500
acctgcctgg tcaaaggctt ctatcccagc gacatcgccg tggagtggga gagcaatggg    1560
cagccggaga acaactacaa gaccacgcct cccgtgctgg actccgacgg ctccttcttc    1620
ctctacagca agctcaccgt ggacaagagc aggtggcagc aggggaacgt cttctcatgc    1680
tccgtgatgc atgaggctct gcacaaccac tacacgcaga agagcctctc tctgtctccg    1740
ggtaaatgat aatctaga                                                  1758
```

<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Gly Gly Ser Gly Gly Gly Gly Ser Gly Gly Gly Gly Ser Gly
1               5                   10                  15

Gly Gly Gly Ser
            20

<210> SEQ ID NO 137
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Gly Gly Ser Gly Gly Gly Gly Ser Gly Gly Gly Gly Ser Gly

Gly Gly Gly Ser Gly Gly Gly Ser
            20              25

<210> SEQ ID NO 138
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Gly Ser Gly Gly Gly Ser Gly Gly Gly Ser Gly
1               5                   10                  15

Gly Gly Gly Ser Gly Gly Gly Gly Ser
            20              25

<210> SEQ ID NO 139
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu

Val Met Leu Lys
            260

<210> SEQ ID NO 140
<211> LENGTH: 260
<212> TYPE: PRT
<213> ORGANISM: Homo sapiens

<400> SEQUENCE: 140

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 141
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr

```
            20                  25                  30
Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
            50                  55                  60

Tyr Val Val Ser Glu Pro Leu Gly Arg Asn Ser Tyr Lys Glu Arg Tyr
 65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
                100                 105                 110

Pro Phe Ile Val Arg Phe Phe Ser Arg Phe Thr Glu Val Arg Glu Phe
                115                 120                 125

Ala Ile Val Pro Leu His Ala Ala Pro Gly Asp Ala Val Ala Glu Ile
                130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Thr Pro Thr His
                195                 200                 205

Cys Ala Tyr Asp Arg Ile Val Val Ala Gly Met Leu Leu Arg Gly Ala
                210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
                260

<210> SEQ ID NO 142
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Leu Lys Ile Ala Ala Phe Asn Ile Gln Thr Phe Gly Glu Thr Lys Met
 1               5                  10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
            50                  55                  60

Tyr Val Val Ser Glu Pro Leu Gly Arg Asn Ser Tyr Lys Glu Arg Tyr
 65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
                100                 105                 110
```

```
Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 143
<211> LENGTH: 260
<212> TYPE: PRT
<213> ORGANISM: Homo sapiens

<400> SEQUENCE: 143

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220
```

```
Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 144
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 145
<211> LENGTH: 233
<212> TYPE: PRT
<213> ORGANISM: Homo sapiens

<400> SEQUENCE: 145
```

```
Leu Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 146
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Asp Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
```

-continued

```
                115                 120                 125

<210> SEQ ID NO 147
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Gly Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys
        275                 280

<210> SEQ ID NO 148
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ser Arg Glu Leu Ala Pro Leu Leu Leu Leu Leu Ser Ile His
```

```
  1               5                  10                 15
Ser Ala Leu Ala Met Arg Ile Cys Ser Phe Asn Val Arg Ser Phe Gly
            20                  25                 30

Glu Ser Lys Gln Glu Asp Lys Asn Ala Met Asp Val Ile Val Lys Val
            35                  40                 45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Ser
            100                 105                110

Val Lys Arg Ser Tyr His Tyr His Asp Tyr Gln Asp Gly Asp Ala Asp
            115                 120                125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
            290                 295                 300

Ser
305

<210> SEQ ID NO 149
<211> LENGTH: 156
<212> TYPE: PRT
<213> ORGANISM: Homo sapiens

<400> SEQUENCE: 149

Met Gly Leu Glu Lys Ser Leu Val Arg Leu Leu Leu Leu Val Leu Ile
 1               5                  10                 15

Leu Leu Val Leu Gly Trp Val Gln Pro Ser Leu Gly Lys Glu Ser Arg
            20                  25                 30

Ala Lys Lys Phe Gln Arg Gln His Met Asp Ser Asp Ser Ser Pro Ser
            35                  40                 45

Ser Ser Ser Thr Tyr Cys Asn Gln Met Met Arg Arg Arg Asn Met Thr
 50                  55                  60
```

```
Gln Gly Arg Cys Lys Pro Val Asn Thr Phe Val His Glu Pro Leu Val
 65                  70                  75                  80

Asp Val Gln Asn Val Cys Phe Gln Glu Lys Val Thr Cys Lys Asn Gly
                 85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155
```

<210> SEQ ID NO 150
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Met Glu Thr Pro Ala Gln Leu Leu Phe Leu Leu Leu Leu Trp Leu Pro
  1               5                  10                  15

Asp Thr Thr Gly Arg Glu Ser Ala Ala Gln Lys Phe Gln Arg Gln His
                 20                  25                  30

Met Asp Pro Asp Gly Ser Ser Ile Asn Ser Pro Thr Tyr Cys Asn Gln
             35                  40                  45

Met Met Lys Arg Arg Asp Met Thr Asn Gly Ser Cys Lys Pro Val Asn
 50                  55                  60

Thr Phe Val His Glu Pro Leu Ala Asp Val Gln Ala Val Cys Ser Gln
 65                  70                  75                  80

Glu Asn Val Thr Cys Lys Asn Arg Lys Ser Asn Cys Tyr Lys Ser Ser
                 85                  90                  95

Ser Ala Leu His Ile Thr Asp Cys His Leu Lys Gly Asn Ser Lys Tyr
            100                 105                 110

Pro Asn Cys Asp Tyr Lys Thr Thr Gln Tyr Gln Lys His Ile Ile Val
        115                 120                 125

Ala Cys Glu Gly Asn Pro Tyr Val Pro Val His Phe Asp Ala Thr Val
    130                 135                 140

Leu Glu Pro Arg Gly Leu Thr Ile Lys Pro Ser Pro Pro Cys Lys Cys
145                 150                 155                 160

Pro Ala Pro Asn Leu Leu Gly Gly Ser Ser Val Phe Ile Phe Pro Pro
                165                 170                 175

Lys Ile Lys Asp Val Leu Met Ile Ser Leu Ser Pro Met Val Thr Cys
            180                 185                 190

Val Val Val Asp Val Ser Glu Asp Asp Pro Asp Val Gln Ile Ser Trp
        195                 200                 205

Phe Val Asn Asn Val Glu Val His Thr Ala Gln Thr Gln Thr His Arg
    210                 215                 220

Glu Asp Tyr Asn Ser Thr Leu Arg Val Val Ser Ala Leu Pro Ile Gln
225                 230                 235                 240

His Gln Asp Trp Met Ser Gly Lys Glu Phe Lys Cys Ser Val Asn Asn
                245                 250                 255

Lys Asp Leu Pro Ala Ser Ile Glu Arg Thr Ile Ser Lys Pro Arg Gly
            260                 265                 270
```

```
Pro Val Arg Ala Pro Gln Val Tyr Val Leu Pro Pro Ala Glu Glu
        275                 280                 285

Met Thr Lys Lys Glu Phe Ser Leu Thr Cys Met Ile Thr Gly Phe Leu
290                 295                 300

Pro Ala Glu Ile Ala Val Asp Trp Thr Ser Asn Gly Arg Thr Glu Gln
305                 310                 315                 320

Asn Tyr Lys Asn Thr Ala Thr Val Leu Asp Ser Asp Gly Ser Tyr Phe
                325                 330                 335

Met Tyr Ser Lys Leu Arg Val Gln Lys Ser Thr Trp Glu Arg Gly Ser
            340                 345                 350

Leu Phe Ala Cys Ser Val Val His Glu Gly Leu His Asn His Leu Thr
        355                 360                 365

Thr Lys Ser Phe Ser Arg Thr Pro Gly Lys
    370                 375

<210> SEQ ID NO 151
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
```

-continued

```
                245                 250                 255
Val Ser Asn Lys Ala Leu Pro Ala Pro Ile Glu Lys Thr Ile Ser Lys
            260                 265                 270
Ala Lys Gly Gln Pro Arg Glu Pro Gln Val Tyr Thr Leu Pro Pro Ser
            275                 280                 285
Arg Asp Glu Leu Thr Lys Asn Gln Val Ser Leu Thr Cys Leu Val Lys
            290                 295                 300
Gly Phe Tyr Pro Ser Asp Ile Ala Val Glu Trp Glu Ser Asn Gly Gln
305                 310                 315                 320
Pro Glu Asn Asn Tyr Lys Thr Thr Pro Pro Val Leu Asp Ser Asp Gly
                325                 330                 335
Ser Phe Phe Leu Tyr Ser Lys Leu Thr Val Asp Lys Ser Arg Trp Gln
                340                 345                 350
Gln Gly Asn Val Phe Ser Cys Ser Val Met His Glu Gly Leu His Asn
                355                 360                 365
His Tyr Thr Gln Lys Ser Leu Ser Leu Ser Pro Gly Lys Val Asp Gly
            370                 375                 380
Ala Ser Ser Pro Val Asn Val Ser Ser Pro Ser Val Gln Asp Ile Leu
385                 390                 395                 400
Lys Ile Ala Ala Phe Asn Ile Gln Thr Phe Gly Glu Thr Lys Met Ser
                    405                 410                 415
Asn Ala Thr Leu Val Ser Tyr Ile Val Gln Ile Leu Ser Arg Tyr Asp
                420                 425                 430
Ile Ala Leu Val Gln Glu Val Arg Asp Ser His Leu Thr Ala Val Gly
                435                 440                 445
Lys Leu Leu Asp Asn Leu Asn Gln Asp Ala Pro Asp Thr Tyr His Tyr
            450                 455                 460
Val Val Ser Glu Pro Leu Gly Arg Asn Ser Tyr Lys Glu Arg Tyr Leu
465                 470                 475                 480
Phe Val Tyr Arg Pro Asp Gln Val Ser Ala Val Asp Ser Tyr Tyr Tyr
                485                 490                 495
Asp Asp Gly Cys Glu Pro Cys Arg Asn Asp Thr Phe Asn Arg Glu Pro
            500                 505                 510
Phe Ile Val Arg Phe Phe Ser Arg Phe Thr Glu Val Arg Glu Phe Ala
            515                 520                 525
Ile Val Pro Leu His Ala Ala Pro Gly Asp Ala Val Ala Glu Ile Asp
            530                 535                 540
Ala Leu Tyr Asp Val Tyr Leu Asp Val Gln Glu Lys Trp Gly Ser Glu
545                 550                 555                 560
Asp Val Met Leu Met Gly Asp Phe Asn Ala Gly Cys Ser Tyr Val Arg
                565                 570                 575
Pro Ser Gln Trp Ser Ser Ile Arg Leu Trp Thr Ser Pro Thr Phe Gln
            580                 585                 590
Trp Leu Ile Pro Asp Ser Ala Asp Thr Thr Ala Thr Pro Thr His Cys
            595                 600                 605
Ala Tyr Asp Arg Ile Val Val Ala Gly Met Leu Leu Arg Gly Ala Val
            610                 615                 620
Val Pro Asp Ser Ala Leu Pro Phe Asn Phe Gln Ala Ala Tyr Gly Leu
625                 630                 635                 640
Ser Asp Gln Leu Ala Gln Ala Ile Ser Asp His Tyr Pro Val Glu Val
                645                 650                 655
Met Leu Lys
```

<210> SEQ ID NO 152
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
                20                  25                  30

Met Asp Ser Asp Ser Ser Pro Ser Ser Ser Ser Thr Tyr Cys Asn Gln
            35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Gly Leu His Asn
        355                 360                 365

His Tyr Thr Gln Lys Ser Leu Ser Leu Ser Pro Gly Lys Val Asp Gly
        370                 375                 380

Ala Ser Ser Pro Val Asn Val Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
        435                 440                 445

Lys Leu Leu Asp Asn Leu Asn Gln Asp Ala Pro Asp Thr Tyr His Tyr
450                 455                 460

Val Val Ser Glu Pro Leu Gly Arg Asn Ser Tyr Lys Glu Arg Tyr Leu
465                 470                 475                 480

Phe Val Tyr Arg Pro Asp Gln Val Ser Ala Val Asp Ser Tyr Tyr Tyr
                485                 490                 495

Asp Asp Gly Cys Glu Pro Cys Gly Asn Asp Thr Phe Asn Arg Glu Pro
            500                 505                 510

Phe Ile Val Arg Phe Phe Ser Arg Phe Thr Glu Val Arg Glu Phe Ala
        515                 520                 525

Ile Val Pro Leu His Ala Ala Pro Gly Asp Ala Val Ala Glu Ile Asp
530                 535                 540

Ala Leu Tyr Asp Val Tyr Leu Asp Val Gln Glu Lys Trp Gly Leu Glu
545                 550                 555                 560

Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
        595                 600                 605

Ala Tyr Asp Arg Ile Val Val Ala Gly Met Leu Leu Arg Gly Ala Val
610                 615                 620

Val Pro Asp Ser Ala Leu Pro Phe Asn Phe Gln Ala Ala Tyr Gly Leu
625                 630                 635                 640

Ser Asp Gln Leu Ala Gln Ala Ile Ser Asp His Tyr Pro Val Glu Val
                645                 650                 655

Met Leu Lys

<210> SEQ ID NO 153
<211> LENGTH: 659
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
                20                  25                  30

Met Asp Ser Asp Ser Ser Pro Ser Ser Ser Thr Tyr Cys Asn Gln
            35                  40                  45

Met Met Arg Arg Arg Asn Met Thr Gln Gly Arg Cys Lys Pro Val Asn
50                  55                  60

```
Thr Phe Val His Glu Pro Leu Val Asp Val Gln Asn Val Cys Phe Gln
 65                  70                  75                  80

Glu Lys Val Thr Cys Lys Asn Gly Gln Gly Asn Cys Tyr Lys Ser Asn
                 85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
            115                 120                 125

Ala Cys Glu Gly Ser Pro Tyr Val Pro Val His Phe Asp Ala Ser Val
            130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
            195                 200                 205

Phe Asn Trp Tyr Val Asp Gly Val Glu Val His Asn Ala Lys Thr Lys
210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
            275                 280                 285

Arg Asp Glu Leu Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Gly Leu His Asn
            355                 360                 365

His Tyr Thr Gln Lys Ser Leu Ser Leu Ser Pro Gly Lys Val Asp Gly
            370                 375                 380

Ala Ser Ser Pro Val Asn Val Ser Ser Pro Ser Val Gln Asp Ile Leu
385                 390                 395                 400

Lys Ile Ala Ala Phe Asn Ile Gln Thr Phe Gly Glu Thr Lys Met Ser
                405                 410                 415

Asn Ala Thr Leu Val Ser Tyr Ile Val Gln Ile Leu Ser Arg Tyr Asp
            420                 425                 430

Ile Ala Leu Val Gln Glu Val Arg Asp Ser His Leu Thr Ala Val Gly
            435                 440                 445

Lys Leu Leu Asp Asn Leu Asn Gln Asp Ala Pro Asp Thr Tyr His Tyr
450                 455                 460

Val Val Ser Glu Pro Leu Gly Arg Asn Ser Tyr Lys Glu Arg Tyr Leu
465                 470                 475                 480
```

Phe Val Tyr Arg Pro Asp Gln Val Ser Ala Val Asp Ser Tyr Tyr Tyr
                485                 490                 495

Asp Asp Gly Cys Glu Pro Cys Gly Asn Asp Thr Phe Asn Arg Glu Pro
            500                 505                 510

Ala Ile Val Arg Phe Phe Ser Arg Phe Thr Glu Val Arg Glu Phe Ala
        515                 520                 525

Ile Val Pro Leu His Ala Ala Pro Gly Asp Ala Val Ala Glu Ile Asp
    530                 535                 540

Ala Leu Tyr Asp Val Tyr Leu Asp Val Gln Glu Lys Trp Gly Leu Glu
545                 550                 555                 560

Asp Val Met Leu Met Gly Asp Phe Asn Ala Gly Cys Ser Tyr Val Arg
                565                 570                 575

Pro Ser Gln Trp Ser Ser Ile Arg Leu Trp Thr Ser Pro Thr Phe Gln
            580                 585                 590

Trp Leu Ile Pro Asp Ser Ala Asp Thr Thr Ala Thr Pro Thr His Cys
        595                 600                 605

Ala Tyr Asp Arg Ile Val Val Ala Gly Met Leu Leu Arg Gly Ala Val
    610                 615                 620

Val Pro Asp Ser Ala Leu Pro Phe Asn Phe Gln Ala Ala Tyr Gly Leu
625                 630                 635                 640

Ser Asp Gln Leu Ala Gln Ala Ile Ser Asp His Tyr Pro Val Glu Val
                645                 650                 655

Met Leu Lys

<210> SEQ ID NO 154
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Gly Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 155
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Glu Thr Pro Ala Gln Leu Leu Phe Leu Leu Leu Leu Trp Leu Pro
1               5                   10                  15

-continued

```
Asp Thr Thr Gly Leu Lys Ile Ala Ala Phe Asn Ile Gln Thr Phe Gly
            20                  25                  30
Glu Thr Lys Met Ser Asn Ala Thr Leu Val Ser Tyr Ile Val Gln Ile
        35                  40                  45
Leu Ser Arg Tyr Asp Ile Ala Leu Val Gln Glu Val Arg Asp Ser His
    50                  55                  60
Leu Thr Ala Val Gly Lys Leu Leu Asp Asn Leu Asn Gln Asp Ala Pro
65                  70                  75                  80
Asp Thr Tyr His Tyr Val Val Ser Glu Pro Leu Gly Arg Asn Ser Tyr
                85                  90                  95
Lys Glu Arg Tyr Leu Phe Val Tyr Arg Pro Asp Gln Val Ser Ala Val
            100                 105                 110
Asp Ser Tyr Tyr Tyr Asp Asp Gly Cys Glu Pro Cys Gly Asn Asp Thr
        115                 120                 125
Phe Asn Arg Glu Pro Phe Ile Val Arg Phe Phe Ser Arg Phe Thr Glu
    130                 135                 140
Val Arg Glu Phe Ala Ile Val Pro Leu His Ala Ala Pro Gly Asp Ala
145                 150                 155                 160
Val Ala Glu Ile Asp Ala Leu Tyr Asp Val Tyr Leu Asp Val Gln Glu
                165                 170                 175
Lys Trp Gly Leu Glu Asp Val Met Leu Met Gly Asp Phe Asn Ala Gly
            180                 185                 190
Cys Ser Tyr Val Arg Pro Ser Gln Trp Ser Ser Ile Arg Leu Trp Thr
        195                 200                 205
Ser Pro Thr Phe Gln Trp Leu Ile Pro Asp Ser Ala Asp Thr Thr Ala
    210                 215                 220
Thr Pro Thr His Cys Ala Tyr Asp Arg Ile Val Val Ala Gly Met Leu
225                 230                 235                 240
Leu Arg Gly Ala Val Val Pro Asp Ser Ala Leu Pro Phe Asn Phe Gln
                245                 250                 255
Ala Ala Tyr Gly Leu Ser Asp Gln Leu Ala Gln Ala Ile Ser Asp His
            260                 265                 270
Tyr Pro Val Glu Val Met Leu Lys Leu Glu Pro Lys Ser Ser Asp Lys
        275                 280                 285
Thr His Thr Cys Pro Pro Cys Pro Ala Pro Glu Leu Leu Gly Gly Pro
    290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
            340                 345                 350
Ala Lys Thr Lys Pro Arg Glu Glu Gln Tyr Asn Ser Thr Tyr Arg Val
        355                 360                 365
Val Ser Val Leu Thr Val Leu His Gln Asp Trp Leu Asn Gly Lys Glu
    370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Asp Glu Leu Thr Lys Asn Gln Val Ser Leu Thr
            420                 425                 430
Cys Leu Val Lys Gly Phe Tyr Pro Ser Asp Ile Ala Val Glu Trp Glu
```

```
                    435                 440                 445
Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
                500                 505                 510

Lys

<210> SEQ ID NO 156
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
```

```
            275                 280                 285
Gly Ser Gly Gly Gly Ser Gly Gly Gly Ser Leu Glu Pro Lys
    290                 295                 300
Ser Ser Asp Lys Thr His Thr Cys Pro Pro Cys Pro Ala Pro Glu Leu
305                 310                 315                 320
Leu Gly Gly Pro Ser Val Phe Leu Phe Pro Pro Lys Pro Lys Asp Thr
                325                 330                 335
Leu Met Ile Ser Arg Thr Pro Glu Val Thr Cys Val Val Val Asp Val
                340                 345                 350
Ser His Glu Asp Pro Glu Val Lys Phe Asn Trp Tyr Val Asp Gly Val
                355                 360                 365
Glu Val His Asn Ala Lys Thr Lys Pro Arg Glu Glu Gln Tyr Asn Ser
    370                 375                 380
Thr Tyr Arg Val Val Ser Val Leu Thr Val Leu His Gln Asp Trp Leu
385                 390                 395                 400
Asn Gly Lys Glu Tyr Lys Cys Lys Val Ser Asn Lys Ala Leu Pro Ala
                405                 410                 415
Pro Ile Glu Lys Thr Ile Ser Lys Ala Lys Gly Gln Pro Arg Glu Pro
                420                 425                 430
Gln Val Tyr Thr Leu Pro Pro Ser Arg Asp Glu Leu Thr Lys Asn Gln
                435                 440                 445
Val Ser Leu Thr Cys Leu Val Lys Gly Phe Tyr Pro Ser Asp Ile Ala
    450                 455                 460
Val Glu Trp Glu Ser Asn Gly Gln Pro Glu Asn Asn Tyr Lys Thr Thr
465                 470                 475                 480
Pro Pro Val Leu Asp Ser Asp Gly Ser Phe Phe Leu Tyr Ser Lys Leu
                485                 490                 495
Thr Val Asp Lys Ser Arg Trp Gln Gln Gly Asn Val Phe Ser Cys Ser
                500                 505                 510
Val Met His Glu Ala Leu His Asn His Tyr Thr Gln Lys Ser Leu Ser
                515                 520                 525
Leu Ser Pro Gly Lys
    530

<210> SEQ ID NO 157
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Glu Thr Pro Ala Gln Leu Leu Phe Leu Leu Leu Leu Trp Leu Pro
1               5                   10                  15
Asp Thr Thr Gly Leu Lys Ile Ala Ala Phe Asn Ile Gln Thr Phe Gly
                20                  25                  30
Glu Thr Lys Met Ser Asn Ala Thr Leu Val Ser Tyr Ile Val Gln Ile
            35                  40                  45
Leu Ser Arg Tyr Asp Ile Ala Leu Val Gln Glu Val Arg Asp Ser His
    50                  55                  60
Leu Thr Ala Val Gly Lys Leu Leu Asp Asn Leu Asn Gln Asp Ala Pro
65                  70                  75                  80
Asp Thr Tyr His Tyr Val Val Ser Glu Pro Leu Gly Arg Asn Ser Tyr
                85                  90                  95
```

-continued

Lys Glu Arg Tyr Leu Phe Val Tyr Arg Pro Asp Gln Val Ser Ala Val
                100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
            195                 200                 205

Ser Pro Thr Phe Gln Trp Leu Ile Pro Asp Ser Ala Asp Thr Thr Ala
        210                 215                 220

Thr Pro Thr His Cys Ala Tyr Asp Arg Ile Val Val Ala Gly Met Leu
225                 230                 235                 240

Leu Arg Gly Ala Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
        450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr 515                 520                 525
Gln Lys Ser Leu Ser Leu Ser Pro Gly Lys
    530                 535

<210> SEQ ID NO 158
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Gly Ser Gly Gly Gly
        275                 280                 285

Gly Ser Gly Gly Gly Gly Ser Gly Gly Gly Ser Gly Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535

<210> SEQ ID NO 159
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Leu Glu Pro Lys Ser Ser Asp Lys
        275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
    450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 160
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

```
Met Glu Thr Pro Ala Gln Leu Leu Phe Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Asp Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380

<210> SEQ ID NO 161
<211> LENGTH: 401
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 161

```
Met Glu Thr Pro Ala Gln Leu Leu Phe Leu Leu Leu Trp Leu Pro
1               5                   10                  15

Asp Thr Thr Gly Lys Glu Ser Arg Ala Lys Lys Phe Gln Arg Gln
            20                  25                  30

His Met Asp Ser Asp Ser Ser Pro Ser Ser Ser Thr Tyr Cys Asn
        35                  40                  45

Gln Met Met Arg Arg Arg Asn Met Thr Gln Gly Arg Cys Lys Pro
    50                  55                  60

Val Asn Thr Phe Val His Glu Pro Leu Val Asp Val Gln Asn Val
65                  70                  75

Cys Phe Gln Glu Lys Val Thr Cys Lys Asn Gly Gln Gly Asn Cys
            80                  85                  90

Tyr Lys Ser Asn Ser Ser Met His Ile Thr Asp Cys Arg Leu Thr
        95                  100                 105

Asn Gly Ser Arg Tyr Pro Asn Cys Ala Tyr Arg Thr Ser Pro Lys
    110                 115                 120

Glu Arg His Ile Ile Val Ala Cys Glu Gly Ser Pro Tyr Val Pro
125                 130                 135

Val His Phe Asp Ala Ser Val Glu Asp Ser Thr Gly Gly Gly Ser
            140                 145                 150

Gly Gly Gly Ser Gly Gly Gly Ser Gly Gly Gly Ser Leu Glu Pro
        155                 160                 165

Lys Ser Ser Asp Lys Thr His Thr Cys Pro Pro Cys Pro Ala Pro
    170                 175                 180

Glu Leu Leu Gly Gly Pro Ser Val Phe Leu Phe Pro Pro Lys Pro
185                 190                 195

Lys Asp Thr Leu Met Ile Ser Arg Thr Pro Glu Val Thr Cys Val
            200                 205                 210

Val Val Asp Val Ser His Glu Asp Pro Glu Val Lys Phe Asn Trp
        215                 220                 225

Tyr Val Asp Gly Val Glu Val His Asn Ala Lys Thr Lys Pro Arg
    230                 235                 240

Glu Glu Gln Tyr Asn Ser Thr Tyr Arg Val Val Ser Val Leu Thr
245                 250                 255

Val Leu His Gln Asp Trp Leu Asn Gly Lys Glu Tyr Lys Cys Lys
            260                 265                 270

Val Ser Asn Lys Ala Leu Pro Ala Pro Ile Glu Lys Thr Ile Ser
        275                 280                 285

Lys Ala Lys Gly Gln Pro Arg Glu Pro Gln Val Tyr Thr Leu Pro
    290                 295                 300

Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu
            325                 330                 335

Ser Asn Gly Gln Pro Glu Asn Asn Tyr Lys Thr Thr Pro Pro Val
        340                 345                 350

Leu Asp Ser Asp Gly Ser Phe Phe Leu Tyr Ser Lys Leu Thr Val
    355                 360                 365

Asp Lys Ser Arg Trp Gln Gln Gly Asn Val Phe Ser Cys Ser Val
370                 375                 380

Met His Glu Ala Leu His Asn His Tyr Thr Gln Lys Ser Leu Ser
            385                 390                 395

Leu Ser Pro Gly
            400
```

Lys

<210> SEQ ID NO 162
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

Met Glu Thr Pro Ala Gln Leu Leu Phe Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
            35                  40                  45

Met Met Arg Arg Arg Asn Met Thr Gln Gly Arg Cys Lys Pro Val Asn
        50                  55                  60

Thr Phe Val His Glu Pro Leu Val Asp Val Gln Asn Val Cys Phe Gln
65              70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Ser Gly Gly Gly Ser Gly Gly
145                 150                 155                 160

Gly Gly Ser Gly Gly Gly Ser Gly Gly Gly Ser Leu Glu Pro
                165                 170                 175

Lys Ser Ser Asp Lys Thr His Thr Cys Pro Pro Cys Pro Ala Pro Glu
            180                 185                 190

Leu Leu Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
    290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

```
Thr Pro Pro Val Leu Asp Ser Asp Gly Ser Phe Phe Leu Tyr Ser Lys
            355                 360                 365

Leu Thr Val Asp Lys Ser Arg Trp Gln Gln Gly Asn Val Phe Ser Cys
        370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 163
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
```

```
                290                 295                 300
Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
                340                 345                 350

Gln Gly Asn Val Phe Ser Cys Ser Val Met His Glu Ala Leu His Asn
            355                 360                 365

His Tyr Thr Gln Lys Ser Leu Ser Leu Ser Pro Gly Lys
        370                 375                 380

<210> SEQ ID NO 164
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Gly Ser Gln Thr Leu Pro His Gly His Met Gln Thr Leu Ile Phe
1               5                   10                  15

Leu Asp Leu Glu Ala Thr Gly Leu Pro Ser Ser Arg Pro Glu Val Thr
            20                  25                  30

Glu Leu Cys Leu Leu Ala Val His Arg Arg Ala Leu Glu Asn Thr Ser
        35                  40                  45

Ile Ser Gln Gly His Pro Pro Pro Val Pro Arg Pro Pro Arg Val Val
    50                  55                  60

Asp Lys Leu Ser Leu Cys Ile Ala Pro Gly Lys Ala Cys Ser Pro Gly
65                  70                  75                  80

Ala Ser Glu Ile Thr Gly Leu Ser Lys Ala Glu Leu Glu Val Gln Gly
                85                  90                  95

Arg Gln Arg Phe Asp Asp Asn Leu Ala Ile Leu Leu Arg Ala Phe Leu
            100                 105                 110

Gln Arg Gln Pro Gln Pro Cys Cys Leu Val Ala His Asn Gly Asp Arg
        115                 120                 125

Tyr Asp Phe Pro Leu Leu Gln Thr Glu Leu Ala Arg Leu Ser Thr Pro
    130                 135                 140

Ser Pro Leu Asp Gly Thr Phe Cys Val Asp Ser Ile Ala Ala Leu Lys
145                 150                 155                 160

Ala Leu Glu Gln Ala Ser Ser Pro Ser Gly Asn Gly Ser Arg Lys Ser
                165                 170                 175

Tyr Ser Leu Gly Ser Ile Tyr Thr Arg Leu Tyr Trp Gln Ala Pro Thr
            180                 185                 190

Asp Ser His Thr Ala Glu Gly Asp Val Leu Thr Leu Leu Ser Ile Cys
        195                 200                 205

Gln Trp Lys Pro Gln Ala Leu Leu Gln Trp Val Asp Glu His Ala Arg
    210                 215                 220

Pro Phe Ser Thr Val Lys Pro Met Tyr Gly Thr Pro Ala Thr Thr Gly
225                 230                 235                 240

Thr Thr Asn Leu Arg Pro His Ala Ala Thr Ala Thr Pro Leu Ala
                245                 250                 255

Thr Ala Asn Gly Ser Pro Ser Asn Gly Arg Ser Arg Pro Lys Ser
            260                 265                 270
```

```
Pro Pro Pro Glu Lys Val Pro Glu Ala Pro Ser Gln Glu Gly Leu Leu
            275                 280                 285

Ala Pro Leu Ser Leu Leu Thr Leu Leu Thr Leu Ala Ile Ala Thr Leu
290                 295                 300

Tyr Gly Leu Phe Leu Ala Ser Pro Gly Gln
305                 310

<210> SEQ ID NO 165
<211> LENGTH: 245
<212> TYPE: PRT
<213> ORGANISM: Mus sp.

<400> SEQUENCE: 165

Met Gly Ser Gln Thr Leu Pro His Gly His Met Gln Thr Leu Ile Phe
1               5                   10                  15

Leu Asp Leu Glu Ala Thr Gly Leu Pro Ser Ser Arg Pro Glu Val Thr
                20                  25                  30

Glu Leu Cys Leu Leu Ala Val His Arg Arg Ala Leu Glu Asn Thr Ser
            35                  40                  45

Ile Ser Gln Gly His Pro Pro Pro Val Pro Arg Pro Pro Arg Val Val
        50                  55                  60

Asp Lys Leu Ser Leu Cys Ile Ala Pro Gly Lys Ala Cys Ser Pro Gly
65                  70                  75                  80

Ala Ser Glu Ile Thr Gly Leu Ser Lys Ala Glu Leu Glu Val Gln Gly
                85                  90                  95

Arg Gln Arg Phe Asp Asp Asn Leu Ala Ile Leu Leu Arg Ala Phe Leu
            100                 105                 110

Gln Arg Gln Pro Gln Pro Cys Cys Leu Val Ala His Asn Gly Asp Arg
        115                 120                 125

Tyr Asp Phe Pro Leu Leu Gln Thr Glu Leu Ala Arg Leu Ser Thr Pro
    130                 135                 140

Ser Pro Leu Asp Gly Thr Phe Cys Val Asp Ser Ile Ala Ala Leu Lys
145                 150                 155                 160

Ala Leu Glu Gln Ala Ser Ser Pro Ser Gly Asn Gly Ser Arg Lys Ser
                165                 170                 175

Tyr Ser Leu Gly Ser Ile Tyr Thr Arg Leu Tyr Trp Gln Ala Pro Thr
            180                 185                 190

Asp Ser His Thr Ala Glu Gly Asp Val Leu Thr Leu Leu Ser Ile Cys
        195                 200                 205

Gln Trp Lys Pro Gln Ala Leu Leu Gln Trp Val Asp Glu His Ala Arg
    210                 215                 220

Pro Phe Ser Thr Val Lys Pro Met Tyr Gly Thr Pro Ala Thr Thr Gly
225                 230                 235                 240

Thr Thr Asp Leu Glu
                245

<210> SEQ ID NO 166
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Glu Thr Pro Ala Gln Leu Leu Phe Leu Leu Leu Leu Trp Leu Pro
1               5                   10                  15
```

```
Asp Thr Thr Gly Met Gly Ser Gln Thr Leu Pro His Gly His Met Gln
             20                  25                  30

Thr Leu Ile Phe Leu Asp Leu Glu Ala Thr Gly Leu Pro Ser Ser Arg
         35                  40                  45

Pro Glu Val Thr Glu Leu Cys Leu Leu Ala Val His Arg Arg Ala Leu
     50                  55                  60

Glu Asn Thr Ser Ile Ser Gln Gly His Pro Pro Val Pro Arg Pro
 65                  70                  75                  80

Pro Arg Val Val Asp Lys Leu Ser Leu Cys Ile Ala Pro Gly Lys Ala
                 85                  90                  95

Cys Ser Pro Gly Ala Ser Glu Ile Thr Gly Leu Ser Lys Ala Glu Leu
            100                 105                 110

Glu Val Gln Gly Arg Gln Arg Phe Asp Asp Asn Leu Ala Ile Leu Leu
        115                 120                 125

Arg Ala Phe Leu Gln Arg Gln Pro Gln Pro Cys Cys Leu Val Ala His
    130                 135                 140

Asn Gly Asp Arg Tyr Asp Phe Pro Leu Leu Gln Thr Glu Leu Ala Arg
145                 150                 155                 160

Leu Ser Thr Pro Ser Pro Leu Asp Gly Thr Phe Cys Val Asp Ser Ile
                165                 170                 175

Ala Ala Leu Lys Ala Leu Glu Gln Ala Ser Ser Pro Ser Gly Asn Gly
            180                 185                 190

Ser Arg Lys Ser Tyr Ser Leu Gly Ser Ile Tyr Thr Arg Leu Tyr Trp
        195                 200                 205

Gln Ala Pro Thr Asp Ser His Thr Ala Glu Gly Asp Val Leu Thr Leu
    210                 215                 220

Leu Ser Ile Cys Gln Trp Lys Pro Gln Ala Leu Leu Gln Trp Val Asp
225                 230                 235                 240

Glu His Ala Arg Pro Phe Ser Thr Val Lys Pro Met Tyr Gly Thr Pro
                245                 250                 255

Ala Thr Thr Gly Thr Thr Gly Gly Gly Ser Gly Gly Gly Gly Ser
            260                 265                 270

Gly Gly Gly Gly Ser Gly Gly Gly Gly Ser Leu Glu Pro Arg Gly Pro
        275                 280                 285

Thr Ile Lys Pro Ser Pro Pro Cys Lys Cys Pro Ala Pro Asn Leu Leu
    290                 295                 300

Gly Gly Ser Ser Val Phe Ile Phe Pro Pro Lys Ile Lys Asp Val Leu
305                 310                 315                 320

Met Ile Ser Leu Ser Pro Met Val Thr Cys Val Val Val Asp Val Ser
                325                 330                 335

Glu Asp Asp Pro Asp Val Gln Ile Ser Trp Phe Val Asn Asn Val Glu
            340                 345                 350

Val His Thr Ala Gln Thr Gln Thr His Arg Glu Asp Tyr Asn Ser Thr
        355                 360                 365

Leu Arg Val Val Ser Ala Leu Pro Ile Gln His Gln Asp Trp Met Ser
    370                 375                 380

Gly Lys Glu Phe Lys Cys Ser Val Asn Asn Lys Asp Leu Pro Ala Ser
385                 390                 395                 400

Ile Glu Arg Thr Ile Ser Lys Pro Arg Gly Pro Val Arg Ala Pro Gln
                405                 410                 415

Val Tyr Val Leu Pro Pro Pro Ala Glu Glu Met Thr Lys Lys Glu Phe
            420                 425                 430

Ser Leu Thr Cys Met Ile Thr Gly Phe Leu Pro Ala Glu Ile Ala Val
```

```
                435                 440                 445
Asp Trp Thr Ser Asn Gly Arg Thr Glu Gln Asn Tyr Lys Asn Thr Ala
    450                 455                 460

Thr Val Leu Asp Ser Asp Gly Ser Tyr Phe Met Tyr Ser Lys Leu Arg
465                 470                 475                 480

Val Gln Lys Ser Thr Trp Glu Arg Gly Ser Leu Phe Ala Cys Ser Val
                485                 490                 495

Val His Glu Gly Leu His Asn His Leu Thr Thr Lys Ser Phe Ser Arg
            500                 505                 510

Thr Pro Gly Lys
            515

<210> SEQ ID NO 167
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Glu Thr Pro Ala Gln Leu Leu Phe Leu Leu Leu Leu Trp Leu Pro
1               5                   10                  15

Asp Thr Thr Gly Met Gly Ser Gln Thr Leu Pro His Gly His Met Gln
            20                  25                  30

Thr Leu Ile Phe Leu Asp Leu Glu Ala Thr Gly Leu Pro Ser Ser Arg
        35                  40                  45

Pro Glu Val Thr Glu Leu Cys Leu Leu Ala Val His Arg Arg Ala Leu
    50                  55                  60

Glu Asn Thr Ser Ile Ser Gln Gly His Pro Pro Val Pro Arg Pro
65                  70                  75                  80

Pro Arg Val Val Asp Lys Leu Ser Leu Cys Ile Ala Pro Gly Lys Ala
                85                  90                  95

Cys Ser Pro Gly Ala Ser Glu Ile Thr Gly Leu Ser Lys Ala Glu Leu
            100                 105                 110

Glu Val Gln Gly Arg Gln Arg Phe Asp Asp Asn Leu Ala Ile Leu Leu
        115                 120                 125

Arg Ala Phe Leu Gln Arg Gln Pro Gln Pro Cys Cys Leu Val Ala His
    130                 135                 140

Asn Gly Asp Arg Tyr Asp Phe Pro Leu Leu Gln Thr Glu Leu Ala Arg
145                 150                 155                 160

Leu Ser Thr Pro Ser Pro Leu Asp Gly Thr Phe Cys Val Asp Ser Ile
                165                 170                 175

Ala Ala Leu Lys Ala Leu Glu Gln Ala Ser Ser Pro Ser Gly Asn Gly
            180                 185                 190

Ser Arg Lys Ser Tyr Ser Leu Gly Ser Ile Tyr Thr Arg Leu Tyr Trp
        195                 200                 205

Gln Ala Pro Thr Asp Ser His Thr Ala Glu Gly Asp Val Leu Thr Leu
    210                 215                 220

Leu Ser Ile Cys Gln Trp Lys Pro Gln Ala Leu Leu Gln Trp Val Asp
225                 230                 235                 240

Glu His Ala Arg Pro Phe Ser Thr Val Lys Pro Met Tyr Gly Thr Pro
                245                 250                 255

Ala Thr Thr Gly Thr Thr Gly Gly Gly Ser Gly Gly Gly Ser
            260                 265                 270
```

```
Gly Gly Gly Gly Ser Gly Gly Gly Ser Gly Gly Gly Ser Leu
            275                 280                 285

Glu Pro Arg Gly Pro Thr Ile Lys Pro Ser Pro Cys Lys Cys Pro
    290                 295                 300

Ala Pro Asn Leu Leu Gly Gly Ser Ser Val Phe Ile Phe Pro Pro Lys
305                 310                 315                 320

Ile Lys Asp Val Leu Met Ile Ser Leu Ser Pro Met Val Thr Cys Val
                325                 330                 335

Val Val Asp Val Ser Glu Asp Asp Pro Asp Val Gln Ile Ser Trp Phe
            340                 345                 350

Val Asn Asn Val Glu Val His Thr Ala Gln Thr Gln Thr His Arg Glu
            355                 360                 365

Asp Tyr Asn Ser Thr Leu Arg Val Val Ser Ala Leu Pro Ile Gln His
    370                 375                 380

Gln Asp Trp Met Ser Gly Lys Glu Phe Lys Cys Ser Val Asn Asn Lys
385                 390                 395                 400

Asp Leu Pro Ala Ser Ile Glu Arg Thr Ile Ser Lys Pro Arg Gly Pro
                405                 410                 415

Val Arg Ala Pro Gln Val Tyr Val Leu Pro Pro Ala Glu Glu Met
            420                 425                 430

Thr Lys Lys Glu Phe Ser Leu Thr Cys Met Ile Thr Gly Phe Leu Pro
    435                 440                 445

Ala Glu Ile Ala Val Asp Trp Thr Ser Asn Gly Arg Thr Glu Gln Asn
    450                 455                 460

Tyr Lys Asn Thr Ala Thr Val Leu Asp Ser Asp Gly Ser Tyr Phe Met
465                 470                 475                 480

Tyr Ser Lys Leu Arg Val Gln Lys Ser Thr Trp Glu Arg Gly Ser Leu
                485                 490                 495

Phe Ala Cys Ser Val Val His Glu Gly Leu His Asn His Leu Thr Thr
            500                 505                 510

Lys Ser Phe Ser Arg Thr Pro Gly Lys
    515                 520

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Val Asp Gly Ala Ser Ser Pro Val Asn Val Ser Ser Pro Ser Val Gln
1               5                   10                  15

Asp Ile

<210> SEQ ID NO 169
<211> LENGTH: 763
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Glu Thr Pro Ala Gln Leu Leu Phe Leu Leu Leu Leu Trp Leu Pro
1               5                   10                  15

Asp Thr Thr Gly Met Gly Ser Gln Thr Leu Pro His Gly His Met Gln
```

```
                20                  25                  30
Thr Leu Ile Phe Leu Asp Leu Glu Ala Thr Gly Leu Pro Ser Ser Arg
            35                  40                  45

Pro Glu Val Thr Glu Leu Cys Leu Leu Ala Val His Arg Arg Ala Leu
 50                  55                  60

Glu Asn Thr Ser Ile Ser Gln Gly His Pro Pro Val Pro Arg Pro
 65                  70                  75                  80

Pro Arg Val Val Asp Lys Leu Ser Leu Cys Ile Ala Pro Gly Lys Ala
                85                  90                  95

Cys Ser Pro Gly Ala Ser Glu Ile Thr Gly Leu Ser Lys Ala Glu Leu
            100                 105                 110

Glu Val Gln Gly Arg Gln Arg Phe Asp Asp Asn Leu Ala Ile Leu Leu
            115                 120                 125

Arg Ala Phe Leu Gln Arg Gln Pro Gln Pro Cys Cys Leu Val Ala His
            130                 135                 140

Asn Gly Asp Arg Tyr Asp Phe Pro Leu Leu Gln Thr Glu Leu Ala Arg
145                 150                 155                 160

Leu Ser Thr Pro Ser Pro Leu Asp Gly Thr Phe Cys Val Asp Ser Ile
                165                 170                 175

Ala Ala Leu Lys Ala Leu Glu Gln Ala Ser Ser Pro Ser Gly Asn Gly
            180                 185                 190

Ser Arg Lys Ser Tyr Ser Leu Gly Ser Ile Tyr Thr Arg Leu Tyr Trp
            195                 200                 205

Gln Ala Pro Thr Asp Ser His Thr Ala Glu Gly Asp Val Leu Thr Leu
            210                 215                 220

Leu Ser Ile Cys Gln Trp Lys Pro Gln Ala Leu Leu Gln Trp Val Asp
225                 230                 235                 240

Glu His Ala Arg Pro Phe Ser Thr Val Lys Pro Met Tyr Gly Thr Pro
                245                 250                 255

Ala Thr Thr Gly Thr Thr Met Gly Ser Gln Thr Leu Pro His Gly His
            260                 265                 270

Met Gln Thr Leu Ile Phe Leu Asp Leu Glu Ala Thr Gly Leu Pro Ser
            275                 280                 285

Ser Arg Pro Glu Val Thr Glu Leu Cys Leu Leu Ala Val His Arg Arg
            290                 295                 300

Ala Leu Glu Asn Thr Ser Ile Ser Gln Gly His Pro Pro Val Pro
305                 310                 315                 320

Arg Pro Pro Arg Val Val Asp Lys Leu Ser Leu Cys Ile Ala Pro Gly
                325                 330                 335

Lys Ala Cys Ser Pro Gly Ala Ser Glu Ile Thr Gly Leu Ser Lys Ala
            340                 345                 350

Glu Leu Glu Val Gln Gly Arg Gln Arg Phe Asp Asp Asn Leu Ala Ile
            355                 360                 365

Leu Leu Arg Ala Phe Leu Gln Arg Gln Pro Gln Pro Cys Cys Leu Val
            370                 375                 380

Ala His Asn Gly Asp Arg Tyr Asp Phe Pro Leu Leu Gln Thr Glu Leu
385                 390                 395                 400

Ala Arg Leu Ser Thr Pro Ser Pro Leu Asp Gly Thr Phe Cys Val Asp
                405                 410                 415

Ser Ile Ala Ala Leu Lys Ala Leu Glu Gln Ala Ser Ser Pro Ser Gly
            420                 425                 430

Asn Gly Ser Arg Lys Ser Tyr Ser Leu Gly Ser Ile Tyr Thr Arg Leu
            435                 440                 445
```

Tyr Trp Gln Ala Pro Thr Asp Ser His Thr Ala Glu Gly Asp Val Leu
            450                 455                 460

Thr Leu Leu Ser Ile Cys Gln Trp Lys Pro Gln Ala Leu Leu Gln Trp
465                 470                 475                 480

Val Asp Glu His Ala Arg Pro Phe Ser Thr Val Lys Pro Met Tyr Gly
                485                 490                 495

Thr Pro Ala Thr Thr Gly Thr Thr Gly Gly Gly Ser Gly Gly Gly
            500                 505                 510

Gly Ser Gly Gly Gly Gly Ser Gly Gly Gly Ser Gly Gly Gly Gly
            515                 520                 525

Ser Leu Glu Pro Arg Gly Pro Thr Ile Lys Pro Ser Pro Pro Cys Lys
530                 535                 540

Cys Pro Ala Pro Asn Leu Leu Gly Gly Ser Ser Val Phe Ile Phe Pro
545                 550                 555                 560

Pro Lys Ile Lys Asp Val Leu Met Ile Ser Leu Ser Pro Met Val Thr
                565                 570                 575

Cys Val Val Val Asp Val Ser Glu Asp Asp Pro Asp Val Gln Ile Ser
                580                 585                 590

Trp Phe Val Asn Asn Val Glu Val His Thr Ala Gln Thr Gln Thr His
            595                 600                 605

Arg Glu Asp Tyr Asn Ser Thr Leu Arg Val Val Ser Ala Leu Pro Ile
610                 615                 620

Gln His Gln Asp Trp Met Ser Gly Lys Glu Phe Lys Cys Ser Val Asn
625                 630                 635                 640

Asn Lys Asp Leu Pro Ala Ser Ile Glu Arg Thr Ile Ser Lys Pro Arg
                645                 650                 655

Gly Pro Val Arg Ala Pro Gln Val Tyr Val Leu Pro Pro Ala Glu
                660                 665                 670

Glu Met Thr Lys Lys Glu Phe Ser Leu Thr Cys Met Ile Thr Gly Phe
            675                 680                 685

Leu Pro Ala Glu Ile Ala Val Asp Trp Thr Ser Asn Gly Arg Thr Glu
690                 695                 700

Gln Asn Tyr Lys Asn Thr Ala Thr Val Leu Asp Ser Asp Gly Ser Tyr
705                 710                 715                 720

Phe Met Tyr Ser Lys Leu Arg Val Gln Lys Ser Thr Trp Glu Arg Gly
                725                 730                 735

Ser Leu Phe Ala Cys Ser Val Val His Glu Gly Leu His Asn His Leu
            740                 745                 750

Thr Thr Lys Ser Phe Ser Arg Thr Pro Gly Lys
            755                 760

<210> SEQ ID NO 170
<211> LENGTH: 570
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Glu Thr Pro Ala Gln Leu Leu Phe Leu Leu Leu Leu Trp Leu Pro
1               5                   10                  15

Asp Thr Thr Gly Met Gly Pro Gly Ala Arg Arg Gln Gly Arg Ile Val
            20                  25                  30

Gln Gly Arg Pro Glu Met Cys Phe Cys Pro Pro Pro Thr Pro Leu Pro

```
            35                  40                  45
Pro Leu Arg Ile Leu Thr Leu Gly Thr His Thr Pro Thr Cys Ser
 50                  55                  60

Ser Pro Gly Ser Ala Ala Gly Thr Tyr Pro Thr Met Gly Ser Gln Ala
 65                  70                  75                  80

Leu Pro Pro Gly Pro Met Gln Thr Leu Ile Phe Phe Asp Met Glu Ala
                 85                  90                  95

Thr Gly Leu Pro Phe Ser Gln Pro Lys Val Thr Glu Leu Cys Leu Leu
                100                 105                 110

Ala Val His Arg Cys Ala Leu Glu Ser Pro Pro Thr Ser Gln Gly Pro
            115                 120                 125

Pro Pro Thr Val Pro Pro Pro Arg Val Val Asp Lys Leu Ser Leu
130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
            195                 200                 205

Leu Gln Ala Glu Leu Ala Met Leu Gly Leu Thr Ser Ala Leu Asp Gly
210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
                260                 265                 270

Glu Gly Asp Val Leu Ala Leu Leu Ser Ile Cys Gln Trp Arg Pro Gln
            275                 280                 285

Ala Leu Leu Arg Trp Val Asp Ala His Ala Arg Pro Phe Gly Thr Ile
            290                 295                 300

Arg Pro Met Tyr Gly Val Thr Ala Ser Ala Arg Thr Lys Gly Gly Gly
305                 310                 315                 320

Gly Ser Gly Gly Gly Ser Gly Gly Gly Ser Gly Gly Gly
                325                 330                 335

Ser Leu Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
            355                 360                 365

Lys Pro Lys Asp Thr Leu Met Ile Ser Arg Thr Pro Glu Val Thr Cys
            370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
            450                 455                 460
```

-continued

```
Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
            485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
            530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
                565                 570
```

<210> SEQ ID NO 171
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Met Glu Thr Pro Ala Gln Leu Leu Phe Leu Leu Leu Leu Trp Leu Pro
1               5                   10                  15

Asp Thr Thr Gly Met Gly Pro Gly Ala Arg Arg Gln Gly Arg Ile Val
            20                  25                  30

Gln Gly Arg Pro Glu Met Cys Phe Cys Pro Pro Thr Pro Leu Pro
        35                  40                  45

Pro Leu Arg Ile Leu Thr Leu Gly Thr His Thr Pro Thr Pro Cys Ser
    50                  55                  60

Ser Pro Gly Ser Ala Ala Gly Thr Tyr Pro Thr Met Gly Ser Gln Ala
65                  70                  75                  80

Leu Pro Pro Gly Pro Met Gln Thr Leu Ile Phe Phe Asp Met Glu Ala
                85                  90                  95

Thr Gly Leu Pro Phe Ser Gln Pro Lys Val Thr Glu Leu Cys Leu Leu
            100                 105                 110

Ala Val His Arg Cys Ala Leu Glu Ser Pro Pro Thr Ser Gln Gly Pro
        115                 120                 125

Pro Pro Thr Val Pro Pro Pro Arg Val Val Asp Lys Leu Ser Leu
    130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
```

```
            245                 250                 255
Ile Tyr Thr Arg Leu Tyr Gly Gln Ser Pro Pro Asp Ser His Thr Ala
            260                 265                 270

Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Ser Gly Gly Gly Ser Gly Gly Gly Gly
            325                 330                 335

Ser Gly Gly Gly Gly Ser Leu Glu Pro Lys Ser Ser Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
            405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Asp Glu Leu Thr Lys Asn Gln Val Ser Leu Thr Cys Leu
            485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
            565                 570                 575

<210> SEQ ID NO 172
<211> LENGTH: 2091
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
gttaagcttg ccaccatgga aaccccagcg cagcttctct tcctcctgct actctggctc     60
ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
```

```
ctggtccagg aggtcagaga cagccacctg actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcagg aacgacacct caaccgaga gccattcatt    420
gtcaggttct ctcccggtt cacagaggtc agggagtttg ccattgttcc cctgcatgcg    480
gccccggggg acgcagtagc cgagatcgac gctctctatg acgtctacct ggatgtccaa    540
gagaaatggg gcttggagga cgtcatgttg atgggcgact caatgcgggg ctgcagctat    600
gtgagaccct cccagtggtc atccatccgc ctgtggacaa gccccacctt ccagtggctg    660
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct ctccggagga ggtggctcag gtggtggagg atctggagga    900
ggtgggagtg gtggaggtgg ttctaccggt ctcgagccca atcttctga caaaactcac    960
acatgtccac cgtgcccagc acctgaactc ctggggggac cgtcagtctt cctcttcccc   1020
ccaaaaccca aggacaccct catgatctcc cggacccctg aggtcacatg cgtggtggtg   1080
gacgtgagcc acgaagaccc tgaggtcaag ttcaactggt acgtggacgg cgtggaggtg   1140
cataatgcca agacaaagcc gcgggaggag cagtacaaca gcacgtaccg tgtggtcagc   1200
gtcctcaccg tcctgcacca ggactggctg aatggcaagg agtacaagtg caaggtctcc   1260
aacaaagccc tcccagcccc catcgagaaa accatctcca aagccaaagg cagcccccga   1320
gaaccacagg tgtacaccct gcccccatcc cgggatgagc tgaccaagaa ccaggtcagc   1380
ctgacctgcc tggtcaaagg cttctatccc agcgacatcg ccgtggagtg ggagagcaat   1440
gggcagccgg agaacaacta caagaccacg cctcccgtgc tggactccga cggctccttc   1500
ttcctctaca gcaagctcac cgtggacaag agcaggtggc agcagggaa cgtcttctca   1560
tgctccgtga tgcatgaggc tctgcacaac cactacacgc agaagagcct ctctctgtct   1620
ccgggtaaag tcgacggagc tagcagcccc gtgaacgtga gcagcccag cgtgcaggat   1680
atcccttccc tgggcaagga atcccgggcc aagaaattcc agcggcagca tatggactca   1740
gacagttccc ccagcagcag ctccacctac tgtaaccaaa tgatgaggcg ccggaatatg   1800
acacaggggc ggtgcaaacc agtgaacacc tttgtgcacg agccctggt agatgtccag   1860
aatgtctgtt tccaggaaaa ggtcacctgc aagaacgggc agggcaactg ctacaagagc   1920
aactccagca tgcacatcac agactgccgc ctgacaaacg gctccaggta ccccaactgt   1980
gcataccgga ccagcccgaa ggagagacac atcattgtgg cctgtgaagg gagcccatat   2040
gtgccagtcc actttgatgc ttctgtggag gactctacct aataatctag a             2091
```

<210> SEQ ID NO 173
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly

-continued

```
                20                  25                  30
Glu Thr Lys Met Ser Asn Ala Thr Leu Val Ser Tyr Ile Val Gln Ile
             35                  40                  45
Leu Ser Arg Tyr Asp Ile Ala Leu Val Gln Glu Val Arg Asp Ser His
         50                  55                  60
Leu Thr Ala Val Gly Lys Leu Leu Asp Asn Leu Asn Gln Asp Ala Pro
 65                  70                  75                  80
Asp Thr Tyr His Tyr Val Val Ser Glu Pro Leu Gly Arg Asn Ser Tyr
                 85                  90                  95
Lys Glu Arg Tyr Leu Phe Val Tyr Arg Pro Asp Gln Val Ser Ala Val
             100                 105                 110
Asp Ser Tyr Tyr Tyr Asp Asp Gly Cys Glu Pro Cys Arg Asn Asp Thr
             115                 120                 125
Phe Asn Arg Glu Pro Phe Ile Val Arg Phe Phe Ser Arg Phe Thr Glu
             130                 135                 140
Val Arg Glu Phe Ala Ile Val Pro Leu His Ala Ala Pro Gly Asp Ala
145                 150                 155                 160
Val Ala Glu Ile Asp Ala Leu Tyr Asp Val Tyr Leu Asp Val Gln Glu
                 165                 170                 175
Lys Trp Gly Leu Glu Asp Val Met Leu Met Gly Asp Phe Asn Ala Gly
             180                 185                 190
Cys Ser Tyr Val Arg Pro Ser Gln Trp Ser Ser Ile Arg Leu Trp Thr
             195                 200                 205
Ser Pro Thr Phe Gln Trp Leu Ile Pro Asp Ser Ala Asp Thr Thr Ala
             210                 215                 220
Thr Pro Thr His Cys Ala Tyr Asp Arg Ile Val Val Ala Gly Met Leu
225                 230                 235                 240
Leu Arg Gly Ala Val Val Pro Asp Ser Ala Leu Pro Phe Asn Phe Gln
                 245                 250                 255
Ala Ala Tyr Gly Leu Ser Asp Gln Leu Ala Gln Ala Ile Ser Asp His
             260                 265                 270
Tyr Pro Val Glu Val Met Leu Lys Gly Gly Gly Ser Gly Gly Gly
             275                 280                 285
Gly Ser Gly Gly Gly Ser Gly Gly Gly Ser Leu Glu Pro Lys
             290                 295                 300
Ser Ser Asp Lys Thr His Thr Cys Pro Pro Cys Pro Ala Pro Glu Leu
305                 310                 315                 320
Leu Gly Gly Pro Ser Val Phe Leu Phe Pro Pro Lys Pro Lys Asp Thr
                 325                 330                 335
Leu Met Ile Ser Arg Thr Pro Glu Val Thr Cys Val Val Val Asp Val
             340                 345                 350
Ser His Glu Asp Pro Glu Val Lys Phe Asn Trp Tyr Val Asp Gly Val
             355                 360                 365
Glu Val His Asn Ala Lys Thr Lys Pro Arg Glu Glu Gln Tyr Asn Ser
             370                 375                 380
Thr Tyr Arg Val Val Ser Val Leu Thr Val Leu His Gln Asp Trp Leu
385                 390                 395                 400
Asn Gly Lys Glu Tyr Lys Cys Lys Val Ser Asn Lys Ala Leu Pro Ala
                 405                 410                 415
Pro Ile Glu Lys Thr Ile Ser Lys Ala Lys Gly Gln Pro Arg Glu Pro
             420                 425                 430
Gln Val Tyr Thr Leu Pro Pro Ser Arg Asp Glu Leu Thr Lys Asn Gln
             435                 440                 445
```

Val Ser Leu Thr Cys Leu Val Lys Gly Phe Tyr Pro Ser Asp Ile Ala
            450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys Val Asp Gly Ala Ser Ser Pro Val Asn Val Ser
530                 535                 540

Ser Pro Ser Val Gln Asp Ile Lys Glu Ser Arg Ala Lys Lys Phe Gln
545                 550                 555                 560

Arg Gln His Met Asp Ser Asp Ser Ser Pro Ser Ser Ser Ser Thr Tyr
                565                 570                 575

Cys Asn Gln Met Met Arg Arg Arg Asn Met Thr Gln Gly Arg Cys Lys
                580                 585                 590

Pro Val Asn Thr Phe Val His Glu Pro Leu Val Asp Val Gln Asn Val
                595                 600                 605

Cys Phe Gln Glu Lys Val Thr Cys Lys Asn Gly Gln Gly Asn Cys Tyr
610                 615                 620

Lys Ser Asn Ser Ser Met His Ile Thr Asp Cys Arg Leu Thr Asn Gly
625                 630                 635                 640

Ser Arg Tyr Pro Asn Cys Ala Tyr Arg Thr Ser Pro Lys Glu Arg His
                645                 650                 655

Ile Ile Val Ala Cys Glu Gly Ser Pro Tyr Val Pro Val His Phe Asp
                660                 665                 670

Ala Ser Val Glu Asp Ser Thr
        675

<210> SEQ ID NO 174
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
gttaagcttg ccaccatgga aaccccagcg cagcttctct tcctcctgct actctggctc    60
ccagatacca ccggtccttc cctgggcaag gaatcccggg ccaagaaatt ccagcggcag   120
catatggact cagacagttc ccccagcagc agctccacct actgtaacca aatgatgagg   180
cgccggaata tgacacaggg gcggtgcaaa ccagtgaaca cctttgtgca cgagcccctg   240
gtagatgtcc agaatgtctg tttccaggaa aaggtcacct gcaagaacgg cagggcaac   300 tgctacaaga gcaactccag catgcacatc acagactgcc gcctgacaaa cgactccagg   360
taccccaact gtgcataccg gaccagcccg aaggagagac acatcattgt ggcctgtgaa   420
gggagcccat atgtgccagt ccactttgat gcttctgtgg aggactctac agatctcgag   480
cccaaatctt ctgacaaaac tcacacatgt ccaccgtgtc cagcacctga actcctgggt   540
ggatcgtcag tcttcctctt ccccccaaaa cccaaggaca ctctcatgat ctcccggacc   600
cctgaggtca cgtgcgtggt ggtggacgtg agccaggaag accccgaggt ccagttcaac   660

-continued

```
tggtacgtgg acggcatgga ggtgcataat gccaagacaa agccacggga ggagcagttc    720
aacagcacgt tccgtgtggt cagcgtcctc accgtcgtgc accaggactg gctgaacggc    780
aaggagtaca agtgcaaggt ctccaacaaa gccctcccag cctccatcga gaaaacaatc    840
tccaaaacca agggcagcc ccgagaacca caggtgtaca ccctgccccc atcccgggag     900
gagatgacca gaaccaggt cagcctgacc tgcctggtca aaggcttcta tcccagcgac     960
atcgccgtgg agtgggagag caatgggcag ccggagaaca actacaacac cacgcctccc   1020
gtgctggact ccgacggctc cttctcgcctc tacagcaagc tcaccgtgga caagagcagg  1080
tggcagcagg ggaacgtctt ctcatgctcc gtgatgcatg aggctctgca caaccactac   1140
acgcagaaga gcctctctct gtctccgggt aaatgataat ctaga                   1185
```

<210> SEQ ID NO 175
<211> LENGTH: 381
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Asp Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Ser Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser Gln Glu Asp Pro Glu Val Gln
        195                 200                 205

Phe Asn Trp Tyr Val Asp Gly Met Glu Val His Asn Ala Lys Thr Lys
    210                 215                 220

Pro Arg Glu Glu Gln Phe Asn Ser Thr Phe Arg Val Val Ser Val Leu
225                 230                 235                 240

Thr Val Val His Gln Asp Trp Leu Asn Gly Lys Glu Tyr Lys Cys Lys
                245                 250                 255

Val Ser Asn Lys Ala Leu Pro Ala Ser Ile Glu Lys Thr Ile Ser Lys
            260                 265                 270
```

```
Thr Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
        290                 295                 300

Gly Phe Tyr Pro Ser Asp Ile Ala Val Glu Trp Glu Ser Asn Gly Gln
305                 310                 315                 320

Pro Glu Asn Asn Tyr Asn Thr Thr Pro Pro Val Leu Asp Ser Asp Gly
                325                 330                 335

Ser Phe Ser Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
        370                 375                 380

<210> SEQ ID NO 176
<211> LENGTH: 2106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
gttaagcttg ccaccatgga acccccagcg cagcttctct tcctcctgct actctggctc      60
ccagatacca ccgtctctgaa gatcgcagcc ttcaacatcc agacatttgg ggagaccaag    120
```

```
aagaaccagg tcagcctgac ctgcctggtc aaaggcttct atcccagcga catcgccgtg   1440
gagtgggaga gcaatgggca gccggagaac aactacaaga ccacgcctcc cgtgctggac   1500
tccgacggct ccttcttcct ctacagcaag ctcaccgtgg acaagagcag gtggcagcag   1560
gggaacgtct tctcatgctc cgtgatgcat gaggctctgc acaaccacta cacgcagaag   1620
agcctctctc tgtctccggg taaagtcgac ggagctagca gccccgtgaa cgtgagcagc   1680
cccagcgtgc aggatatccc ttccctgggc aaggaatccc gggccaagaa attccagcgg   1740
cagcatatgg actcagacag ttcccccagc agcagctcca cctactgtaa ccaaatgatg   1800
aggcgccgga atatgacaca ggggcggtgc aaaccagtga acacctttgt gcacgagccc   1860
ctggtagatg tccagaatgt ctgtttccag gaaaaggtca cctgcaagaa cgggcagggc   1920
aactgctaca agagcaactc cagcatgcac atcacagact gccgcctgac aaacggctcc   1980
aggtacccca actgtgcata ccggaccagc ccgaaggaga gacacatcat tgtggcctgt   2040
gaagggagcc catatgtgcc agtccacttt gatgcttctg tggaggactc tacctaataa   2100
tctaga                                                              2106
```

<210> SEQ ID NO 177
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220
```

```
Thr Pro Thr His Cys Ala Tyr Asp Arg Ile Val Ala Gly Met Leu
225                 230                 235                 240

Leu Arg Gly Ala Val Pro Asp Ser Ala Leu Pro Phe Asn Phe Gln
        245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Ser Gly Gly Gly
        275                 280                 285

Gly Ser Gly Gly Gly Ser Gly Gly Gly Ser Gly Gly Gly
    290                 295                 300

Ser Leu Glu Pro Lys Ser Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
                340                 345                 350

Val Val Val Asp Val Ser His Glu Asp Pro Glu Val Lys Phe Asn Trp
                355                 360                 365

Tyr Val Asp Gly Val Glu Val His Asn Ala Lys Thr Lys Pro Arg Glu
        370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
                420                 425                 430

Gln Pro Arg Glu Pro Gln Val Tyr Thr Leu Pro Pro Ser Arg Asp Glu
                435                 440                 445

Leu Thr Lys Asn Gln Val Ser Leu Thr Cys Leu Val Lys Gly Phe Tyr
                450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
                500                 505                 510

Val Phe Ser Cys Ser Val Met His Glu Ala Leu His Asn His Tyr Thr
                515                 520                 525

Gln Lys Ser Leu Ser Leu Ser Pro Gly Lys Val Asp Gly Ala Ser Ser
                530                 535                 540

Pro Val Asn Val Ser Ser Pro Ser Val Gln Asp Ile Lys Glu Ser Arg
545                 550                 555                 560

Ala Lys Lys Phe Gln Arg Gln His Met Asp Ser Asp Ser Ser Pro Ser
                565                 570                 575

Ser Ser Ser Thr Tyr Cys Asn Gln Met Met Arg Arg Arg Asn Met Thr
                580                 585                 590

Gln Gly Arg Cys Lys Pro Val Asn Thr Phe Val His Glu Pro Leu Val
                595                 600                 605

Asp Val Gln Asn Val Cys Phe Gln Glu Lys Val Thr Cys Lys Asn Gly
                610                 615                 620

Gln Gly Asn Cys Tyr Lys Ser Asn Ser Ser Met His Ile Thr Asp Cys
625                 630                 635                 640

Arg Leu Thr Asn Gly Ser Arg Tyr Pro Asn Cys Ala Tyr Arg Thr Ser
```

645                 650                 655
Pro Lys Glu Arg His Ile Ile Val Ala Cys Glu Gly Ser Pro Tyr Val
            660                 665                 670
Pro Val His Phe Asp Ala Ser Val Glu Asp Ser Thr
        675                 680

<210> SEQ ID NO 178
<211> LENGTH: 2100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

| | | | | | |
|---|---|---|---|---|---|
| gttaagcttg | ccaccatgga | aaccccagcg | cagcttctct | tcctcctgct | actctggctc | 60 |
| ccagatacca | ccggtctgaa | gatcgcagcc | ttcaacatcc | agacatttgg | ggagaccaag | 120 |
| atgtccaatg | ccaccctcgt | cagctacatt | gtgcagatcc | tgagccgcta | tgacatcgcc | 180 |
| ctggtccagg | aggtcagaga | cagccacctg | actgccgtgg | ggaagctgct | ggacaacctc | 240 |
| aatcaggatg | caccagacac | ctatcactac | gtggtcagtg | agccactggg | acggaacagc | 300 |
| tataaggagc | gctacctgtt | cgtgtacagg | cctgaccagg | tgtctgcggt | ggacagctac | 360 |
| tactacgatg | atggctgcga | gccctgcagg | aacgacacct | tcaaccgaga | gccattcatt | 420 |
| gtcaggttct | tctcccggtt | cacagaggtc | agggagtttg | ccattgttcc | cctgcatgcg | 480 |
| gccccggggg | acgcagtagc | cgagatcgac | gctctctatg | acgtctacct | ggatgtccaa | 540 |
| agaaatgggg | gcttggagga | cgtcatgttg | atgggcgact | tcaatgcggg | ctgcagctat | 600 |
| gtgagaccct | ccagtggtc | atccatccgc | ctgtggacaa | gccccacctt | ccagtggctg | 660 |
| atccccgaca | gcgctgacac | cacagctaca | cccacgcact | gtgcctatga | caggatcgtg | 720 |
| gttgcaggga | tgctgctccg | aggcgccgtt | gttcccgact | cggctcttcc | ctttaacttc | 780 |
| caggctgcct | atggcctgag | tgaccaactg | gcccaagcca | tcagtgacca | ctatccagtg | 840 |
| gaggtgatgc | tgaaagatct | ctccggagga | ggtggctcag | gtggtggagg | atctggagga | 900 |
| ggtggctcag | gtggtggagg | atctggagga | ggtgggagtc | tcgagcccaa | atcttctgac | 960 |
| aaaactcaca | catgtccacc | gtgcccagca | cctgaactcc | tggggggacc | gtcagtcttc | 1020 |
| ctcttccccc | caaaacccaa | ggacaccctc | atgatctccc | ggacccctga | ggtcacatgc | 1080 |
| gtggtggtgg | acgtgagcca | cgaagaccct | gaggtcaagt | tcaactggta | cgtggacggc | 1140 |
| gtggaggtgc | ataatgccaa | gacaaagccg | cgggaggagc | agtacaacag | cacgtaccgt | 1200 |
| gtggtcagcg | tcctcaccgt | cctgcaccag | gactggctga | atggcaagga | gtacaagtgc | 1260 |
| aaggtctcca | acaaagccct | cccagccccc | atcgagaaaa | ccatctccaa | agccaaaggg | 1320 |
| cagccccgag | aaccacaggt | gtacaccctg | cccccatccc | gggatgagct | gaccaagaac | 1380 |
| caggtcagcc | tgacctgcct | ggtcaaaggc | ttctatccca | gcgacatcgc | cgtggagtgg | 1440 |
| gagagcaatg | ggcagccgga | gaacaactac | aagaccacgc | ctcccgtgct | ggactccgac | 1500 |
| ggctccttct | tcctctacag | caagctcacc | gtggacaaga | gcaggtggca | gcaggggaac | 1560 |
| gtcttctcat | gctccgtgat | gcatgaggct | ctgcacaacc | actacacgca | gaagagcctc | 1620 |
| tctctgtctc | cgggtaaagt | cgacggagct | agcagccccg | tgaacgtgag | cagccccagc | 1680 |
| gtgcaggata | tcccttccct | gggcaaggaa | tcccgggcca | agaaattcca | gcggcagcat | 1740 |
| atggactcag | acagttcccc | cagcagcagc | tccacctact | gtaaccaaat | gatgaggcgc | 1800 |

```
cggaatatga cacaggggcg gtgcaaacca gtgaacacct ttgtgcacga gcccctggta    1860
gatgtccaga atgtctgttt ccaggaaaag gtcacctgca agaacgggca gggcaactgc    1920
tacaagagca actccagcat gcacatcaca gactgccgcc tgacaaacgg ctccaggtac    1980
cccaactgtg cataccggac cagcccgaag gagagacaca tcattgtggc ctgtgaaggg    2040
agcccatatg tgccagtcca ctttgatgct tctgtggagg actctaccta ataatctaga    2100
```

<210> SEQ ID NO 179
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 179

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Gly Gly Gly Ser Gly Gly Gly
        275                 280                 285

Gly Ser Gly Gly Gly Ser Gly Gly Gly Ser Gly Gly Gly
    290                 295                 300

Ser Leu Glu Pro Lys Ser Ser Asp Lys Thr His Thr Cys Pro Pro Cys
```

```
305                 310                 315                 320
Pro Ala Pro Glu Leu Leu Gly Gly Pro Ser Val Phe Leu Phe Pro Pro
                325                 330                 335
Lys Pro Lys Asp Thr Leu Met Ile Ser Arg Thr Pro Glu Val Thr Cys
            340                 345                 350
Val Val Val Asp Val Ser His Glu Asp Pro Glu Val Lys Phe Asn Trp
            355                 360                 365
Tyr Val Asp Gly Val Glu Val His Asn Ala Lys Thr Lys Pro Arg Glu
        370                 375                 380
Glu Gln Tyr Asn Ser Thr Tyr Arg Val Val Ser Val Leu Thr Val Leu
385                 390                 395                 400
His Gln Asp Trp Leu Asn Gly Lys Glu Tyr Lys Cys Lys Val Ser Asn
                405                 410                 415
Lys Ala Leu Pro Ala Pro Ile Glu Lys Thr Ile Ser Lys Ala Lys Gly
            420                 425                 430
Gln Pro Arg Glu Pro Gln Val Tyr Thr Leu Pro Pro Ser Arg Asp Glu
            435                 440                 445
Leu Thr Lys Asn Gln Val Ser Leu Thr Cys Leu Val Lys Gly Phe Tyr
        450                 455                 460
Pro Ser Asp Ile Ala Val Glu Trp Glu Ser Asn Gly Gln Pro Glu Asn
465                 470                 475                 480
Asn Tyr Lys Thr Thr Pro Pro Val Leu Asp Ser Asp Gly Ser Phe Phe
                485                 490                 495
Leu Tyr Ser Lys Leu Thr Val Asp Lys Ser Arg Trp Gln Gln Gly Asn
            500                 505                 510
Val Phe Ser Cys Ser Val Met His Glu Ala Leu His Asn His Tyr Thr
            515                 520                 525
Gln Lys Ser Leu Ser Leu Ser Pro Gly Lys Val Asp Gly Ala Ser Ser
        530                 535                 540
Pro Val Asn Val Ser Ser Pro Ser Val Gln Asp Ile Lys Glu Ser Arg
545                 550                 555                 560
Ala Lys Lys Phe Gln Arg Gln His Met Asp Ser Asp Ser Ser Pro Ser
                565                 570                 575
Ser Ser Ser Thr Tyr Cys Asn Gln Met Met Arg Arg Arg Asn Met Thr
            580                 585                 590
Gln Gly Arg Cys Lys Pro Val Asn Thr Phe Val His Glu Pro Leu Val
            595                 600                 605
Asp Val Gln Asn Val Cys Phe Gln Glu Lys Val Thr Cys Lys Asn Gly
        610                 615                 620
Gln Gly Asn Cys Tyr Lys Ser Asn Ser Ser Met His Ile Thr Asp Cys
625                 630                 635                 640
Arg Leu Thr Asn Gly Ser Arg Tyr Pro Asn Cys Ala Tyr Arg Thr Ser
                645                 650                 655
Pro Lys Glu Arg His Ile Ile Val Ala Cys Glu Gly Ser Pro Tyr Val
            660                 665                 670
Pro Val His Phe Asp Ala Ser Val Glu Asp Ser Thr
        675                 680

<210> SEQ ID NO 180
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 180

```
gttaagcttg ccaccatgga aacccagcg cagcttctct tcctcctgct actctggctc      60
ccagatacca ccggtctgaa gatcgcagcc ttcaacatcc agacatttgg ggagaccaag    120
atgtccaatg ccaccctcgt cagctacatt gtgcagatcc tgagccgcta tgacatcgcc    180
ctggtccagg aggtcagaga cagccacctg actgccgtgg ggaagctgct ggacaacctc    240
aatcaggatg caccagacac ctatcactac gtggtcagtg agccactggg acggaacagc    300
tataaggagc gctacctgtt cgtgtacagg cctgaccagg tgtctgcggt ggacagctac    360
tactacgatg atggctgcga gccctgcagg aacgacacct caaccgaga gccattcatt    420
gtcaggttct tctcccggtt cacagaggtc agggagtttg ccattgttcc cctgcatgcg    480
gccccggggg acgcagtagc cgagatcgac gctctctatg acgtctacct ggatgtccaa    540
gagaaatggg gcttggagga cgtcatgttg atgggcgact tcaatgcggg ctgcagctat    600
gtgagaccct cccagtggtc atccatccgc ctgtggacaa gccccacctt ccagtggctg    660
atccccgaca gcgctgacac cacagctaca cccacgcact gtgcctatga caggatcgtg    720
gttgcaggga tgctgctccg aggcgccgtt gttcccgact cggctcttcc ctttaacttc    780
caggctgcct atggcctgag tgaccaactg gcccaagcca tcagtgacca ctatccagtg    840
gaggtgatgc tgaaagatct cgagcccaaa tcttctgaca aaactcacac atgtccaccg    900
tgcccagcac ctgaactcct ggggggaccg tcagtcttcc tcttcccccc aaaacccaag    960
gacaccctca tgatctcccg gaccctgag gtcacatgcg tggtggtgga cgtgagccac   1020
gaagaccctg aggtcaagtt caactggtac gtggacggcg tggaggtgca taatgccaag   1080
acaaagccgc gggaggagca gtacaacagc acgtaccgtg tggtcagcgt cctcaccgtc   1140
ctgcaccagg actggctgaa tggcaaggag tacaagtgca aggtctccaa caaagccctc   1200
ccagccccca tcgagaaaac catctccaaa gccaaagggc agccccgaga accacaggtg   1260
tacaccctgc cccatcccg ggatgagctg accaagaacc aggtcagcct gacctgcctg   1320
gtcaaaggct tctatcccag cgacatcgcc gtggagtggg agagcaatgg gcagccggag   1380
aacaactaca agaccacgcc tcccgtgctg gactccgacg gctccttctt cctctacagc   1440
aagctcaccg tggacaagag caggtggcag caggggaacg tcttctcatg ctccgtgatg   1500
catgaggctc tgcacaacca ctacacgcag aagagcctct ctctgtctcc gggtaaagtc   1560
gacggagcta gcagccccgt gaacgtgagc agccccagcg tgcaggatat cccttccctg   1620
ggcaaggaat cccgggccaa gaaattccag cggcagcata tggactcaga cagttccccc   1680
agcagcagct ccacctactg taaccaaatg atgaggcgcc ggaatatgac acagggcggg   1740
tgcaaaccag tgaacacctt tgtgcacgag cccctggtag atgtccagaa tgtctgtttc   1800
caggaaaagg tcacctgcaa gaacgggcag ggcaactgct acaagagcaa ctccagcatg   1860
cacatcacag actgccgcct gacaaacggc tccaggtacc caactgtgc ataccggacc   1920
agcccgaagg agagacacat cattgtggcc tgtgaaggga gcccatatgt gccagtccac   1980
tttgatgctt ctgtggagga ctctacctaa taatctaga                         2019
```

<210> SEQ ID NO 181
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

| | | | | | | | | | | | | | | |
|---|---|---|---|---|---|---|---|---|---|---|---|---|---|---|
|Met|Glu|Thr|Pro|Ala|Gln|Leu|Leu|Phe|Leu|Leu|Leu|Trp|Leu|Pro|
|1| | | |5| | | | |10| | | | |15|
|Asp|Thr|Thr|Gly|Leu|Lys|Ile|Ala|Ala|Phe|Asn|Ile|Gln|Thr|Phe|Gly|
| | | |20| | | | |25| | | | |30| | |
|Glu|Thr|Lys|Met|Ser|Asn|Ala|Thr|Leu|Val|Ser|Tyr|Ile|Val|Gln|Ile|
| | |35| | | | |40| | | | |45| | | |
|Leu|Ser|Arg|Tyr|Asp|Ile|Ala|Leu|Val|Gln|Glu|Val|Arg|Asp|Ser|His|
| |50| | | | |55| | | | |60| | | | |
|Leu|Thr|Ala|Val|Gly|Lys|Leu|Leu|Asp|Asn|Leu|Asn|Gln|Asp|Ala|Pro|
|65| | | | |70| | | | |75| | | | |80|
|Asp|Thr|Tyr|His|Tyr|Val|Val|Ser|Glu|Pro|Leu|Gly|Arg|Asn|Ser|Tyr|
| | | | |85| | | | |90| | | | |95| |
|Lys|Glu|Arg|Tyr|Leu|Phe|Val|Tyr|Arg|Pro|Asp|Gln|Val|Ser|Ala|Val|
| | | |100| | | | |105| | | | |110| | |
|Asp|Ser|Tyr|Tyr|Tyr|Asp|Asp|Gly|Cys|Glu|Pro|Cys|Arg|Asn|Asp|Thr|
| | |115| | | | |120| | | | |125| | | |
|Phe|Asn|Arg|Glu|Pro|Phe|Ile|Val|Arg|Phe|Phe|Ser|Arg|Phe|Thr|Glu|
| |130| | | | |135| | | | |140| | | | |
|Val|Arg|Glu|Phe|Ala|Ile|Val|Pro|Leu|His|Ala|Ala|Pro|Gly|Asp|Ala|
|145| | | | |150| | | | |155| | | | |160|
|Val|Ala|Glu|Ile|Asp|Ala|Leu|Tyr|Asp|Val|Tyr|Leu|Asp|Val|Gln|Glu|
| | | | |165| | | | |170| | | | |175| |
|Lys|Trp|Gly|Leu|Glu|Asp|Val|Met|Leu|Met|Gly|Asp|Phe|Asn|Ala|Gly|
| | | |180| | | | |185| | | | |190| | |
|Cys|Ser|Tyr|Val|Arg|Pro|Ser|Gln|Trp|Ser|Ser|Ile|Arg|Leu|Trp|Thr|
| | |195| | | | |200| | | | |205| | | |
|Ser|Pro|Thr|Phe|Gln|Trp|Leu|Ile|Pro|Asp|Ser|Ala|Asp|Thr|Thr|Ala|
| |210| | | | |215| | | | |220| | | | |
|Thr|Pro|Thr|His|Cys|Ala|Tyr|Asp|Arg|Ile|Val|Val|Ala|Gly|Met|Leu|
|225| | | | |230| | | | |235| | | | |240|
|Leu|Arg|Gly|Ala|Val|Val|Pro|Asp|Ser|Ala|Leu|Pro|Phe|Asn|Phe|Gln|
| | | | |245| | | | |250| | | | |255| |
|Ala|Ala|Tyr|Gly|Leu|Ser|Asp|Gln|Leu|Ala|Gln|Ala|Ile|Ser|Asp|His|
| | | |260| | | | |265| | | | |270| | |
|Tyr|Pro|Val|Glu|Val|Met|Leu|Lys|Leu|Glu|Pro|Lys|Ser|Ser|Asp|Lys|
| | |275| | | | |280| | | | |285| | | |
|Thr|His|Thr|Cys|Pro|Pro|Cys|Pro|Ala|Pro|Glu|Leu|Leu|Gly|Gly|Pro|
| |290| | | | |295| | | | |300| | | | |
|Ser|Val|Phe|Leu|Phe|Pro|Pro|Lys|Pro|Lys|Asp|Thr|Leu|Met|Ile|Ser|
|305| | | | |310| | | | |315| | | | |320|
|Arg|Thr|Pro|Glu|Val|Thr|Cys|Val|Val|Val|Asp|Val|Ser|His|Glu|Asp|
| | | | |325| | | | |330| | | | |335| |
|Pro|Glu|Val|Lys|Phe|Asn|Trp|Tyr|Val|Asp|Gly|Val|Glu|Val|His|Asn|
| | | |340| | | | |345| | | | |350| | |
|Ala|Lys|Thr|Lys|Pro|Arg|Glu|Glu|Gln|Tyr|Asn|Ser|Thr|Tyr|Arg|Val|
| | |355| | | | |360| | | | |365| | | |
|Val|Ser|Val|Leu|Thr|Val|Leu|His|Gln|Asp|Trp|Leu|Asn|Gly|Lys|Glu|
| |370| | | | |375| | | | |380| | | | |
|Tyr|Lys|Cys|Lys|Val|Ser|Asn|Lys|Ala|Leu|Pro|Ala|Pro|Ile|Glu|Lys|
|385| | | | |390| | | | |395| | | | |400|
|Thr|Ile|Ser|Lys|Ala|Lys|Gly|Gln|Pro|Arg|Glu|Pro|Gln|Val|Tyr|Thr|

Leu Pro Pro Ser Arg Asp Glu Leu Thr Lys Asn Gln Val Ser Leu Thr
    420                 425                 430

Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys Val Asp Gly Ala Ser Ser Pro Val Asn Val Ser Ser Pro Ser Val
        515                 520                 525

Gln Asp Ile Lys Glu Ser Arg Ala Lys Lys Phe Gln Arg Gln His Met
    530                 535                 540

Asp Ser Asp Ser Ser Pro Ser Ser Ser Thr Tyr Cys Asn Gln Met
545                 550                 555                 560

Met Arg Arg Arg Asn Met Thr Gln Gly Arg Cys Lys Pro Val Asn Thr
                565                 570                 575

Phe Val His Glu Pro Leu Val Asp Val Gln Asn Val Cys Phe Gln Glu
            580                 585                 590

Lys Val Thr Cys Lys Asn Gly Gln Gly Asn Cys Tyr Lys Ser Asn Ser
        595                 600                 605

Ser Met His Ile Thr Asp Cys Arg Leu Thr Asn Gly Ser Arg Tyr Pro
    610                 615                 620

Asn Cys Ala Tyr Arg Thr Ser Pro Lys Glu Arg His Ile Ile Val Ala
625                 630                 635                 640

Cys Glu Gly Ser Pro Tyr Val Pro Val His Phe Asp Ala Ser Val Glu
                645                 650                 655

Asp Ser Thr

<210> SEQ ID NO 182
<211> LENGTH: 1652
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
gaccaagctt gccaccatgg aaacccagc gcagcttctc ttcctcctgc tactctggct      60
cccagatacc accggtctaa ggctctgctc cttcaatgtg aggtcctttg agcgagcaa     120 gaaggaaaac catgaagcca tggatatcat tgtgaagatc atcaaacgct gtgaccttat    180
actgttgatg gaaatcaagg acagcagcaa caacatctgt cccatgctga tggagaagct    240
gaatggaaat tcacgaagaa gcacaacata caactatgtg attagttctc gacttggaag    300
aaacacgtac aaagagcagt atgccttcgt ctacaaggag aagctggtgt ctgtgaagac    360
aaaataccac taccatgact atcaggatgg agacacagac gtgttttcca gggagccctt    420
tgtggtttgg ttccattccc cctttactgc tgtcaaggac ttcgtgattg tccccttgca    480
cacaactccc gagacctccg ttaaagagat agatgagctg gtcgatgtct acacggatgt    540
gagaagccag tggaagacag agaatttcat cttcatgggt gatttcaacg ccggctgtag    600

```
ctatgtcccc aagaaggcct ggcagaacat tcgtttgagg acggacccca agtttgtttg      660
gctgattggg gaccaagagg acactacggt caagaagagt accagctgtg cctatgacag      720
gattgtgctt tgtggacaag agatagtcaa ctccgtggtt ccccgttcca gtggcgtctt      780
tgactttcag aaagcttatg acttgtctga agaggaggcc ctggatgtca gtgatcactt      840
tccagttgag tttaagctac agtcttcaag ggccttcacc aacaacagaa atctgtttc       900 tctcaaaaag agaaaaaaag gcaatcgctc ctcagatctc gagcccagag gtctcacaat      960
caagccctct cctccatgca aatgcccagc acctaacctc ttgggtggat catccgtctt     1020
catcttccct ccaaagatca aggatgtact catgatctcc ctgagcccca tggtcacatg     1080
tgtggtggtg gatgtgagcg aggatgaccc agacgtccag atcagctggt ttgtgaacaa     1140
cgtggaagta cacacagctc agacacaaac ccatagagag gattacaaca gtactctccg     1200
ggtggtcagt gccctcccca tccagcacca ggactggatg agtggcaagg agttcaaatg     1260
ctcggtcaac aacaaagacc tcccagcgtc catcgagaga accatctcaa aacccagagg     1320
gccagtaaga gctccacagg tatatgtctt gcctccacca gcagaagaga tgactaagaa     1380
agagttcagt ctgacctgca tgatcacagg cttcttacct gccgaaattg ctgtggactg     1440
gaccagcaat gggcgtacag agcaaaacta caagaacacc gcaacagtcc tggactctga     1500
tggttcttac ttcatgtaca gcaagctcag agtacaaaag agcacttggg aaagaggaag     1560
tcttttcgcc tgctcagtgg tccacgaggg tctgcacaat caccttacga ctaagagctt     1620
ctctcggact ccgggtaaat gataatctag aa                                   1652
```

<210> SEQ ID NO 183
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Met Glu Thr Pro Ala Gln Leu Leu Phe Leu Leu Leu Trp Leu Pro
1               5                   10                  15

Asp Thr Thr Gly Leu Arg Leu Cys Ser Phe Asn Val Arg Ser Phe Gly
                20                  25                  30

Ala Ser Lys Lys Glu Asn His Glu Ala Met Asp Ile Val Lys Ile
            35                  40                  45

Ile Lys Arg Cys Asp Leu Ile Leu Leu Met Glu Ile Lys Asp Ser Ser
50                  55                  60

Asn Asn Ile Cys Pro Met Leu Met Glu Lys Leu Asn Gly Asn Ser Arg
65                  70                  75                  80

Arg Ser Thr Thr Tyr Asn Tyr Val Ile Ser Ser Arg Leu Gly Arg Asn
                85                  90                  95

Thr Tyr Lys Glu Gln Tyr Ala Phe Val Tyr Lys Glu Lys Leu Val Ser
            100                 105                 110

Val Lys Thr Lys Tyr His Tyr His Asp Tyr Gln Asp Gly Asp Thr Asp
        115                 120                 125

Val Phe Ser Arg Glu Pro Phe Val Val Trp Phe His Ser Pro Phe Thr
    130                 135                 140

Ala Val Lys Asp Phe Val Ile Val Pro Leu His Thr Thr Pro Glu Thr
145                 150                 155                 160

Ser Val Lys Glu Ile Asp Glu Leu Val Asp Val Tyr Thr Asp Val Arg
```

```
                165                 170                 175
Ser Gln Trp Lys Thr Glu Asn Phe Ile Phe Met Gly Asp Phe Asn Ala
            180                 185                 190

Gly Cys Ser Tyr Val Pro Lys Lys Ala Trp Gln Asn Ile Arg Leu Arg
            195                 200                 205

Thr Asp Pro Lys Phe Val Trp Leu Ile Gly Asp Gln Glu Asp Thr Thr
            210                 215                 220

Val Lys Lys Ser Thr Ser Cys Ala Tyr Asp Arg Ile Val Leu Cys Gly
225                 230                 235                 240

Gln Glu Ile Val Asn Ser Val Val Pro Arg Ser Ser Gly Val Phe Asp
                245                 250                 255

Phe Gln Lys Ala Tyr Asp Leu Ser Glu Glu Ala Leu Asp Val Ser
                260                 265                 270

Asp His Phe Pro Val Glu Phe Lys Leu Gln Ser Ser Arg Ala Phe Thr
                275                 280                 285

Asn Asn Arg Lys Ser Val Ser Leu Lys Lys Arg Lys Lys Gly Asn Arg
            290                 295                 300

Ser Ser Asp Leu Glu Pro Arg Gly Leu Thr Ile Lys Pro Ser Pro Pro
305                 310                 315                 320

Cys Lys Cys Pro Ala Pro Asn Leu Leu Gly Ser Ser Val Phe Ile
                325                 330                 335

Phe Pro Pro Lys Ile Lys Asp Val Leu Met Ile Ser Leu Ser Pro Met
            340                 345                 350

Val Thr Cys Val Val Val Asp Val Ser Glu Asp Asp Pro Asp Val Gln
            355                 360                 365

Ile Ser Trp Phe Val Asn Asn Val Glu Val His Thr Ala Gln Thr Gln
        370                 375                 380

Thr His Arg Glu Asp Tyr Asn Ser Thr Leu Arg Val Val Ser Ala Leu
385                 390                 395                 400

Pro Ile Gln His Gln Asp Trp Met Ser Gly Lys Glu Phe Lys Cys Ser
                405                 410                 415

Val Asn Asn Lys Asp Leu Pro Ala Ser Ile Glu Arg Thr Ile Ser Lys
            420                 425                 430

Pro Arg Gly Pro Val Arg Ala Pro Gln Val Tyr Val Leu Pro Pro Pro
        435                 440                 445

Ala Glu Glu Met Thr Lys Lys Glu Phe Ser Leu Thr Cys Met Ile Thr
    450                 455                 460

Gly Phe Leu Pro Ala Glu Ile Ala Val Asp Trp Thr Ser Asn Gly Arg
465                 470                 475                 480

Thr Glu Gln Asn Tyr Lys Asn Thr Ala Thr Val Leu Asp Ser Asp Gly
                485                 490                 495

Ser Tyr Phe Met Tyr Ser Lys Leu Arg Val Gln Lys Ser Thr Trp Glu
            500                 505                 510

Arg Gly Ser Leu Phe Ala Cys Ser Val Val His Glu Gly Leu His Asn
            515                 520                 525

His Leu Thr Thr Lys Ser Phe Ser Arg Thr Pro Gly Lys
    530                 535                 540

<210> SEQ ID NO 184
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (832)..(832)
<223> OTHER INFORMATION: a, c, t, g, unknown or other

<400> SEQUENCE: 184

```
gagaccagct tgccccatgt ccctgcaccc agcttcccca cgcctggcct ccctgctgct    60
cttcatcctt gccctccatg acaccctggc cctaaggctc tgctccttca atgtgaggtc   120
ctttggagcg agcaagaagg aaaaccatga agccatggat atcattgtga agatcatcaa   180
acgctgtgac cttatactgt tgatggaaat caaggacagc agcaacaaca tctgtcccat   240
gctgatggag aagctgaatg gaaattcacg aagaagcaca acatacaact atgtgattag   300
ttctcgactt ggaagaaaca cgtacaaaga gcagtatgcc ttcgtctaca aggagaagct   360
ggtgtctgtg aagacaaaat accactacca tgactatcag gatggagaca cagacgtgtt   420
ttccagggag cccttttgtgg tttggttcca ttcccccttt actgctgtca aggacttcgt   480
gattgtcccc ttgcacacaa ctcccgagac ctccgttaaa gagatagatg agctggtcga   540
tgtctacacg gatgtgagaa gccagtggaa gacagagaat tcatcttca tgggtgattt   600
caacgccggc tgtagctatg tccccaagaa ggcctggcag aacattcgtt tgaggacgga   660
ccccaagttt gtttggctga ttggggacca agaggacact acggtcaaga gagtaccag   720
ctgtgcctat gacaggattg tgctttgtgg acaagagata gtcaactccg tggttccccg   780
ttccagtggc gtctttgact ttcagaaagc ttatgacttg tctgangagg angccctgga   840
tgtcagtgat cactttccag ttgagtttaa gctacagtct tcaagggcct tcaccaacaa   900
cagaaaatct gtttctctca aaagagaaa aaaggcaat cgctcctcag atctcgagcc   960
cagaggtctc acaatcaagc cctctcctcc atgcaaatgc ccagcaccta acctcttggg  1020
tggatcatcc gtcttcatct tccctccaaa gatcaaggat gtactcatga tctccctgag  1080
ccccatggtc acatgtgtgg tggtggatgt gagcgaggat gacccagacg tccagatcag  1140
ctggtttgtg aacaacgtgg aagtacacac agctcagaca caaacccata gagaggatta  1200
caacagtact ctccgggtgg tcagtgccct ccccatccag caccaggact ggatgagtgg  1260
caaggagttc aaatgctcgg tcaacaacaa agacctccca cgtccatcg agagaaccat  1320
ctcaaaaccc agagggccag taagagctcc acaggtatat gtcttgcctc caccagcaga  1380
agagatgact aagaaagagt tcagtctgac ctgcatgatc acaggcttct acctgccga  1440
aattgctgtg gactggacca gcaatgggcg tacagagcaa aactacaaga acaccgcaac  1500
agtcctggac tctgatggtt cttacttcat gtacagcaag ctcagagtac aaaagagcac  1560
ttgggaaaga ggaagtcttt tcgcctgctc agtggtccac gagggtctgc acaatcacct  1620
tacgactaag agcttctctc ggactccggg taaatgataa tctagaa         1667
```

<210> SEQ ID NO 185
<211> LENGTH: 546
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (270)..(270)
<223> OTHER INFORMATION: Any amino acid

```
<220> FEATURE:
<221> NAME/KEY: MOD_RES
<222> LOCATION: (272)..(272)
<223> OTHER INFORMATION: Any amino acid

<400> SEQUENCE: 185

Met Ser Leu His Pro Ala Ser Pro Arg Leu Ala Ser Leu Leu Phe
1               5                   10                  15

Ile Leu Ala Leu His Asp Thr Leu Ala Leu Arg Leu Cys Ser Phe Asn
            20                  25                  30

Val Arg Ser Phe Gly Ala Ser Lys Lys Glu Asn His Glu Ala Met Asp
                35                  40                  45

Ile Ile Val Lys Ile Ile Lys Arg Cys Asp Leu Ile Leu Leu Met Glu
50                  55                  60

Ile Lys Asp Ser Ser Asn Asn Ile Cys Pro Met Leu Met Glu Lys Leu
65                  70                  75                  80

Asn Gly Asn Ser Arg Arg Ser Thr Thr Tyr Asn Tyr Val Ile Ser Ser
                85                  90                  95

Arg Leu Gly Arg Asn Thr Tyr Lys Glu Gln Tyr Ala Phe Val Tyr Lys
            100                 105                 110

Glu Lys Leu Val Ser Val Lys Thr Lys Tyr His Tyr His Asp Tyr Gln
            115                 120                 125

Asp Gly Asp Thr Asp Val Phe Ser Arg Glu Pro Phe Val Val Trp Phe
130                 135                 140

His Ser Pro Phe Thr Ala Val Lys Asp Phe Val Ile Val Pro Leu His
145                 150                 155                 160

Thr Thr Pro Glu Thr Ser Val Lys Glu Ile Asp Glu Leu Val Asp Val
                165                 170                 175

Tyr Thr Asp Val Arg Ser Gln Trp Lys Thr Glu Asn Phe Ile Phe Met
            180                 185                 190

Gly Asp Phe Asn Ala Gly Cys Ser Tyr Val Pro Lys Lys Ala Trp Gln
            195                 200                 205

Asn Ile Arg Leu Arg Thr Asp Pro Lys Phe Val Trp Leu Ile Gly Asp
210                 215                 220

Gln Glu Asp Thr Thr Val Lys Lys Ser Thr Ser Cys Ala Tyr Asp Arg
225                 230                 235                 240

Ile Val Leu Cys Gly Gln Glu Ile Val Asn Ser Val Val Pro Arg Ser
                245                 250                 255

Ser Gly Val Phe Asp Phe Gln Lys Ala Tyr Asp Leu Ser Xaa Glu Xaa
            260                 265                 270

Ala Leu Asp Val Ser Asp His Phe Pro Val Glu Phe Lys Leu Gln Ser
            275                 280                 285

Ser Arg Ala Phe Thr Asn Asn Arg Lys Ser Val Ser Leu Lys Lys Arg
            290                 295                 300

Lys Lys Gly Asn Arg Ser Ser Asp Leu Glu Pro Arg Gly Leu Thr Ile
305                 310                 315                 320

Lys Pro Ser Pro Pro Cys Lys Cys Pro Ala Pro Asn Leu Leu Gly Gly
                325                 330                 335

Ser Ser Val Phe Ile Phe Pro Pro Lys Ile Lys Asp Val Leu Met Ile
            340                 345                 350

Ser Leu Ser Pro Met Val Thr Cys Val Val Asp Val Ser Glu Asp
            355                 360                 365

Asp Pro Asp Val Gln Ile Ser Trp Phe Val Asn Val Glu Val His
    370                 375                 380
```

Thr Ala Gln Thr Gln Thr His Arg Glu Asp Tyr Asn Ser Thr Leu Arg
385                 390                 395                 400

Val Val Ser Ala Leu Pro Ile Gln His Gln Asp Trp Met Ser Gly Lys
            405                 410                 415

Glu Phe Lys Cys Ser Val Asn Asn Lys Asp Leu Pro Ala Ser Ile Glu
            420                 425                 430

Arg Thr Ile Ser Lys Pro Arg Gly Pro Val Arg Ala Pro Gln Val Tyr
            435                 440                 445

Val Leu Pro Pro Pro Ala Glu Glu Met Thr Lys Lys Glu Phe Ser Leu
    450                 455                 460

Thr Cys Met Ile Thr Gly Phe Leu Pro Ala Glu Ile Ala Val Asp Trp
465                 470                 475                 480

Thr Ser Asn Gly Arg Thr Glu Gln Asn Tyr Lys Asn Thr Ala Thr Val
            485                 490                 495

Leu Asp Ser Asp Gly Ser Tyr Phe Met Tyr Ser Lys Leu Arg Val Gln
            500                 505                 510

Lys Ser Thr Trp Glu Arg Gly Ser Leu Phe Ala Cys Ser Val Val His
            515                 520                 525

Glu Gly Leu His Asn His Leu Thr Thr Lys Ser Phe Ser Arg Thr Pro
    530                 535                 540

Gly Lys
545

<210> SEQ ID NO 186
<211> LENGTH: 2094
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
gttaagcttg ccaccatgga aaccccagcg cagcttctct tcctcctgct actctggctc      60
ccagatacca ccggtatgag gatctgctcc ttcaacgtca ggtcctttgg ggaaagcaag     120
caggaagaca agaatgccat ggatgtcatt gtgaaggtca tcaaacgctg tgacatcata     180
ctcgtgatgg aaatcaagga cagcaacaac aggatctgcc ccatactgat ggagaagctg     240
aacagaaatt caaggagagg cataacatac aactatgtga ttagctctcg gcttggaaga     300
aacacatata agaacaata tgcctttctc tacaaggaaa agctggtgtc tgtgaagagg     360
agttatcact accatgacta tcaggatgga gacgcagatg tgttttccag ggagcccttt     420
gtggtctggt ccaatctccc ccacactgct gtcaaagact tcgtgattat ccccctgcac     480
accaccccag agacatccgt taaggagatc gatgagttgg ttgaggtcta cacggacgtg     540
aaacaccgct ggaaggcgga gaatttcatt ttcatgggtg acttcaatgc cggctgcagc     600
tacgtcccca agaaggcctg gaagaacatc cgcttgagga ctgacccag gtttgtttgg     660 ctgatcgggg accaagagga caccacggtg aagaagagca ccaactgtgc atatgacagg     720
attgtgctta gaggacaaga aatcgtcagt tctgttgttc ccagtcaaa cagtgttttt     780 gacttccaga agcttacaa gctgactgaa gaggaggccc tggatgtcag cgaccacttt     840
ccagttgaat ttaaactaca gtcttcaagg gccttcacca acagcaaaaa atctgtcact     900
ctaaggaaga aaacaaagag caaacgctca gatctcgagc ccaaatcttc tgacaaaact     960
cacacatgtc caccgtgccc agcacctgaa ctcctggggg gaccgtcagt cttcctcttc    1020
cccccaaaac ccaaggacac cctcatgatc tcccggaccc ctgaggtcac atgcgtggtg    1080

```
gtggacgtga gccacgaaga ccctgaggtc aagttcaact ggtacgtgga cggcgtggag    1140
gtgcataatg ccaagacaaa gccgcgggag gagcagtaca acagcacgta ccgtgtggtc    1200
agcgtcctca ccgtcctgca ccaggactgg ctgaatggca aggagtacaa gtgcaaggtc    1260
tccaacaaag ccctcccagc ccccatcgag aaaaccatct ccaaagccaa agggcagccc    1320
cgagaaccac aggtgtacac cctgccccca tcccgggatg agctgaccaa gaaccaggtc    1380
agcctgacct gcctggtcaa aggcttctat cccagcgaca tcgccgtgga gtgggagagc    1440
aatgggcagc cggagaacaa ctacaagacc acgcctcccg tgctggactc cgacggctcc    1500
ttcttcctct acagcaagct caccgtggac aagagcaggt ggcagcaggg gaacgtcttc    1560
tcatgctccg tgatgcatga ggctctgcac aaccactaca cgcagaagag cctctctctg    1620
tctccgggta aagtcgacgg agctagcagc cccgtgaacg tgagcagccc cagcgtgcag    1680
gatatccctt ccctgggcaa ggaatcccgg gccaagaaat ccagcggca gcatatggac    1740 tcagacagtt cccccagcag cagctccacc tactgtaacc aaatgatgag cgccggaat    1800 atgacacagg ggcggtgcaa accagtgaac acctttgtgc acgagcccct ggtagatgtc    1860
cagaatgtct gtttccagga aaaggtcacc tgcaagaacg ggcagggcaa ctgctacaag    1920
agcaactcca gcatgcacat cacagactgc cgcctgacaa acggctccag gtaccccaac    1980
tgtgcatacc ggaccagccc gaaggagaga cacatcattg tggcctgtga agggagccca    2040
tatgtgccag tccactttga tgcttctgtg gaggactcta cctaataatc taga          2094
```

<210> SEQ ID NO 187
<211> LENGTH: 684
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

```
Met Glu Thr Pro Ala Gln Leu Leu Phe Leu Leu Leu Leu Trp Leu Pro
1               5                  10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175
```

```
His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Val Val Pro Lys Ser Asn Ser Val Phe Asp
                245                 250                 255

Phe Gln Lys Ala Tyr Lys Leu Thr Glu Glu Ala Leu Asp Val Ser
        260                 265                 270

Asp His Phe Pro Val Glu Phe Lys Leu Gln Ser Ser Arg Ala Phe Thr
    275                 280                 285

Asn Ser Lys Lys Ser Val Thr Leu Arg Lys Lys Thr Lys Ser Lys Arg
    290                 295                 300

Ser Leu Glu Pro Lys Ser Ser Asp Lys Thr His Thr Cys Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
                340                 345                 350

Val Val Val Asp Val Ser His Glu Asp Pro Glu Val Lys Phe Asn Trp
                355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
                420                 425                 430

Gln Pro Arg Glu Pro Gln Val Tyr Thr Leu Pro Pro Ser Arg Asp Glu
            435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Lys Glu Ser Arg
545                 550                 555                 560

Ala Lys Lys Phe Gln Arg Gln His Met Asp Ser Asp Ser Ser Pro Ser
                565                 570                 575

Ser Ser Ser Thr Tyr Cys Asn Gln Met Met Arg Arg Arg Asn Met Thr
                580                 585                 590

Gln Gly Arg Cys Lys Pro Val Asn Thr Phe Val His Glu Pro Leu Val
```

```
                    595                 600                 605
Asp Val Gln Asn Val Cys Phe Gln Glu Lys Val Thr Cys Lys Asn Gly
        610                 615                 620

Gln Gly Asn Cys Tyr Lys Ser Asn Ser Ser Met His Ile Thr Asp Cys
625                 630                 635                 640

Arg Leu Thr Asn Gly Ser Arg Tyr Pro Asn Cys Ala Tyr Arg Thr Ser
                645                 650                 655

Pro Lys Glu Arg His Ile Ile Val Ala Cys Glu Gly Ser Pro Tyr Val
            660                 665                 670

Pro Val His Phe Asp Ala Ser Val Glu Asp Ser Thr
            675                 680
```

<210> SEQ ID NO 188
<211> LENGTH: 1620
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188

```
aagcttgccg ccatggaaac cccagcgcag cttctcttcc tcctgctact ctggctccca      60
gataccaccg gtaaggaatc ccgggccaag aaattccagc ggcagcatat ggactcagac     120
agttccccca gcagcagctc cacctactgt aaccaaatga tgaggcgccg aatatgaca     180
caggggcggt gcaaaccagt gaacaccttt gtgcacgagc cctggtaga tgtccagaat     240
gtctgtttcc aggaaaaggt cacctgcaag aacgggcagg gcaactgcta caagagcaac     300
tccagcatgc acatcacaga ctgccgcctg acaaacggct ccaggtaccc caactgtgca     360
taccggacca gcccgaagga gagacacatc attgtggcct gtgaagggag cccatatgtg     420
ccagtccact ttgatgcttc tgtggaggac tctacagatc tcgagcccaa atcttctgac     480
aaaactcaca catgtccacc gtgcccagca cctgaactcc tggggggacc gtcagtcttc     540
ctcttccccc caaaacccaa ggacaccctc atgatctccc ggacccctga ggtcacatgc     600
gtggtggtgg acgtgagcca cgaagaccct gaggtcaagt tcaactggta cgtggacggc     660
gtggaggtgc ataatgccaa gacaaagccg cgggaggagc agtacaacag cacgtaccgt     720
gtggtcagcg tcctcaccgt cctgcaccag gactggctga atggcaagga gtacaagtgc     780
aaggtctcca acaaagccct cccagccccc atcgagaaaa ccatctccaa agccaaaggg     840
cagccccgag aaccacaggt gtacaccctg cccccatccc gggatgagct gaccaagaac     900
caggtcagcc tgacctgcct ggtcaaaggc ttctatccca gcgacatcgc cgtggagtgg     960
gagagcaatg ggcagccgga gaacaactac aagaccacgc ctcccgtgct ggactccgac    1020
ggctccttct tcctctacag caagctcacc gtggacaaga gcaggtggca gcaggggaac    1080
gtcttctcat gctccgtgat gcatgagggt ctgcacaacc actacacgca gaagagcctc    1140
tctctgtctc cgggtaaagt cgacggtgct agcagccatg tgaatgtgag cagccctagc    1200
gtgcaggata tcccttccct gggcaaggaa tcccgggcca agaaattcca gcggcagcat    1260
atggactcag acagttcccc cagcagcagc tccacctact gtaaccaaat gatgaggcgc    1320
cggaatatga cacaggggcg gtgcaaacca gtgaacacct ttgtgcacga gccctggta    1380
gatgtccaga atgtctgttt ccaggaaaag gtcacctgca agaacgggca gggcaactgc    1440
tacaagagca actccagcat gcacatcaca gactgccgcc tgacaaacgg ctccaggtac    1500
cccaactgtg cataccggac cagcccgaag gagagacaca tcattgtggc ctgtgaaggg    1560
```
agcccatatg tgccagtcca ctttgatgct tctgtggagg actctaccta ataatctaga    1620

<210> SEQ ID NO 189
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350
```

Gln Gly Asn Val Phe Ser Cys Ser Val Met His Glu Gly Leu His Asn
            355                 360                 365

His Tyr Thr Gln Lys Ser Leu Ser Leu Ser Pro Gly Lys Val Asp Gly
        370                 375                 380

Ala Ser Ser His Val Asn Val Ser Ser Pro Ser Val Gln Asp Ile Lys
385                 390                 395                 400

Glu Ser Arg Ala Lys Lys Phe Gln Arg Gln His Met Asp Ser Asp Ser
            405                 410                 415

Ser Pro Ser Ser Ser Ser Thr Tyr Cys Asn Gln Met Met Arg Arg Arg
            420                 425                 430

Asn Met Thr Gln Gly Arg Cys Lys Pro Val Asn Thr Phe Val His Glu
        435                 440                 445

Pro Leu Val Asp Val Gln Asn Val Cys Phe Gln Glu Lys Val Thr Cys
    450                 455                 460

Lys Asn Gly Gln Gly Asn Cys Tyr Lys Ser Asn Ser Ser Met His Ile
465                 470                 475                 480

Thr Asp Cys Arg Leu Thr Asn Gly Ser Arg Tyr Pro Asn Cys Ala Tyr
            485                 490                 495

Arg Thr Ser Pro Lys Glu Arg His Ile Ile Val Ala Cys Glu Gly Ser
            500                 505                 510

Pro Tyr Val Pro Val His Phe Asp Ala Ser Val Glu Asp Ser Thr
        515                 520                 525

<210> SEQ ID NO 190
<211> LENGTH: 1692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
aagcttgccg ccatggaaac ccagcgcag cttctcttcc tcctgctact ctggctccca      60
gataccaccg gtaaggaatc ccgggccaag aaattccagc ggcagcatat ggactcagac    120
agttccccca gcagcagctc cacctactgt aaccaaatga tgaggcgccg gaatatgaca    180
caggggcggt gcaaaccagt gaacaccttt gtgcacgagc ccctggtaga tgtccagaat    240
gtctgtttcc aggaaaaggt cacctgcaag aacgggcagg gcaactgcta caagagcaac    300
tccagcatgc acatcacaga ctgccgcctg acaaacggct ccaggtaccc caactgtgca    360
taccggacca gcccgaagga gagacacatc attgtggcct gtgaagggag cccatatgtg    420
ccagtccact tgatgcttc tgtggaggac tctacagatc tctccggagg aggtggctca    480
ggtggtggag atctggagg aggtgggagt ggtggaggtg gttctaccgg tctcgagccc    540
aaatcttctg acaaaactca cacatgtcca ccgtgcccag cacctgaact cctgggggga    600
ccgtcagtct tcctcttccc cccaaaaccc aaggacaccc tcatgatctc ccggacccct    660
gaggtcacat gcgtggtggt ggacgtgagc cacgaagacc ctgaggtcaa gttcaactgg    720
tacgtggacg gcgtggaggt gcataatgcc aagacaaagc cgcgggagga gcagtacaac    780
agcacgtacc gtgtggtcag cgtcctcacc gtcctgcacc aggactggct gaatggcaag    840
gagtacaagt gcaaggtctc caacaaagcc ctcccagccc ccatcgagaa aaccatctcc    900
aaagccaaag gcagccccg agaaccacag gtgtacaccc tgcccccatc ccgggatgag    960
ctgaccaaga accaggtcag cctgacctgc ctggtcaaag gcttctatcc cagcgacatc   1020

```
gccgtggagt gggagagcaa tgggcagccg agaacaact acaagaccac gcctcccgtg    1080
ctggactccg acggctcctt cttcctctac agcaagctca ccgtggacaa gagcaggtgg    1140
cagcagggga acgtcttctc atgctccgtg atgcatgagg gtctgcacaa ccactacacg    1200
cagaagagcc tctctctgtc tccgggtaaa gtcgacggtg ctagcagcca tgtgaatgtg    1260
agcagcccta gcgtgcagga tatcccttcc ctgggcaagg aatcccgggc caagaaattc    1320
cagcggcagc atatggactc agacagttcc cccagcagca gctccaccta ctgtaaccaa    1380
atgatgaggc gccggaatat gacacagggg cggtgcaaac cagtgaacac ctttgtgcac    1440
gagcccctgg tagatgtcca gaatgtctgt ttccaggaaa aggtcacctg caagaacggg    1500
cagggcaact gctacaagag caactccagc atgcacatca cagactgccg cctgacaaac    1560
ggctccaggt accccaactg tgcataccgg accagcccga aggagagaca catcattgtg    1620
gcctgtgaag ggagcccata tgtgccagtc cactttgatg cttctgtgga ggactctacc    1680
taataatcta ga                                                      1692
```

<210> SEQ ID NO 191
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
130                 135                 140

Glu Asp Ser Thr Gly Gly Gly Ser Gly Gly Gly Ser Gly Gly
145                 150                 155                 160

Gly Gly Ser Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240
```

```
Ala Lys Thr Lys Pro Arg Glu Glu Gln Tyr Asn Ser Thr Tyr Arg Val
            245                 250                 255

Val Ser Val Leu Thr Val Leu His Gln Asp Trp Leu Asn Gly Lys Glu
        260                 265                 270

Tyr Lys Cys Lys Val Ser Asn Lys Ala Leu Pro Ala Pro Ile Glu Lys
    275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Gly Leu His Asn His Tyr Thr Gln Lys Ser Leu Ser Leu Ser Pro Gly
385                 390                 395                 400

Lys Val Asp Gly Ala Ser Ser His Val Asn Val Ser Pro Ser Val
                405                 410                 415

Gln Asp Ile Lys Glu Ser Arg Ala Lys Lys Phe Gln Arg Gln His Met
            420                 425                 430

Asp Ser Asp Ser Ser Pro Ser Ser Ser Thr Tyr Cys Asn Gln Met
        435                 440                 445

Met Arg Arg Arg Asn Met Thr Gln Gly Arg Cys Lys Pro Val Asn Thr
    450                 455                 460

Phe Val His Glu Pro Leu Val Asp Val Gln Asn Val Cys Phe Gln Glu
465                 470                 475                 480

Lys Val Thr Cys Lys Asn Gly Gln Gly Asn Cys Tyr Lys Ser Asn Ser
                485                 490                 495

Ser Met His Ile Thr Asp Cys Arg Leu Thr Asn Gly Ser Arg Tyr Pro
            500                 505                 510

Asn Cys Ala Tyr Arg Thr Ser Pro Lys Glu Arg His Ile Ile Val Ala
        515                 520                 525

Cys Glu Gly Ser Pro Tyr Val Pro Val His Phe Asp Ala Ser Val Glu
    530                 535                 540

Asp Ser Thr
545

<210> SEQ ID NO 192
<211> LENGTH: 2199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
aagcttgcca ccatggaaac ccagcgcag cttctcttcc tcctgctact ctggctccca      60
gataccaccg gtatgggccc tggagctcgc agacagggca ggattgtgca gggaaggcct    120
gagatgtgct ctgcccacc ccctacccca ctccctcccc ttcggatctt aacactgggc     180
actcacacac ccaccccatg ctcctctcca ggctcagcag caggtacgta cccaaccatg    240
```

```
ggctcgcagg ccctgccccc ggggcccatg cagaccctca tcttttcga catggaggcc      300 actggcttgc ccttctccca gcccaaggtc acggagctgt gcctgctggc tgtccacaga      360
tgtgccctgg agaccccccc cacctctcag gggccacctc ccacagttcc tccaccaccg      420
cgtgtggtag acaagctctc cctgtgtgtg gctccgggga aggcctgcag ccctgcagcc      480
agcgagatca caggtctgag cacagctgtg ctggcagcgc atgggcgtca atgttttgat      540
gacaacctgg ccaacctgct cctagccttc tgcggcgcc agccacagcc ctggtgcctg      600
gtggcacaca atggtgaccg ctacgacttc ccctgctcc aagcagagct ggctatgctg      660
ggcctcacca gtgctctgga tggtgccttc tgtgtggata gcatcactgc gctgaaggcc      720
ctggagcgag caagcagccc ctcagaacac ggcccaagga gagctacag cctaggcagc      780 atctacactc gcctgtatgg gcagtcccct ccagactcgc acacggctga gggtgatgtc      840
ctggccctgc tcagcatctg tcagtggaga ccacaggccc tgctgcggtg ggtggatgct      900
cacgccaggc ctttcggcac catcaggccc atgtatgggg tcacagcctc tgctaggacc      960
aaagatctct ccggaggagg tggctcaggt ggtggaggat ctggaggagg tgggagtggt     1020
ggaggtggtt ctaccggtct cgagcccaaa tcttctgaca aaactcacac atgtccaccg     1080
tgcccagcac ctgaactcct gggggaccg tcagtcttcc tcttcccccc aaaacccaag     1140
gacaccctca tgatctcccg gacccctgag gtcacatgcg tggtggtgga cgtgagccac     1200
gaagaccctg aggtcaagtt caactggtac gtggacggcg tggaggtgca taatgccaag     1260
acaaagccgc gggaggagca gtacaacagc acgtaccgtg tggtcagcgt cctcaccgtc     1320
ctgcaccagg actggctgaa tggcaaggag tacaagtgca aggtctccaa caaagccctc     1380 ccagcccca tcgagaaaac catctccaaa gccaagggc agccccgaga accacaggtg     1440
tacaccctgc ccccatcccg ggatgagctg accaagaacc aggtcagcct gacctgcctg     1500
gtcaaaggct tctatcccag cgacatcgcc gtggagtggg agagcaatgg gcagccggag     1560
aacaactaca agaccacgcc tcccgtgctg gactccgacg gctccttctt cctctacagc     1620
aagctcaccg tggacaagag caggtggcag caggggaacg tcttctcatg ctccgtgatg     1680
catgaggctc tgcacaacca ctacacgcag aagagcctct ctctgtctcc gggtaaagtc     1740
gacggagcta gcagccccgt gaacgtgagc agccccagcg tgcaggatat cccttccctg     1800
ggcaaggaat cccgggccaa gaaattccag cggcagcata tggactcaga cagttccccc     1860
agcagcagct ccacctactg taaccaaatg atgaggcgcc ggaatatgac acaggggcgg     1920
tgcaaaccag tgaacacctt tgtgcacgag cccctggtag atgtccagaa tgtctgtttc     1980
caggaaaagg tcacctgcaa gaacgggcag ggcaactgct acaagagcaa ctccagcatg     2040
cacatcacag actgccgcct gacaaacggc tccaggtacc caactgtgc ataccggacc     2100 agcccgaagg agagacacat cattgtggcc tgtgaaggga gcccatatgt gccagtccac     2160
tttgatgctt ctgtggagga ctctacctaa taatctaga                             2199
```

<210> SEQ ID NO 193
<211> LENGTH: 716
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

Met Glu Thr Pro Ala Gln Leu Leu Phe Leu Leu Leu Leu Trp Leu Pro

-continued

```
1               5                   10                  15
Asp Thr Thr Gly Met Gly Pro Gly Ala Arg Arg Gln Gly Arg Ile Val
                20                  25                  30

Gln Gly Arg Pro Glu Met Cys Phe Cys Pro Pro Thr Pro Leu Pro
                35                  40                  45

Pro Leu Arg Ile Leu Thr Leu Gly Thr His Thr Pro Thr Pro Cys Ser
        50                  55                  60

Ser Pro Gly Ser Ala Ala Gly Thr Tyr Pro Thr Met Gly Ser Gln Ala
65                      70                  75                  80

Leu Pro Pro Gly Pro Met Gln Thr Leu Ile Phe Phe Asp Met Glu Ala
                    85                  90                  95

Thr Gly Leu Pro Phe Ser Gln Pro Lys Val Thr Glu Leu Cys Leu Leu
                100                 105                 110

Ala Val His Arg Cys Ala Leu Glu Ser Pro Pro Thr Ser Gln Gly Pro
            115                 120                 125

Pro Pro Thr Val Pro Pro Pro Arg Val Val Asp Lys Leu Ser Leu
        130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
            260                 265                 270

Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Gly Ser Gly Gly Gly Ser Gly Gly Gly Gly
                325                 330                 335

Ser Leu Glu Pro Lys Ser Ser Asp Lys Thr His Thr Cys Pro Pro Cys
                340                 345                 350

Pro Ala Pro Glu Leu Leu Gly Gly Pro Ser Val Phe Leu Phe Pro Pro
                355                 360                 365

Lys Pro Lys Asp Thr Leu Met Ile Ser Arg Thr Pro Glu Val Thr Cys
                370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
                420                 425                 430
```

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
    450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
                500                 505                 510

Asn Tyr Lys Thr Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys Val Asp Gly Ala Ser Ser
                565                 570                 575

Pro Val Asn Val Ser Ser Pro Ser Val Gln Asp Ile Lys Glu Ser Arg
                580                 585                 590

Ala Lys Lys Phe Gln Arg Gln His Met Asp Ser Asp Ser Ser Pro Ser
            595                 600                 605

Ser Ser Ser Thr Tyr Cys Asn Gln Met Met Arg Arg Arg Asn Met Thr
        610                 615                 620

Gln Gly Arg Cys Lys Pro Val Asn Thr Phe Val His Glu Pro Leu Val
625                 630                 635                 640

Asp Val Gln Asn Val Cys Phe Gln Glu Lys Val Thr Cys Lys Asn Gly
                645                 650                 655

Gln Gly Asn Cys Tyr Lys Ser Asn Ser Ser Met His Ile Thr Asp Cys
            660                 665                 670

Arg Leu Thr Asn Gly Ser Arg Tyr Pro Asn Cys Ala Tyr Arg Thr Ser
        675                 680                 685

Pro Lys Glu Arg His Ile Ile Val Ala Cys Glu Gly Ser Pro Tyr Val
    690                 695                 700

Pro Val His Phe Asp Ala Ser Val Glu Asp Ser Thr
705                 710                 715

<210> SEQ ID NO 194
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
aagcttgccg ccatggaaac cccagcgcag cttctcttcc tcctgctact ctggctccca      60
gataccaccg gtaaggaatc ccgggccaag aaattccagc ggcagcatat ggactcagac     120
agttccccca gcagcagctc cacctactgt aaccaaatga tgaggcgccg gaatatgaca     180
caggggcggt gcaaaccagt gaacaccttt gtgcacgagc cctggtaga tgtccagaat      240 gtctgtttcc aggaaaaggt cacctgcaag aacgggcagg gcaactgcta caagagcaac     300
tccagcatgc acatcacaga ctgccgcctg acaaacggct ccaggtaccc caactgtgca     360
taccggacca gcccgaagga gagacacatc attgtggcct gtgaagggag cccatatgtg     420

-continued

```
ccagtccact tgatgcttc tgtggaggac tctacagatc tcgagcccaa atcttctgac    480
aaaactcaca catgtccacc gtgcccagca cctgaactcc tgggggggacc gtcagtcttc   540 ctcttccccc caaaacccaa ggacaccctc atgatctccc ggaccctga ggtcacatgc     600 gtggtggtgg acgtgagcca cgaagaccct gaggtcaagt tcaactggta cgtggacggc   660
gtggaggtgc ataatgccaa gacaaagccg cgggaggagc agtacaacag cacgtaccgt   720
gtggtcagcg tcctcaccgt cctgcaccag gactggctga atggcaagga gtacaagtgc   780
aaggtctcca acaaagccct cccagccccc atcgagaaaa ccatctccaa agccaaaggg   840
cagccccgag aaccacaggt gtacaccctg cccccatccc gggatgagct gaccaagaac   900
caggtcagcc tgacctgcct ggtcaaaggc ttctatccca gcgacatcgc cgtggagtgg   960
gagagcaatg ggcagccgga gaacaactac aagaccacgc ctcccgtgct ggactccgac  1020
ggctccttct tcctctacag caagctcacc gtggacaaga gcaggtggca gcaggggaac  1080
gtcttctcat gctccgtgat gcatgagggt ctgcacaacc actacacgca gaagagcctc  1140
tctctgtctc cgggtaaagt cgacggtgct agcagccatg tgaatgtgag cagccctagc  1200
gtgcaggata tcatgggccc tggagctcgc agacagggca ggattgtgca gggaaggcct  1260
gagatgtgct tctgcccacc ccctacccca ctccctcccc ttcggatctt aacactgggc  1320
actcacacac ccaccccatg ctcctctcca ggctcagcag caggtacgta cccaaccatg  1380
ggctcgcagg ccctgccccc ggggcccatg cagaccctca tcttttcga catggaggcc  1440 actggcttgc ccttctccca gcccaaggtc acggagctgt gcctgctggc tgtccacaga  1500
tgtgccctgg agagccccc cacctctcag gggccacctc ccacagttcc tccaccaccg  1560
cgtgtggtag acaagctctc cctgtgtgtg gctccgggga aggcctgcag ccctgcagcc  1620
agcgagatca caggtctgag cacagctgtg ctggcagcgc atgggcgtca atgttttgat  1680
gacaacctgg ccaacctgct cctagccttc ctgcggcgcc agccacagcc ctggtgcctg  1740
gtggcacaca atggtgaccg ctacgacttc cccctgctcc aagcagagct ggctatgctg  1800
ggcctcacca gtgctctgga tggtgccttc tgtgtggata gcatcactgc gctgaaggcc  1860
ctggagcgag caagcagccc ctcagaacac ggcccaagga agagctacag cctaggcagc  1920
atctacactc gcctgtatgg gcagtcccct ccagactcgc acacggctga gggtgatgtc  1980
ctggccctgc tcagcatctg tcagtggaga ccacaggccc tgctgcggtg gtggatgct   2040 cacgccaggc ctttcggcac catcaggccc atgtatgggg tcacagcctc tgctaggacc  2100
aaatgataat ctaga                                                     2115
```

<210> SEQ ID NO 195
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
                20                  25                  30

Met Asp Ser Asp Ser Ser Pro Ser Ser Ser Thr Tyr Cys Asn Gln
            35                  40                  45

```
Met Met Arg Arg Arg Asn Met Thr Gln Gly Arg Cys Lys Pro Val Asn
    50                  55                  60
Thr Phe Val His Glu Pro Leu Val Asp Val Gln Asn Val Cys Phe Gln
65                  70                  75                  80
Glu Lys Val Thr Cys Lys Asn Gly Gln Gly Asn Cys Tyr Lys Ser Asn
                85                  90                  95
Ser Ser Met His Ile Thr Asp Cys Arg Leu Thr Asn Gly Ser Arg Tyr
            100                 105                 110
Pro Asn Cys Ala Tyr Arg Thr Ser Pro Lys Glu Arg His Ile Ile Val
        115                 120                 125
Ala Cys Glu Gly Ser Pro Tyr Val Pro Val His Phe Asp Ala Ser Val
    130                 135                 140
Glu Asp Ser Thr Leu Glu Pro Lys Ser Ser Asp Lys Thr His Thr Cys
145                 150                 155                 160
Pro Pro Cys Pro Ala Pro Glu Leu Leu Gly Gly Pro Ser Val Phe Leu
                165                 170                 175
Phe Pro Pro Lys Pro Lys Asp Thr Leu Met Ile Ser Arg Thr Pro Glu
            180                 185                 190
Val Thr Cys Val Val Val Asp Val Ser His Glu Asp Pro Glu Val Lys
        195                 200                 205
Phe Asn Trp Tyr Val Asp Gly Val Glu Val His Asn Ala Lys Thr Lys
    210                 215                 220
Pro Arg Glu Glu Gln Tyr Asn Ser Thr Tyr Arg Val Val Ser Val Leu
225                 230                 235                 240
Thr Val Leu His Gln Asp Trp Leu Asn Gly Lys Glu Tyr Lys Cys Lys
                245                 250                 255
Val Ser Asn Lys Ala Leu Pro Ala Pro Ile Glu Lys Thr Ile Ser Lys
            260                 265                 270
Ala Lys Gly Gln Pro Arg Glu Pro Gln Val Tyr Thr Leu Pro Pro Ser
        275                 280                 285
Arg Asp Glu Leu Thr Lys Asn Gln Val Ser Leu Thr Cys Leu Val Lys
    290                 295                 300
Gly Phe Tyr Pro Ser Asp Ile Ala Val Glu Trp Glu Ser Asn Gly Gln
305                 310                 315                 320
Pro Glu Asn Asn Tyr Lys Thr Thr Pro Pro Val Leu Asp Ser Asp Gly
                325                 330                 335
Ser Phe Phe Leu Tyr Ser Lys Leu Thr Val Asp Lys Ser Arg Trp Gln
            340                 345                 350
Gln Gly Asn Val Phe Ser Cys Ser Val Met His Glu Gly Leu His Asn
        355                 360                 365
His Tyr Thr Gln Lys Ser Leu Ser Leu Ser Pro Gly Lys Val Asp Gly
    370                 375                 380
Ala Ser Ser His Val Asn Val Ser Ser Pro Ser Val Gln Asp Ile Met
385                 390                 395                 400
Gly Pro Gly Ala Arg Arg Gln Gly Arg Ile Val Gln Gly Arg Pro Glu
                405                 410                 415
Met Cys Phe Cys Pro Pro Thr Pro Leu Pro Pro Leu Arg Ile Leu
            420                 425                 430
Thr Leu Gly Thr His Thr Pro Thr Pro Cys Ser Ser Pro Gly Ser Ala
        435                 440                 445
Ala Gly Thr Tyr Pro Thr Met Gly Ser Gln Ala Leu Pro Pro Gly Pro
    450                 455                 460
Met Gln Thr Leu Ile Phe Phe Asp Met Glu Ala Thr Gly Leu Pro Phe
```

```
            465                 470                 475                 480
Ser Gln Pro Lys Val Thr Glu Leu Cys Leu Leu Ala Val His Arg Cys
                485                 490                 495

Ala Leu Glu Ser Pro Pro Thr Ser Gln Gly Pro Pro Thr Val Pro
                500                 505                 510

Pro Pro Pro Arg Val Val Asp Lys Leu Ser Leu Cys Val Ala Pro Gly
                515                 520                 525

Lys Ala Cys Ser Pro Ala Ala Ser Glu Ile Thr Gly Leu Ser Thr Ala
            530                 535                 540

Val Leu Ala Ala His Gly Arg Gln Cys Phe Asp Asp Asn Leu Ala Asn
545                 550                 555                 560

Leu Leu Leu Ala Phe Leu Arg Arg Gln Pro Gln Pro Trp Cys Leu Val
                565                 570                 575

Ala His Asn Gly Asp Arg Tyr Asp Phe Pro Leu Leu Gln Ala Glu Leu
                580                 585                 590

Ala Met Leu Gly Leu Thr Ser Ala Leu Asp Gly Ala Phe Cys Val Asp
            595                 600                 605

Ser Ile Thr Ala Leu Lys Ala Leu Glu Arg Ala Ser Ser Pro Ser Glu
            610                 615                 620

His Gly Pro Arg Lys Ser Tyr Ser Leu Gly Ser Ile Tyr Thr Arg Leu
625                 630                 635                 640

Tyr Gly Gln Ser Pro Pro Asp Ser His Thr Ala Glu Gly Asp Val Leu
                645                 650                 655

Ala Leu Leu Ser Ile Cys Gln Trp Arg Pro Gln Ala Leu Leu Arg Trp
                660                 665                 670

Val Asp Ala His Ala Arg Pro Phe Gly Thr Ile Arg Pro Met Tyr Gly
            675                 680                 685

Val Thr Ala Ser Ala Arg Thr Lys
            690                 695

<210> SEQ ID NO 196
<211> LENGTH: 2166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gttaagcttg ccaccatgga aaccccagcg cagcttctct tcctcctgct actctggctc      60
ccagatacca ccggtatgag gatctgctcc ttcaacgtca ggtcctttgg ggaaagcaag     120
caggaagaca agaatgccat ggatgtcatt gtgaaggtca tcaaacgctg tgacatcata     180
ctcgtgatgg aaatcaagga cagcaacaac aggatctgcc ccatactgat ggagaagctg     240
aacagaaatt caaggagagg cataacatac aactatgtga ttagctctcg gcttggaaga     300
aacacatata agaacaata tgcctttctc tacaaggaaa agctggtgtc tgtgaagagg     360
agttatcact accatgacta tcaggatgga gacgcagatg tgttttccag ggagcccttt     420
gtggtctggt ccaatctccc ccacactgct gtcaaagact cgtgattat ccccctgcac     480 accacccag agacatccgt taaggagatc gatgagttgg ttgaggtcta cacgacgtg     540 aaacaccgct ggaaggcgga gaatttcatt ttcatgggtg acttcaatgc cggctgcagc     600
tacgtcccca gaaggcctg gaagaacatc cgcttgagga ctgacccag gtttgtttgg     660 ctgatcgggg accaagagga caccacggtg aagaagagca ccaactgtgc atatgacagg     720
```

```
attgtgctta gaggacaaga aatcgtcagt tctgttgttc ccaagtcaaa cagtgttttt      780
gacttccaga aagcttacaa gctgactgaa gaggaggccc tggatgtcag cgaccacttt      840
ccagttgaat ttaaactaca gtcttcaagg gccttcacca acagcaaaaa atctgtcact      900
ctaaggaaga aaacaaagag caaacgctca gatctctccg gaggaggtgg ctcaggtggt      960
ggaggatctg gaggaggtgg gagtggtgga ggtggttcta ccggtctcga gcccaaatct     1020
tctgacaaaa ctcacacatg tccaccgtgc ccagcacctg aactcctggg gggaccgtca     1080
gtcttcctct tccccccaaa acccaaggac accctcatga tctcccggac ccctgaggtc     1140
acatgcgtgg tggtggacgt gagccacgaa gaccctgagg tcaagttcaa ctggtacgtg     1200
gacggcgtgg aggtgcataa tgccaagaca agccgcggg aggagcagta caacagcacg      1260
taccgtgtgg tcagcgtcct caccgtcctg caccaggact ggctgaatgg caaggagtac     1320
aagtgcaagg tctccaacaa agccctccca gcccccatcg agaaaaccat ctccaaagcc     1380
aaagggcagc cccgagaacc acaggtgtac accctgcccc catcccggga tgagctgacc     1440
aagaaccagg tcagcctgac ctgcctggtc aaaggcttct atcccagcga catcgccgtg     1500
gagtgggaga gcaatgggca gccggagaac aactacaaga ccacgcctcc cgtgctggac     1560
tccgacggct ccttcttcct ctacagcaag ctcaccgtgg acaagagcag gtggcagcag     1620
gggaacgtct tctcatgctc cgtgatgcat gagggtctgc acaaccacta cacgcagaag     1680
agcctctctc tgtctccggg taaagtcgac ggtgctagca gccatgtgaa tgtgagcagc     1740
cctagcgtgc aggatatccc ttccctgggc aaggaatccc gggccaagaa attccagcgg     1800
cagcatatgg actcagacag ttccccccagc agcagctcca cctactgtaa ccaaatgatg     1860
aggcgccgga atatgacaca ggggcggtgc aaaccagtga acacctttgt gcacgagccc     1920
ctggtagatg tccagaatgt ctgtttccag gaaaaggtca cctgcaagaa cgggcagggc     1980
aactgctaca agagcaactc cagcatgcac atcacagact gccgcctgac aaacggctcc     2040
aggtaccccca actgtgcata ccggaccagc ccgaaggaga gacacatcat tgtggcctgt     2100
gaagggagcc catatgtgcc agtccacttt gatgcttctg tggaggactc tacctaataa     2160
tctaga                                                                2166
```

<210> SEQ ID NO 197
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Met Glu Thr Pro Ala Gln Leu Leu Phe Leu Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95
```

```
Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                    165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
            210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                    245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
290                 295                 300

Ser Gly Gly Gly Gly Ser Gly Gly Gly Ser Gly Gly Gly Gly Ser
305                 310                 315                 320

Gly Gly Gly Gly Ser Leu Glu Pro Lys Ser Ser Asp Lys Thr His Thr
            325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
            355                 360                 365

Glu Val Thr Cys Val Val Val Asp Val Ser His Glu Asp Pro Glu Val
            370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
            405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
            435                 440                 445

Lys Ala Lys Gly Gln Pro Arg Glu Pro Gln Val Tyr Thr Leu Pro Pro
450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
            485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
```

|  |  | 515 |  |  |  | 520 |  |  |  | 525 |  |
|---|---|---|---|---|---|---|---|---|---|---|---|
| Gln | Gln | Gly | Asn | Val | Phe | Ser | Cys | Ser | Val | Met | His | Glu | Gly | Leu | His |
|  |  | 530 |  |  |  | 535 |  |  |  | 540 |  |

Asn His Tyr Thr Gln Lys Ser Leu Ser Leu Ser Pro Gly Lys Val Asp
545                 550                 555                 560

Gly Ala Ser Ser His Val Asn Val Ser Ser Pro Ser Val Gln Asp Ile
                565                 570                 575

Lys Glu Ser Arg Ala Lys Lys Phe Gln Arg Gln His Met Asp Ser Asp
            580                 585                 590

Ser Ser Pro Ser Ser Ser Ser Thr Tyr Cys Asn Gln Met Met Arg Arg
        595                 600                 605

Arg Asn Met Thr Gln Gly Arg Cys Lys Pro Val Asn Thr Phe Val His
    610                 615                 620

Glu Pro Leu Val Asp Val Gln Asn Val Cys Phe Gln Glu Lys Val Thr
625                 630                 635                 640

Cys Lys Asn Gly Gln Gly Asn Cys Tyr Lys Ser Asn Ser Ser Met His
                645                 650                 655

Ile Thr Asp Cys Arg Leu Thr Asn Gly Ser Arg Tyr Pro Asn Cys Ala
            660                 665                 670

Tyr Arg Thr Ser Pro Lys Glu Arg His Ile Ile Val Ala Cys Glu Gly
        675                 680                 685

Ser Pro Tyr Val Pro Val His Phe Asp Ala Ser Val Glu Asp Ser Thr
    690                 695                 700

<210> SEQ ID NO 198
<211> LENGTH: 2154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198

```
gttaagcttg ccaccatgga accccagcg cagcttctct tcctcctgct actctggctc      60
ccagatacca ccgtaagga atcccgggcc aagaaattcc agcggcagca tatggactca     120
gacagttccc ccagcagcag ctccacctac tgtaaccaaa tgatgaggcg ccggaatatg     180
acacaggggc ggtgcaaacc agtgaacacc tttgtgcacg agcccctggt agatgtccag     240
aatgtctgtt tccaggaaaa ggtcacctgc aagaacgggc agggcaactg ctacaagagc     300
aactccagca tgcacatcac agactgccgc ctgacaaacg gctccaggta ccccaactgt     360
gcataccgga ccagcccgaa ggagagacac atcattgtgg cctgtgaagg agcccatat      420
gtgccagtcc actttgatgc ttctgtggag gactctacag atctctccgg aggaggtggc     480
tcaggtggtg gaggatctgg aggaggtggg agtggtggag gtggttctac cggtctcgag     540
cccaaatctt ctgacaaaac tcacacatgt ccaccgtgcc cagcacctga actcctgggg     600
ggaccgtcag tcttcctctt ccccccaaaa cccaaggaca cctcatgat ctcccggacc      660
cctgaggtca catgcgtggt ggtggacgtg agccacgaag accctgaggt caagttcaac     720
tggtacgtgg acggcgtgga ggtgcataat gccaagacaa agccgcggga ggagcagtac     780
aacagcacgt accgtgtggt cagcgtcctc accgtcctgc accaggactg gctgaatggc     840
aaggagtaca agtgcaaggt ctccaacaaa gccctcccag cccccatcga gaaaaccatc     900
tccaaagcca agggcagccc cgagaaccca caggtgtaca ccctgccccc atccgggat      960
gagctgacca agaaccaggt cagcctgacc tgcctggtca aaggcttcta tcccagcgac    1020
```

```
atcgccgtgg agtgggagag caatgggcag ccggagaaca actacaagac cacgcctccc    1080
gtgctggact ccgacggctc cttcttcctc tacagcaagc tcaccgtgga caagagcagg    1140
tggcagcagg ggaacgtctt ctcatgctcc gtgatgcatg aggctctgca caaccactac    1200
acgcagaaga gcctctctct gtctccgggt aaagtcgacg tgctagcagc catgtgaat     1260 gtgagcagcc ctagcgtgca ggatatcatg aggatctgct ccttcaacgt caggtccttt    1320
ggggaaagca agcaggaaga caagaatgcc atggatgtca ttgtgaaggt catcaaacgc    1380
tgtgacatca tactcgtgat ggaaatcaag acagcaaca acaggatctg ccccatactg      1440
atggagaagc tgaacagaaa ttcaaggaga ggcataacat acaactatgt gattagctct    1500
cggcttggaa gaaacacata taagaacaa tatgcctttc tctacaagga aaagctggtg     1560
tctgtgaaga ggagttatca ctaccatgac tatcaggatg agacgcaga tgtgttttcc      1620 agggagccct ttgtggtctg gttccaatct ccccacactg ctgtcaaaga cttcgtgatt    1680
atccccctgc acaccacccc agagacatcc gttaaggaga tcgatgagtt ggttgaggtc    1740
tacacggacg tgaaacaccg ctggaaggcg gagaatttca ttttcatggg tgacttcaat    1800
gccggctgca gctacgtccc caagaaggcc tggaagaaca tccgcttgag gactgacccc    1860
aggtttgttt ggctgatcgg ggaccaagag gacaccacgg tgaagaagag caccaactgt    1920
gcatatgaca ggattgtgct tagaggacaa gaaatcgtca gttctgttgt tcccaagtca    1980
aacagtgttt ttgacttcca gaaagcttac aagctgactg aagaggaggc cctggatgtc   2040
agcgaccact ttccagttga atttaaacta cagtcttcaa gggccttcac caacagcaaa   2100
aaatctgtca ctctaaggaa gaaaacaaag agcaaacgct cctaatgatc taga          2154
```

<210> SEQ ID NO 199  
<211> LENGTH: 704  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 199

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Gly Ser Gly Gly Gly Ser Gly Gly
145                 150                 155                 160
```

-continued

```
Gly Gly Ser Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
            195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
            275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
            355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys Val Asp Gly Ala Ser Ser His Val Asn Val Ser Ser Pro Ser Val
                405                 410                 415

Gln Asp Ile Met Arg Ile Cys Ser Phe Asn Val Arg Ser Phe Gly Glu
            420                 425                 430

Ser Lys Gln Glu Asp Lys Asn Ala Met Asp Val Ile Val Lys Val Ile
            435                 440                 445

Lys Arg Cys Asp Ile Ile Leu Val Met Glu Ile Lys Asp Ser Asn Asn
    450                 455                 460

Arg Ile Cys Pro Ile Leu Met Glu Lys Leu Asn Arg Asn Ser Arg Arg
465                 470                 475                 480

Gly Ile Thr Tyr Asn Tyr Val Ile Ser Ser Arg Leu Gly Arg Asn Thr
                485                 490                 495

Tyr Lys Glu Gln Tyr Ala Phe Leu Tyr Lys Glu Lys Leu Val Ser Val
            500                 505                 510

Lys Arg Ser Tyr His Tyr His Asp Tyr Gln Asp Gly Asp Ala Asp Val
            515                 520                 525

Phe Ser Arg Glu Pro Phe Val Val Trp Phe Gln Ser Pro His Thr Ala
    530                 535                 540

Val Lys Asp Phe Val Ile Ile Pro Leu His Thr Thr Pro Glu Thr Ser
545                 550                 555                 560

Val Lys Glu Ile Asp Glu Leu Val Glu Val Tyr Thr Asp Val Lys His
                565                 570                 575
```

Arg Trp Lys Ala Glu Asn Phe Ile Phe Met Gly Asp Phe Asn Ala Gly
            580                 585                 590

Cys Ser Tyr Val Pro Lys Ala Trp Lys Asn Ile Arg Leu Arg Thr
        595                 600                 605

Asp Pro Arg Phe Val Trp Leu Ile Gly Asp Gln Glu Asp Thr Thr Val
    610                 615                 620

Lys Lys Ser Thr Asn Cys Ala Tyr Asp Arg Ile Val Leu Arg Gly Gln
625                 630                 635                 640

Glu Ile Val Ser Ser Val Val Pro Lys Ser Asn Ser Val Phe Asp Phe
                645                 650                 655

Gln Lys Ala Tyr Lys Leu Thr Glu Glu Ala Leu Asp Val Ser Asp
            660                 665                 670

His Phe Pro Val Glu Phe Lys Leu Gln Ser Ser Arg Ala Phe Thr Asn
    675                 680                 685

Ser Lys Lys Ser Val Thr Leu Arg Lys Lys Thr Lys Ser Lys Arg Ser
690                 695                 700

<210> SEQ ID NO 200
<211> LENGTH: 2586
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
gttaagcttg ccaccatgga aaccccagcg cagcttctct tcctcctgct actctggctc      60
ccagatacca ccggtctgaa gatcgcagcc ttcaacatcc agacatttgg ggagaccaag     120
atgtccaatg ccaccctcgt cagctacatt gtgcagatcc tgagccgcta tgacatcgcc     180
ctggtccagg aggtcagaga cagccacctg actgccgtgg ggaagctgct ggacaacctc     240
aatcaggatg caccagacac ctatcactac gtggtcagtg agccactggg acggaacagc     300
tataaggagc gctacctgtt cgtgtacagg cctgaccagg tgtctgcggt ggacagctac     360
tactacgatg atggctgcga gccctgcagg aacgacacct caaccgaga gccattcatt     420 gtcaggttct tctcccggtt cacagaggtc agggagtttg ccattgttcc cctgcatgcg     480
gccccggggg acgcagtagc cgagatcgac gctctctatg acgtctacct ggatgtccaa     540
gagaaatggg gcttggagga cgtcatgttg atgggcgact tcaatgcggg ctgcagctat     600
gtgagaccct cccagtggtc atccatccgc ctgtggacaa gccccacctt ccagtggctg     660
atccccgaca cgcgctgaca cacagctaca cccacgcact gtgcctatga caggatcgtg     720
gttgcaggga tgctgctccg aggcgccgtt gttcccgact cggctcttcc ctttaacttc     780
caggctgcct atgcctgag tgaccaactg gcccaagcca tcagtgacca ctatccagtg     840
gaggtgatgc tgaaagatct ctccggagga ggtggctcag gtggtggagg atctggagga     900
ggtgggagtg gtgagtgg ttctaccggt ctcgagccca atcttctga caaaactcac     960 acatgtccac cgtgcccagc acctgaactc ctggggggac cgtcagtctt cctcttcccc    1020
ccaaaaccca aggacaccct catgatctcc cggacccctg aggtcacatg cgtggtggtg    1080
gacgtgagcc acgaagaccc tgaggtcaag ttcaactggt acgtggacgg cgtggaggtg    1140
cataatgcca agacaaagcc gcgggaggag cagtacaaca gcacgtaccg tgtggtcagc    1200
gtcctcaccg tcctgcacca ggactggctg aatggcaagg agtacaagtg caaggtctcc    1260
aacaaagccc tcccagcccc catcgagaaa accatctcca agccaaagg gcagccccga    1320

```
gaaccacagg tgtacaccct gccccatcc cgggatgagc tgaccaagaa ccaggtcagc    1380
ctgacctgcc tggtcaaagg cttctatccc agcgacatcg ccgtggagtg ggagagcaat    1440
gggcagccgg agaacaacta caagaccacg cctcccgtgc tggactccga cggctccttc    1500
ttcctctaca gcaagctcac cgtggacaag agcaggtggc agcaggggaa cgtcttctca    1560
tgctccgtga tgcatgaggc tctgcacaac cactacacgc agaagagcct ctctctgtct    1620
ccgggtaaag tcgacggtgc tagcagccat gtgaatgtga gcagccctag cgtgcaggat    1680
atcatgggcc tggagctcg cagacagggc aggattgtgc agggaaggcc tgagatgtgc    1740
ttctgcccac ccctacccc actccctccc cttcggatct aaacactggg cactcacaca    1800
cccaccccat gctcctctcc aggctcagca gcaggtacgt acccaaccat gggctcgcag    1860
gccctgcccc cggggcccat gcagaccctc atctttttcg acatggaggc cactggcttg    1920
cccttctccc agcccaaggt cacggagctg tgcctgctgg ctgtccacag atgtgccctg    1980
gagagccccc ccacctctca ggggccacct cccacagttc ctccaccacc gcgtgtggta    2040
gacaagctct ccctgtgtgt ggctccgggg aaggcctgca gccctgcagc cagcgagatc    2100
acaggtctga gcacagctgt gctggcagcg catgggcgtc aatgttttga tgacaacctg    2160
gccaacctgc tcctagcctt cctgcggcgc cagccacagc cctggtgcct ggtggcacac    2220
aatggtgacc gctacgactt ccccctgctc caagcagagc tggctatgct gggcctcacc    2280
agtgctctgg atggtgcctt ctgtgtggat agcatcactg cgctgaaggc cctggagcga    2340
gcaagcagcc cctcagaaca cggcccaagg aagagctaca gcctaggcag catctacact    2400
cgcctgtatg ggcagtcccc tccagactcg cacacggctg agggtgatgt cctggccctg    2460
ctcagcatct gtcagtggag accacaggcc ctgctgcggt gggtggatgc tcacgccagg    2520
cctttcggca ccatcaggcc catgtatggg gtcacagcct tgctaggac caaatgataa    2580 tctaga                                                              2586
```

<210> SEQ ID NO 201  
<211> LENGTH: 848  
<212> TYPE: PRT  
<213> ORGANISM: Artificial Sequence  
<220> FEATURE:  
<223> OTHER INFORMATION: Description of Artificial Sequence: Synthetic  
polypeptide

<400> SEQUENCE: 201

```
Met Glu Thr Pro Ala Gln Leu Leu Phe Leu Leu Leu Trp Leu Pro
 1               5                  10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
        50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125
```

-continued

```
Phe Asn Arg Glu Pro Phe Ile Val Arg Phe Phe Ser Arg Phe Thr Glu
    130                 135                 140
Val Arg Glu Phe Ala Ile Val Pro Leu His Ala Ala Pro Gly Asp Ala
145                 150                 155                 160
Val Ala Glu Ile Asp Ala Leu Tyr Asp Val Tyr Leu Asp Val Gln Glu
                165                 170                 175
Lys Trp Gly Leu Glu Asp Val Met Leu Met Gly Asp Phe Asn Ala Gly
                180                 185                 190
Cys Ser Tyr Val Arg Pro Ser Gln Trp Ser Ser Ile Arg Leu Trp Thr
        195                 200                 205
Ser Pro Thr Phe Gln Trp Leu Ile Pro Asp Ser Ala Asp Thr Thr Ala
210                 215                 220
Thr Pro Thr His Cys Ala Tyr Asp Arg Ile Val Val Ala Gly Met Leu
225                 230                 235                 240
Leu Arg Gly Ala Val Pro Asp Ser Ala Leu Pro Phe Asn Phe Gln
                245                 250                 255
Ala Ala Tyr Gly Leu Ser Asp Gln Leu Ala Gln Ala Ile Ser Asp His
                260                 265                 270
Tyr Pro Val Glu Val Met Leu Lys Gly Gly Gly Ser Gly Gly Gly
        275                 280                 285
Gly Ser Gly Gly Gly Ser Gly Gly Gly Ser Leu Glu Pro Lys
    290                 295                 300
Ser Ser Asp Lys Thr His Thr Cys Pro Pro Cys Pro Ala Pro Glu Leu
305                 310                 315                 320
Leu Gly Gly Pro Ser Val Phe Leu Phe Pro Pro Lys Pro Lys Asp Thr
                325                 330                 335
Leu Met Ile Ser Arg Thr Pro Glu Val Thr Cys Val Val Val Asp Val
                340                 345                 350
Ser His Glu Asp Pro Glu Val Lys Phe Asn Trp Tyr Val Asp Gly Val
        355                 360                 365
Glu Val His Asn Ala Lys Thr Lys Pro Arg Glu Glu Gln Tyr Asn Ser
    370                 375                 380
Thr Tyr Arg Val Val Ser Val Leu Thr Val Leu His Gln Asp Trp Leu
385                 390                 395                 400
Asn Gly Lys Glu Tyr Lys Cys Lys Val Ser Asn Lys Ala Leu Pro Ala
                405                 410                 415
Pro Ile Glu Lys Thr Ile Ser Lys Ala Lys Gly Gln Pro Arg Glu Pro
                420                 425                 430
Gln Val Tyr Thr Leu Pro Pro Ser Arg Asp Glu Leu Thr Lys Asn Gln
        435                 440                 445
Val Ser Leu Thr Cys Leu Val Lys Gly Phe Tyr Pro Ser Asp Ile Ala
450                 455                 460
Val Glu Trp Glu Ser Asn Gly Gln Pro Glu Asn Asn Tyr Lys Thr Thr
465                 470                 475                 480
Pro Pro Val Leu Asp Ser Asp Gly Ser Phe Phe Leu Tyr Ser Lys Leu
                485                 490                 495
Thr Val Asp Lys Ser Arg Trp Gln Gln Gly Asn Val Phe Ser Cys Ser
                500                 505                 510
Val Met His Glu Ala Leu His Asn His Tyr Thr Gln Lys Ser Leu Ser
        515                 520                 525
Leu Ser Pro Gly Lys Val Asp Gly Ala Ser Ser His Val Asn Val Ser
    530                 535                 540
Ser Pro Ser Val Gln Asp Ile Met Gly Pro Gly Ala Arg Arg Gln Gly
```

```
                    545                 550                 555                 560
Arg Ile Val Gln Gly Arg Pro Glu Met Cys Phe Cys Pro Pro Thr
                565                 570                 575

Pro Leu Pro Pro Leu Arg Ile Leu Thr Leu Gly Thr His Thr Pro Thr
                580                 585                 590

Pro Cys Ser Ser Pro Gly Ser Ala Ala Gly Thr Tyr Pro Thr Met Gly
                595                 600                 605

Ser Gln Ala Leu Pro Pro Gly Pro Met Gln Thr Leu Ile Phe Phe Asp
                610                 615                 620

Met Glu Ala Thr Gly Leu Pro Phe Ser Gln Pro Lys Val Thr Glu Leu
625                 630                 635                 640

Cys Leu Leu Ala Val His Arg Cys Ala Leu Glu Ser Pro Pro Thr Ser
                645                 650                 655

Gln Gly Pro Pro Pro Thr Val Pro Pro Pro Arg Val Val Asp Lys
                660                 665                 670

Leu Ser Leu Cys Val Ala Pro Gly Lys Ala Cys Ser Pro Ala Ala Ser
                675                 680                 685

Glu Ile Thr Gly Leu Ser Thr Ala Val Leu Ala Ala His Gly Arg Gln
                690                 695                 700

Cys Phe Asp Asp Asn Leu Ala Asn Leu Leu Leu Ala Phe Leu Arg Arg
705                 710                 715                 720

Gln Pro Gln Pro Trp Cys Leu Val Ala His Asn Gly Asp Arg Tyr Asp
                725                 730                 735

Phe Pro Leu Leu Gln Ala Glu Leu Ala Met Leu Gly Leu Thr Ser Ala
                740                 745                 750

Leu Asp Gly Ala Phe Cys Val Asp Ser Ile Thr Ala Leu Lys Ala Leu
                755                 760                 765

Glu Arg Ala Ser Ser Pro Ser Glu His Gly Pro Arg Lys Ser Tyr Ser
                770                 775                 780

Leu Gly Ser Ile Tyr Thr Arg Leu Tyr Gly Gln Ser Pro Pro Asp Ser
785                 790                 795                 800

His Thr Ala Glu Gly Asp Val Leu Ala Leu Leu Ser Ile Cys Gln Trp
                805                 810                 815

Arg Pro Gln Ala Leu Leu Arg Trp Val Asp Ala His Ala Arg Pro Phe
                820                 825                 830

Gly Thr Ile Arg Pro Met Tyr Gly Val Thr Ala Ser Ala Arg Thr Lys
                835                 840                 845

<210> SEQ ID NO 202
<211> LENGTH: 2583
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2500)..(2500)
<223> OTHER INFORMATION: a, c, t, g, unknown or other

<400> SEQUENCE: 202
aagcttgcca ccatggaaac ccagcgcag cttctcttcc tcctgctact ctggctccca    60
gataccaccg gtatgggccc tggagctcgc agacagggca ggattgtgca gggaaggcct   120
gagatgtgct ctgcccacc cctaccccca ctccctcccc ttcggatctt aacactgggc   180
actcacacac ccaccccatg ctcctctcca ggctcagcag caggtacgta cccaaccatg   240
```

```
ggctcgcagg ccctgccccc ggggcccatg cagaccctca tcttttttcga catggaggcc      300 actggcttgc ccttctccca gcccaaggtc acggagctgt gcctgctggc tgtccacaga      360
tgtgccctgg agagccccc cacctctcag gggccacctc ccacagttcc tccaccaccg       420
cgtgtggtag acaagctctc cctgtgtgtg gctccgggga aggcctgcag ccctgcagcc      480
agcgagatca caggtctgag cacagctgtg ctggcagcgc atgggcgtca atgttttgat      540
gacaacctgg ccaacctgct cctagccttc ctgcggcgcc agccacagcc ctggtgcctg      600
gtggcacaca atggtgaccg ctacgacttc ccctgctcc aagcagagct ggctatgctg       660
ggcctcacca gtgctctgga tggtgccttc tgtgtggata gcatcactgc gctgaaggcc      720
ctggagcgag caagcagccc ctcagaacac ggcccaagga gagctacag cctaggcagc       780 atctacactc gcctgtatgg gcagtcccct ccagactcgc acacggctga gggtgatgtc      840
ctggccctgc tcagcatctg tcagtggaga ccacaggccc tgctgcggtg gtggatgct      900 cacgccaggc ctttcggcac catcaggccc atgtatgggg tcacagcctc tgctaggacc      960
aaagatctct ccggaggagg tggctcaggt ggtggaggat ctggaggagg tgggagtggt     1020
ggaggtggtt ctaccggtct cgagcccaaa tcttctgaca aaactcacac atgtccaccg     1080
tgcccagcac ctgaactcct gggggaccg tcagtcttcc tcttcccccc aaaacccaag      1140 gacacccctca tgatctcccg gacccctgag gtcacatgcg tggtggtgga cgtgagccac     1200
gaagaccctg aggtcaagtt caactggtac gtggacggcg tggaggtgca taatgccaag     1260
acaaagccgc gggaggagca gtacaacagc acgtaccgtg tggtcagcgt cctcaccgtc     1320
ctgcaccagg actggctgaa tggcaaggag tacaagtgca aggtctccaa caaagccctc     1380
ccagccccca tcgagaaaac catctccaaa gccaagggc agccccgaga accacaggtg      1440
tacaccctgc cccatcccg ggatgagctg accaagaacc aggtcagcct gacctgcctg      1500
gtcaaaggct tctatcccag cgacatcgcc gtggagtggg agagcaatgg gcagccggag     1560
aacaactaca agaccacgcc tcccgtgctg gactccgacg gctccttctt cctctacagc     1620
aagctcaccg tggacaagag caggtggcag caggggaacg tcttctcatg ctccgtgatg     1680
catgaggctc tgcacaacca ctacacgcag aagagcctct ctctgtctcc gggtaaagtc     1740
gacggtgcta gcagccatgt gaatgtgagc agccctagcg tgcaggatat cctgaagatc     1800
gcagccttca acatccagac atttggggag accaagatgt ccaatgccac cctcgtcagc     1860
tacattgtgc agatcctgag ccgctatgac atcgccctgg tccaggaggt cagagacagc     1920
cacctgactg ccgtggggaa gctgctggac aacctcaatc aggatgcacc agacacctat     1980
cactacgtgg tcagtgagcc actgggacgg aacagctata aggagcgcta cctgttcgtg     2040
tacaggcctg accaggtgtc tgcggtggac agctactact acgatgatgg ctgcgagccc     2100
tgcgggaacg acaccttcaa ccgagagcca gccattgtca ggttcttctc ccggttcaca     2160
gaggtcaggg agtttgccat tgttcccctg catgcggccc cggggacgc agtagccgag      2220 atcgacgctc tctatgacgt ctacctggat gtccaagaga atgggggctc ggaggacgtc     2280
atgttgatgg gcgacttcaa tgcgggctgc agctatgtga ccctcccca gtggtcatcc      2340 atccgcctgt ggacaagccc caccttccag tggctgatcc ccgacagcgc tgacaccaca     2400
gctacaccca cgcactgtgc ctatgacagg atcgtggttg cagggatgct gctccgaggc     2460
gccgttgttc ccgactcggc tcttcccttt aacttccagn ctgcctatgg cctgagtgac     2520
caactggccc aagccatcag tgaccactat ccagtggagg tgatgctgaa gtgataatct     2580
aga                                                                    2583
```

<210> SEQ ID NO 203
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (825)..(825)
<223> OTHER INFORMATION: Any amino acid

<400> SEQUENCE: 203

```
Met Glu Thr Pro Ala Gln Leu Leu Phe Leu Leu Leu Leu Trp Leu Pro
1               5                   10                  15

Asp Thr Thr Gly Met Gly Pro Gly Ala Arg Arg Gln Gly Arg Ile Val
            20                  25                  30

Gln Gly Arg Pro Glu Met Cys Phe Cys Pro Pro Thr Pro Leu Pro
        35                  40                  45

Pro Leu Arg Ile Leu Thr Leu Gly Thr His Thr Pro Thr Pro Cys Ser
    50                  55                  60

Ser Pro Gly Ser Ala Ala Gly Thr Tyr Pro Thr Met Gly Ser Gln Ala
65                  70                  75                  80

Leu Pro Pro Gly Pro Met Gln Thr Leu Ile Phe Phe Asp Met Glu Ala
                85                  90                  95

Thr Gly Leu Pro Phe Ser Gln Pro Lys Val Thr Glu Leu Cys Leu Leu
            100                 105                 110

Ala Val His Arg Cys Ala Leu Glu Ser Pro Pro Thr Ser Gln Gly Pro
        115                 120                 125

Pro Pro Thr Val Pro Pro Pro Arg Val Val Asp Lys Leu Ser Leu
    130                 135                 140

Cys Val Ala Pro Gly Lys Ala Cys Ser Pro Ala Ala Ser Glu Ile Thr
145                 150                 155                 160

Gly Leu Ser Thr Ala Val Leu Ala Ala His Gly Arg Gln Cys Phe Asp
                165                 170                 175

Asp Asn Leu Ala Asn Leu Leu Leu Ala Phe Leu Arg Arg Gln Pro Gln
            180                 185                 190

Pro Trp Cys Leu Val Ala His Asn Gly Asp Arg Tyr Asp Phe Pro Leu
        195                 200                 205

Leu Gln Ala Glu Leu Ala Met Leu Gly Leu Thr Ser Ala Leu Asp Gly
    210                 215                 220

Ala Phe Cys Val Asp Ser Ile Thr Ala Leu Lys Ala Leu Glu Arg Ala
225                 230                 235                 240

Ser Ser Pro Ser Glu His Gly Pro Arg Lys Ser Tyr Ser Leu Gly Ser
                245                 250                 255

Ile Tyr Thr Arg Leu Tyr Gly Gln Ser Pro Pro Asp Ser His Thr Ala
            260                 265                 270

Glu Gly Asp Val Leu Ala Leu Leu Ser Ile Cys Gln Trp Arg Pro Gln
        275                 280                 285

Ala Leu Leu Arg Trp Val Asp Ala His Ala Arg Pro Phe Gly Thr Ile
    290                 295                 300

Arg Pro Met Tyr Gly Val Thr Ala Ser Ala Arg Thr Lys Gly Gly Gly
305                 310                 315                 320

Gly Ser Gly Gly Gly Gly Ser Gly Gly Gly Ser Gly Gly Gly Gly
                325                 330                 335
```

```
Ser Leu Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
            355                 360                 365

Lys Pro Lys Asp Thr Leu Met Ile Ser Arg Thr Pro Glu Val Thr Cys
370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
            485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys Val Asp Gly Ala Ser Ser
            565                 570                 575

His Val Asn Val Ser Ser Pro Ser Val Gln Asp Ile Leu Lys Ile Ala
            580                 585                 590

Ala Phe Asn Ile Gln Thr Phe Gly Glu Thr Lys Met Ser Asn Ala Thr
            595                 600                 605

Leu Val Ser Tyr Ile Val Gln Ile Leu Ser Arg Tyr Asp Ile Ala Leu
            610                 615                 620

Val Gln Glu Val Arg Asp Ser His Leu Thr Ala Val Gly Lys Leu Leu
625                 630                 635                 640

Asp Asn Leu Asn Gln Asp Ala Pro Asp Thr Tyr His Tyr Val Val Ser
            645                 650                 655

Glu Pro Leu Gly Arg Asn Ser Tyr Lys Glu Arg Tyr Leu Phe Val Tyr
            660                 665                 670

Arg Pro Asp Gln Val Ser Ala Val Asp Ser Tyr Tyr Tyr Asp Asp Gly
            675                 680                 685

Cys Glu Pro Cys Gly Asn Asp Thr Phe Asn Arg Glu Pro Ala Ile Val
            690                 695                 700

Arg Phe Phe Ser Arg Phe Thr Glu Val Arg Glu Phe Ala Ile Val Pro
705                 710                 715                 720

Leu His Ala Ala Pro Gly Asp Ala Val Ala Glu Ile Asp Ala Leu Tyr
            725                 730                 735

Asp Val Tyr Leu Asp Val Gln Glu Lys Trp Gly Ser Glu Asp Val Met
            740                 745                 750

Leu Met Gly Asp Phe Asn Ala Gly Cys Ser Tyr Val Arg Pro Ser Gln
```

|  |  | 755 |  |  | 760 |  |  | 765 |  |
| --- | --- | --- | --- | --- | --- | --- | --- | --- | --- |

Trp Ser Ser Ile Arg Leu Trp Thr Ser Pro Thr Phe Gln Trp Leu Ile
 770                 775                 780

Pro Asp Ser Ala Asp Thr Thr Ala Thr Pro Thr His Cys Ala Tyr Asp
785                 790                 795                 800

Arg Ile Val Val Ala Gly Met Leu Leu Arg Gly Ala Val Val Pro Asp
                805                 810                 815

Ser Ala Leu Pro Phe Asn Phe Gln Xaa Ala Tyr Gly Leu Ser Asp Gln
            820                 825                 830

Leu Ala Gln Ala Ile Ser Asp His Tyr Pro Val Glu Val Met Leu Lys
        835                 840                 845

<210> SEQ ID NO 204
<211> LENGTH: 2190
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204

```
gttaagcttg ccaccatgga aacccccagcg cagcttctct tcctcctgct actctggctc      60
```



```
gttaagcttg ccaccatgga aacccagcg cagcttctct tcctcctgct actctggctc        60
ccagatacca ccggtaagga atcccgggcc aagaaattcc agcggcagca tatggactca      120
gacagttccc ccagcagcag ctccacctac tgtaaccaaa tgatgaggcg ccggaatatg      180
acacaggggc ggtgcaaacc agtgaacacc tttgtgcacg agcccctggt agatgtccag      240
aatgtctgtt tccaggaaaa ggtcacctgc aagaacgggc agggcaactg ctacaagagc      300
aactccagca tgcacatcac agactgccgc ctgacaaacg gctccaggta ccccaactgt      360
gcataccgga ccagcccgaa ggagagacac atcattgtgg cctgtgaagg agcccatat       420 gtgccagtcc actttgatgc ttctgtggag gactctacag atctctccgg aggaggtggc      480
tcaggtggtg gaggatctgg aggaggtggg agtggtggag tggttctac cggtctcgag       540 cccaaatctt ctgacaaaac tcacacatgt ccaccgtgcc cagcacctga actcctgggg      600
ggaccgtcag tcttcctctt cccccccaaaa cccaaggaca ccctcatgat ctcccggacc      660
cctgaggtca catgcgtggt ggtggacgtg agccacgaag accctgaggt caagttcaac      720
tggtacgtgg acggcgtgga ggtgcataat gccaagacaa agccgcggga ggagcagtac      780
aacagcacgt accgtgtggt cagcgtcctc accgtcctgc accaggactg gctgaatggc      840
aaggagtaca agtgcaaggt ctccaacaaa gccctcccag cccccatcga gaaaaccatc      900
tccaaagcca agggcagccc cgagaaccca caggtgtaca ccctgccccc atcccgggat      960
gagctgacca agaaccaggt cagcctgacc tgcctggtca aaggcttcta tcccagcgac     1020
atcgccgtgg agtgggagag caatgggcag ccggagaaca actacaagac cacgcctccc     1080
gtgctggact ccgacggctc cttcttcctc tacagcaagc tcaccgtgga caagagcagg     1140
tggcagcagg ggaacgtctt ctcatgctcc gtgatgcatg aggctctgca caaccactac     1200
acgcagaaga gcctctctct gtctccgggt aaagtcgacg gtgctagcag ccatgtgaat     1260
gtgagcagcc ctagcgtgca ggatatcatg ggccctggag ctcgcagaca gggcaggatt     1320
gtgcagggaa ggcctgagat gtgcttctgc ccaccccta ccccactccc tcccttcgg      1380 atcttaacac tgggcactca cacccccacc ccatgctcct ctccaggctc agcagcaggt     1440
acgtacccaa ccatgggctc gcaggccctg ccccgggc ccatgcagac cctcatcttt      1500
ttcgacatgg aggccactgg cttgcccttc tcccagccca aggtcacgga gctgtgcctg     1560
```

```
ctggctgtcc acagatgtgc cctggagagc ccccccacct ctcagggcc acctcccaca   1620 gttcctccac caccgcgtgt ggtagacaag ctctccctgt gtgtggctcc ggggaaggcc   1680
tgcagccctg cagccagcga gatcacaggt ctgagcacag ctgtgctggc agcgcatggg   1740
cgtcaatgtt ttgatgacaa cctggccaac ctgctcctag ccttcctgcg cgcgcagcca   1800
cagccctggt gcctggtggc acacaatggt gaccgctacg acttcccct gctccaagca    1860 gagctggcta tgctgggcct caccagtgct ctggatggtg ccttctgtgt ggatagcatc   1920
actgcgctga aggccctgga gcgagcaagc agcccctcag aacacggccc aaggaagagc   1980
tacagcctag gcagcatcta cactcgcctg tatgggcagt cccctccaga ctcgcacacg   2040
gctgagggtg atgtcctggc cctgctcagc atctgtcagt ggagaccaca ggccctgctg   2100
cggtgggtgg atgctcacgc caggcctttc ggcaccatca ggcccatgta tgggtcaca    2160 gcctctgcta ggaccaaatg ataatctaga                                    2190
```

<210> SEQ ID NO 205
<211> LENGTH: 716
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Gly Gly Gly Ser Gly Gly Gly Ser Gly Gly
145                 150                 155                 160

Gly Gly Ser Gly Gly Gly Gly Ser Leu Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240
```

-continued

```
Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
    290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys Val Asp Gly Ala Ser Ser His Val Asn Val Ser Ser Pro Ser Val
                405                 410                 415

Gln Asp Ile Met Gly Pro Gly Ala Arg Arg Gly Arg Ile Val Gln
            420                 425                 430

Gly Arg Pro Glu Met Cys Phe Cys Pro Pro Thr Pro Leu Pro Pro
        435                 440                 445

Leu Arg Ile Leu Thr Leu Gly Thr His Thr Pro Thr Pro Cys Ser Ser
    450                 455                 460

Pro Gly Ser Ala Ala Gly Thr Tyr Pro Thr Met Gly Ser Gln Ala Leu
465                 470                 475                 480

Pro Pro Gly Pro Met Gln Thr Leu Ile Phe Phe Asp Met Glu Ala Thr
                485                 490                 495

Gly Leu Pro Phe Ser Gln Pro Lys Val Thr Glu Leu Cys Leu Leu Ala
            500                 505                 510

Val His Arg Cys Ala Leu Glu Ser Pro Pro Thr Ser Gln Gly Pro Pro
        515                 520                 525

Pro Thr Val Pro Pro Pro Arg Val Val Asp Lys Leu Ser Leu Cys
    530                 535                 540

Val Ala Pro Gly Lys Ala Cys Ser Pro Ala Ala Ser Glu Ile Thr Gly
545                 550                 555                 560

Leu Ser Thr Ala Val Leu Ala Ala His Gly Arg Gln Cys Phe Asp Asp
                565                 570                 575

Asn Leu Ala Asn Leu Leu Ala Phe Leu Arg Arg Gln Pro Gln Pro
            580                 585                 590

Trp Cys Leu Val Ala His Asn Gly Asp Arg Tyr Asp Phe Pro Leu Leu
        595                 600                 605

Gln Ala Glu Leu Ala Met Leu Gly Leu Thr Ser Ala Leu Asp Gly Ala
    610                 615                 620

Phe Cys Val Asp Ser Ile Thr Ala Leu Lys Ala Leu Glu Arg Ala Ser
625                 630                 635                 640

Ser Pro Ser Glu His Gly Pro Arg Lys Ser Tyr Ser Leu Gly Ser Ile
                645                 650                 655

Tyr Thr Arg Leu Tyr Gly Gln Ser Pro Pro Asp Ser His Thr Ala Glu
```

| | | | |
|---|---|---|---|
| | 660 | 665 | 670 |
| Gly Asp Val Leu Ala Leu Leu Ser Ile Cys Gln Trp Arg Pro Gln Ala | | | |
| | 675 | 680 | 685 |
| Leu Leu Arg Trp Val Asp Ala His Ala Arg Pro Phe Gly Thr Ile Arg | | | |
| | 690 | 695 | 700 |
| Pro Met Tyr Gly Val Thr Ala Ser Ala Arg Thr Lys | | | |
| 705 | | 710 | 715 |

<210> SEQ ID NO 206
<211> LENGTH: 2589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206

```
gttaagcttg ccaccatgga aaccccagcg cagcttctct tcctcctgct actctggctc      60
ccagatacca ccggtatgag gatctgctcc ttcaacgtca ggtcctttgg ggaaagcaag     120
caggaagaca agaatgccat ggatgtcatt gtgaaggtca tcaaacgctg tgacatcata     180
ctcgtgatgg aaatcaagga cagcaacaac aggatctgcc ccatactgat ggagaagctg     240
aacagaaatt caaggagagg cataacatac aactatgtga ttagctctcg gcttggaaga     300
aacacatata agaacaata tgcctttctc tacaaggaaa gctggtgtc tgtgaagagg     360
agttatcact accatgacta tcaggatgga gacgcagatg tgttttccag ggagcccttt     420
gtggtctggt ccaatctcc ccacactgct gtcaaagact cgtgattat ccccctgcac     480
accaccccag agacatccgt taaggagatc gatgagttgg ttgaggtcta cacggacgtg     540
aaacaccgct ggaaggcgga gaatttcatt ttcatgggtg acttcaatgc cggctgcagc     600
tacgtcccca gaaggcctg gaagaacatc cgcttgagga ctgaccccag gtttgtttgg     660
ctgatcgggg accaagagga caccacggtg aagaagagca ccaactgtgc atatgacagg     720
attgtgctta gaggacaaga aatcgtcagt tctgttgttc ccaagtcaaa cagtgttttt     780
gacttccaga aagcttacaa gctgactgaa gaggaggccc tggatgtcag cgaccacttt     840
ccagttgaat ttaaactaca gtcttcaagg gccttcacca acagcaaaaa atctgtcact     900
ctaaggaaga aaacaaagag caaacgctca gatctcgagc ccaaatcttc tgacaaaact     960
cacacatgtc caccgtgccc agcacctgaa ctcctggggg gaccgtcagt cttcctcttc    1020
cccccaaaac ccaaggacac cctcatgatc tcccggaccc ctgaggtcac atgcgtggtg    1080
gtggacgtga gccacgaaga ccctgaggtc aagttcaact ggtacgtgga cggcgtggag    1140
gtgcataatg ccaagacaaa gccgcgggag gagcagtaca acagcacgta ccgtgtggtc    1200
agcgtcctca ccgtcctgca ccaggactgg ctgaatggca aggagtacaa gtgcaaggtc    1260
tccaacaaag ccctcccagc ccccatcgag aaaaccatct ccaaagccaa agggcagccc    1320
cgagaaccac aggtgtacac cctgccccca tcccgggatg agctgaccaa gaaccaggtc    1380
agcctgacct gcctggtcaa aggcttctat cccagcgaca tcgccgtgga gtgggagagc    1440
aatgggcagc cggagaacaa ctacaagacc acgcctcccg tgctggactc cgacggctcc    1500
ttcttcctct acagcaagct caccgtggac aagagcaggt ggcagcaggg gaacgtcttc    1560
tcatgctccg tgatgcatga ggctctgcac aaccactaca cgcagaagag cctctctctg    1620
tctccgggta aagtcgacgg agctagcagc cccgtgaacg tgagcagccc cagcgtgcag    1680
gatatcatgg gccctggagc tcgcagacag ggcaggattg tgcagggaag gcctgagatg    1740
```

```
tgcttctgcc cacccccta cccactccct cccttcgga tcttaacact gggcactcac    1800
acacccaccc catgctcctc tccaggctca gcagcaggta cgtacccaac catgggctcg    1860
caggccctgc ccccggggcc catgcagacc ctcatctttt tcgacatgga ggccactggc    1920
ttgcccttct cccagcccaa ggtcacggag ctgtgcctgc tggctgtcca cagatgtgcc    1980
ctggagagcc ccccacctc tcagggcca cctcccacag ttcctccacc accgcgtgtg    2040
gtagacaagc tctccctgtg tgtggctccg gggaaggcct gcagccctgc agccagcgag    2100
atcacaggtc tgagcacagc tgtgctggca gcgcatgggc gtcaatgttt tgatgacaac    2160
ctggccaacc tgctcctagc cttcctgcgg cgccagccac agccctggtg cctggtggca    2220
cacaatggtg accgctacga cttccccctg ctccaagcag agctggctat gctgggcctc    2280
accagtgctc tggatggtgc cttctgtgtg gatagcatca ctgcgctgaa ggccctggag    2340
cgagcaagca gcccctcaga acacggccca aggaagagct acagcctagg cagcatctac    2400
actcgcctgt atgggcagtc ccctccagac tcgcacacgg ctgagggtga tgtcctggcc    2460
ctgctcagca tctgtcagtg gagaccacag gccctgctgc ggtgggtgga tgctcacgcc    2520
aggcctttcg gcaccatcag gcccatgtat ggggtcacag cctctgctag gaccaaatga    2580
taatctaga                                                            2589
```

<210> SEQ ID NO 207
<211> LENGTH: 854
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

```
Met Glu Thr Pro Ala Gln Leu Leu Phe Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
```

```
                195                 200                 205
Thr Asp Pro Arg Phe Val Trp Leu Ile Gly Asp Gln Glu Asp Thr Thr
210                 215                 220
Val Lys Lys Ser Thr Asn Cys Ala Tyr Asp Arg Ile Val Leu Arg Gly
225                 230                 235                 240
Gln Glu Ile Val Ser Val Val Pro Lys Ser Asn Ser Val Phe Asp
                245                 250                 255
Phe Gln Lys Ala Tyr Lys Leu Thr Glu Glu Ala Leu Asp Val Ser
                260                 265                 270
Asp His Phe Pro Val Glu Phe Lys Leu Gln Ser Ser Arg Ala Phe Thr
                275                 280                 285
Asn Ser Lys Lys Ser Val Thr Leu Arg Lys Lys Thr Lys Ser Lys Arg
290                 295                 300
Ser Asp Leu Glu Pro Lys Ser Ser Asp Lys Thr His Thr Cys Pro Pro
305                 310                 315                 320
Cys Pro Ala Pro Glu Leu Leu Gly Gly Pro Ser Val Phe Leu Phe Pro
                325                 330                 335
Pro Lys Pro Lys Asp Thr Leu Met Ile Ser Arg Thr Pro Glu Val Thr
                340                 345                 350
Cys Val Val Val Asp Val Ser His Glu Asp Pro Glu Val Lys Phe Asn
                355                 360                 365
Trp Tyr Val Asp Gly Val Glu Val His Asn Ala Lys Thr Lys Pro Arg
370                 375                 380
Glu Glu Gln Tyr Asn Ser Thr Tyr Arg Val Val Ser Val Leu Thr Val
385                 390                 395                 400
Leu His Gln Asp Trp Leu Asn Gly Lys Glu Tyr Lys Cys Lys Val Ser
                405                 410                 415
Asn Lys Ala Leu Pro Ala Pro Ile Glu Lys Thr Ile Ser Lys Ala Lys
                420                 425                 430
Gly Gln Pro Arg Glu Pro Gln Val Tyr Thr Leu Pro Pro Ser Arg Asp
                435                 440                 445
Glu Leu Thr Lys Asn Gln Val Ser Leu Thr Cys Leu Val Lys Gly Phe
450                 455                 460
Tyr Pro Ser Asp Ile Ala Val Glu Trp Glu Ser Asn Gly Gln Pro Glu
465                 470                 475                 480
Asn Asn Tyr Lys Thr Thr Pro Pro Val Leu Asp Ser Asp Gly Ser Phe
                485                 490                 495
Phe Leu Tyr Ser Lys Leu Thr Val Asp Lys Ser Arg Trp Gln Gln Gly
                500                 505                 510
Asn Val Phe Ser Cys Ser Val Met His Glu Ala Leu His Asn His Tyr
                515                 520                 525
Thr Gln Lys Ser Leu Ser Leu Ser Pro Gly Lys Val Asp Gly Ala Ser
                530                 535                 540
Ser Pro Val Asn Val Ser Ser Pro Ser Val Gln Asp Ile Met Gly Pro
545                 550                 555                 560
Gly Ala Arg Arg Gln Gly Arg Ile Val Gln Gly Arg Pro Glu Met Cys
                565                 570                 575
Phe Cys Pro Pro Pro Thr Pro Leu Pro Pro Leu Arg Ile Leu Thr Leu
                580                 585                 590
Gly Thr His Thr Pro Thr Pro Cys Ser Ser Pro Gly Ser Ala Ala Gly
                595                 600                 605
Thr Tyr Pro Thr Met Gly Ser Gln Ala Leu Pro Pro Gly Pro Met Gln
610                 615                 620
```

```
Thr Leu Ile Phe Phe Asp Met Glu Ala Thr Gly Leu Pro Phe Ser Gln
625                 630                 635                 640

Pro Lys Val Thr Glu Leu Cys Leu Leu Ala Val His Arg Cys Ala Leu
            645                 650                 655

Glu Ser Pro Pro Thr Ser Gln Gly Pro Pro Thr Val Pro Pro Pro
        660                 665                 670

Pro Arg Val Val Asp Lys Leu Ser Leu Cys Val Ala Pro Gly Lys Ala
            675                 680                 685

Cys Ser Pro Ala Ala Ser Glu Ile Thr Gly Leu Ser Thr Ala Val Leu
        690                 695                 700

Ala Ala His Gly Arg Gln Cys Phe Asp Asp Asn Leu Ala Asn Leu Leu
705                 710                 715                 720

Leu Ala Phe Leu Arg Arg Gln Pro Gln Pro Trp Cys Leu Val Ala His
            725                 730                 735

Asn Gly Asp Arg Tyr Asp Phe Pro Leu Leu Gln Ala Glu Leu Ala Met
            740                 745                 750

Leu Gly Leu Thr Ser Ala Leu Asp Gly Ala Phe Cys Val Asp Ser Ile
            755                 760                 765

Thr Ala Leu Lys Ala Leu Glu Arg Ala Ser Ser Pro Ser Glu His Gly
    770                 775                 780

Pro Arg Lys Ser Tyr Ser Leu Gly Ser Ile Tyr Thr Arg Leu Tyr Gly
785                 790                 795                 800

Gln Ser Pro Pro Asp Ser His Thr Ala Glu Gly Asp Val Leu Ala Leu
            805                 810                 815

Leu Ser Ile Cys Gln Trp Arg Pro Gln Ala Leu Leu Arg Trp Val Asp
                820                 825                 830

Ala His Ala Arg Pro Phe Gly Thr Ile Arg Pro Met Tyr Gly Val Thr
            835                 840                 845

Ala Ser Ala Arg Thr Lys
    850

<210> SEQ ID NO 208
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 0 to 5 "GGGGS"
      repeating units

<400> SEQUENCE: 208

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209
```

-continued

```
Gly Gly Gly Gly Ser Gly Gly Gly Gly Ser Gly Gly Gly Ser Gly
1               5                   10                  15

Gly Gly Gly Ser Gly Gly Gly Gly Ser
            20                  25

<210> SEQ ID NO 210
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "GGGGS"
      repeating units

<400> SEQUENCE: 210

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Gly Gly Ser Gly Gly Gly Gly Ser Gly Gly Gly Gly Ser
1               5                   10                  15

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Gly Gly Gly Ser Gly Gly Gly Gly Ser Gly Gly Gly Gly Ser Gly
1               5                   10                  15

Gly Gly Gly Ser
        20

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Gly Gly Gly Ser
1               5
```

```
<210> SEQ ID NO 214
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(51)
<223> OTHER INFORMATION: This region may encompass 1 to 10 "GGGGS"
      repeating units

<400> SEQUENCE: 214

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Gly Gly Gly Gly Ser Gly Gly Gly Gly Ser Gly Gly Gly Gly Ser
1               5                   10                  15

<210> SEQ ID NO 216
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 217
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(31)
<223> OTHER INFORMATION: This region may encompass 1 to 6 "GGGGS"
      repeating units

<400> SEQUENCE: 217

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
```

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 3 to 5 "GGGGS"
      repeating units

<400> SEQUENCE: 218

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 1 to 5 "GGGGS"
      repeating units

<400> SEQUENCE: 219

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: This sequence may encompass 1 to 12 repeating
      "t" nucleotides

<400> SEQUENCE: 220
tttttttttt tttttttt                                                 18

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Gly Gly
1               5

-continued

```
<210> SEQ ID NO 222
<211> LENGTH: 1177
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(1164)

<400> SEQUENCE: 222
gttaagcttg ccacc atg ggt ctg gag aag tcc ctc att ctg ttt cca ttg       51
               Met Gly Leu Glu Lys Ser Leu Ile Leu Phe Pro Leu
                 1               5                  10 ttt ttc ctg ctg ctt gga tgg gtc cag cct tcc ccg ggc agg gaa tct        99
Phe Phe Leu Leu Leu Gly Trp Val Gln Pro Ser Pro Gly Arg Glu Ser
            15                  20                  25 gca gca cag aag ttt cag cgg cag cac atg gat cca gat ggt tcc tcc       147
Ala Ala Gln Lys Phe Gln Arg Gln His Met Asp Pro Asp Gly Ser Ser
         30                  35                  40 atc aac agc ccc acc tac tgc aac caa atg atg aaa cgc cgg gat atg       195
Ile Asn Ser Pro Thr Tyr Cys Asn Gln Met Met Lys Arg Arg Asp Met
 45                  50                  55                  60 aca aat ggg tca tgc aag ccc gtg aac acc ttc gtg cat gag ccc ttg       243
Thr Asn Gly Ser Cys Lys Pro Val Asn Thr Phe Val His Glu Pro Leu
                 65                  70                  75 gca gat gtc cag gcc gtc tgc tcc cag gaa aat gtc acc tgc aag aac       291
Ala Asp Val Gln Ala Val Cys Ser Gln Glu Asn Val Thr Cys Lys Asn
             80                  85                  90 agg aag agc aac tgc tac aag agc agc tct gcc ctg cac atc act gac       339
Arg Lys Ser Asn Cys Tyr Lys Ser Ser Ser Ala Leu His Ile Thr Asp
         95                 100                 105 tgc cac ctg aag ggc aac tcc aag tat ccc aac tgt gac tac aag acc       387
Cys His Leu Lys Gly Asn Ser Lys Tyr Pro Asn Cys Asp Tyr Lys Thr
    110                 115                 120 act caa tac cag aag cac atc att gtg gcc tgt gaa ggg aac ccc tac       435
Thr Gln Tyr Gln Lys His Ile Ile Val Ala Cys Glu Gly Asn Pro Tyr
125                 130                 135                 140 gta cca gtc cac ttt gat gct act gtg ctc gag ccc aga ggt ctc aca       483
Val Pro Val His Phe Asp Ala Thr Val Leu Glu Pro Arg Gly Leu Thr
                145                 150                 155 atc aag ccc tct cct cca tgc aaa tgc cca gca cct aac ctc ttg ggt       531
Ile Lys Pro Ser Pro Pro Cys Lys Cys Pro Ala Pro Asn Leu Leu Gly
            160                 165                 170 gga tca tcc gtc ttc atc ttc cct cca aag atc aag gat gta ctc atg       579
Gly Ser Ser Val Phe Ile Phe Pro Pro Lys Ile Lys Asp Val Leu Met
        175                 180                 185 atc tcc ctg agc ccc atg gtc aca tgt gtg gtg gtg gat gtg agc gag       627
Ile Ser Leu Ser Pro Met Val Thr Cys Val Val Val Asp Val Ser Glu
    190                 195                 200 gat gac cca gac gtc cag atc agc tgg ttt gtg aac aac gtg gaa gta       675
Asp Asp Pro Asp Val Gln Ile Ser Trp Phe Val Asn Asn Val Glu Val
205                 210                 215                 220 cac aca gct cag aca caa acc cat aga gag gat tac aac agt act ctc       723
His Thr Ala Gln Thr Gln Thr His Arg Glu Asp Tyr Asn Ser Thr Leu
                225                 230                 235 cgg gtg gtc agt gcc ctc ccc atc cag cac cag gac tgg atg agt ggc       771
Arg Val Val Ser Ala Leu Pro Ile Gln His Gln Asp Trp Met Ser Gly
            240                 245                 250 aag gag ttc aaa tgc tcg gtc aac aac aaa gac ctc cca gcg tcc atc       819
Lys Glu Phe Lys Cys Ser Val Asn Asn Lys Asp Leu Pro Ala Ser Ile
```

| | | |
|---|---|---|
| gag aga acc atc tca aaa ccc aga ggg cca gta aga gct cca cag gta<br>Glu Arg Thr Ile Ser Lys Pro Arg Gly Pro Val Arg Ala Pro Gln Val<br>270                         275                     280 | 867 | |
| tat gtc ttg cct cca cca gca gaa gag atg act aag aaa gag ttc agt<br>Tyr Val Leu Pro Pro Pro Ala Glu Glu Met Thr Lys Lys Glu Phe Ser<br>285                     290                     295                     300 | 915 | |
| ctg acc tgc atg atc aca ggc ttc tta cct gcc gaa att gct gtg gac<br>Leu Thr Cys Met Ile Thr Gly Phe Leu Pro Ala Glu Ile Ala Val Asp<br>                     305                     310                     315 | 963 | |
| tgg acc agc aat ggg cgt aca gag caa aac tac aag aac acc gca aca<br>Trp Thr Ser Asn Gly Arg Thr Glu Gln Asn Tyr Lys Asn Thr Ala Thr<br>             320                     325                     330 | 1011 | |
| gtc ctg gac tct gat ggt tct tac ttc atg tac agc aag ctc aga gta<br>Val Leu Asp Ser Asp Gly Ser Tyr Phe Met Tyr Ser Lys Leu Arg Val<br>             335                     340                     345 | 1059 | |
| caa aag agc act tgg gaa aga gga agt ctt ttc gcc tgc tca gtg gtc<br>Gln Lys Ser Thr Trp Glu Arg Gly Ser Leu Phe Ala Cys Ser Val Val<br>350                         355                     360 | 1107 | |
| cac gag ggt ctg cac aat cac ctt acg act aag agc ttc tct cgg act<br>His Glu Gly Leu His Asn His Leu Thr Thr Lys Ser Phe Ser Arg Thr<br>365                         370                     375                     380 | 1155 | |
| ccg ggt aaa tgataatcta gaa<br>Pro Gly Lys | 1177 | |

<210> SEQ ID NO 223
<211> LENGTH: 383
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 223

Met Gly Leu Glu Lys Ser Leu Ile Leu Phe Pro Leu Phe Phe Leu Leu
1                5                    10                  15

Leu Gly Trp Val Gln Pro Ser Pro Gly Arg Glu Ser Ala Ala Gln Lys
               20                    25                    30

Phe Gln Arg Gln His Met Asp Pro Asp Gly Ser Ser Ile Asn Ser Pro
           35                    40                    45

Thr Tyr Cys Asn Gln Met Met Lys Arg Arg Asp Met Thr Asn Gly Ser
 50                   55                    60

Cys Lys Pro Val Asn Thr Phe Val His Glu Pro Leu Ala Asp Val Gln
65                    70                    75                    80

Ala Val Cys Ser Gln Glu Asn Val Thr Cys Lys Asn Arg Lys Ser Asn
               85                    90                    95

Cys Tyr Lys Ser Ser Ser Ala Leu His Ile Thr Asp Cys His Leu Lys
           100                   105                   110

Gly Asn Ser Lys Tyr Pro Asn Cys Asp Tyr Lys Thr Thr Gln Tyr Gln
         115                   120                   125

Lys His Ile Ile Val Ala Cys Glu Gly Asn Pro Tyr Val Pro Val His
 130                  135                   140

Phe Asp Ala Thr Val Leu Glu Pro Arg Gly Leu Thr Ile Lys Pro Ser
145                  150                  155                  160

Pro Pro Cys Lys Cys Pro Ala Pro Asn Leu Leu Gly Gly Ser Ser Val
         165                   170                   175

Phe Ile Phe Pro Pro Lys Ile Lys Asp Val Leu Met Ile Ser Leu Ser
           180                   185                   190

```
Pro Met Val Thr Cys Val Val Asp Val Ser Glu Asp Asp Pro Asp
        195                 200             205
Val Gln Ile Ser Trp Phe Val Asn Asn Val Glu Val His Thr Ala Gln
        210                 215             220
Thr Gln Thr His Arg Glu Asp Tyr Asn Ser Thr Leu Arg Val Val Ser
225             230                 235                 240
Ala Leu Pro Ile Gln His Gln Asp Trp Met Ser Gly Lys Glu Phe Lys
            245                 250                 255
Cys Ser Val Asn Asn Lys Asp Leu Pro Ala Ser Ile Glu Arg Thr Ile
                260                 265                 270
Ser Lys Pro Arg Gly Pro Val Arg Ala Pro Gln Val Tyr Val Leu Pro
            275                 280                 285
Pro Pro Ala Glu Glu Met Thr Lys Lys Glu Phe Ser Leu Thr Cys Met
        290                 295                 300
Ile Thr Gly Phe Leu Pro Ala Glu Ile Ala Val Asp Trp Thr Ser Asn
305             310                 315                 320
Gly Arg Thr Glu Gln Asn Tyr Lys Asn Thr Ala Thr Val Leu Asp Ser
                325                 330                 335
Asp Gly Ser Tyr Phe Met Tyr Ser Lys Leu Arg Val Gln Lys Ser Thr
            340                 345                 350
Trp Glu Arg Gly Ser Leu Phe Ala Cys Ser Val Val His Glu Gly Leu
        355                 360                 365
His Asn His Leu Thr Thr Lys Ser Phe Ser Arg Thr Pro Gly Lys
        370                 375                 380

<210> SEQ ID NO 224
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Met Gly Leu Glu Lys Ser Leu Val Arg Leu Leu Leu Leu Val Leu Ile
1               5                   10                  15
Leu Leu Val Leu Gly Trp Val Gln Pro Ser Leu Gly
            20                  25

<210> SEQ ID NO 225
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Met Glu Thr Pro Ala Gln Leu Leu Phe Leu Leu Leu Leu Trp Leu Pro
1               5                   10                  15
Asp Thr Thr Gly
            20
```